US009327137B2

(12) United States Patent
Audonnet et al.

(10) Patent No.: US 9,327,137 B2
(45) Date of Patent: May 3, 2016

(54) RECOMBINANT CDV COMPOSITIONS AND USES THEREOF

(75) Inventors: Jean-Christophe Audonnet, Lyons (FR); Jules Minke, Corbas (FR)

(73) Assignee: MERIAL, INC., Duluth, GA (US)

( * ) Notice: Subject to any disclaimer, the term of this patent is extended or adjusted under 35 U.S.C. 154(b) by 162 days.

(21) Appl. No.: 13/035,904

(22) Filed: Feb. 25, 2011

(65) Prior Publication Data

US 2011/0236419 A1  Sep. 29, 2011

Related U.S. Application Data

(60) Provisional application No. 61/308,620, filed on Feb. 26, 2010.

(51) Int. Cl.
| | |
|---|---|
| *A61K 39/12* | (2006.01) |
| *C07K 14/005* | (2006.01) |
| *C07K 14/535* | (2006.01) |
| *A61N 5/06* | (2006.01) |
| *A61K 39/00* | (2006.01) |

(52) U.S. Cl.
CPC .............. *A61N 5/0613* (2013.01); *A61K 39/12* (2013.01); *C07K 14/005* (2013.01); *C07K 14/535* (2013.01); *A61K 2039/53* (2013.01); *A61K 2039/545* (2013.01); *A61K 2039/552* (2013.01); *A61K 2039/55522* (2013.01); *C12N 2710/24043* (2013.01); *C12N 2750/14334* (2013.01); *C12N 2760/18422* (2013.01); *C12N 2760/18434* (2013.01); *C12N 2760/18471* (2013.01); *C12N 2800/22* (2013.01)

(58) Field of Classification Search
None
See application file for complete search history.

(56) References Cited

U.S. PATENT DOCUMENTS

| 5,606,024 A | 2/1997 | Boone et al. |
|---|---|---|
| 5,702,919 A | 12/1997 | Nash et al. |
| 5,756,102 A | 5/1998 | Paoletti et al. |
| 6,228,846 B1 | 5/2001 | Audonnet et al. |
| 6,309,647 B1 | 10/2001 | Paoletti et al. |
| 7,250,161 B2 | 7/2007 | Bublot et al. |
| 7,682,619 B2 * | 3/2010 | Dubovi ...................... 424/209.1 |
| 2001/0036928 A1 * | 11/2001 | Chamberlain et al. .......... 514/44 |
| 2005/0255127 A1 | 11/2005 | Loosmore et al. |

FOREIGN PATENT DOCUMENTS

| FR | 2 775 601 | 9/2001 |
|---|---|---|
| WO | WO97/49825 | 12/1997 |

OTHER PUBLICATIONS

GenBank Accession # AAQ05830, haemagglutinin [Canine distemper virus], May 4, 2004.*
GenBank Accession # NP_001003245, colony stimulating factor 2 [Canis lupus familiaris], Jun. 26, 2007.*
GenBank Accession# AF478545, Canine distemper virus isolate B haemagglutinin (H) gene, complete cds., May 4, 2004.*
GenBank Accession# NM_001003245, Canis familiaris granulocyte-macrophage colony-stimulating factor (CSF2), mRNA, Aug. 5, 2004.*
Puigbo et al., Optimizer: a web server for optimizing the codon usage of DNA sequences, 2007, Nucleic Acids Research, vol. 35, pp. W126-W131.*
Fenner, et al., 1987, Veterinary Virology, Academic Press, Inc., pp. 485-503.
Graves et al., "Measles Virus Polypeptide Synthesis in Infected Cells", 1978, Virology 86:254-263.
Diallo A., "Morbillivirus group genome organization and proteins", 1990, Vet. Micro. 23: 155-163.
Burgess et al., "Purification and Properties of Colony-stimulating Factor form Mouse Lung-conditioned Medium", 1977, J. Biol. Chem.252:1998-2003.
Cantrell et al., "Cloning, Sequence, and Expression of a Human Granulocyte/Macrophage Colony-Stimulating Factor", 1985, Proc. Natl. Acad. Sci. USA 82:6250-6254.
U.S. Appl. No. 09/587,964, Fischer et al.
Saldarriaga et al. "Immunogenicity of a multicomponent DNA vaccine against visceral leishmaniasis in dogs", 2006, Vaccine 24, 1928-1940.
Fischer L. et al., "vaccination of puppies born to Immune dams with a canine adenovirus-based vaccine protects against a canine distemper virus challenge", Vaccine, vol. 20. No. 29-30, Oct. 4, 2002, pp. 3485-3497).
Nielsen Line et al., "Changes in the receptor binding haemagglutinin protein of wild-type morbilliviruses are not required for adaptation to Vero cells", Virus Genes, vol. 27, No. 2 Oct. 2003 pp. 157-162.
Nash Ra et al., "Molecular cloning and in-vivo evaluation of canine granulocyte-macrophage colony-stimulating factor", Blood, vol. 78, 1991, pp. 930-937.
Jones T, et al., "Potential role of granulocyte-macrophage colony-stimulating factor as vaccine adjuvant", European Journal of Clinical Microbiology & Infectiour Disease, vol. 13, No. suppl 02, Jan. 1, 1994, pp. 47-53.

* cited by examiner

*Primary Examiner* — Benjamin P Blumel
(74) *Attorney, Agent, or Firm* — Judy Jarecki-Black; Ruoying Chen; Merial, Inc.

(57) ABSTRACT

The present invention provides vectors that contain and express in vivo or in vitro CDV polypeptides or antigens that elicit an immune response in animal against CDV, compositions comprising said vectors and/or CDV polypeptides, and methods of vaccination against CDV. The invention further provides methods for inducing an immunogenic or protective response against CDV and other canine virus, as well as methods for preventing or treating CDV and other canine virus or disease state(s) caused by CDV and other canine virus.

15 Claims, 40 Drawing Sheets

Figure 1A

| SEQ ID NO | Type | Gene Description |
|---|---|---|
| 1 | DNA | Codon-optimized CDV HA gene |
| 2 | Protein | CDV HA protein (encoded by codon-optimized DNA) |
| 3 | DNA | Codon-optimized canine GM-CSF |
| 4 | Protein | Codon-optimized canine GM-CSF |
| 5 | Protein | CDV HA protein in vCP258 |
| 6 | DNA | Part of pCXL1557.1 containing arms and insert (forward strand) |
| 7 | DNA | The entire pCXL1557.1 DNA sequence |
| 8 | DNA | Part of pJSY2218.1 containing arms and insert (forward strand) |
| 9 | DNA | The entire pJSY2218.1 DNA sequence |
| 10 | oligo | 13220CXL primer for synthetic CDV HA probe |
| 11 | oligo | 13225CXL primer for synthetic CDV HA probe |
| 12 | oligo | 7931DC primer for PCR amplification |
| 13 | oligo | 7932DC primer for PCR amplification |
| 14 | DNA | Part of vCP2263 containing arms and insert (forward strand) |
| 15 | oligo | 18071BK primer for amplifying canine GM-CSF probe |
| 16 | oligo | 18073BK primer for amplifying canine GM-CSF probe |
| 17 | oligo | 8103JY primer for PCR amplification of C3L-Canine GM-CSF-C3R |
| 18 | oligo | 8104JY primer for PCR amplification of C3L-Canine GM-CSF-C3R |
| 19 | DNA | Part of vCP2391 containing C3L-H6 promoter-Canine GM-CSF-C3R |
| 20 | Protein | AAQ05828 |
| 21 | Protein | ABF55673 |
| 22 | Protein | CAA55672 |
| 23 | Protein | AAQ96308 |
| 24 | Protein | ABF55671 |
| 25 | Protein | ACS88240 |
| 26 | Protein | ABK35770 |
| 27 | Protein | ACD92997 |
| 28 | Protein | ACI28389 |
| 29 | Protein | ACI28390 |
| 30 | Protein | ACN58242 |
| 31 | Protein | ABB51156 |
| 32 | Protein | ABK35780 |
| 33 | Protein | ACJ46470 |
| 34 | Protein | ABX84040 |

| Figure 1B | | |
|---|---|---|
| 35 | DNA | AF478545, wildtype DNA encoding CDV HA (AAQ05830) |
| 36 | DNA | AF478543 DNA encoding CDV HA AAQ05828 |
| 37 | DNA | DQ494318 DNA encoding CDV HA ABF55672 |
| 38 | DNA | AY386316 DNA encoding CDV HA AAQ96308 |
| 39 | DNA | DQ494317 DNA encoding CDV HA ABF55671 |
| 40 | DNA | GQ214376 DNA encoding CDV HAACS88240 |
| 41 | DNA | DQ889177 DNA encoding CDV HA ABK35770 |
| 42 | DNA | EU716337 DNA encoding CDV HA ACD92997 |
| 43 | DNA | FJ011004 DNA encoding CDV HA ACI28389 |
| 44 | DNA | FJ011005 DNA encoding CDV HA ACI28390 |
| 45 | DNA | FJ705233 DNA encoding CDV HA ACN58242 |
| 46 | DNA | DQ228166 DNA encoding CDV HA ABB51156 |
| 47 | DNA | DQ889187 DNA encoding CDV HA ABK35780 |
| 48 | DNA | FJ423608 DNA encoding CDV HA ACJ46470 |
| 49 | DNA | EU325730 DNA encoding CDV HA ABX84040 |
| 50 | DNA | Part of vCP2392 containing C3L-H6 promoter-Canine GM-CSF-C3R |
| 51 | DNA | Part of vCP2392 containing H6 promoter-Canine GM-CSF |

Figure 2

Comparison of synthetic CDV HA and CDV HA in vCP258 synthetic CDV HA: SEQ ID NO:2;   vCP258 CDV HA : SEQ ID NO:5
Sequence identity between SEQ ID NO:2 and SEQ ID NO:5 is 90.0% (Vector NTI program)

Figure 3
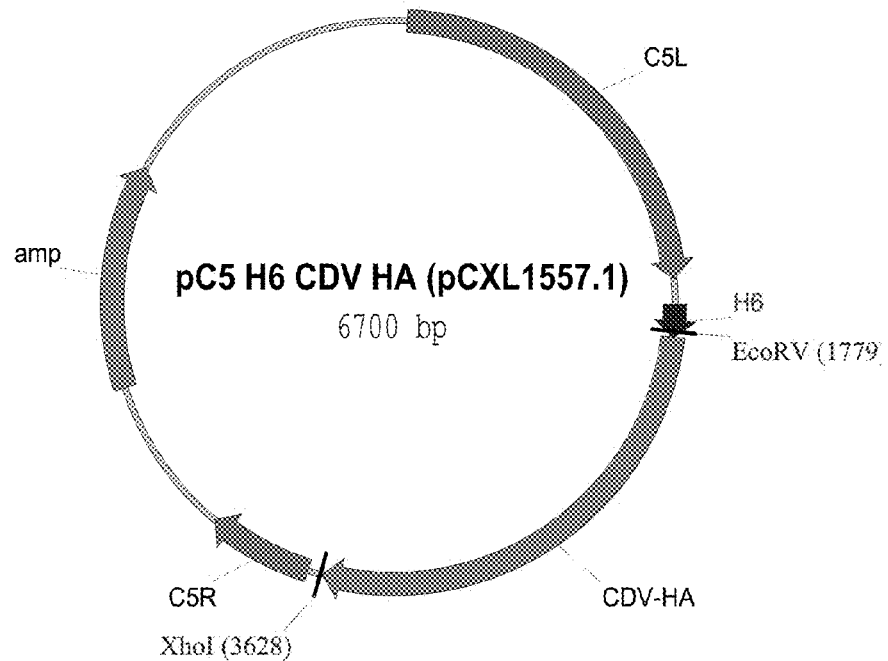
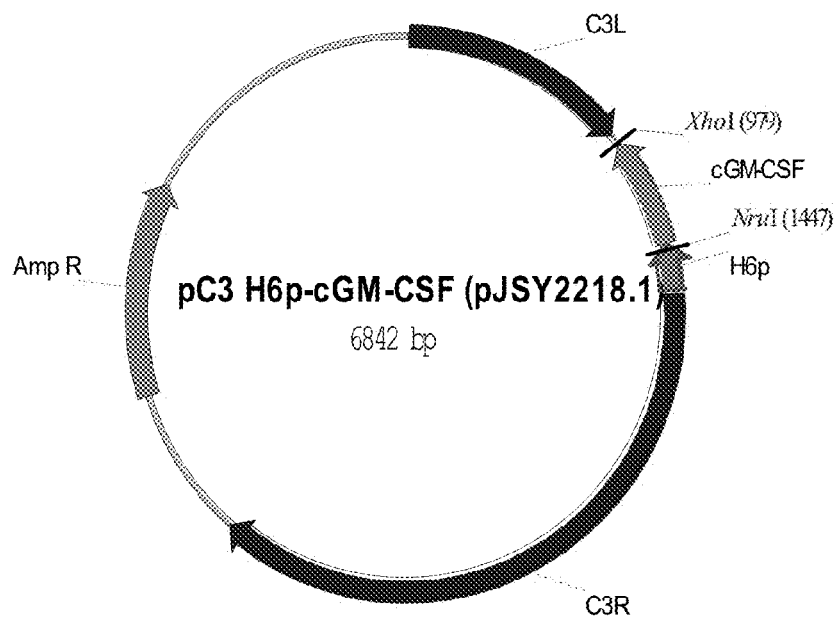

vCP2263 Southern blot analysis

Bands hybridized with CDV HA probe
VCP2263
 &nb vCP2263 Western blot analysis

1. Fermentas Prestain protein marker
2. ALVAC cell pellet
3. vCP2263.1211 cell pellet
4. vCP2263.6111 cell pellet
5. space
6. ALVAC supernatant
7. vCP2263.1211 supernatant
8. vCP2263.6111 supernatant

Figure 6 vCP2263 Immunoplaque assay

Rabbit anti-CDV HA antibody ( Rabbit A151 and A152 at wk 23) at 1/100 dilution

VCP2263.1.2.1.1 P3 stock, replica membranes, unstained, vCP2391 Western blot vCP2392 Western blot for GM-CSF Western blot of vCP2391 and vCP2392 for GM-CSF vCP2391:
Lane 1: pellet
Lane 2: supernatant
Lane 3: crude vCP2392:
Lane 4: pellet
Lane 5: supernatant
Lane 6: crude vCP65 – negative control:
Lane 7: pellet
Lane 8: supernatant
Lane 9: crude

Figure 10

Western blot of vCP2392 for CDV HA

Lane markers: 1 2 3 4 5 6

Molecular weights: 178, 114, 81, 60, 47, 36, 25, 19, 15

← CDV HA
← Non-specific band

Lane 1: vCP2392 CEF cell lysate
Lane 2: vCP2263 CEF cell lysate
Lane 3: vCP2287 CEF Cell lysate
Lane 4: vCP2392 culture medium
Lane 5: vCP2263 culture medium
Lane 6: vCP2287 culture medium Primary antibody: goat anti-CDV antibody 1:1000 vCP2263: ALVAC C5 H6p-CDV HA
vCP2287: ALVAC C5 CDV HA/C3 H6p-CPV VP2 as positive control for western blot Serology Results

Figure 13A

```
                  1                                                  50
AAQ05828   (1)   MLSYQDKVGAFYKDNARANSSKLSLVTEEQGGRRPPYLLFVLLILLVGIM
AAQ96308   (1)   MLSYQDKVGAFYKDNARANSSKLSLVTEEQGGRRPPYLLFVLLILLVGIM
ABB51156   (1)   MLSYQDKVGAFYKDNARANSSKLSLVTEEQGGRRPPFLLFVLLVLLVGIM
ABF55671   (1)   MLSYQDKVGAFYKDNARANSSKLSLVTEEQGGRRPPYLLFVLLILLVGVM
ABF55672   (1)   MLSYQDKVGAFYKDNARANSSKLSLVTEEQGGRRPPYLLFVLLILLVGIM
ABF55673   (1)   MLSYQDKVGAFYKDNARANSSKLSLVTEEQGGRRPPYLLFVLLILLVGIM
ABK35770   (1)   MLSYQDKVGAFYKDNARANSSKLSLVTEEQGGRRPPYLLFVLLILLVGIM
ABK35780   (1)   MLSYQDKVSAFYKDNARANSSKLSLVTEEHGSRRPPYLLFILLILLVGIM
ABX84040   (1)   MLSYQDKVGAFYKDNARANSSKLSLVTEEQGGRRPPYLLFVLLILLIGIM
ACD92997   (1)   MLSYQDKVGAFYKDNARANSSKLSSVTEEQGGRRPPYLLFVLLILLVGIM
ACI28389   (1)   MLSYQDKVGAFYKDNARANSSKLSLVTEEQGGRRPPYLLFVLLILLVGIM
ACI28390   (1)   MLSYQDKVGAFYKDNARANSSKLSLVTEEQGGRRPPYLLFVLLILLVGIM
ACJ46470   (1)   MLSYQDKVGAFYKDNARANSSKLSLVTEEQGGRRPPYLFFVLLTLLIGII
ACN58242   (1)   MLSYQDKVGAFYKDNARANSSKLSLVTEEQGGRRPPYLLFVLLILLTGIM
ACS88240   (1)   MLSYQDKVGAFYKDNARANSSKLSLVTEEQGGRRPPYLLFVLLILLVGIM
CDV HA     (1)   MLSYQDKVGAFYKDNARANSSKLSLVTEEQGGRRPPYLLFVLLILLVGIM 51                                                 100
AAQ05828   (51)  TLLAITGVRFHQVSTSNMEFSRLLKEDMEKSEAVHRQVIDVLTPLFKIIG
AAQ96308   (51)  TLLAITGVRFHQVSTSNMEFSRLLKEDMEKSEAVHRQVIDVLTPLFKIIG
ABB51156   (51)  ALLAITGVRFHQVSTSNMEFSRLLKEDMEKSEAVHRQVIDVLTPLFKIIG
ABF55671   (51)  TLXAITGVRIHQVSTSNMEFSRLLKEDMEKSEAVHRQVIDVLTPLFKIIG
ABF55672   (51)  TLLAITGVRFHQVSTSNMEFSRLLKEDMEKSEAVHRQVIDVLTPLFKIIG
ABF55673   (51)  TLLAITGVRFHQVSTSNMEFSRLLKEDMEKSEAVHRQVIDVLTPLFKIIG
ABK35770   (51)  TLLAITGVRFHQVSTSNMEFSRLLKEDMEKSEAVHRQVIDVLTPLFKIIG
ABK35780   (51)  ALLAITGARFHQVSTSNMEFSRLLKEDMEKSEAVHRQVIDVLTPLFKIIG
ABX84040   (51)  ALLAITGVRFHQVSTSNMEFSRLLKEDMEKSEAVHRQVIDVLTPLFKIIG
ACD92997   (51)  ALLAITGVRFHQVSTNNMEFSRLLKEDMEKSEAVHRQVIDVLTPLFKIIG
ACI28389   (51)  TLLAITGVRFHQVSTSNMEFSRLLKEDMEKSEAVHRQVIDVLTPLFKIIG
ACI28390   (51)  TLLAITGVRFHQVSTSNMEFSRLLKEDMEKSEAVHRQVMDVLTPLFKIIG
ACJ46470   (51)  ALLAITGVRFHQVSTSNMEFSRLLKEDMEKSEAVHRQVIDVLTPLFKIIG
ACN58242   (51)  ALLAITRVRFHQVSTSNMEFSRLLKEDMEKSEAVHRQVIDVLTPLFKIIG
ACS88240   (51)  TLLAITGVRFHQVSTSNMEFSRLLKEDMEKSEAVHRQVIDVLTPLFKIIG
CDV HA     (51)  TLLAITGVRFHQVSTSNMEFSRLLKEDMEKSEAVHRQVIDVLTPLFKIIG 101                                                150
AAQ05828  (101)  DEVGLRLPQKLNEIKQFILQKTNFFNPNREFDFRDLHWCINPPSKIKVNF
AAQ96308  (101)  DEVGLQLPQKLNEIKQFILQKTNFFNPNREFDFRDLHWCINPPSKIKVNF
ABB51156  (101)  DEIGLRLPQKLNEIKQFILQKTNFFNPNREFDFRDLHWCINPPSKIKVNF
ABF55671  (101)  DEVGLRLPQKLNEIKQFILQKTNFFNPNREFDFRDLHWCINPPSKIKVNF
ABF55672  (101)  DEVGLRLPQKLNEIKQFILQKTNFFNPNREFDFRDLHWCINPPSKIKVNF
ABF55673  (101)  DEVGLRLPQKLNEIKQFILQKTNFFNPNREFDFRDLHWCINPPSKIKVNF
ABK35770  (101)  DEVGLRLPQKLNEIKQFILQKTNFFNPNREFDFRDLHWCINPPSKIKVNF
ABK35780  (101)  DEIGLRLPQKLNEIKQFILQKTNFFNPKREFDFRDLHWCINPPSKIKVNF
ABX84040  (101)  DEIGLRLPQKLNEIKQFILQKTNFFNPNREFDFRDLHWCINPPSKIKVNF
ACD92997  (101)  DEVGLRLPQKLNEIKQFILQKTNFFNPNREFDFRDLHWCINPPSKIKVNF
ACI28389  (101)  DEVGLRLPQKLNEIKQFILQKTNFFNPNREFDFRDLHWCINPPSKIKVNF
```

Figure 13A (continued)

```
ACI28390(101)  DEVGLRLPQKLNEIKQFILQKTNFFNPNREFDFRDLHWCINPPSKIKVNF
ACJ46470(101)  DEIGLRLPQKLNEIKQFILQKTNFFNPNREFDFRDLHWCINPPSKIKVNF
ACN58242(101)  DEIGLRLPQKLNEIKQFILQKTNFFNPNREFDFRDLHWCINPPSKIKVNF
ACS88240(101)  DEVGLRLPQKLNEIKQFILQKTNFFNPNREFDFRDLHWCINPPSKIKVNF
   CDV HA(101) DEVGLRLPQKLNEIKQFILQKTNFFNPNREFDFRDLHWCINPPSKIKVNF 151                                            200
AAQ05828(151)  TNYCDTIGIRKSIASAVNPILLSALSGGRGDIFPPYRCSGATTSVGRVFP
AAQ96308(151)  TNYCDTIGIKKSIASAANPILLSALSGGRGDIFPPYRCSGATTSVGRVFP
ABB51156(151)  TNYCDTIGIRKSIASAANPILLSALSGGRGDIFPPYKCNGAATSVGRVFP
ABF55671(151)  TNYCDTVGIRKSIASAANPILLSALSGGRGDIFPPYRCSGATTSVGRVFP
ABF55672(151)  TNYCDTIGIRKSIASAANPILLSALSGGRGDIFPPYRCSGATTSVGRVFP
ABF55673(151)  TNYCDTIGIRKSIASAANPILLSALSGGRGDIFPPYRCSGATTSVGRVFP
ABK35770(151)  TNYCDTIGIRKSIASAANPILLSALSGGRGDIFPPYRCSGATTSVGRVFP
ABK35780(151)  TNYCDTIGIRKSIALAANPILLSALSRGRGDIFPPYRCSGAATSVGRVFP
ABX84040(151)  TNYCDTVGVRKSIASAANPILLSALSGARGDIFPPYRCSGATTSVGRVFP
ACD92997(151)  TNYCDTIEIRKSIALAANPILLSALSGGRGDIFPPYSCSGATTSVGRVFP
ACI28389(151)  TNYCDTIEIRKSIASAANPILLSALSGGRGDIFPPYRCSGATTSVGRVFP
ACI28390(151)  SNYCDTIGIRKSIASAANPILLSALSGGRGDIFPPYRCNGAATSIGRVFP
ACJ46470(151)  TNYCDTVGVRKSITSAANPILLSALSGARGDIFPPYRCSGATTSVGRVFP
ACN58242(151)  TNYCDTVGVRKSIASAANPILLSALSGARGDIFPPCRCSGATTSVGRVFP
ACS88240(151)  TNYCDTIGIRQSIASAANPILLSALSGGRGDIFPPYRCSGATTSVGRVFP
   CDV HA(151) TNYCDTIGIRKSIASAVNPILLSALSGGRGDIFPPYRCSGATTSVGRVFP 201                                            250
AAQ05828(201)  LSVSLSMSLISKTSEITNMLTAISDGVYGKTYLLVPDYIEGEFDTQKIRV
AAQ96308(201)  LSVSLSMSLISKTSEITSMLTAISDGVYGKTYLLVPDYIEGEFDTQKIRV
ABB51156(201)  LSVSLSMSLISKTSGIINMLTAISDGVYGKTYLLMPDYIEGEFDTQKIRV
ABF55671(201)  LSVSLSMSLISKTSEITNMLTAISDGVYGKTYLLVPDYIEGEFDTQKIRV
ABF55672(201)  LSVSLSMSLISKTSEITNMLTAISDGVYGKTYLLVPDYIEGEFDTQMIRV
ABF55673(201)  LSVSLSMSLISKTSEITNMLTAISDGVYGKTYLLVPDYIEGEFDTQKIRV
ABK35770(201)  LSVSLSMSLISKTSGITNMLTAISDGVYGKTYLLVPDYIEGEFDTQKIRV
ABK35780(201)  LSVSLSMSLISKTSEIINMLTAISDGVYGKTYLLVPDYIEGEFDTQKIRV
ABX84040(201)  LSVSLSMSLISKTSEIINMLTAISDGVYGKTYMLVPDYIEGEFDSQKIRV
ACD92997(201)  LSVSLSMSLISKTSEIINMLTAISDGVYGKTYLLVPDYIEGGFDTQKIRV
ACI28389(201)  LSVSLSMSLISKTSEITNMLTAISDGVYGKTYLLVPDYFEGEFDTQKIRV
ACI28390(201)  LSVSLSMSLISRTAEIINMLTAISDGVDGKTYLLVPDYIEGEFETQKIRV
ACJ46470(201)  LSVSLSMSLISRTSEIINMLTAISDGVYGKTYLLVPDYIEGEFDSQKIRV
ACN58242(201)  LSVSLSMSLISRTSEIINMLTAISDGMYGKTYLLVPDYIEGEFDSQKIRV
ACS88240(201)  LSVSLSMSVISKTSEITNMLTAISDGVYGKTYLLVPDYIEGEFDTQKIRV
   CDV HA(201) LSVSLSMSLISKTSEITNMLTAISDGVYGKTYLLVPDYIEGEFDTQKIRV 251                                            300
AAQ05828(251)  FEIGFIKRWLNDMPLLQTTNYMVLPENSKAKVCTIAVGELTLASLCVDES
AAQ96308(251)  FEIGFIKRWLNDMPLLQTTNYMVLPENSKAKVCTIAVGELTLASLCVDES
ABB51156(251)  FEIGFIKRWLNDMPLLQTTNYIVLPENSKAKVCTIAVGELTLASLCVDES
ABF55671(251)  FEIGFIKRWLNDMPLLQTTNYMVLPENSKAKVCTIAVGELTLASLCVDES
ABF55672(251)  FEIGFIKRWLNDMPLLQTTNYMVLPENSKAKVCTIAVGELTLASLCVDES
```

Figure 13A (continued)

```
ABF55673(251) FEIGFIKRWLNNMPLLQTTNYMVLPENSKAKVCTIAVGELTLASLCVDES
ABK35770(251) FEIGFIKRWLNNMPLFQTTNYMVLPENSKAKVCTIAVGELTLASLCVDES
ABK35780(251) FEIGFIKRWLNDMPLLQTTNYMVLPENSKAKVCTIAVGELTLASLCVDES
ABX84040(251) FEIGFIKRWLNNMLLQTTNYMVLPETSKAKVCTIAVGELTLASLCVDES
ACD92997(251) FEIGFIKRWLNDMPLLQTTNYMVLPENSKAKVCTIAVGELTLASLCVDES
ACI28389(251) FEIGFIKRWLNDMPLLQTTNYMFLPENSKAKVCTIAVGELTLASLCVDES
ACI28390(251) FEIGFIKRWLNDMSLLQTTNYMVLPENSKAKVCTIAVGELTLASLCVDES
ACJ46470(251) FEIGFIKRWLNDMPLLQTTNYMVLPETSKAKVCTIAVGELTLASLCVDES
ACN58242(251) FEIGFIKRWLNDMPLLQTTNYMVLPETSKAKVCTIAVGELTLASLCVDES
ACS88240(251) FEIGFIKRWLNNMPLLQTTNYMVLPENSKAKVCTIAVGELTLASLCVDEN
   CDV HA(251) FEIGFIKRWLNNMPLLQTTNYMVLPENSKAKVCTIAVGELTLASLCVDES 301                                              350
AAQ05828(301) TVLLYHDSNGSQDGILVVTLGIFGATPMDQVEEVIPVAHPSVEKIHITNH
AAQ96308(301) TVLLYHDSNGSQDGILVVTLGIFGATPMDQVEEVIPVAHPSVEKIHITNH
ABB51156(301) TVLLYHDSNGSQDGILVVTLGIFGATPMDQVEEVIPVAHPSVXKIHITNH
ABF55671(301) TVLLYHDSNGSQDGILVVTLGIFGATPMDQVEEVIPVAHPSVEKIHITNH
ABF55672(301) TVLLYHDSNGSQDGILVVTLGIFGATPMDQVGEVIPVAHPSVEKIHITNH
ABF55673(301) TVLLYHDSNGSQDGILVVTLGIFGATPMDQVGEVIPVAHPSVEKIHITNH
ABK35770(301) TVLLYHDSNGSQGGVLVVTLGIFGATPMDQVEEMIPVAHPSVEKIHITNH
ABK35780(301) TVLLYHDSNGSQDGILVVTLGIFGATPMDQVEEVIPVAHPSVEKIHITNH
ABX84040(301) TVLLYHDSNGSQNGILVVTLGIFGATPMDQVEEVIPIAHPSVERIHITNH
ACD92997(301) TVLLYHDSDGSQDGILVVTLGIFGATPMDQVEEVIPVAHPSVEKIHITNH
ACI28389(301) TVSLYHDGSGSQDGILVVTLGIFGATPMDQVEEVIPVAHPSVEKIHITNH
ACI28390(301) TVLLYHDSNGSQDGILVVTLGIFWGTPMDQVEEVIPVAHPSVEKIHITNH
ACJ46470(301) TVLLYHDSNGSQNGILVVTLGIFGATSMDQVEEVIPIAHPSVERIHITNH
ACN58242(301) TVLLYHDSNGSQNGILVVTLGIFGATPMDQVEEVIPIAHPSVERIHITNH
ACS88240(301) TVLLYHDSNGSQDGILVVTLGIFGATPMDQVEEVIPVAHPSIEKIHITNH
   CDV HA(301) TVLLYHDSNGSQDGILVVTLGIFGATPMDQVEEVIPVAHPSVEKIHITNH 351                                              400
AAQ05828(351) RGFIKDSIATWMVPALVSEKQEEQKNCLESACQRKTYPMCNQTSWEPFGG
AAQ96308(351) RGFIKDSIATWMVPALVSEKQEEQKNCLESACQRKTYPMCNQTSWEPFGG
ABB51156(351) RGFIKDSIATWMVPALSGEQEEQKNCLESACQRKSYPMCNQTSWKPFGG
ABF55671(351) RGFIKDAIATWMVPALVSEKQEEQKNCLESACQRKTYPMCNQTSWEPFGG
ABF55672(351) RGFIKDSIATWMVPALVSEKQEEQKNCLESACQRKTYPMCNQTSWEPFGG
ABF55673(351) RGFIKDSIATWMVPALVSEKQEEQKNCLESACQRKTYPMCNQTSWEPFGG
ABK35770(351) RGFIKDSIATWMVPVLVSEKQEEQKNCLESACQRKTYPMCNQTSWEPFGG
ABK35780(351) RGFIKDSIATWMVPVLVSENQEEQKNCLESACQRKSYPMCNQTSWEPFGG
ABX84040(351) RGFIKDSVVTWMVPVLVSEKQEEQKNCLESACQRKSYPMCNQTSWEPFGG
ACD92997(351) RGFIKDSIATWMVPALVSEKQEEQKNCLESACQRKSYPMCNQTSWEPFGG
ACI28389(351) RGFIKDSIATWMVPALVSEKQEEQKNCLESACQRKTYPMCNQTSWEPFGG
ACI28390(351) RGFIKDSKAIWMVPALVSEKQEEQKNCLESACQRKTYPMCNQTSWEPFGG
ACJ46470(351) RGFIKDSIVTWMVPVLVSEKQEEQKNCLESACQRKSYPMCNQTSWEPFGG
ACN58242(351) RGFIKDSIVTWMVPVLVSEKQEEQKNCLESACQRKTYPMCNQTSWEPFGG
ACS88240(351) RGFIKDSIATWMVPALVSEKQEEQKNCLESACQRKTYPMCNQTSWEPFGG
   CDV HA(351) RGFIKDSIATWMVPALVSEKQEEQKNCLESACQRKTYPMCNQTSWEPFGG
```

Figure 13A (continued)

```
                401                                                    450
AAQ05828(401)   GQLPSYGRLTLSLDPSIDLQLNISPTYGPVILNGDGMDYYGSSLSDSGWL
AAQ96308(401)   GQLPSYGRLTLELDPSIDLQLNISPTYGPVILNGDGMDYYESPLSDSGWL
ABB51156(401)   GQLPSYGRLTLELDPGIDLQLNISPTYGPVILNGDGMDYYESPLLDSGWL
ABF55671(401)   GQLPSYGRLTLELDPSIDLQLNISPTYGPVILNGDGMDYYESSLSDSGWL
ABF55672(401)   GQLPSYGRLTLELDPSIDPQLNISPTYGPVILNGDGMDYYESSLSDSGWL
ABF55673(401)   GQLPSYGRLTLELDPSIDPQLNISPTYGPVILNGDGMDYYESSLSDSGWL
ABK35770(401)   GQLPSYGRLTLELDPSIDLQLNISPTYGPVILNGDGMDYYESPLLDSGWL
ABK35780(401)   GQLPSYGRLTLELDPGIDLQLNISPTYGPIILNGDGMDYYESPLNSGWL
ABX84040(401)   GQLPSYGRLTLELDPSVDLQLNISPTYGPVILNGDGMDYYESPLLSGWL
ACD92997(401)   GQLPSYGRLTLELDPSIDLQLNISPTYGPVILNGDGMDYYESPLLDSGWL
ACI28389(401)   GQLPSYGRWTLELDPSIDLQLNISVTYGPVILNGDGMDYYESPLSDSGWL
ACI28390(401)   GQLPSYGRLTLELDPSIDLQLNISPTYGPVILNGDGMDYYESPLLDSGWL
ACJ46470(401)   GQLPSYGRLTLELDPSIDLQLNISPTYGPVILNGDGMDYYESPLLSGWL
ACN58242(401)   GQLPSYGRLTLELDPSIDLQLNISPTYGPVILNGDGMDYYESPLLDSGWL
ACS88240(401)   RQLPSYGRLTLELDPSMDLQLNISPTYGPVILNGDGMDYYESPLPDSGWL
CDV HA(401)     GQLPSYGRLTLSLDPSIDLQLNISPTYGPVILNGDGMDYYGSSLSDSGWL 451                                                    500
AAQ05828(451)   TIPPKNGTVLGLINKASRGDQFTVIPHVLTFAPRESSGNCYLPIQTSQIM
AAQ96308(451)   TIPPRNGTVLGLINKASRGDQFTVIPHVLTFAPRESSGNCYLPIQTSQIM
ABB51156(451)   TIPPKNGTILGLINKASRGDQFTVIPHVLTFAPRESSGNCYLPIQTSQIM
ABF55671(451)   TIPPKNGTVLGLINKASRGDQFTVTPHVLTSAPRESSGNCYLPIQTSQIM
ABF55672(451)   TIPPKNGTVLGLINKASRGDQFTVIPHVLTFAPRESSGNCYLPIQTSQIM
ABF55673(451)   TIPPKNGTVLGLINKASRGDQFTVIPHVLTFAPRESSGNCYLPIQTSQIM
ABK35770(451)   TIPPKNGTVLGLINKASRGDQFTVIPHVLTFAPRESSGNCYLPIQTSQIM
ABK35780(451)   TIPPKNGTILGLINKASRGDQFTVTPHVLTFAPRESSGNCYLPIQTSQIM
ABX84040(451)   AIPPKNGTVLGLINKASRGDQFTVTPHVLTFAPRESSGNCYLPIQTSQIM
ACD92997(451)   TIPPKNGTVLGLINKASRGDQFTVIPHVLTFAPRESSGNCYLPIQTSQIM
ACI28389(451)   TIPPKNGTILGLINKASRGDQFTVIPHVLTFAPRESSGNCYLPIQTSQIM
ACI28390(451)   TIPPKNGTVLGLMNKASRGDQFTVIPHVLTFAPRESGGNCYLPIQTSQIM
ACJ46470(451)   TIPPKNGTVLGLINKASRGDQFTATPHVLTFAPRESSGNCYLPIQTSQIM
ACN58242(451)   TIPPKNGTVLGLINKASRGDQFTVTPHVLTFAPRESSGNCYLPIQTSQIM
ACS88240(451)   TIPPKNGTVLGLINKASRGDQFTVIPHVLTFAPRESSGNCYLPIQTSQIM
CDV HA(451)     TIPPKNGTVLGLINKASRGDQFTVIPHVLTFAPRESSGNCYLPIQTSQIM 501                                                    550
AAQ05828(501)   DKDVLTESNLVVLPTQNFRYVIATYDISRGDHAIVYDVYDPIRTISYTHP
AAQ96308(501)   DKDVLTESNLVVLPTQNFRYVIATYDISRGDHAIVYIVYDPIRTISYTHP
ABB51156(501)   DKDVLTESNLVVLPTQNFRYVIATYDISRNDHAIVYIVYDPIRTISYTHP
ABF55671(501)   DKDVLTESNLVVLPTQNFRYVIATYDISRGDHAIVYIVYDPIRTISYTYP
ABF55672(501)   DKDVLTESNLVVLPTQNFRYVIATYDISRGDHAIVYIVYDPIRTISYTYP
ABF55673(501)   DKDVLTESNLVVLPTQNFRYVIATYDISRGDHAIVYIVYDPIRTISYTYP
ABK35770(501)   DKDVLTESNLVVLPTQNFRYVIATYDISRGDHAIVYIVYDPIRTISYTYP
ABK35780(501)   DKDVLTESNLVVLPTQNFRYVIATYDISRDDHAIVYIVYDPIRTISYTYP
ABX84040(501)   DKDVLTESNLVVLPTQNFRYVIATYDISRGDHAIVYIVYDPIRTISYTYP
ACD92997(501)   DKDVLTESNLVVLPTQNFRYVIATYDISRGDHAIVYIVYDPIRAISYTYP
ACI28389(501)   DKDVLTESNLVVLPTQNFRYVIATYDISRGDHAIVYIVYDPIRTISYTYP
```

Figure 13A (continued)

```
ACI28390(501)  DKDVLAESNLVVLPTQNFRYVIATYDISRDDHAIVYIVYDPIRTISYTYP
ACJ46470(501)  DKDVLFESNLVVLPTQNFRYVIATYDISRGDHAIVYIVYDPIRTISYTYP
ACN58242(501)  DKDVLFESNLVVLPTQNFRYVIATYDISRGDHAIVYIVYDPIRTISYTYP
ACS88240(501)  DKDVLFESNLVVLPTQNFRYVIATYDISRGDHAIVYIVYDPIRTISYTYP
   CDV HA(501) DKDVLFESNLVVLPTQNFRYVIATYDISRGDHAIVYIVYDPIRTISYTYP 551                                              600
AAQ05828(551)  FRLTTKGRPDFLRIECFVWDDDLWCHQFYRFEADITNSTTSVENLVRIRF
AAQ96308(551)  FRLTTKGRPDFLRIECFVWDDDLWCHQFYRFEADITNSTTSVENLVRIRF
ABB51156(551)  FRLTTKGRPDFLRIECFVWDDDLWCHQFYRFEADITNSATSVENLVRIRF
ABF55671(551)  FRLTTKGRPDFLRIECFVWDDDMWCHQFYRFEADITNSTTSVENLVRIRF
ABF55672(551)  FRLTTKGRPDFLRIECFVWDDDLWCHQFYRFEADITNSTTSVENLVRIRF
ABF55673(551)  FRLTTKGRPDFLRIECFVWDDDLWCHQFYRFEADITNSTTSVENLVRIRF
ABK35770(551)  FRLTTKGRPEFLRIECFVWDDDLWCHQFYRFEADITNSTISVENLVHIRF
ABK35780(551)  FRLTTKGRPDFLRIECFVWDYDLWCHQFYRFEADITNSTTSVENLVRIRF
ABX84040(551)  FRLTTKGRPDFLRIECFVWDDDLWCHQFYRFEANITNSTTSVENLVRIRF
ACD92997(551)  FRLTTKGRPDFLRIECFVWDDDLWCHQFYRFEADSTNSTTSVENLVRIRF
ACI28389(551)  FRLTTKGRPVSLRIECFVWDDDLWCHQFYQFEADITNSTTSVENLVRIRF
ACI28390(551)  FRLTTKGRPDFLRIECFVWDDDLWCHQFYRFEADITNSTTSVENLVRIRF
ACJ46470(551)  FRLTTKGRPDFLRIECFVWDDDLWCHQFYRFEANITNSTTSVENLVRIRF
ACN58242(551)  FRLTTKGRPDFLRIECFVWDDDLWCHQFYRFEANITNSTTSVENLVRIRF
ACS88240(551)  FRLTTKGRPDFLRIECFVWDDDLWCHQFYRFEADITNSTTSVENLVCIRF
   CDV HA(551) FRLTTKGRPDFLRIECFVWDDDLWCHQFYRFEADITNSTTSVENLVRIRF

601
AAQ05828(601)  SCDRSKP
AAQ96308(601)  SCNRSKP
ABB51156(601)  SCNRSKP
ABF55671(601)  SCNRSKP
ABF55672(601)  SCNRSKP
ABF55673(601)  SCNRSKP
ABK35770(601)  SCNRSKP
ABK35780(601)  SCNRSKP
ABX84040(601)  SCNRSKP
ACD92997(601)  SCNRSKP
ACI28389(601)  SCNRSKP
ACI28390(601)  SCNRSKP
ACJ46470(601)  SCNRSKP
ACN58242(601)  SCNRSKP
ACS88240(601)  SCNRSKP
   CDV HA(601) SCDRSKP
```

AAQ05828:SEQ ID NO:20;   AAQ96308:SEQ ID NO:23;   ABB51156:SEQ ID NO:31;
ABF55671:SEQ ID NO:24;   ABF55672:SEQ ID NO:22;   ABF55673:SEQ ID NO:21;
ABK35770:SEQ ID NO:26;   ABK35780:SEQ ID NO:32;   ABX84040:SEQ ID NO:34;
ACD92997:SEQ ID NO:27;   ACI28389:SEQ ID NO:28;   ACI28390:SEQ ID NO:29;
ACJ46470:SEQ ID NO:33;   ACN58242:SEQ ID NO:30;   ACS88240:SEQ ID NO:25;
   CDV HA:SEQ ID NO:2.

Figure 13B

Sequence identity percetage of CDV HA proteins

| SEQ ID NO: | 2 | 20 | 21 | 22 | 23 | 24 | 25 | 26 | 27 | 28 | 29 | 30 | 31 | 32 | 33 | 34 |
|---|---|---|---|---|---|---|---|---|---|---|---|---|---|---|---|---|
| 2 |  | 100 | 99 | 99 | 98 | 98 | 98 | 98 | 97 | 97 | 96 | 95 | 95 | 95 | 94 | 95 |
| 20 |  |  | 99 | 98 | 98 | 98 | 98 | 97 | 96 | 96 | 95 | 94 | 95 | 94 | 94 | 94 |
| 21 |  |  |  | 98 | 98 | 98 | 98 | 97 | 97 | 97 | 96 | 95 | 96 | 95 | 95 | 95 |
| 22 |  |  |  |  | 98 | 98 | 98 | 98 | 97 | 97 | 96 | 95 | 95 | 95 | 94 | 95 |
| 23 |  |  |  |  |  | 98 | 98 | 98 | 97 | 97 | 96 | 95 | 95 | 94 | 95 | 95 |
| 24 |  |  |  |  |  |  | 97 | 97 | 96 | 96 | 95 | 95 | 94 | 94 | 94 | 94 |
| 25 |  |  |  |  |  |  |  | 97 | 96 | 96 | 95 | 94 | 95 | 94 | 94 | 94 |
| 26 |  |  |  |  |  |  |  |  | 96 | 96 | 95 | 95 | 95 | 95 | 94 | 95 |
| 27 |  |  |  |  |  |  |  |  |  | 96 | 95 | 95 | 96 | 95 | 94 | 94 |
| 28 |  |  |  |  |  |  |  |  |  |  | 95 | 94 | 94 | 94 | 94 | 94 |
| 29 |  |  |  |  |  |  |  |  |  |  |  | 94 | 94 | 94 | 93 | 93 |
| 30 |  |  |  |  |  |  |  |  |  |  |  |  | 93 | 94 | 94 | 98 |
| 31 |  |  |  |  |  |  |  |  |  |  |  |  |  | 95 | 93 | 93 |
| 32 |  |  |  |  |  |  |  |  |  |  |  |  |  |  | 94 | 94 |
| 33 |  |  |  |  |  |  |  |  |  |  |  |  |  |  |  | 98 |
| 34 |  |  |  |  |  |  |  |  |  |  |  |  |  |  |  |  |

Vector NTI (Invitrogen, Calsbad, CA, USA)

Figure 14A

```
                        1                                                  50
SEQ ID NO:35    (1)  ATGCTCTCCTACCAAGACAAGGTGGGTGCCTTCTATAAGGATAATGCAAG
SEQ ID NO:1     (1)  ATGCTGAGCTACCAGGACAAAGTGGGCGCCTTCTACAAGGACAACGCCAG 51                                                 100
SEQ ID NO:35    (51) AGCTAATTCATCCAAGCTGTCCTTAGTGACAGAAGAGCAAGGGGGCAGGA
SEQ ID NO:1     (51) GGCCAATAGCAGCAAGCTGAGCCTGGTGACCGAGGAGCAGGGCGGCAGGA 101                                                150
SEQ ID NO:35   (101) GACCACCCTATTTGCTGTTTGTCCTTCTCATCCTTCTGGTTGGAATCATG
SEQ ID NO:1    (101) GACCCCCCTACCTGCTGTTCGTGCTGCTGATCCTTCTTGTGGGCATCATG 151                                                200
SEQ ID NO:35   (151) ACCTTGCTTGCTATCACTGGAGTTCGATTTCACCAAGTATCAACTAGCAA
SEQ ID NO:1    (151) ACCCTGCTGGCCATCACCGGAGTGAGATTCCACCAGGTGTCCACCTCCAA 201                                                250
SEQ ID NO:35   (201) TATGGAATTTAGCAGATTGCTGAAAGAGGATATGGAGAAATCAGAGGCCG
SEQ ID NO:1    (201) CATGGAGTTCAGCCGGCTGCTGAAAGAGGACATGGAGAAGAGCGAGGCCG 251                                                300
SEQ ID NO:35   (251) TACATCACCAAGTCATAGATGTCTTGACACCGCTCTTCAAAATTATTGGA
SEQ ID NO:1    (251) TGCACCACCAGGTGATCGATGTGCTGACCCCCCTGTTCAAGATCATCGGC 301                                                350
SEQ ID NO:35   (301) GATGAGGTTGGGTTACGGTTGCCACAAAAACTAAACGAGATCAAACAATT
SEQ ID NO:1    (301) GACGAAGTGGGCCTGAGACTGCCCCAGAAGCTGAACGAGATCAAGCAGTT 351                                                400
SEQ ID NO:35   (351) TATCCTTCAAAAGACAAACTTCTTCAATCCGAACAGGGAATTCGACTTCC
SEQ ID NO:1    (351) CATCCTGCAGAAAAACCAACTTCTTCAACCCCAACCGGGAGTTCGACTTCA 401                                                450
SEQ ID NO:35   (401) GCGATCTCCACTGGTGCATTAATCCACCTAGTAAGATCAAGGTGAATTTT
SEQ ID NO:1    (401) GACACCTGCACTGGTGCATCAACCCCCCAGCAAGATCAAAGTGAACTTC 451                                                500
SEQ ID NO:35   (451) ACTAATTACTGCGATACAATTGGATCAGAAAATCTATTGCATCGGCAGT
SEQ ID NO:1    (451) ACCAACTACTGCGACACCATCGGCATCAGGAAGAGCATCGCCAGCGCCGT 501                                                550
SEQ ID NO:35   (501) AAATCCCATCCTTTTATCAGCACTCTCGGAGGCAGAGGTGACATATTCC
SEQ ID NO:1    (501) GAATCCCATCCTGCTGAGCGCCCTGAGCGGCGGCAGAGGCGACATCTTCC 551                                                600
SEQ ID NO:35   (551) CACCATACAGATGCAGTGGAGCTACTACTTCAGTGGGCAGAGTTTTCCCC
SEQ ID NO:1    (551) CCCCCTACAGATGCAGCGGCGCCACCACCTCTGTGGGCAGAGTGTTCCCT 601                                                650
SEQ ID NO:35   (601) CTATCAGTATCATTGTCCATGTCTTTGACCTCAAAAACATCAGAGATAAC
SEQ ID NO:1    (601) CTGAGCGTGTCCCTGAGCATGAGCCTGACAGCAAGACCAGCGAGATCAC
```

Figure 14B

```
                   651                                                  700
SEQ ID NO:35 (651) CAATATGCTAACTGCTATCTCAGACGGAGTGTATGGTAAAACCTATTTGC
SEQ ID NO:1  (651) CAACATGCTGACCGCCATCAGCGACGGCGTGTACGGCAAGACCTATCTGC 701                                                  750
SEQ ID NO:35 (701) TAGTGCCTGATTACATTGAAGGGCAGTTCGACACGCAAAAGATTCGAGTC
SEQ ID NO:1  (701) TGGTGCCCGACTACATCGAGGGCGAGTTCGACACCCAGAAGATCCGCGTG 751                                                  800
SEQ ID NO:35 (751) TTTGAGATAGGGTTCATCAAACGGTGGCTGAATAACATGCCATTACTCCA
SEQ ID NO:1  (751) TTCGAGATCGGCTTCATCAAGCGGTGGCTGAACAACATGCCCCTGCTGCA 801                                                  850
SEQ ID NO:35 (801) GACAACCAACTACATGGTCCTCCCGGAGAATTCCAAAGCCAAGGTATGTA
SEQ ID NO:1  (801) GACCACCAACTACATGGTGCTGCCCGAGAACAGCAAGGCCAAAGTGTGCA 851                                                  900
SEQ ID NO:35 (851) CTATAGCAGTGGGCGAGTTGACACTGGCTTCCTTGTGTGTAGATGAGAGC
SEQ ID NO:1  (851) CCATCGCTGTGGGCGAGCTGACCCTGGCCAGCCTGTGCGTGGACGAGAGC 901                                                  950
SEQ ID NO:35 (901) ACCGTATTGTTATATCATGACAGCAATGGTTCACAAGATGGTATTCTAGT
SEQ ID NO:1  (901) ACCGTGCTGCTGTACCACGACAGCAACGGCAGCCAGGACGGCATCCTGGT 951                                                 1000
SEQ ID NO:35 (951) AGTGACGCTGGGGATATTTGGGCAACACCTATGGATCAAGTTGAAGAAG
SEQ ID NO:1  (951) GGTGACCCTGGGCATCTTCGGCGCCACCCCTATGGACCAGGTGGAGGAAG 1001                                                 1050
SEQ ID NO:35 (1001) TGATACCTGTCGCTCACCCATCAGTAGAAAAATACATATAACAAATCAC
SEQ ID NO:1  (1001) TGATCCCCGTGGCCCACCCCAGCGTGGAGAAGATCCACATCACCAACCAC 1051                                                 1100
SEQ ID NO:35 (1051) CGTCGGTTCATAAAAGATTCAATAGCAACCTGGATGGTGCCTGCATTGGT
SEQ ID NO:1  (1051) CGGGGCTTTATCAAGGACAGCATCGCCACCTGGATGGTGCCCGCCCTGGT 1101                                                 1150
SEQ ID NO:35 (1101) CTCTGAGAAACAAGAGGAACAAAAAAATTGTCTGGAGTCGGCTTGTCAAA
SEQ ID NO:1  (1101) GTCTGAGAAGCAGGAGGAGCAGAAGAACTGCCTGGAGAGCGCCTGCCAGA 1151                                                 1200
SEQ ID NO:35 (1151) GAAAAACCTACCCTATGTGCAACCAAACGTCATGGGAACCCTTTGGAGGG
SEQ ID NO:1  (1151) GAAAGACCTACCCCATGTGCAACCAGACCAGCTGGGAGCCCTTTGGCGGC 1201                                                 1250
SEQ ID NO:35 (1201) GGACAGTTGCCATCTTATGGGCGGTTGACATTATCTTAGATCCAAGCAT
SEQ ID NO:1  (1201) GGACAGCTGCCCAGCTACGGCAGACTGACCCTGAGCCTGGACCCTAGCAT 1251                                                 1300
SEQ ID NO:35 (1251) TGACCTTCAACTTAACATATCATTTACATACGGTCCAGTTATACTGAATG
SEQ ID NO:1  (1251) CGACCTGCAGCTGAACATCAGCTTCACCTACGGCCCCGTGATCCTGAACG
```

Figure 14C

```
                       1301                                              1350
SEQ ID NO:35 (1301)    GAGACGGTATGGATTATTATGAAGCTCACTTTCGGACTCCGGATGGCTT
SEQ ID NO:1  (1301)    GCGACGGCATGGATTACTACGGCAGCAGCCTGAGCGACAGCGGCTGGCTG 1351                                              1400
SEQ ID NO:35 (1351)    ACCATTCCTCCCAAGAATGGAACAGTCCTTGGATTGATAAACAAAGCAAG
SEQ ID NO:1  (1351)    ACCATCCCTCCCAAGAACGGCACAGTGCTGGGCCTGATCAACAAGGCCTC 1401                                              1450
SEQ ID NO:35 (1401)    TAGAGGAGACCAGTTCACTGTAATCCCCATGTGTTGACATTTGCGCCA
SEQ ID NO:1  (1401)    CAGGGGCGACCAGTTCACCGTGATCCCTACGTGCTGACCTTCGCCCCA 1451                                              1500
SEQ ID NO:35 (1451)    GGCAATCAAGTGGAAATTGTTATTTACCTATTCAAACATCCCAGATTATG
SEQ ID NO:1  (1451)    GAGAGCAGCGGCAACTGCTACCTGCCTATCCAGACCTCCCAGATCATG 1501                                              1550
SEQ ID NO:35 (1501)    GATAAAGATGTCCTGACTGAGTCCAATTTAGTGGTGTTGCCTACACAGAA
SEQ ID NO:1  (1501)    GACAAGGACGTGCTGACAGAGAGCAACCTGGTGGTGCTGCCTACCCAGAA 1551                                              1600
SEQ ID NO:35 (1551)    TTTTAGATATGTCATAGCAACATATGATATCTCGGGCGATCATGCAA
SEQ ID NO:1  (1551)    CTTCCGGTACGTGATCGCCACCTACGGCACAGCAGAGCGATCACGCCA 1601                                              1650
SEQ ID NO:35 (1601)    TTGTTTATTATGTTTATGACCCAATCCGGACGATTTCTTATACGTACCCA
SEQ ID NO:1  (1601)    TCGTGTACTACGTGTACGACCCCATCCGGACCATCAGCTACACATACCCC 1651                                              1700
SEQ ID NO:35 (1651)    TTTAGACTAACTACCAAGGGTAGACCTGATTTCCTAAGAATTGAATGTTT
SEQ ID NO:1  (1651)    TTCCGGCTGACCACCAAGGGCAGACCCGACTTCCTGCGGATCGAGTGCTT 1701                                              1750
SEQ ID NO:35 (1701)    TGTGTGGATGACGATTTGTGGTGTCACCAATTTACCGATTTGAGGCTG
SEQ ID NO:1  (1701)    TGTGTGGACGACGACCTGTGGTGCCACCAGTTCTACAGATTCGAGGCCG 1751                                              1800
SEQ ID NO:35 (1751)    ACATCACCAACTCTACAACCAGTGTTGAGAATTTAGTCCGTATAACATTC
SEQ ID NO:1  (1751)    ACATCACCAATAGCACCACCTCCGTGGAGAACCTTGTGAGGATCCGGTTC 1801              1824
SEQ ID NO:35 (1801)    TCAGGTGACCGTTCAAAACTTGA
SEQ ID NO:1  (1801)    AGCTGCGACAGAAGCAAGCCC---
```

Sequence identity between SEQ ID NO:1 and SEQ ID NO:35: 73%

Figure 15A

|  | | 1 | 50 |
|---|---|---|---|
| AF478543 | (1) | ATGCTCTCCTACCAAGACAAGGTGGGTGCCTTCTATAAGGATAATGCAAG | |
| AF478545 | (1) | ATGCTCTCCTACCAAGACAAGGTGGGTGCCTTCTATAAGGATAATGCAAG | |
| AY386316 | (1) | ATGCTCTCCTACCAAGACAAGGTGGGTGCCTTCTATAAGGATAATGCAAG | |
| ca CDV HA | (1) | ATGCTGAGCTACCAGGACAAAGTGGGCGCCTTCTACAAGGACAACGCCAG | |
| DQ228166 | (1) | ATGCTCTCCTACCAAGACAAGGTGGGTGCCTTCTATAAAGATAATGCAAG | |
| DQ494317 | (1) | ATGCTCTCCTACCAAGACAAGGTGGGTGCCTTCTATAAGGATAATGCAAG | |
| DQ494318 | (1) | ATGCTCTCCTACCAAGACAAGGTGGGTGCCTTCTATAAGGATAATGCAAG | |
| DQ889177 | (1) | ATGCTCTCCTACCAAGACAAGGTGGGTGCCTTCTATAAGGATAATGCAAG | |
| DQ889187 | (1) | ATGCTCTCCTACCAAGACAAGGTGAGTGCCTTCTATAAGGATAATGCAAG | |
| EU325730 | (1) | ATGCTCTCTTACCAAGACAAGGTGGGTGCCTTCTATAAGGACAATGCAAG | |
| EU716337 | (1) | ATGCTCTCCTACCAAGACAAGGTGGGTGCCTTCTATAAGGATAATGCAAG | |
| FJ011004 | (1) | ATGCTCTCCTACCAAGACAAGGTGGGTGCCTTCTATAAGGATAATGCAAG | |
| FJ011005 | (1) | ATGCTCTCCTACCAAGACAAGGTGGGTGCCTTTATAAGGATAATGCAAG | |
| FJ423608 | (1) | ATGCTCTCTTACCAAGACAAGGTGGGTGCCTTCTATAAGGATAATGCAAG | |
| FJ705233 | (1) | ATGCTCTCCTACCAAGACAAGGTGGGTGCCTTCTATAAGGATAATGCAAG | |
| GQ214376 | (1) | ATGCTCTCCTACCAAGACAAGGTGGGTGCCTTCTATAAGGATAATGCAAG | |

|  | | 51 | 100 |
|---|---|---|---|
| AF478543 | (51) | AGCTAATTCATCCAAGCTGTCCTTAGTGACAGAAGAGCAAGGGGCAGGA | |
| AF478545 | (51) | AGCTAATTCATCCAAGCTGTCCTTAGTGACAGAAGAGCAAGGGGCAGGA | |
| AY386316 | (51) | AGCTAATTCATCCAAGCTGTCCTTAGTGACAGAAGAGCAAGGGGCAGGA | |
| ca CDV HA | (51) | GGCCAATAGCAGCAAGCTGAGCCTGGTGACCGAGGAGCAGGGCGCAGGA | |
| DQ228166 | (51) | AGCCAATTCATCCAAGCTGTCCTTAGTGACAGAAGAGCAAGGGGTACAA | |
| DQ494317 | (51) | AGCTAATTCATCCAAGCTGTCCTTAGTGACAGAAGAGCAAGGGGCAGGA | |
| DQ494318 | (51) | AGCTAATTCATCCAAGCTGTCCTTAGTGACAGAAGAGCAAGGGGCAGGA | |
| DQ889177 | (51) | AGCTAATTCATCCAAGCTGTCCTTAGTGACAGAAGAGCAAGGGGCAGGA | |
| DQ889187 | (51) | AGCCAATTCATCCAAACTGTCCTTAGTGACAGAAGAACATGGGACCAGGA | |
| EU325730 | (51) | AGCTAATTCATCCAAGCTGTCCTTAGTGACAGAAGAGCAAGGGGAAGGA | |
| EU716337 | (51) | AGCTAATTCATCCAAGCTGTCCTCAGTGACAGAAGAGCAAGGGGCAGGA | |
| FJ011004 | (51) | AGCTAATTCATCCAAGCTGTCCTTAGTGACAGAAGAGCAAGGGGCCGGA | |
| FJ011005 | (51) | AGCCAATTCATCCAAGCTGTCTCAGTGACAGAAGAGCAAGGGGTACGA | |
| FJ423608 | (51) | AGCTAATTCATCCAAGCTGTCCTTAGTGACAGAAGAGCAAGGGGCAAGA | |
| FJ705233 | (51) | AGCTAATTCATCCAAGCTGTCCTTAGTGACAGAAGAGCAAGGGGCAAGA | |
| GQ214376 | (51) | AGCTAATTCATCCAAGCTGTCCTTAGTGACAGAAGAGCAAGGGGCAGGA | |

|  | | 101 | 150 |
|---|---|---|---|
| AF478543 | (101) | GACCACCCTATTTGCTGTTTGTCCTTCTCATCCTTCTGGTTGGAATCATG | |
| AF478545 | (101) | GACCACCCTATTTGCTGTTTGTCCTTCTCATCCTTCTGGTTGGAATCATG | |
| AY386316 | (101) | GACCACCCTATTTGCTGTTTGTCCTTCTCATCCTTCTGGTTGGAATCATG | |
| ca CDV HA | (101) | GACCCCCCTACCTGCTGTTCGTGCTGCTGATCCTTCTTGTGGCATCATG | |
| DQ228166 | (101) | GACCACCCTTTTGCTGTTTGTCCTTCTCGTCCTACTGGTTGGAATCATG | |
| DQ494317 | (101) | GACCACCCTATTTGCTGTTTGTCCTTCTCATCCTTCTGGTTGGAGTCATG | |
| DQ494318 | (101) | GACCACCCTATTTGCTGTTTGTCCTTCTCATCCTTCTGGTCGGAATCATG | |
| DQ889177 | (101) | GACCACCCTATTTGCTGTTTGTCCTTCTCATCCTTCTGGTTGGAATCATG | |
| DQ889187 | (101) | GACCACCCTATTGCTGTTATCCTTCTCATCCTACTGGTTGGAATCATG | |
| EU325730 | (101) | GACCACCCTATTTGCTGTTTGTCCTTCTCATCCTACTGATTGGAATCCTG | |
| EU716337 | (101) | GACCACCCTATTTGCTGTTTGTCCTTCTCATCCTACTGGTTGGAATCCTG | |
| FJ011004 | (101) | GACCACCCTATTTGCTGTTTGTCCTTCTCATCCTTCTGGTTGGAATCATG | |
| FJ011005 | (101) | GACCACCCTATCTGCTGTTTGTCCTTCTCATCCTACTGGTTGGAATCATG | |
| FJ423608 | (101) | GACCACCCTACTTGTTTTTGTCTTCTCACCCTACTGATTGGAATCCTG | |
| FJ705233 | (101) | GACCACCCTATTTGCTGTTTGTCCTTCTCATCCTACTGACTGGAATCCTG | |
| GQ214376 | (101) | GACCACCCTATTTGCTGTTTGTCCTTCATCCTTCTGGTTGGAATCATG | |

Figure 15A (continued)

```
                     151                                                  200
AF478543   (151)  ACCTTGCTTGCTATCACTGGAGTTCGATTTCACCAAGTATCAACTAGCAA
AF478545   (151)  ACCTTGCTTGCTATCACTGGAGTTCGATTTCACCAAGTATCAACTAGCAA
AY386316   (151)  ACCTTGCTTGCTATCACTGGAGTTCGATTTCACCAAGTATCAACTAGCAA
ca CDV HA  (151)  ACCCTGCTGGCCATCACCGGAGTGAGATTCCACCAGGTGTCCACCTCCAA
DQ228166   (151)  GCCTTGCTTGCTATCACTGGAGTTCGATTTCATCAAGTATCAACCAGCAA
DQ494317   (151)  ACCTTGCNTGCTATCACTGGAGTTCGAATTCACCAAGTATCAACTAGCAA
DQ494318   (151)  ACCTTGCTTGCTATCACTGGAGTTCGATTTCACCAAGTATCAACTAGCAA
DQ889177   (151)  ACCTTGCTTGCTATCACTGGAGTTCGATTTCACCAAGTATCAACTAGCAA
DQ889187   (151)  GCCTTGCTTGCTATCACTGGAGCTCGATTTCACCAAGTATCAACTAGCAA
EU325730   (151)  GCCTTGCTTGCCATCACTGGAGTTCGATTTCACCAAGTATCAACTAGCAA
EU716337   (151)  GCCTTGCTTGCTATCACTGGAGTTCGATTTCACCAAGTATCAACTAACAA
FJ011004   (151)  ACCTTGCTTGCTATCACTGGAGTTCGATTTCACCAAGTATCAACTAGCAA
FJ011005   (151)  ACCTTGCTTGCTATCACCGGAGTTCGATTCACCAGGTATCAACTAGCAA
FJ423608   (151)  GCCTTGCTTGCCATCACTGGAGTTCGATTTCACCAAGTATCAACTAGCAA
FJ705233   (151)  GCCTTGCTTGCCATCACTAGAGTTCGATTTCACCAAGTATCAACTAGCAA
GQ214376   (151)  ACCTTGCTTGCTATCACTGGAGTTCGATTTCACCAAGTATCAACTAGCAA 201                                                  250
AF478543   (201)  TATGGAATTTAGCAGATTGCTGAAAGAGGATATGGAGAAATCAGAGGCCG
AF478545   (201)  TATGGAATTTAGCAGATTGCTGAAAGAGGATATGGAGAAATCAGAGGCCG
AY386316   (201)  TATGGAATTTAGCAGATTGCTGAAAGAGGATATGGAGAAATCAGAGGCCG
ca CDV HA  (201)  CATGGAGTTCAGCCGGCTGCTGAAAGAGGACATGGAGAAGAGCGAGGCCG
DQ228166   (201)  TATGGAATTTAGTAGATTGCTGAAAGAGGATATGGAGAAATCTGAGGCCG
DQ494317   (201)  TATGGAATTTAGCAGATTGCTGAAAGAGGATATGGAGAAATCAGAGGCCG
DQ494318   (201)  TATGGAATTTAGCAGATTGTTGAAAGAGGATATGGAGAAATCAGAGGCCG
DQ889177   (201)  TATGGAATTTAGCAGATTACTGAAAGAGGATATGGAGAAATCAGAGGCCG
DQ889187   (201)  TATGGAATTTAGCAGATTGCTGAAAGAGGATATGGAGAAATCAGAGGCCG
EU325730   (201)  TATGGAATTTAGCAGATTGCTGAAAGAGGATATGGAGAAATCAGAGGCCG
EU716337   (201)  TATGGAATTTAGCAGATTGCTGAAAGAGGATATGGAGAAGTCAGAGGCCG
FJ011004   (201)  TATGGAATTTAGCAGATTGCTGAAAGAGGATATGGAGAAATCAGAGGCCG
FJ011005   (201)  TATGGAATTCAGCAGATTGCTGAAAGAGGATATGGAGAAATCAGAGGCCG
FJ423608   (201)  TATGGAATTTAGCAGATTGCTGAAAGAGGATATGGAGAAATCAGAGGCCG
FJ705233   (201)  TATGGAATTTAGCAGATTGCTGAAAGAGGATATGGAGAAATCAGAGGCCG
GQ214376   (201)  TATGGAATTTAGCAGATTGCTGAAAGAGGATATGGAGAAATCAGAGGCCG 251                                                  300
AF478543   (251)  TACATCACCAAGTCATAGATGTCTTGACACCGCTCTTCAAAATTATTGGA
AF478545   (251)  TACATCACCAAGTCATAGATGTCTTGACACCGCTCTTCAAAATTATTGGA
AY386316   (251)  TACATCACCAAGTCATAGATGTCTTGACACCGCTCTTCAAAATTATTGGA
ca CDV HA  (251)  TGCACCACCAGGTGATCGATGTGCTGACCCCCTGTTCAAGATCATCGGC
DQ228166   (251)  TACATCATCAAGTCATAGATGTTTTGACACCGCTCTTCAAAATCATCGGA
DQ494317   (251)  TACATCACCAAGTCATAGATGTCTTGACACCGCTCTTCAAAATTATTGGA
DQ494318   (251)  TACATCACCAAGTCATAGATGTCTTGACACCGCTCTTCAAAATTATTGGA
DQ889177   (251)  TACATCACCAAGTCATAGATGTCTTGACACCGCTCTTCAAAATTATTGGA
DQ889187   (251)  TACATCACCAAGTCATAGATGTCTTGACACCGCTCTTTAAAATTATTGGT
EU325730   (251)  TACATCACCAAGTCATAGATGTCTTGACACCGCTCTTCAAAATTATTGGA
EU716337   (251)  TACATCACCAAGTCATAGATGTCTTGACACCGCTCTTCAAGATTATTGGA
FJ011004   (251)  TACATCACCAAGTCATAGATGTCTTGACACCGCTCTTCAAAATTATTGGA
FJ011005   (251)  TACACCACCAAGTCATGGATGTCTTGACACCGCTCTTCAAAATTATTGGA
FJ423608   (251)  TACATCACCAAGTCATAGATGTCTTGACACCGCTCTTCAAAATTATTGGA
FJ705233   (251)  TACATCACCAAGTCATAGATGTCTTGACGCCGCTCTTCAAAATTATTGGA
GQ214376   (251)  TACATCACCAAGTCATAGATGTCTTGACACCGCTCTTCAAAATTATTGGA
```

|  |  | 451 | 500 |
|---|---|---|---|
| AF478543 | (451) | ACTAATTACTGCGATACAATTGGATCAGAAAATCTATTGCATCGGCAGT |  |
| AF478545 | (451) | ACTAATTACTGCGATACAATTGGATCAGAAAATCTATTGCATCGGCAGT |  |
| AY386316 | (451) | ACTAATTACTGCGATACAATTGGATCAAAAGTCTATTGCATCGGCAGC |  |
| ca CDV HA | (451) | ACCAACTACTGCGACACCATCGGCATCAGGAAGAGCATCGCCAGCGCCGT |  |
| DQ228166 | (451) | ACTAATTACTGCGATACAATTGGATCAGAAAATCTATTGCATCGGCAGC |  |
| DQ494317 | (451) | ACTAATTACTGCGATACAGTTGGATCAGAAAATCTATTGCATCGGCAGC |  |
| DQ494318 | (451) | ACTAATTACTGCGATACAATTGGATCAGAAAATCTATTGCATCGGCAGC |  |
| DQ889177 | (451) | ACTAATTACTGCGATACAATTGGATCAGAAAATCTATTGCATCGGCAGC |  |
| DQ889187 | (451) | ACTAATTACTGCGATACAATTGGATCAGAAAATCTATTGCATTGGCAGC |  |
| EU325730 | (451) | ACTAATTACTGTGATACAGTTGGGTCAAAAATCTATTGCATCGGCAGC |  |
| EU716337 | (451) | ACTAATTACTGCGATACAATTGAGATCAGAAAATCTATTGCATTGGCAGC |  |
| FJ011004 | (451) | ACTAATTACTGTGATACAATTGAGATCAGAAAATCTATTGCATCGGCAGC |  |
| FJ011005 | (451) | TCTAATTACTGTGATACAATTGGATCAGAAAATCTATTGCATCAGCAGC |  |
| FJ423608 | (451) | ACTAATTACTGTCATACAGTTGGGTCAAAAATCTATTACATCGGCAGC |  |
| FJ705233 | (451) | ACTAATTACTGTGATACAGTTGGGTCAAAAATCTATTGCATCGGCAGC |  |
| GQ214376 | (451) | ACTAATTACTGCGATACAATTGGATCAGACAATCTATTGCATCGGCAGC |  |

|  |  | 501 | 550 |
|---|---|---|---|
| AF478543 | (501) | AAATCCCATCCTTTTATCAGCACTCTCCGGAGGCAGAGGTGACATATTCC |  |
| AF478545 | (501) | AAATCCCATCCTTTTATCAGCACTCTCCGGAGGCAGAGGTGACATATTCC |  |
| AY386316 | (501) | AAATCCCATCCTTTTATCAGCACTCTCCGGAGGCAGAGGTGACATATTCC |  |
| ca CDV HA | (501) | GAATCCCATCCTGCTGAGCGCCCTGAGCGGCGGCAGAGGCGACATCTTCC |  |
| DQ228166 | (501) | AAATCCTATCCTTTTATCAGCACTTTCTGGAGGCAGAGGTGACATATTCC |  |
| DQ494317 | (501) | AAATCCCATCCTTTTATCAGCACTCTCCGGAGGCAGAGGTGACATATTCC |  |
| DQ494318 | (501) | AAATCCCATCCTTTTATCAGCACTCTCCGGGAGGCAGAGGTGACATATTCC |  |
| DQ889177 | (501) | AAATCCCATCCTTTTATCAGCACTCTCGGAGGCAGAGGTGACATATTCC |  |
| DQ889187 | (501) | AAATCCCATCCTTTTGTCGGCACTCTCCAGAGGCAGGGGTGACATATTCC |  |
| EU325730 | (501) | AAATCCCATCATTTTATCAGCACTCTCCGGAGCCAGAGGCGACATATTCC |  |
| EU716337 | (501) | AAATCCCATCCTTTTATCAGCACTCTCCGGTGGCAGAGGTGACATATTCC |  |
| FJ011004 | (501) | AAATCCCATCCTTTTATCAGCACTCTCCGGAGGCAGAGGTGACATATTCC |  |
| FJ011005 | (501) | AAATCCTATCCTTTTATCAGCACTCTCCGGAGGCAGAGGTGACATATTCC |  |
| FJ423608 | (501) | AAATCCCATCATTTTATCAGCACTCTCCGGAGCCAGAGGTGACATATTCC |  |
| FJ705233 | (501) | AAATCCCATCATTTTATCAGCACTCTCCGGAGCCAGAGGTGACATATTCC |  |
| GQ214376 | (501) | AAATCCCATCCTTTTATCAGCACTCTCCGGAGGCAGAGGTGACATATTCC |  |

|  |  | 551 | 600 |
|---|---|---|---|
| AF478543 | (551) | CACCATACAGATGCAGTGGAGCTACTACTTCAGTGGGCAGAGTTTTCCCG |  |
| AF478545 | (551) | CACCATACAGATGCAGTGGAGCTACTACTTCAGTGGGCAGAGTTTTCCCG |  |
| AY386316 | (551) | CACCATACAGATGCAGTGGAGCTACTACTTCAGTGGGCAGAGTTTTCCCG |  |
| ca CDV HA | (551) | CCCCCTACAGATGGAGCGGCGCCACCACCTCTGTGGGCAGAGCTGTTCCCT |  |
| DQ228166 | (551) | CACCATACAAGTCCAATGGAGCTGCTACTTCAGTAGGCAGAGTTTTCCCG |  |
| DQ494317 | (551) | CACCATACAGATGCAGTGGAGCTACTACTTCAGTGGGCAGAGTTTTCCCG |  |
| DQ494318 | (551) | CACCATACAGATGCAGTGGAGCTACTACTTCAGTGGGCAGAGTTTTCCCG |  |
| DQ889177 | (551) | CACCATACAGATGCAGTGGAGCTACTACTTCAGTGGGCAGAGTTTTCCCG |  |
| DQ889187 | (551) | CACCATACAGATGTAGTGGAGCTGCTACTTCAGTAGGCAGAGTTTTCCCG |  |
| EU325730 | (551) | CGCCGTACAGATGCAGTGGAGCTACTACTTCAGTAGGCAGAGTATTCCCG |  |
| EU716337 | (551) | CACCATACAGTTGCAGTGGAGCTACTACTTCAGTAGGCAGAGTTTTCCCT |  |
| FJ011004 | (551) | CACCATACAGATGCAGTGGAGCTACTACTTCAGTGGGCAGAGTTTTCCCG |  |
| FJ011005 | (551) | CTCCATACAGATGCAATGGAGCTGCTACTTCAATAGGCAGAGTTTTCCCT |  |
| FJ423608 | (551) | CGCCGTACAGATGCAGTGGAGCTACTACTTCAGTAGGCAGAGTATTCCCG |  |
| FJ705233 | (551) | CGCCGTGCAGATGCAGTGGAGCTACTACTTCAGTAGGCAGAGTATTCCCG |  |
| GQ214376 | (551) | CACCATACAGATGCAGTGGAGCTACTACTTCAGTGGGCAGAGTTTTCCCG |  |

Figure 15A (continued)

```
              601                                                    650
AF478543 (601) CTATCAGTATCATTGTCCATGTCTTTGATCT-CAAAAACATCAGAGATAA
AF478545 (601) CTATCAGTATCATTGTCCATGTCTTTGATCT-CAAAAACATCAGAGATAA
AY386316 (601) CTATCAGTATCATTGTCCATGTCTTTGATCT-CAAAAACATCAGAGATAA
ca CDV HA (601) CTGAGCGTGTCCCTGAGCATGAGCCTGATCAGCAAGACCAGC-GAGATCA
DQ228166 (601) CTTTCAGTATCATTGTCCATGTCTTTGATCT-CAAAAACATCAGGGATAA
DQ494317 (601) CTATCAGTATCATTGTCCATGTCTTTGATCT-CAAAAACATCAGAGATAA
DQ494318 (601) CTATCAGTATCATTGTCCATGTCTTTGATCT-CAAAAACATCAGAGATAA
DQ889177 (601) CTATCAGTATCATTGTCCATGTCTTTGATTT-CAAAAACATCAGGGATAA
DQ889187 (601) CTCTCAGTATCATTGTCCATGTCTTTGATCT-CAAGAACATCAGAGATAA
EU325730 (601) CTATCCGTATCATTATCCATGTCTTTGATAT-CAAGAACATCAGAGATAA
EU716337 (601) CTATCAGTATCATTGTCCATGTCTTTGATCT-CAAAAACATCAGAGATAA
FJ011004 (601) CTATCAGTATCATTGTCCATGTCTTTGATCT-CAAGAACATCAGAGATAA
FJ011005 (601) CTATCTGTGTCATTGTCCATGTCCTTGATCT-CCAGAACAGCAGAGATAA
FJ423608 (601) CTATCTGTATCATTATCCATGTCTTTGATAT-CAAGAACATCAGAGATAA
FJ705233 (601) CTATCCGTATCATTATCCATGTCTTTGATAT-CAAGAACATCAGAGATAA
GQ214376 (601) CTGTCAGTATCATTGTCCATGTCTGTGATCT-CAAAAACATCAGAGATAA 651                                                    700
AF478543 (650) GCAATATGCTAACTGCTATCTCAGACGGAGTGTATGGTAAAACCTATTTG
AF478545 (650) GCAATATGCTAACTGCTATCTCAGACGGAGTGTATGGTAAAACCTATTTG
AY386316 (650) GCAGTATGCTAACTGCTATCTCAGACGGAGTGTATGGTAAAACCTATTTG
ca CDV HA (650) GCAACATGCTGACCGCCATCAGCGACGGCGTGTACGGCAAGACCTATCTG
DQ228166 (650) TCAATATGCTAACCGCTATCTCAGACGGAGTGTATGGTAAAACTTACTTG
DQ494317 (650) GCAATATGCTAACTGCTATCTCAGACGGAGTGTATGGTAAAACCTATTTG
DQ494318 (650) GCAATATGCTAACTGCTATCTCAGACGGAGTGTATGGTAAAACCTATTTG
DQ889177 (650) GCAATATGCTAACTGCCATCTCAGACGGAGTGTATGGTAAAACCTATTTG
DQ889187 (650) TCAATATGCTAACCGCTATCTCAGATGGAGTGTATGGTAAAACTTACTTG
EU325730 (650) TCAATATGCTAACCGCTATCTCAGACGGAGTGTATGGTAAAACTTATATG
EU716337 (650) TCAATATGCTAACCGCTATCTCAGACGGGGTGTATGGTAAAACTTATTTG
FJ011004 (650) GCAATATGCTAACTGCTATCTCAGACGGAGTGTATGGTAAAACCTATTTG
FJ011005 (650) TCAATATGCTAACCGCTATCTCAGACGGAGTTGATGGTAAAACTTACTTG
FJ423608 (650) TCAATATGCTAACCGCTATCTCAGACGGAGTGTATGGTAAAACTTATTTG
FJ705233 (650) TCAATATGCTAACCGCTATCTCAGACGGAATGTATGGTAAAACTTATTTG
GQ214376 (650) GCAATATGCTAACTGCTATCTCAGACGGAGTGTATGGTAAAACCTATTTG 701                                                    750
AF478543 (700) CTAGTGCCTGATTACATTGAAGGGGAGTTCGACACGCAAAAGATTCGAGT
AF478545 (700) CTAGTGCCTGATTACATTGAAGGGGAGTTCGACACGCAAAAGATTCGAGT
AY386316 (700) CTAGTGCCTGATTACATTGAAGGGGAGTTCGACACGCAAAAGATTCGAGT
ca CDV HA (700) CTGGTGCCCGACTACATCGAGGGCGAGTTCGACACCCAGAAGATCCGCGT
DQ228166 (700) CTAATGCCTGATTATATTGAAGGGGAGTTCGACACGCAAAAGATTCGAGT
DQ494317 (700) CTAGTGCCTGATTACATTGAAGGGGAGTTCGACACGCAAAAGATTCGAGT
DQ494318 (700) CTAGTGCCTGATTACATTGAAGGGGAGTTCGACACGCAAATGATTCGAGT
DQ889177 (700) CTAGTGCCTGATTACATTGAAGGGGAGTTCGACACGCAAAAGATTCGAGT
DQ889187 (700) CTAGTGCCTGATTATATTGAAGGGGAATTCGACACACAAAAGATTCGAGT
EU325730 (700) CTAGTGCCTGATTATATTGAAGGGGAGTTCGACTCGCAAAAGATTCGAGT
EU716337 (700) CTAGTTCCTGATTATATTGAAGGGGGTTCGACACGCAAAAGATTCGAGT
FJ011004 (700) CTAGTGCCTGATTACTTTGAAGGGGAGTTCGACACGCAAAAGATTCGGGT
FJ011005 (700) CTAGTGCCTGATTATATTGAAGGGGAGTTCGAAACGCAGAAGATTCGAGT
FJ423608 (700) CTAGTGCCTGATTATATTGAAGGGGAGTTCGACTCGCAAAAGATTCGAGT
FJ705233 (700) CTAGTGCCTGATTATATTGAAGGGGAGTTCGACTCGCAAAAGATTCGAGT
GQ214376 (700) CTAGTGCCTGATTACATTGAAGGGGAGTTCGACACGCAAAAGATTCGAGT
```

Figure 15A (continued)

```
              751                                                      800
AF478543 (750) GTTTGAGATAGGGTTCATCAAACGGTGGCTGAATAACATGCCATTACTCC
AF478545 (750) GTTTGAGATAGGGTTCATCAAACGGTGGCTGAATAACATGCCATTACTCC
AY386316 (750) GTTTGAGATAGGGTTCATCAAACGGTGGCTGAATAACATGCCATTACTCC
ca CDV HA (750) GTTCGAGATCGGCTTCATCAAGCGGTGGCTGAACAACATGCCCCTGCTGC
DQ228166 (750) GTTTGAGATAGGGTTCATCAAACGGTGGCTGAATGACATGCCATTACTCC
DQ494317 (750) GTTTGAGATTGGGTTCATCAGACGGTGGCTGAATAACATGCCATTACTCC
DQ494318 (750) GTTTGAGATAGGGTTCATCAAACGGTGGCTGAATAACATGCCATTACTCC
DQ889177 (750) GTTTGAGATAGGGTTCATTAAACGGTGGCTGAATAACATGCCATTATTCC
DQ889187 (750) GTTTGAGATAGGGTTCATCAAACGGTGGCTGAATGACATGCCATTACTCC
EU325730 (750) GTTTGAGATAGGGTTTATCAAACGGTGGCTGAATAACATGCCTTTACTCC
EU716337 (750) GTTTGAGATAGGGTTCATCAAACGGTGGCTGAATGACATGCCATTACTCC
FJ011004 (750) GTTTGAGATAGGGTTCATCAAACGGTGGCTGAATGACATGCCATTACTCC
FJ011005 (750) GTTTGAGATCGGGTTCATCAAACGGTGGCTGAATGACATGTCATTACTCC
FJ423608 (750) GTTTGAGATAGGGTTTATCAAACGGTGGCTGAATGACATGCCTTTACTCC
FJ705233 (750) GTTTGAGATAGGGTTTATCAGACGGTGGCTGAATGACATGCCTTTACTCC
GQ214376 (750) GTTTGAGATAGGGTTCATCAAACGGTGGCTGAATAACATGCCATTACTCC 801                                                      850
AF478543 (800) AGACAACCAACTACATGGTCCTGCCGGAGAATTCCAAAGCCAAGGTATGT
AF478545 (800) AGACAACCAACTACATGGTCCTGCCGGAGAATTCCAAAGCCAAGGTATGT
AY386316 (800) AGACAACCAACTACATGGTCCTGCCGGAGAATTCCAAAGCCAAGGTATGT
ca CDV HA (800) AGACCACCAACTACATGGTGCTGCCCGAGAACAGCAAGGCCAAAGTGTGC
DQ228166 (800) AGACAACCAACTATATTGTCCTGCCGGAGAATTCCAAAGCCAAGGTATGT
DQ494317 (800) AGACAACCAACTACATGGTCCTGCCGGAGAATTCCAAAGCCAAGGTATGT
DQ494318 (800) AGACAACCAACTACATGGTCCTGCCGGAGAATTCCAAAGCCAAGGTATGT
DQ889177 (800) AGACAACCAACTACATGGTCCTGCCGGAGAATTCCAAAGCCAAGGTATGT
DQ889187 (800) AGACAACCAACTATATGGTCCTGCCGGAGAATTCCAAAGCCAAGGTATGT
EU325730 (800) AGACAACCAACTATATGGTCCTGCCGGAAACTTCCAAAGCCAAGGTATGT
EU716337 (800) AGACAACCAACTATATGGTCCTGCCGGAGAATTCCAAAGCCAAGGTATGT
FJ011004 (800) AGACAACCAACTACATGTTCCTGCCGGAGAATTCCAAAGCCAAGGTATGT
FJ011005 (800) AGACAACCAACTATATGGTCCTGCCGGAGAATTCCAAAGCCAAGGTATGT
FJ423608 (800) AGACAACCAACTATATGGTTCTGCCGGAAACTTCCAAAGCCAAGGTATGT
FJ705233 (800) AGACAACCAACTATATGGTCCTCCGGAAACTTCCAAAGCCAAGGTATGT
GQ214376 (800) AGACAACCAACTATATGGTCCTGCCGGAGAATTCCAAAGCCAAGGTATGT 851                                                      900
AF478543 (850) ACTATAGCAGTGGGCGAGTTGACAACTGGCTTCCTTGTGTGTAGATGAGAG
AF478545 (850) ACTATAGCAGTGGGCGAGTTGACAACTGGCTTCCTTGTGTGTAGATGAGAG
AY386316 (850) ACTATAGCAGTGGGCGAGTTGACAACTGGCTTCCTTGTGTGTAGATGAGAG
ca CDV HA (850) ACCATCGCTGTGGGCGAGCTGACCCTGGCCAGCCTGTGCGTGGACGAGAG
DQ228166 (850) ACTATAGCAGTGGGTGAGTTGACAACTGGCTTCCTTGTGTGTAGATGAGAG
DQ494317 (850) ACTATAGCAGTGGGCGAGTTGACAACTGGCTTCCTTGTGTGTAGATGAGAG
DQ494318 (850) ACTATAGCAGTGGGCGAGTTGACAACTAGCTTCCTTGTGTGTAGATGAGAG
DQ889177 (850) ACTATAGCAGTGGGCGAATTGACAACTAGCTTCCTTGTGTGTAGATGAGAG
DQ889187 (850) ACTATAGCAGTGGGCGAGTTGACAACTGGCTTCCTTGTGTGTAGATGAGAG
EU325730 (850) ACTATAGCAGTGGGCGAGCTGACAACTAGCTTCCTTGTGTGTAGATGAGAG
EU716337 (850) ACTATAGCGGTGGGCGAGTTGACAACTGGCTTCCTTGTGTGTAGATGAGAG
FJ011004 (850) ACTATAGCAGTGGGCGAGTTGACAACTGGCTTCCTTGTGTGTAGATGAGAG
FJ011005 (850) ACTATAGCAGTGGGCGAGTTGACAACTGGCTTCCTTGTGTGTAGATGAGAG
FJ423608 (850) ACTATAGCAGTGGGCGAGCTGACAACTAGCTTCCTTGTGTGTAGATGAGAG
FJ705233 (850) ACTATAGCAGTGGGCGAGCTGACAACTAGCTTCCTTGTGTGTAGATGAGAG
GQ214376 (850) ACTATAGCAGTGGGCGAGTTGACAACTGGCTTCCTTGTGTGTAGATGAGAA
```

Figure 15A (continued)

```
             901                                                  950
AF478543 (900) CACCGTATTGTTATATCAGGACAGCAATGGTTCACAAGATGGTATTCTAG
AF478545 (900) CACCGTATTGTTATATCAGGACAGCAATGGTTCACAAGATGGTATTCTAG
AY386316 (900) CACCGTATTGTTATATCAGGACAGCAATGGTTCACAAGATGGTATTCTAG
ca CDV HA (900) CACCGTGCTGCTGTACCACGACAGCAACGGCAGCCAGGACGGCATCCTGG
DQ228166 (900) CACCGTATTGTTATATCAGGACAGCAATGGTTCACAAGATGGTATTCTAG
DQ494317 (900) CACCGTATTGTTATATCAGGACAGCAATGGTTCACAAGATGGTATTCTAG
DQ494318 (900) CACCGTATTGTTATATCAGGACAGCAATGGTTCACAAGATGGTATTCTAG
DQ889177 (900) CACCGTATTGTTATATCAGGATAGCAATGGTTCACAAGGTGGTGTTCTAG
DQ889187 (900) CACTGTATTACTATATCAGGACAGCAATGGTTCACAAGATGGTATTCTAG
EU325730 (900) CACCGTATTGTTATATCAGACAGCAATGGTTCACAAAATGGTATTCTAG
EU716337 (900) CACCGTATTGTTATATCAGACAGCGATGGTTCACAAGATGGTATTCTAG
FJ011004 (900) CACCGTATCGTTATATCAGACGGCAGTGGTTCACAAGATGGTATTCTAG
FJ011005 (900) CACTGTATTGTTATATCAGGACAGCAATGGTTCACAAGATGGTATTCTAG
FJ423608 (900) CACTGTATTATTATATCAGGACAGCAATGGTTCACAAAATGGTATTCTAG
FJ705233 (900) CACCGTATTGTTATATCAGGACAGCAATGGTTCACAAAATGGTATTCTAG
GQ214376 (900) CACCGTATTGTTATATCAGGACAGCAATGGTTCACAAGATGGTATTCTAG 951                                                 1000
AF478543 (950) TAGTGACGCTGGGGATATTTGGGGCAACACCTATGGATCAAGTTGAAGAA
AF478545 (950) TAGTGACGCTGGGGATATTTGGGGCAACACCTATGGATCAAGTTGAAGAA
AY386316 (950) TAGTGACGCTGGGGATATTTGGAGCAACACCTATGGATCAAGTTGAAGAA
ca CDV HA (950) TGGTGACCCTGGGCATCTTCGGCGGCACCCCTATGGACCAGGTGGAGGAA
DQ228166 (950) TAGTGACACTGGGAATATTCGGGGCAACACCTATGGATCAAGTTGAAGAG
DQ494317 (950) TAGTGACGCTGGGGATATTTGGGGCAACACCTATGGATCAAGTTGAAGAA
DQ494318 (950) TAGTGACGCTGGGGATATTTGGGGCAACACCTATGGATCAAGTTGGAGAA
DQ889177 (950) TAGTGACGCTGGGGATATTTGGGGCAACACCTATGGATCAAGTTGAAGAA
DQ889187 (950) TAGTGACGCTGGGAATATTTGGGGCAACACCTATGGATCAAGTTGAAGAG
EU325730 (950) TAGTGACATTGGGAATATTTGGGGCAACACCTATGGATCAAGTTGAAGAG
EU716337 (950) TGGTGACGCTGGGAATATTTGGGGCAACACCTATGGATCAAGTTGAAGAG
FJ011004 (950) TAGTGACGCTGGGGATATTTGGGGCAACACCTATGGATCAAGTTGAAGAG
FJ011005 (950) TAGTGACGCTGGGAATATTTTGGGCACACCTATGGATCAAGTTGAAGAG
FJ423608 (950) TAGTGACATTGGGAATATTTGGGGCAACATCTATGGATCAAGTTGAAGAG
FJ705233 (950) TAGTGACATTGGGAATATTTGGGGCAACACCTATGGATCAAGTTGAAGAG
GQ214376 (950) TAGTGACGCTGGGGATATTTGGGGCAACACCTATGGATCAAGTTGAAGAA 1001                                                1050
AF478543 (1000) GTGATACCTGTCGCTCAGCCATCAGTAGAAAAAATACATATAACAAATCA
AF478545 (1000) GTGATACCTGTCGCTCAGCCATCAGTAGAAAAAATACATATAACAAATCA
AY386316 (1000) GTGATACCTGTCGCTCAGCCATCAGTAGAAAAAATACATATAACAAATCA
ca CDV HA (1000) GTGATCCCCGTGGCCCAGCCCAGCGTGGAGAAGATCCACATCACCAACCA
DQ228166 (1000) GTGATACCTGTCGCTCAGCCATCAGTANAAAAAATACATATAACAAATCA
DQ494317 (1000) GTGATACCTGTCGCTCAGCCATCAGTAGAAAAAATACATATAACAAATCA
DQ494318 (1000) GTGATACCTGTCGCTCAGCCCTCAGTAGAAAAAATACATATAACAAATCA
DQ889177 (1000) ATGATACCTGTCGCTCAGCCATCAGTAGAAAAAATACATATAACAAATCA
DQ889187 (1000) GTGATACCTGTCGCTCATCCATCAGTAGAAAAAATACATATAACAAATCA
EU325730 (1000) GTGATACCTATGGCTCAGCCATCAGTGGAGAGAATACATATAACAAATCA
EU716337 (1000) GTGATACCTGTTGCTCAGCCATCAGTAGAAAAAATACATATAACAAATCA
FJ011004 (1000) GTGATACCTGTCGCTCAGCCATCAGTAGAGAAAATACATATAACCAATCA
FJ011005 (1000) GTGATACCTGTCGCTCAGCCATCAGTAGAAAAAATACATATAACAAATCA
FJ423608 (1000) GTGATACCTATGGCTCAGCCATCAGTGGAGAGAATACATATAACAAATCA
FJ705233 (1000) GTGATACCTATGGCTCAGCCATCAGTGGAGAGAATACATATAACAAATCA
GQ214376 (1000) GTGATACCTGTCGCCCAGCCATCAATAGAAAAAATACATATAACAAATCA
```

Figure 15A (continued)

```
                    1051                                              1100
AF478543   (1050)   CCGTGGGTTCATAAAAGATTCAATAGCAACCTGGATGGTGCCTGCATTGG
AF478545   (1050)   CCGTGGGTTCATAAAAGATTCAATAGCAACCTGGATGGTGCCTGCATTGG
AY386316   (1050)   CCGTGGGTTCATAAAAGATTCAATAGCAACCTGGATGGTGCCTGCATTGG
ca CDV HA  (1050)   CCGGGGCTTTATCAAGGACAGCATCGCCACCTGGATGGTGCCCGCCCTGG
DQ228166   (1050)   CCGTGGGTTCATAAAAGATTCAATAGCAACCTGGATGGTGCCTGCATTGA
DQ494317   (1050)   CCGTGGGTTCATAAAAGATGCAATAGCAACCTGGATGGTGCCTGCATTGG
DQ494318   (1050)   CCGTGGGTTCATAAAAGATTCAATAGCAACCTGGATGGTGCCTGCATTGG
DQ889177   (1050)   CCGTGGGTTCATAAAAGATTCAATAGCAACCTGGATGGTGCCTGTATTGG
DQ889187   (1050)   CCGTGGGTTCATAAAAGATTCAATAGCAACCTGGATGGTGCCTGTATTGG
EU325730   (1050)   CCGTGGGTTCATAAAAGATTCAGTAGTAACCTGGATGGTGCCTGTATTGG
EU716337   (1050)   CCGTGGGTTCATAAAAGATTCAATAGCAACCTGGATGGTGCCTGCATTGG
FJ011004   (1050)   CCGTGGATTCATAAAAGATTCAATCGCAACCTGGATGGTGCCTGCATTGG
FJ011005   (1050)   CCGTGGGTTCATAAAAGATTCAAAAGCAATCTGGATGGTGCCTGCATTGG
FJ423608   (1050)   CCGTGGGTTCATAAAAGATTCAATAGTAACCTGGATGGTGCCTGTATTGG
FJ705233   (1050)   CCGTGGGTTCATAAAAGATTCAATAGTAACCTGGATGGTGCCTGTATTGG
GQ214376   (1050)   CCGTGGGTTCATAAAAGATTCAATAGCAACCTGGATGGTGCCTGCATTGG 1101                                              1150
AF478543   (1100)   TCTCTGAGAAACAAGAGGAACAAAAAAATTGTCTGGAGTCGGCTTGTCAA
AF478545   (1100)   TCTCTGAGAAACAAGAGGAACAAAAAAATTGTCTGGAGTCGGCTTGTCAA
AY386316   (1100)   TCTCTGAGAAACAAGAGGAACAAAAAAATTGTCTGGAGTCGGCTTGTCAA
ca CDV HA  (1100)   TGTCTGAGAAGCAGGAGGAGCAGAAGAACTGCCTGGAGAGCGCCTGCCAG
DQ228166   (1100)   TCTCTGGGAAACAAGAGGAACAAAAAAATTGTCTGGAGTCGGCTTGTCAA
DQ494317   (1100)   TCTCTGAGAAACAAGAGGAACAAAAAAATTGTCTGGAGTCGGCTTGTCAA
DQ494318   (1100)   TCTCTGAGAAACAAGAGGAACAAAAAAATTGTCTGGAGTCGGCTTGTCAA
DQ889177   (1100)   TCTCTGAGAAACAAGAGGAACAAAAAAATTGTCTGGAGTCGGCTTGTCAA
DQ889187   (1100)   TCTCTGAGAACCAAGAGGAACAAAAAAATTGTCTGGAGTCGGCTTGTCAA
EU325730   (1100)   TCTCTGAGAAACAAGAGGAGCAAAAAAACTGTCTGGAGTCTGCTTGTCAA
EU716337   (1100)   TATCTGAGAAACAAGAGGAACAAAAAAATTGTCTGGAGTCGGCTTGTCAA
FJ011004   (1100)   TCTCTGAGAAACAAGAGGAACAAAAAAATTGTCTGGAGTCGGCTTGTCAA
FJ011005   (1100)   TCTCTGAGAAACAAGAGGAACAAAAAAATTGTCTGGAGTCGGCTTGTCAA
FJ423608   (1100)   TCTCTGAGAAACAAGAGGAGCAAAAAAACTGTCTGGAGTCTGCTTGTCAA
FJ705233   (1100)   TCTCAGAGAAACAAGAGGAGCAAAAAAACTGTCTGGAGTCTGCTTGTCAA
GQ214376   (1100)   TCTCTGAGAAACAAGAGGAACAAAAAAATTGTCTGGAGTCGGCTTGTCAA 1151                                              1200
AF478543   (1150)   AGAAAAACCTACCCTATGTGCAACCAAACGTCATGGGAACCCTTTGGAGG
AF478545   (1150)   AGAAAAACCTACCCTATGTGCAACCAAACGTCATGGGAACCCTTTGGAGG
AY386316   (1150)   AGAAAAACTTACCCTATGTGCAACCAAACGTCATGGGAACCCTTTGGAGG
ca CDV HA  (1150)   AGAAAGACCTACCCCATGTGCAACCAGACCAGCTGGGAGCCCTTTGGCGG
DQ228166   (1150)   AGAAAATCCTACCCTATGTGCAACCAAACGTCATGGAAACCCTTTGGAGG
DQ494317   (1150)   AGAAAAACCTATCCTATGTGCAACCAAACGTCATGGGAACCCTTTGGAGG
DQ494318   (1150)   AGAAAAACCTACCCAATGTGCAACCAAACGTCATGGGAACCCTTTGGAGG
DQ889177   (1150)   AGAAAAACCTACCCTATGTGCAACCAAACGTCATGGGAACCCTTTGGAGG
DQ889187   (1150)   AGAAAATCCTACCCTATGTGCAACCAAACGTCATGGGAACCCTTTGGAGG
EU325730   (1150)   AGAAAATCCTACCCGATGTGCAACCAAACGTCATGGGAACCCTTTGGAGG
EU716337   (1150)   AGAAAATCCTACCCTATGTGCAACCAAACGTCATGGGAACCCTTTGGAGG
FJ011004   (1150)   AGAAAAACCTACCCTATGTGCAACCAAACGTCATGGGAACCCTTTGGAGG
FJ011005   (1150)   AGAAAAACCTACCCTATGTGCAACCAAACGTCATGGGAACCCTTTGGGGG
FJ423608   (1150)   AGAAAATCCTACCCTATGTGCAACCAAACGTCATGGGAACCCTTTGGAGG
FJ705233   (1150)   AGAAAAACCTATCCTATGTGCAACCAAACGTCATGGGAACCCTTTGGAGG
GQ214376   (1150)   AGAAAAACCTACCCTATGTGCAACCAAACGTCATGGGAACCCTTTGGAGG
```

Figure 15A (continued)

```
                 1201                                              1250
AF478543 (1200)  GGGACAGTTGCCATCTTATGGGCGGTTGACATTATCTCTAGATCCAAGCA
AF478545 (1200)  GGGACAGTTGCCATCTTATGGGCGGTTGACATTATCTCTAGATCCAAGCA
AY386316 (1200)  GGGACAGTTGCCATCTTATGGGCGGTTGACATTACCTCTAGATCCAAGCA
ca CDV HA(1200)  CGGACAGCTGCCCAGCTACGGCAGACTGACCCTGAGCCTGGACCCTAGCA
DQ228166 (1200)  AGGACAGTTGCCATCTTATGGGCGGTTGACATTACCTCTAGATCCAGGCA
DQ494317 (1200)  AGGACAGTTGCCATCTTATGGGCGGTTGACATTACCTCTAGATCCAAGCA
DQ494318 (1200)  GGGACAGTTACCATCTTATGGGCGGTTGACATTACCTCTAGATCCAAGCA
DQ889177 (1200)  GGGACAGTTGCCATCTTATGGGCGGTTGACATTACCTCTAGATCCGAGCA
DQ889187 (1200)  AGGACAGCTGCCATCTTATGGGCGGTTGACATTACCTCTAGATCCAGGCA
EU325730 (1200)  AGGACAGTTGCCTTCTTATGGGCGGTTGACATTACCTCTAGATCCAAGCG
EU716337 (1200)  AGGACAGTTGCCATCTTATGGGCGGTTGACATTACCTCTAGATCCAAGCA
FJ011004 (1200)  AGGACAGTTGCCATCTTATGGGCGGTGACATTACCTCTAGATCCAAGCA
FJ011005 (1200)  AGGACAATTGCCATCCTATGGGCGGCTGACATTACCTCTAGATCCAAGTA
FJ423608 (1200)  AGGACAGTTGCCTTCTTATGGGCGGTTGACATTACCTCTAGATCCAAGCA
FJ705233 (1200)  GGACAGTTGCCCTCTTATGGGCGGTTGACATTACCTCTAGATCCAAGCA
GQ214376 (1200)  GAGACAGTTGCCATCTTATGGGCGGTTGACATTACCTCTAGATCCAAGTA 1251                                              1300
AF478543 (1250)  TTGACCTTCAACTTAACATATCATTTACATACGGTCCAGTTATACTGAAT
AF478545 (1250)  TTGACCTTCAACTTAACATATCATTTACATACGGTCCAGTTATACTGAAT
AY386316 (1250)  TTGACCTTCAACTTAACATATCATTTACATACGGTCCGGTTATACTGAAT
ca CDV HA(1250)  TCGACCTGCAGCTGAACATCAGCTTCACCTACGGCCCCGTGATCCTGAAC
DQ228166 (1250)  TTGACCTTCAACTTAACATATCATTTACATACGGTCCGGTTATACTGAAT
DQ494317 (1250)  TTGACCTTCAACTTAACATATCATTTACATACGGTCCAGTTATACTGAAT
DQ494318 (1250)  TTGACCCTCAACTTAACATATCATTTACATACGGTCCAGTTATACTGAAT
DQ889177 (1250)  TTGACCTTCAACTTAACATATCATTTACATACGGTCCAGTTATACTGAAT
DQ889187 (1250)  TTGACCTTCAACTTAATCTATCGTTTACATACGGTCCGATTATACTGAAT
EU325730 (1250)  TTGACCTTCAACTTAACATATCATTTACATATGGTCCGGTTATACTGAAC
EU716337 (1250)  TTGACCTTCAACTTAACATCTCGTTTACATACGGTCCGGTTATACTGAAT
FJ011004 (1250)  TTGACCTTCAACTTAACATATCAGTTACATACGGTCCAGTTATACTGAAT
FJ011005 (1250)  TTGACCTTCAACTTAACATATCGTTTACATACGGTCCGGTTATACTGAAT
FJ423608 (1250)  TTGACCTTCAACTTAACATATCATTTACATATGGTCCGGTTATACTGAAC
FJ705233 (1250)  TTGACCTTCAGCTTAACATATCATTTACATATGGTCCGGTTATACTGAAC
GQ214376 (1250)  TGGACCTTCAACTTAACATATCATTTACATACGGTCCAGTTATACTGAAT 1301                                              1350
AF478543 (1300)  GGAGACGGTATGGATTATTATGGAAGCTCACTTTCGGACTCCGGATGGCT
AF478545 (1300)  GGAGACGGTATGGATTATTATGGAAGCTCACTTTCGGACTCCGGATGGCT
AY386316 (1300)  GGAGACGGTATGGATTATTATGAAAGCCCACTTTCGGACTCCGGATGGCT
ca CDV HA(1300)  GGCGACGGCATGGATTACTACGGCAGCAGCCTGAGCGACAGCGGCTGGCT
DQ228166 (1300)  GGAGACGGTATGGATTATTATGAAAGCCCACTTTTGGACTCCGGATGGCT
DQ494317 (1300)  GGACACGGTATGGATTATTATGAAAGCTCACTTTCGGACTCCGGATGGCT
DQ494318 (1300)  GGAGACGGTATGGATTATTATGAAAGCTCACTTTCGGACTCTGGATGGCT
DQ889177 (1300)  GGAGACGGTATGGATTACTATGAAAGCCCACTTTTGGACTCTGGGTGGCT
DQ889187 (1300)  GGAGACGGTATGGATTATTATGAAAGCCCACTTTTGAACTCCGGATGGCT
EU325730 (1300)  GGAGACGGTATGGATTATTATGAAAGCCCACTTTTGGAATCCGGATGGCT
EU716337 (1300)  GGAGACGGTATGGATTATTATGAAAGCCCACTTTTGGACTCCGGATGGCT
FJ011004 (1300)  GGAGACGGTATGGATTATTATGAAAGCCCACTTTCAGACTCCGGATGGCT
FJ011005 (1300)  GGAGACGGTATGGATTATTATGAAAGCCCACTTTTGGACTCCGGATGGCT
FJ423608 (1300)  GGGGACGGTATGGATTATTATGAAAGCCCACTTTTGGAATCCGGATGGCT
FJ705233 (1300)  GGAGACGGTATGGATTATTATGAAAGCCCGCTTTTGGACTCCGGATGGCT
GQ214376 (1300)  GGAGACGGTATGGATTATTATGAAAGCCCACTTCCGGACTCCGGATGGCT
```

Figure 15A (continued)

```
                1351                                              1400
AF478543  (1350) TACCATTCCTCCCAAGAATGGAACAGTCCTTGGATTGATAAACAAAGCAA
AF478545  (1350) TACCATTCCTCCCAAGAATGGAACAGTCCTTGGATTGATAAACAAAGCAA
AY386316  (1350) TACCATTCCTCCCAGGAACGGAACAGTCCTTGGATTGATAAACAAAGCAA
ca CDV HA (1350) GACCATCCCTCCCAAGAACGGCACAGTGCTGGGCCTGATCAACAAGGCCT
DQ228166  (1350) TACCATTCCTCCCAAGAACGGAACAATTCTTGGATTGATAAACAAGGCAA
DQ494317  (1350) TACCATTCCTCCCAAGAACGGAACAGTCCTTGGATTGATAAACAAAGCAA
DQ494318  (1350) TACCATTCCTCCCAAGAACGGAACAGTCCTTGGATTGATAAACAAAGCAA
DQ889177  (1350) TACCATTCCTCCCAAGAACGGAACAGTCCTTGGATTGATAAACAAAGCAA
DQ889187  (1350) TACCATTCCTCCCAAGAACGGGACAATTCTTGGATTGATAAACAAAGCAA
EU325730  (1350) TGCCATACCCCCTAAGAACGGAACAGTCCTTGGATTGATAAACAAAGCAA
EU716337  (1350) TACCATTCCCCCCAAGAACGGAACAGTCCTTGGATTGATAAACAAAGCAA
FJ011004  (1350) TACCATTCCTCCCAAGAACGGAACAATCCTTGGATTGATAAACAAAGCAA
FJ011005  (1350) TACCATTCCTCCCAAAAACGGAACAGTTCTTGGATTGATGAACAAAGCAA
FJ423608  (1350) TACCATACCCCCTAAGAACGGAACAGTCCTTGGATTGATAAACAAAGCAA
FJ705233  (1350) TACCATACCTCCTAAGAACGGAACAGTCCTTGGATTGATAAACAAAGCAA
GQ214376  (1350) TACCATTCCACCCAAGAACGGAACAGTCCTTGGACTGATAAACAAAGCAA 1401                                              1450
AF478543  (1400) GTAGAGGAGACCAGTTCACTGTAATCCCCCATGTGTTGACATTTGCGCCC
AF478545  (1400) GTAGAGGAGACCAGTTCACTGTAATCCCCCATGTGTTGACATTTGCGCCC
AY386316  (1400) GTAGAGGAGACCAGTTCACTGTAATCCCCCATGTGTTGACATTTGCGCCC
ca CDV HA (1400) CCAGGGGCGACCAGTTCACCGTGATCCCTCACGTGCTGACCTTCGCCCCC
DQ228166  (1400) GTAGAGGAGACCAGTTCACTGTAATCCCCCATGTGTTGACATTTGCGCCC
DQ494317  (1400) GTAGAGGAGACCAGTTCACTGTAACCCCCCATGTGTTGACATCTGCGCCC
DQ494318  (1400) GTAGAGGAGACCAGTTCACTGTAATCCCCCATGTGTTGACATTTGCGCCC
DQ889177  (1400) GTAGAGGAGACCAGTTCACTGTAATCCCCCATGTGTTAACATTTGCGCCC
DQ889187  (1400) GTAGAGGAGACCAGTTCACTGTAACCCCCCATGTGTTGACATTTGCGCCT
EU325730  (1400) GTAGAGGAGACCAGTTCACTGTGACCCCCCATGTGTTGACATTTGCGCCC
EU716337  (1400) GTAGAGGAGACCAATTCACTGTAATCCCCCATGTGTTGACATTTGCGCCC
FJ011004  (1400) GTAGAGGAGACCAGTTCACTGTAATCCCCCATGTGTTGACATTTGCGCCC
FJ011005  (1400) GTAGAGGAGACCAGTTCACTGTAATCCCCCATGTGTTGACATTTGCGCCT
FJ423608  (1400) GTAGAGGAGACCAGTTCACTGCGACCCCCCATGTGTTGACATTTGCGCCC
FJ705233  (1400) GTAGAGGAGACCAGTTCACTGTGACCCCCCATGTGTTGACATTTGCGCCC
GQ214376  (1400) GTAGAGGAGACCAGTTCACTGTAATCCCCCATGTGTTGACATTTGCGCCC 1451                                              1500
AF478543  (1450) AGGGAATCAAGTGGAAATTGTTATTTACCTATTCAAACATCCCAGATTAT
AF478545  (1450) AGGGAATCAAGTGGAAATTGTTATTTACCTATTCAAACATCCCAGATTAT
AY386316  (1450) AGGGAATCAAGTGGAAATTGTTATTTACCTATTCAAACATCCCAGATTAT
ca CDV HA (1450) AGAGAGAGCAGCGGCAACTGCTACCTGCCTATCCAGACCTCCCAGATCAT
DQ228166  (1450) AGGGAATCAAGTGGGAATTGTTATTTACCTATTCAAACATCTCAGATTAT
DQ494317  (1450) AGGGAATCAAGTGGAAATTGTTATTTACCTATTCAAACATCCCAGATTAT
DQ494318  (1450) AGGGAATCAAGTGGAAATTGTTATTTACCTATTCAAACATCCCAGATTAT
DQ889177  (1450) AGGGAATCAAGTGGAAATTGTTATTTACCTATTCAAACATCCCAGATTAT
DQ889187  (1450) AGGGAATCAAGTGGGAATTGTTATTTACCTATTCAAACATCTCAGATTAT
EU325730  (1450) AGGGAATCAAGTGGGAATTGTTATTTGCCTATTCAAACATCCCAGATTAT
EU716337  (1450) AGGGAATCAAGTGGAAATTGTTATTTACCTATTCAAACATCCCAGATTAT
FJ011004  (1450) AGGGAATCAAGTGGAAATTGTTATTTACCTATTCAAACATCCCAGATTAT
FJ011005  (1450) AGGGAATCAGGTGGAAATTGTTATTTACCTATTCAAACCTCCCAGATTAT
FJ423608  (1450) AGGGAATCAAGTGGAAATTGTTATTTGCCTATTCAAACATCCCAGATTAT
FJ705233  (1450) AGGGAATCAAGTGGAAATTGTTATTTGCCTATTCAAACATCCCAGATTAT
GQ214376  (1450) AGGGAATCAAGTGGAAATTGTTATTTACCTATTCAAACATCCCAGATTAT
```

```
                 1801                      1825
AF478543 (1800)  CTCATGTGACCGTTCAAAACCTTGA
AF478545 (1800)  CTCATGTGACCGTTCAAAACCTTGA
AY386316 (1800)  CTCATGTAACCGTTCAAAACCTTGA
ca CDV HA(1800)  CAGCTGCGACAGAAGCAAGCCC---
DQ228166 (1800)  CTCATGTAACCGTTCAAAACCTTGA
DQ494317 (1800)  CTCATGTAACCGTTCAAAACCTTGA
DQ494318 (1800)  CTCATGTAATCGTTCAAAACCTTGA
DQ889177 (1800)  CTCATGTAACCGTTCAAAACCTTGA
DQ889187 (1800)  CTCATGTAACCGTTCAAAACCTTGA
EU325730 (1800)  CTCATGTAACCGTTCAAAACCTTGA
EU716337 (1800)  CTCATGTAATCGTTCAAAACCTTGA
FJ011004 (1800)  CTCATGTAACCGTTCAAAACCT---
FJ011005 (1800)  CTCATGTAACCGTTCAAAACCT---
FJ423608 (1800)  CTCATGTAACCGTTCAAAACCTTGA
FJ705233 (1800)  CTCATGTAACCGTTCAAAACCTTGA
GQ214376 (1800)  CTCATGTAACCGTTCAAAACCTTGA
```

AF478543:SEQ ID NO:36;   AF478545:SEQ ID NO:35;   AY386316:SEQ ID NO:38;
ca CDV HA:SEQ ID NO:1;   DQ228166:SEQ ID NO:46;   DQ494317:SEQ ID NO:39;
DQ494318:SEQ ID NO:37;   DQ889177:SEQ ID NO:41;   DQ889187:SEQ ID NO:47;
EU325730:SEQ ID NO:49;   EU716337:SEQ ID NO:42;   FJ011004:SEQ ID NO:43;
FJ011005:SEQ ID NO:44;   FJ423608:SEQ ID NO:48;   FJ705233:SEQ ID NO:45;
GQ214376:SEQ ID NO:40.

Figure 15B

Sequence Identity Percentage of CDV HA DNA

| SEQ ID NO: | 1 | 35 | 36 | 37 | 38 | 39 | 40 | 41 | 42 | 43 | 44 | 45 | 46 | 47 | 48 | 49 |
|---|---|---|---|---|---|---|---|---|---|---|---|---|---|---|---|---|
| 1 |  | 73 | 73 | 72 | 73 | 72 | 72 | 72 | 72 | 72 | 72 | 71 | 71 | 71 | 71 | 71 |
| 35 |  |  | 99 | 99 | 99 | 99 | 99 | 98 | 97 | 98 | 95 | 95 | 96 | 96 | 95 | 95 |
| 36 |  |  |  | 99 | 99 | 99 | 98 | 98 | 97 | 98 | 95 | 95 | 96 | 96 | 95 | 95 |
| 37 |  |  |  |  | 98 | 99 | 98 | 98 | 97 | 97 | 95 | 95 | 95 | 95 | 94 | 95 |
| 38 |  |  |  |  |  | 99 | 98 | 98 | 97 | 98 | 95 | 95 | 96 | 96 | 95 | 95 |
| 39 |  |  |  |  |  |  | 98 | 98 | 97 | 98 | 95 | 95 | 95 | 96 | 95 | 95 |
| 40 |  |  |  |  |  |  |  | 98 | 97 | 98 | 95 | 95 | 96 | 96 | 95 | 95 |
| 41 |  |  |  |  |  |  |  |  | 96 | 97 | 95 | 94 | 95 | 95 | 94 | 95 |
| 42 |  |  |  |  |  |  |  |  |  | 96 | 95 | 95 | 96 | 96 | 95 | 95 |
| 43 |  |  |  |  |  |  |  |  |  |  | 95 | 95 | 95 | 95 | 94 | 95 |
| 44 |  |  |  |  |  |  |  |  |  |  |  | 94 | 95 | 95 | 94 | 94 |
| 45 |  |  |  |  |  |  |  |  |  |  |  |  | 94 | 94 | 98 | 98 |
| 46 |  |  |  |  |  |  |  |  |  |  |  |  |  | 96 | 94 | 94 |
| 47 |  |  |  |  |  |  |  |  |  |  |  |  |  |  | 94 | 94 |
| 48 |  |  |  |  |  |  |  |  |  |  |  |  |  |  |  | 99 |
| 49 |  |  |  |  |  |  |  |  |  |  |  |  |  |  |  |  |

Figure 16

Monitoring of Cellular Immune Response

| Group | Dog ID | D13 | D42 | D70 |
|---|---|---|---|---|
| A<br>vCP2392<br>(CDV HA –<br>GM CSF) | 1 | 6 | 0 | 0 |
| | 2 | 0 | 0 | 2 |
| | 3 | ND | 0 | 0 |
| | 4 | 0 | 1 | 0 |
| | 5 | 3 | 18 | 3 |
| | 6 | 2 | 45 | 0 |
| B<br>vCP2263<br>(CDV HA) | 7 | 0 | 0 | 0 |
| | 8 | 1 | 29 | 1 |
| | 9 | ND | ND | 4 |
| | 10 | 4 | ND | 0 |
| | 11 | ND | ND | 2 |
| | 12 | 0 | 2 | 3 |
| C<br>unvaccinated | 13 | 1 | 0 | 0 |
| | 14 | ND | 0 | 0 |
| | 15 | ND | ND | 0 |
| | 16 | 0 | ND | 0 |
| | 17 | 1 | 0 | 0 |
| | 18 | ND | ND | 0 |

Units: number of CDV HA specific IFNγ-spot forming cell/500 x $10^3$ PBMCs.
ND: not determined Figure 17
A. CPV2 ELISA serology kinetics
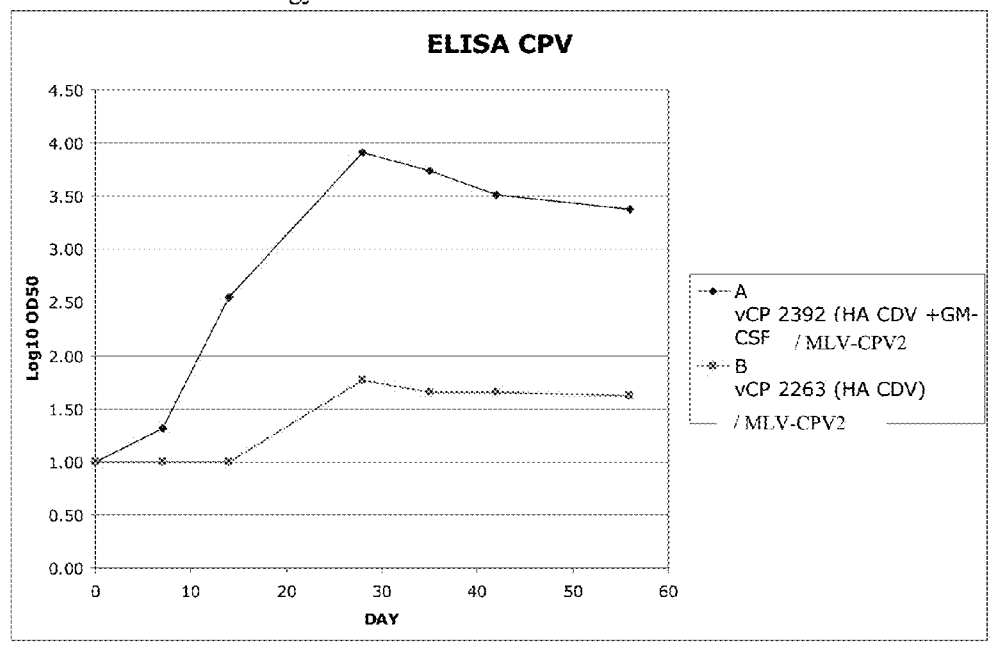
B. Box and whisker plot showing CPV2 serology on D28
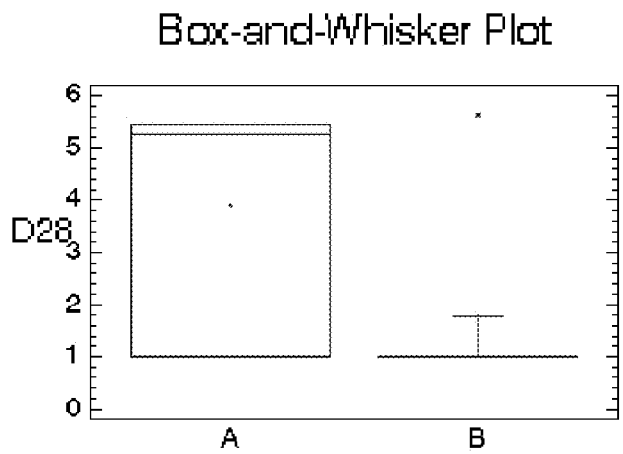

Figure 18

CDV SN antibodies using a homologous SN test

SN CDV on VERO SLAM

- vCP2392 (HA CDV + GM-CSF) / MLV-CPV2
- vCP2263 (HA CDV) / MLV-CPV2

Figure 19

CDV SN antibodies using a heterologous SN test

RECOMBINANT CDV COMPOSITIONS AND USES THEREOF

CROSS-REFERENCE TO RELATED APPLICATIONS

This application claims benefit of U.S. provisional application Ser. No. 61/308,620 filed Feb. 26, 2010.

FIELD OF THE INVENTION

The present invention relates to formulations for combating canine distemper virus and other canine virus infections in animals. Specifically, the present invention provides vectors that contain and express in vivo or in vitro CDV HA that elicit an immune response in animals against canine distemper virus, including compositions comprising said vectors, methods of vaccination against canine distemper virus, and kits for use with such methods and compositions. The present invention also provides vectors that contain and express in vivo or in vitro CDV HA and GM-CSF that elicit an immune response in animals against canine distemper virus and other canine virus, and compositions comprising said vectors.

BACKGROUND OF THE INVENTION

Canine distemper (CD) is a highly infectious, febrile disease of dogs and other carnivores (Fenner, et al., 1987, Veterinary Virology, Academic Press, Inc., pp. 485-503). The mortality rate is high, ranging between 30 and 80 percent. Dogs survived often have permanent central nerve system damage (Fenner, et al., 1987). The established etiology of CD is infection by a member of the Paramyxovirus family, morbillivirus genus known as CD virus (CDV). In general, Paramyxoviruses are enveloped viruses containing an 18-20 kb single stranded RNA genome of negative polarity. The genome encodes 5 to 7 structural proteins including a fusion (F) and either a hemagglutinin-neuraminidase (HN) or hemagglutinin (HA) glycoprotein. The membrane glycoprotein hemagglutinin (HA) is responsible for hemagglutination and attachment of the virus to the host cell, and the fusion glycoprotein (F) causes membrane fusion between the virus and the infected cell or between the infected and adjacent uninfected cells (Graves et al., 1978, Virology 86:254-263). For CDV, both F and HA glycoproteins are found present in the viral envelope and on the surface of infected cells. By inference from analyses with other morbillivirus members, the CDV F and HA glycoproteins appear important for CDV infection and its immunobiology (Diallo A., 1990, Vet. Micro. 23: 155-163). Poxvirus based recombinant CDV vaccines have been developed to protect and treat dogs (U.S. Pat. No. 5,756,102). U.S. patent application Ser. No. 09/232,477 disclosed DNA plasmid based vaccines expressing CDV antigens.

Granulocyte-macrophage colony-stimulating factor (GM-CSF) was first discovered in 1977 (Burgess et al., 1977, J. Biol. Chem. 252:1998-2003). GM-CSF has many physiological roles. In particular, GM-CSF stimulates the production, the development and the formation of colonies of granulocyes, macrophages, eosinophils and megakaryocytes. (Dy M., in "les Cytokines" Cavailon 1995 ed. Masson, Paris, France, 43-56). GM-CSF induces in particular a macrophagic cytotoxocity, stimulates antibody-dependent cytotoxic activity (ADCC) and the recruitment of leukocytes at the level of the sites of inflammation.

The sizes of the nucleotide sequences encoding the known GM-CSFs from various species vary from 381 to 432 nucleotides. The human and murine nucleotide sequences have a degree of homology of 69%. The degree of homology is 54% at the level of the amino acid sequence (Cantrell et al., 1985, Proc. Natl. Acad. Sci. USA 82:6250-6254). An equine GM-CSF was identified which has a size of 144 amino acids (U.S. Pat. No. 7,250,161). Two canine GM-CSFs were identified in U.S. Pat. No. 5,702,919 and U.S. Pat. No. 5,606,024, which have 127 amino acids and 174 amino acids respectively.

The administration of heterologous GM-CSF does not make it possible to obtain an optimum adjuvant effect, in particular a stimulation of the activity of the haematopoietic cells and a substantial increase in the immune response.

There is thus a general need for an improvement in efficacy and safety of the CDV vaccines and for more effective protection in field conditions.

The invention provides a solution for optimizing the immunological effect of caGM-CSF while retaining high safety for the vaccinated dogs.

SUMMARY OF THE INVENTION

An object of this invention can be any one or all of providing recombinant vectors or viruses as well as methods for making such viruses, and providing compositions and/or vaccines as well as methods for treatment and prophylaxis of infection by CDV and other canine virus.

The invention provides a recombinant vector, such as a recombinant virus, that contains and expresses at least one exogenous nucleic acid molecule and, the at least one exogenous nucleic acid molecule may comprise a nucleic acid molecule encoding an immunogen or epitope of interest from CDV, such as CDV HA.

The invention provides a recombinant vector, such as a recombinant poxvirus that contains a first polynucleotide encoding a CDV HA polypeptide and/or variant or fragment thereof and a second polynucleotide encoding a canine GM-CSF polypeptide and/or variant or fragment thereof.

The invention further provides compositions or vaccines comprising such an expression vector or the expression product(s) of such an expression vector.

The invention further provides methods for inducing an immunological (or immunogenic) or protective response against CDV and other canine virus, as well as methods for preventing or treating CDV and other canine virus or disease state(s) caused by CDV and other canine virus, comprising administering the expression vector or an expression product of the expression vector, or a composition comprising the expression vector, or a composition comprising an expression product of the expression vector.

The invention also relates to expression products from the virus as well as antibodies generated from the expression products or the expression thereof in vivo and uses for such products and antibodies, e.g., in diagnostic applications.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings, in which:

FIG. 1 provides a table identifying the SEQ ID NO assigned to the polynucleotide and protein sequence.

FIG. 2 provides sequence alignment between SEQ ID NO:2 and SEQ ID NO:5.

FIG. 3 depicts the plasmid maps of pCXL1557.1 and pJSY2218.1.

FIG. 6 shows the immunoplaque assay of vCP2263.

FIG. 10 shows the western blot of vCP2392 for CDV HA protein.

FIGS. 13*a* and 13*b* provide the sequence alignment of CDV HA proteins and sequence identity percentage at the amino acid level.

FIG. 14 provides the sequence alignment of codon-optimized CDV HA DNA and wild-type CDV HA DNA.

Figure 15A:
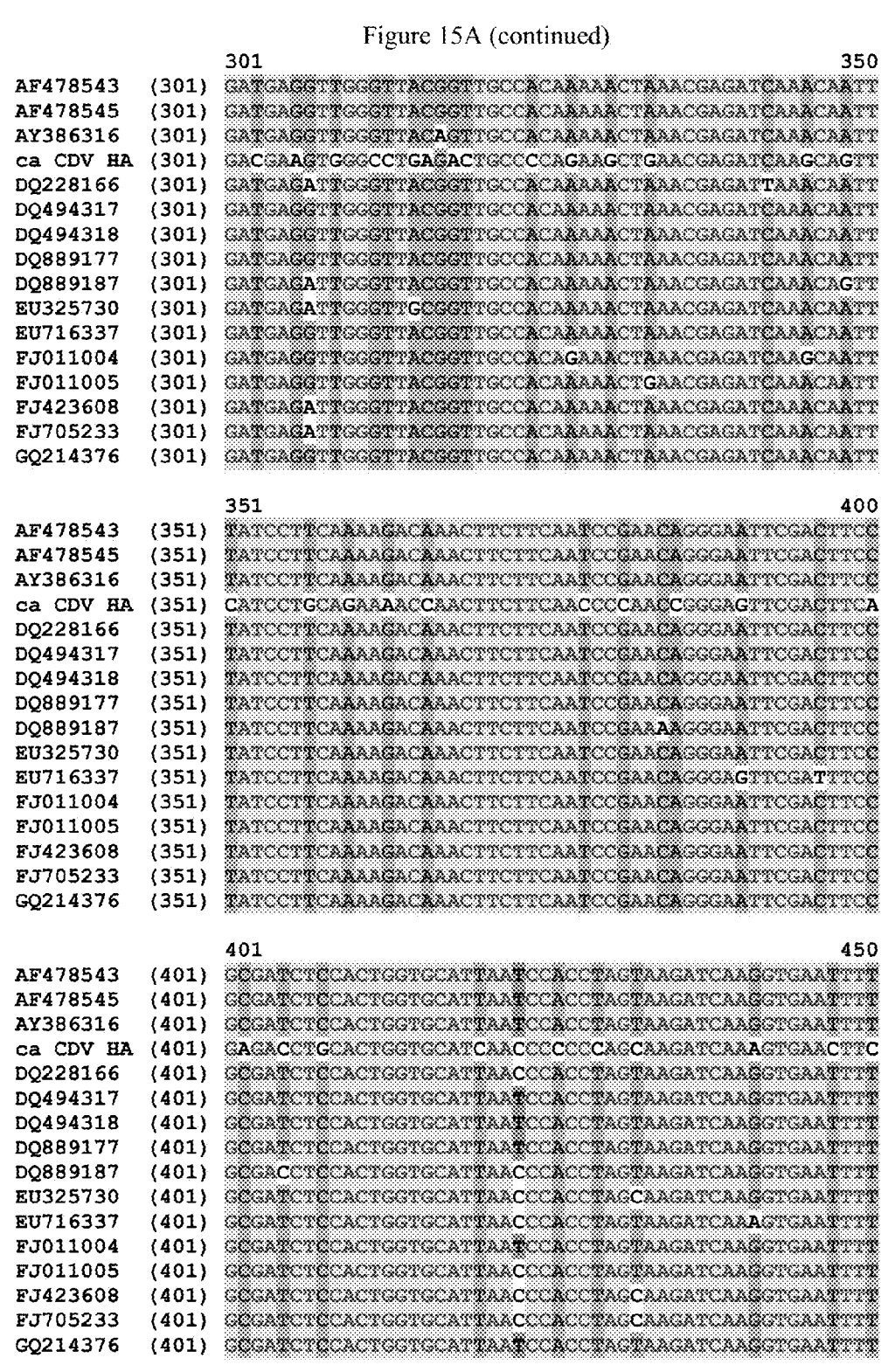
Figure 15A:
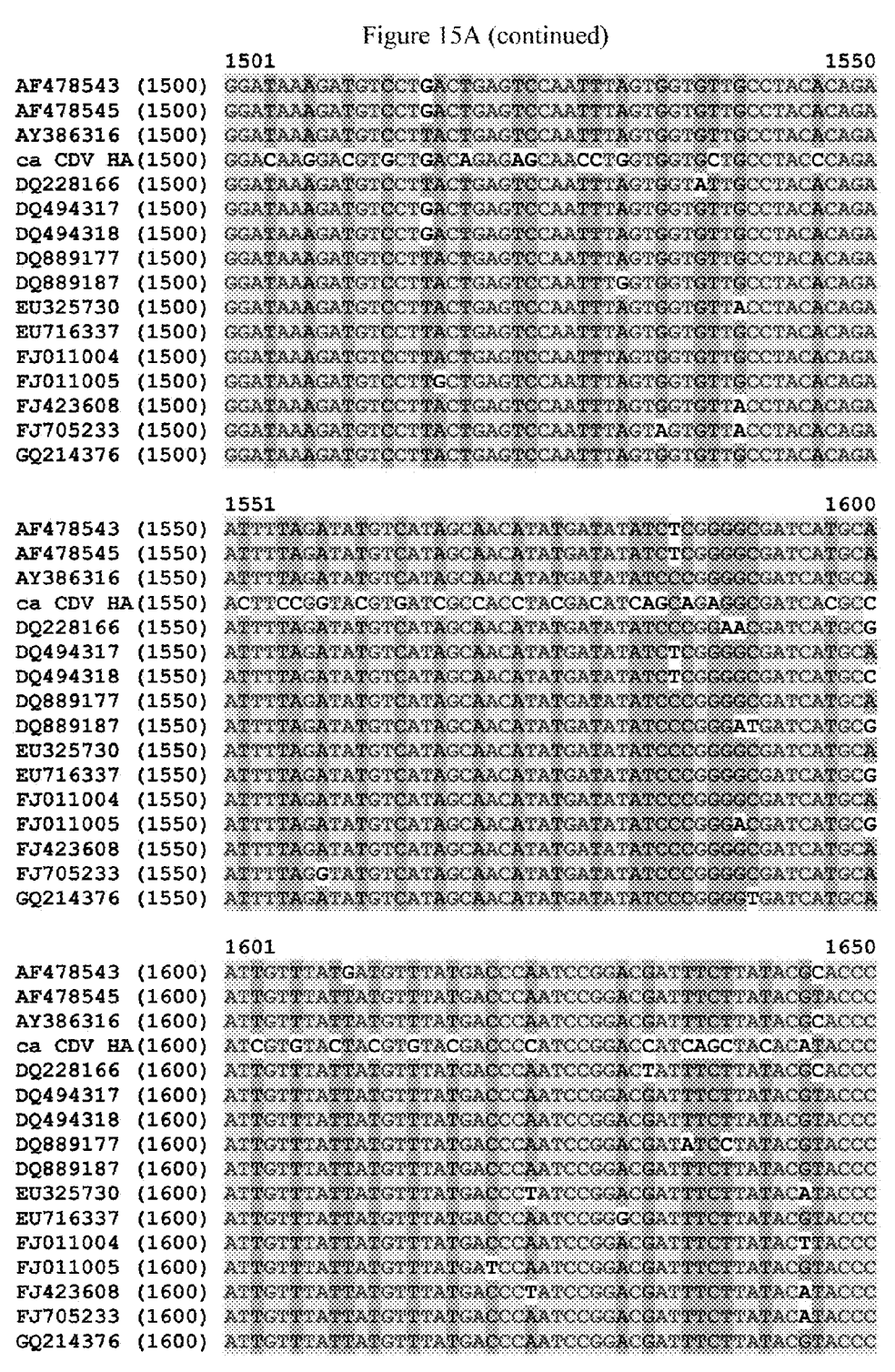
Figure 15A:
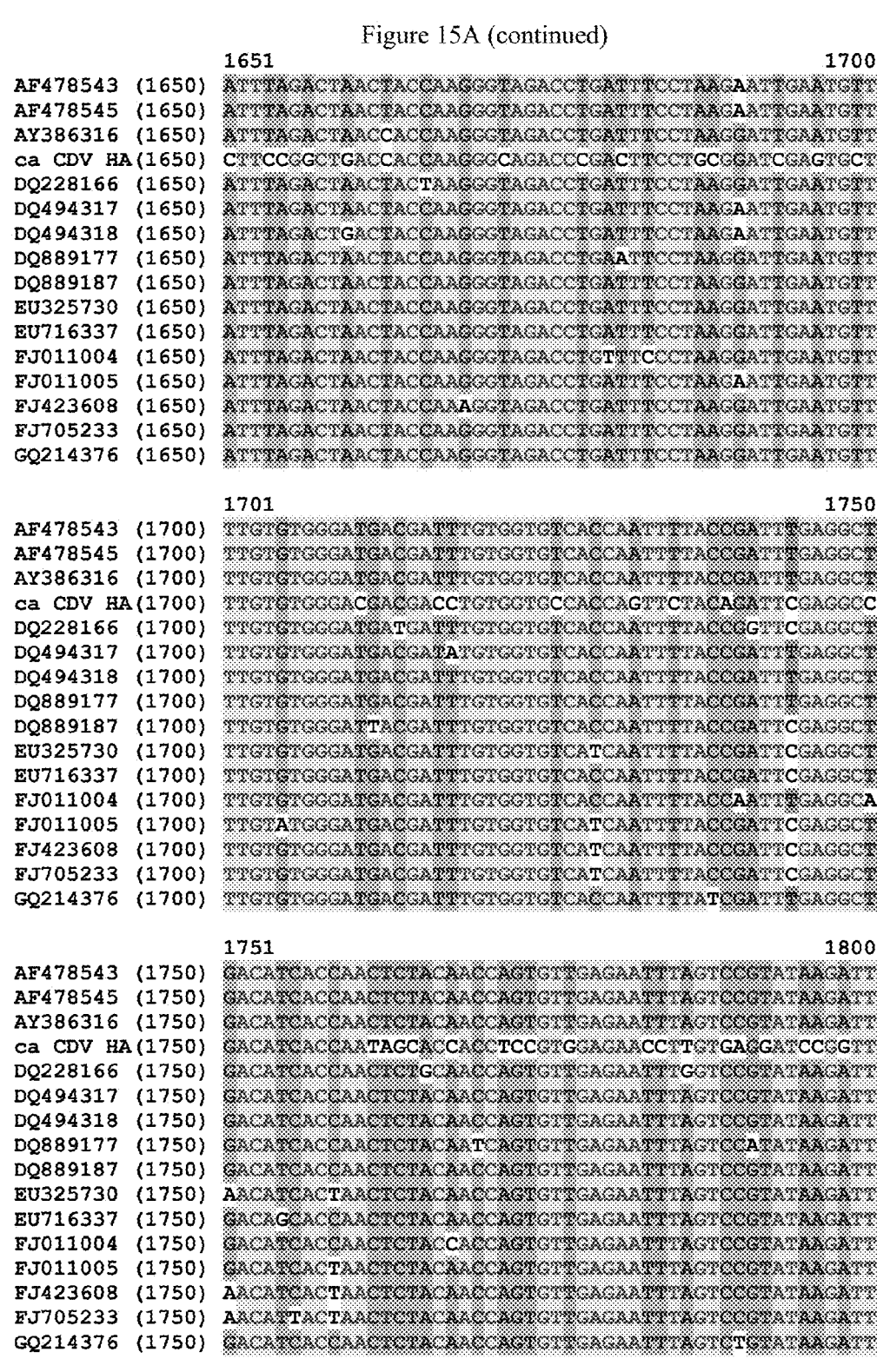

FIGS. 15*a* and 15*b* provide the sequence alignment of CDV HA DNA and sequence identity percentage at the DNA level.

FIG. 16 provides the result of cellular immune response.

FIG. 17 provides CPV2 ELISA result.

FIG. 18 depicts the homologous SN test result of CDV SN antibodies.

FIG. 19 depicts the heterologous SN test result of CDV SN antibodies.

DETAILED DESCRIPTION

Figure 4:
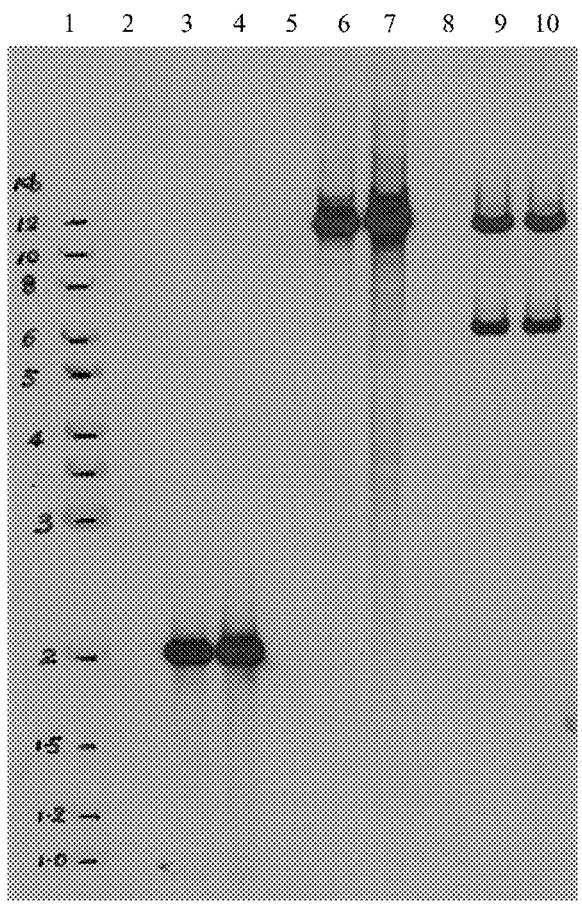
FIG. 4 shows the Southern blot of vCP2263.

Compositions comprising an expression vector comprising a polynucleotide encoding a CDV polypeptide and fragments and variants thereof that elicit an immunogenic response in an animal are provided. The expression vector comprising the polynucleotide encoding CDV polypeptide or fragments or variants may be formulated into vaccines or pharmaceutical compositions and used to elicit or stimulate a protective response in an animal. In one embodiment the CDV polypeptide is a CDV hemagglutinin (HA) polypeptide or active fragment or variant thereof.

Compositions comprising an expression vector comprising a polynucleotide encoding a CDV HA polypeptide or active fragments or variants thereof and a polynucleotide encoding a GM-CSF polypeptide or active fragments or variants thereof are provided.

It is recognized that the polypeptides of the invention may be full length polypeptides or active fragments or variants thereof. By "active fragments" or "active variants" is intended that the fragments or variants retain the antigenic nature of the polypeptide. Thus, the present invention encompasses any CDV polypeptide, antigen, epitope or immunogen that elicits an immunogenic response in an animal. The CDV polypeptide, antigen, epitope or immunogen may be any CDV polypeptide, antigen, epitope or immunogen, such as, but not limited to, a protein, peptide or fragment or variant thereof, that elicits, induces or stimulates a response in an animal.

A particular CDV polypeptide of interest is CDV hemagglutinin (HA). CDV HA refers to a type of hemagglutinin found on the surface of the CDV. It is an antigenic glycoprotein and is responsible for binding the virus to the cell that is being infected. There are different HA antigens, associated with the different CDV strains which circulate in the field, any of which can be used in the practice of the invention. However, there are different antigens, such as the Fusion (F) glycoprotein and Nucleoprotein (NP), any of which can be used in the practice of the invention. It is further recognized that precursors of any of these antigens can be used. The antigenic polypeptides of the invention are capable of protecting against CDV. That is, they are capable of stimulating an immune response in an animal.

The term "antigen" or "immunogen" means a substance that induces a specific immune response in a host animal. The antigen may comprise a whole organism, killed, attenuated or live; a subunit or portion of an organism; a recombinant vector containing an insert with immunogenic properties; a piece or fragment of DNA capable of inducing an immune response upon presentation to a host animal; a polypeptide, an epitope, a hapten, or any combination thereof. Alternately, the immunogen or antigen may comprise a toxin or antitoxin.

The terms "protein", "peptide", "polypeptide" and "polypeptide fragment" are used interchangeably herein to refer to polymers of amino acid residues of any length. The polymer can be linear or branched, it may comprise modified amino acids or amino acid analogs, and it may be interrupted by chemical moieties other than amino acids. The terms also encompass an amino acid polymer that has been modified naturally or by intervention; for example disulfide bond formation, glycosylation, lipidation, acetylation, phosphorylation, or any other manipulation or modification, such as conjugation with a labeling or bioactive component.

The term "CDV HA polypeptide or polynucleotide" refers to any native or optimized CDV HA polypeptide or polynucleotide, and their derivatives and variants.

The term "GM-CSF polypeptide or polynucleotide" refers to any native or optimized GM-CSF polypeptide or polynucleotide, and their derivatives and variants.

The term "immunogenic or antigenic polypeptide" as used herein includes polypeptides that are immunologically active in the sense that once administered to the host, it is able to evoke an immune response of the humoral and/or cellular type directed against the protein. Preferably the protein fragment is such that it has substantially the same immunological activity as the total protein. Thus, a protein fragment according to the invention comprises or consists essentially of or consists of at least one epitope or antigenic determinant. An "immunogenic" protein or polypeptide, as used herein, includes the full-length sequence of the protein, analogs thereof, or immunogenic fragments thereof. By "immunogenic fragment" is meant a fragment of a protein which includes one or more epitopes and thus elicits the immunological response described above. Such fragments can be identified using any number of epitope mapping techniques well known in the art. See, e.g., Epitope Mapping Protocols in Methods in Molecular Biology, Vol. 66 (Glenn E. Morris, Ed., 1996). For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al., 1984; Geysen et al., 1986. Similarly, conformational epitopes are readily identified by determining spatial conformation of amino acids such as by, e.g., x-ray crystallography and 2-dimensional nuclear magnetic resonance. See, e.g., Epitope Mapping Protocols, supra.

As discussed herein, the invention encompasses active fragments and variants of the antigenic polypeptide. Thus, the term "immunogenic or antigenic polypeptide" further contemplates deletions, additions and substitutions to the sequence, so long as the polypeptide functions to produce an immunological response as defined herein.

The term "conservative variation" denotes the replacement of an amino acid residue by another biologically similar residue, or the replacement of a nucleotide in a nucleic acid sequence such that the encoded amino acid residue does not change or is another biologically similar residue. In this regard, particularly preferred substitutions will generally be conservative in nature, i.e., those substitutions that take place within a family of amino acids. For example, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cystine, serine, threonine, tyrosine. Phenylalanine, tryptophan, and tyrosine are sometimes classified as aromatic amino acids. Examples of conservative variations include the substitution of one hydrophobic residue such as isoleucine, valine, leucine or methionine for another hydrophobic residue, or the substitution of one polar residue for another polar residue, such as the substitution of arginine for lysine, glutamic acid for aspartic acid, or glutamine for asparagine, and the like; or a similar conservative replacement of an amino acid with a structurally related amino acid that will not have a major effect on the biological activity. Proteins having substantially the same amino acid sequence as the reference molecule but possessing minor amino acid substitutions that do not substantially affect the immunogenicity of the protein are, therefore, within the definition of the reference polypeptide. All of the polypeptides produced by these modifications are included herein. The term "conservative variation" also includes the use of a substituted amino acid in place of an unsubstituted parent amino acid provided that antibodies raised to the substituted polypeptide also immunoreact with the unsubstituted polypeptide.

The term "epitope" refers to the site on an antigen or hapten to which specific B cells and/or T cells respond. The term is also used interchangeably with "antigenic determinant" or "antigenic determinant site". Antibodies that recognize the same epitope can be identified in a simple immunoassay showing the ability of one antibody to block the binding of another antibody to a target antigen.

An "immunological response" to a composition or vaccine is the development in the host of a cellular and/or antibody-mediated immune response to a composition or vaccine of interest. Usually, an "immunological response" includes but is not limited to one or more of the following effects: the production of antibodies, B cells, helper T cells, and/or cytotoxic T cells, directed specifically to an antigen or antigens included in the composition or vaccine of interest. Preferably, the host will display either a therapeutic or protective immunological response such that resistance to new infection will be enhanced and/or the clinical severity of the disease reduced. Such protection will be demonstrated by either a reduction or lack of symptoms normally displayed by an infected host, a quicker recovery time and/or a lowered viral titer in the infected host.

By "animal" is intended mammals, birds, and the like. Animal or host as used herein includes mammals and human. The animal may be selected from the group consisting of equine (e.g., horse), canine (e.g., dogs, wolves, foxes, coyotes, jackals), feline (e.g., lions, tigers, domestic cats, wild cats, other big cats, and other felines including cheetahs and lynx), ovine (e.g., sheep), bovine (e.g., cattle), porcine (e.g., pig), avian (e.g., chicken, duck, goose, turkey, quail, pheasant, parrot, finches, hawk, crow, ostrich, emu and cassowary), primate (e.g., prosimian, tarsier, monkey, gibbon, ape), ferrets, seals, and fish. The term "animal" also includes an individual animal in all stages of development, including embryonic and fetal stages.

Unless otherwise explained, all technical and scientific terms used herein have the same meaning as commonly understood by one of ordinary skill in the art to which this disclosure belongs. The singular terms "a", "an", and "the" include plural referents unless context clearly indicates otherwise. Similarly, the word "or" is intended to include "and" unless the context clearly indicate otherwise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

Compositions

The present invention relates to a CDV vaccine or composition which may comprise a recombinant or expression vector comprising a polynucleotide encoding a CDV polypeptide, antigen, epitope or immunogen and a pharmaceutically or veterinarily acceptable carrier, excipient, adjuvant, or vehicle. The CDV polypeptide, antigen, epitope or immunogen may be any CDV polypeptide, antigen, epitope or immunogen, such as, but not limited to, a protein, peptide or fragment thereof, that elicits, induces or stimulates a response in an animal.

The present invention relates to a CDV vaccine or composition which may comprise a recombinant or expression vector comprising a polynucleotide encoding a CDV HA polypeptide and a pharmaceutically or veterinarily acceptable carrier, excipient, adjuvant, or vehicle. In one embodiment, the expression vector may further comprise a polynucleotide encoding a GM-CSF polypeptide.

In another embodiment, the pharmaceutically or veterinarily acceptable carrier, excipient, adjuvant, or vehicle may be a water-in-oil emulsion. In yet another embodiment, the water-in-oil emulsion may be a water/oil/water (W/O/W) triple emulsion. In yet another embodiment, the pharmaceutically or veterinarily acceptable carrier, excipient, adjuvant, or vehicle may be an oil-in-water emulsion.

In an embodiment, the CDV polypeptide, antigen or fragment or variant thereof may be a CDV HA polypeptide or fragment or variant thereof. In an aspect of this embodiment, the CDV HA polypeptide or fragment or variant thereof is a recombinant polypeptide produced by a CDV HA gene. In another aspect of this embodiment, the CDV HA gene has at least 70% identity to the sequence as set forth in SEQ ID NO: 1, 35, 36, 37, 38, 39, 40, 41, 42, 43, 44, 45, 46, 47, 48, or 49. In another aspect of this embodiment, the CDV HA polypeptide or fragment or variant thereof has at least 80% identity to the sequence as set forth in SEQ ID NO: 2, 5, 20, 21, 22, 23, 24, 25, 26, 27, 28, 29, 30, 31, 32, 33, or 34.

In another embodiment, the GM-CSF polypeptide, antigen or fragment or variant is a recombinant polypeptide produced by a GM-CSF gene. In another aspect of this embodiment, the GM-CSF gene has at least 70% identity to the sequence as set forth in SEQ ID NO: 3. In another aspect of this embodiment, the GM-CSF polypeptide or fragment or variant thereof has at least 80% identity to the sequence as set forth in SEQ ID NO: 4.

Synthetic antigens are also included within the definition, for example, polyepitopes, flanking epitopes, and other recombinant or synthetically derived antigens. See, e.g., Bergmann et al., 1993; Bergmann et al., 1996; Suhrbier, 1997; Gardner et al., 1998. Immunogenic fragments, for purposes of the present invention, will usually include at least about 3 amino acids, at least about 5 amino acids, at least about 10-15 amino acids, or about 15-25 amino acids or more amino acids, of the molecule. There is no critical upper limit to the length of the fragment, which could comprise nearly the full-length of the protein sequence, or even a fusion protein comprising at least one epitope of the protein.

Accordingly, a minimum structure of a polynucleotide expressing an epitope is that it comprises or consists essentially of or consists of nucleotides encoding an epitope or antigenic determinant of a CDV polypeptide. A polynucleotide encoding a fragment of a CDV polypeptide may comprise or consist essentially of or consist of a minimum of 15 nucleotides, about 30-45 nucleotides, about 45-75, or at least 75, 87 or 150 consecutive or contiguous nucleotides of the sequence encoding the polypeptide. Epitope determination procedures, such as, generating overlapping peptide libraries (Hemmer et al., 1998), Pepscan (Geysen et al., 1984; Geysen et al., 1985; Van der Zee R. et al., 1989; Geysen, 1990; Multipin™ Peptide Synthesis Kits de Chiron) and algorithms (De Groot et al., 1999; PCT/US2004/022605) can be used in the practice of the invention.

The term "nucleic acid" and "polynucleotide" refers to RNA or DNA that is linear or branched, single or double stranded, or a hybrid thereof. The term also encompasses RNA/DNA hybrids. The following are non-limiting examples of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes and primers. A polynucleotide may comprise modified nucleotides, such as methylated nucleotides and nucleotide analogs, uracyl, other sugars and linking groups such as fluororibose and thiolate, and nucleotide branches. The sequence of nucleotides may be further modified after polymerization, such as by conjugation, with a labeling component. Other types of modifications included in this definition are caps, substitution of one or more of the naturally occurring nucleotides with an analog, and introduction of means for attaching the polynucleotide to proteins, metal ions, labeling components, other polynucleotides or solid support. The polynucleotides can be obtained by chemical synthesis or derived from a microorganism.

The term "gene" is used broadly to refer to any segment of polynucleotide associated with a biological function. Thus, genes include introns and exons as in genomic sequence, or just the coding sequences as in cDNAs and/or the regulatory sequences required for their expression. For example, gene also refers to a nucleic acid fragment that expresses mRNA or functional RNA, or encodes a specific protein, and which includes regulatory sequences.

The invention further comprises a complementary strand to a polynucleotide encoding a CDV antigen, epitope or immunogen or to a polynucleotide encoding a GM-CSF antigen, epitope or immunogen. The complementary strand can be polymeric and of any length, and can contain deoxyribonucleotides, ribonucleotides, and analogs in any combination.

An "isolated" biological component (such as a nucleic acid or protein or organelle) refers to a component that has been substantially separated or purified away from other biological components in the cell of the organism in which the component naturally occurs, for instance, other chromosomal and extra-chromosomal DNA and RNA, proteins, and organelles. Nucleic acids and proteins that have been "isolated" include nucleic acids and proteins purified by standard purification methods. The term also embraces nucleic acids and proteins prepared by recombinant technology as well as chemical synthesis.

The term "purified" as used herein does not require absolute purity; rather, it is intended as a relative term. Thus, for example, a partially purified polypeptide preparation is one in which the polypeptide is more enriched than the polypeptide is in its natural environment. That is the polypeptide is separated from cellular components. By "substantially purified" is intended that at least 60%, at least 70%, at least 80%, at least 90%, at least 95%, or at least 98%, or more of the cellular components or materials have been removed. Likewise, a polypeptide may be partially purified. By "partially purified" is intended that less than 60% of the cellular components or material is removed. The same applies to polynucleotides. The polypeptides disclosed herein can be purified by any of the means known in the art.

Moreover, homologs of CDV HA polypeptides and homologs of GM-CSF polypeptides are intended to be within the scope of the present invention. As used herein, the term "homologs" includes orthologs, analogs and paralogs. The term "anologs" refers to two polynucleotides or polypeptides that have the same or similar function, but that have evolved separately in unrelated organisms. The term "orthologs" refers to two polynucleotides or polypeptides from different species, but that have evolved from a common ancestral gene by speciation. Normally, orthologs encode polypeptides having the same or similar functions. The term "paralogs" refers to two polynucleotides or polypeptides that are related by duplication within a genome. Paralogs usually have different functions, but these functions may be related. For example, analogs, orthologs, and paralogs of a wild-type CDV polypeptide can differ from the wild-type CDV polypeptide by post-translational modifications, by amino acid sequence differences, or by both. In particular, homologs of the invention will generally exhibit at least 80-85%, 85-90%, 90-95%, or 95%, 96%, 97%, 98%, 99% sequence identity, with all or part of the wild-type CDV polypeptide or polynucleotide sequences, and will exhibit a similar function.

In one embodiment, the present invention provides an expression vector comprising one or more polynucleotides encoding one or more polypeptides having at least 70%, at least 75%, at least 80%, at least 85%, at least 90%, at least 95%, 96%, 97%, 98% or 99% sequence identity to a polypeptide having a sequence as set forth in SEQ ID NO: 2, 4, 5, 20, 21, 22, 23, 24, 25, 26, 27, 28, 29, 30, 31, 32, 33, or 34. In another embodiment, the present invention provides fragments and variants of the CDV polypeptides or GM-CSF identified above (SEQ ID NO: 2, 4, 5, 20, 21, 22, 23, 24, 25, 26, 27, 28, 29, 30, 31, 32, 33, or 34) which may readily be prepared by one of skill in the art using well-known molecular biology techniques. Variants are homologous polypeptides having amino acid sequences at least 75%, 80%, 85%, 90%, 95%, 96%, 97%, 98%, or 99% identity to the amino acid sequences as set forth in SEQ ID NO: 2, 4, 5, 20, 21, 22, 23, 24, 25, 26, 27, 28, 29, 30, 31, 32, 33, or 34.

Variants include allelic variants. The term "allelic variant" refers to a polynucleotide or a polypeptide containing polymorphisms that lead to changes in the amino acid sequences of a protein and that exist within a natural population (e.g., a virus species or variety). Such natural allelic variations can typically result in 1-5% variance in a polynucleotide or a polypeptide. Allelic variants can be identified by sequencing the nucleic acid sequence of interest in a number of different species, which can be readily carried out by using hybridization probes to identify the same gene genetic locus in those species. Any and all such nucleic acid variations and resulting amino acid polymorphisms or variations that are the result of natural allelic variation and that do not alter the functional activity of gene of interest, are intended to be within the scope of the invention.

As used herein, the term "derivative" or "variant" refers to a polypeptide, or a nucleic acid encoding a polypeptide, that has one or more conservative amino acid variations or other minor modifications such that (1) the corresponding polypeptide has substantially equivalent function when compared to the wild type polypeptide or (2) an antibody raised against the polypeptide is immunoreactive with the wild-type polypeptide. These variants or derivatives include polypeptides having minor modifications of the CDV polypeptide or GM-CSF primary amino acid sequences that may result in peptides which have substantially equivalent activity as compared to the unmodified counterpart polypeptide. Such modifications may be deliberate, as by site-directed mutagenesis, or may be spontaneous. The term "variant" further contemplates deletions, additions and substitutions to the sequence, so long as the polypeptide functions to produce an immunological response as defined herein.

An immunogenic fragment of a CDV polypeptide or GM-CSF polypeptide includes at least 8, 10, 13, 14, 15, or 20 consecutive amino acids, at least 21 amino acids, at least 23 amino acids, at least 25 amino acids, or at least 30 amino acids of a CDV HA polypeptide having a sequence as set forth in SEQ ID NO: 2, 5, 20, 21, 22, 23, 24, 25, 26, 27, 28, 29, 30, 31, 32, 33, or 34 or variants thereof, or of a GM-CSF polypeptide having a sequence as set forth in SEQ ID NO:4 or variants thereof.

In another aspect, the present invention provides an expression vector comprising a polynucleotide encoding a CDV HA polypeptide, such as a polynucleotide encoding a polypeptide having a sequence as set forth in SEQ ID NO: 2, 5, 20, 21, 22, 23, 24, 25, 26, 27, 28, 29, 30, 31, 32, 33, or 34. In yet another aspect, the present invention provides an expression vector comprising a polynucleotide encoding a polypeptide having at least 70%, at least 75%, at least 80%, at least 85%, at least 90%, at least 95%, 96%, 97%, 98% or 99% sequence identity to a polypeptide having a sequence as set forth in SEQ ID NO: 2, 5, 20, 21, 22, 23, 24, 25, 26, 27, 28, 29, 30, 31, 32, 33, or 34, or a conservative variant, an allelic variant, a homolog or an immunogenic fragment comprising at least eight or at east ten consecutive amino acids of one of these polypeptides, or a combination of these polypeptides.

In yet another aspect, the present invention provides an expression vector comprising a polynucleotide encoding a GM-CSF polypeptide, such as a polynucleotide encoding a polypeptide having a sequence as set forth in SEQ ID NO: 4. In yet another aspect, the present invention provides an expression vector comprising a polynucleotide encoding a polypeptide having at least 70%, at least 75%, at least 80%, at least 85%, at least 90%, at least 95%, 96%, 97%, 98% or 99% sequence identity to a polypeptide having a sequence as set forth in SEQ ID NO: 4, or a conservative variant, an allelic variant, a homolog or an immunogenic fragment comprising at least eight or at east ten consecutive amino acids of one of these polypeptides, or a combination of these polypeptides.

In one embodiment the polynucleotide of the present invention includes a polynucleotide having a nucleotide sequence as set forth in SEQ ID NO: 1, 3, 6, 7, 8, 9, 14, 19, 35, 36, 37, 38, 39, 40, 41, 42, 43, 44, 45, 46, 47, 48, or 49, or a variant thereof. In another embodiment, the polynucleotide of the present invention includes a polynucleotide having at least 70%, at least 75%, at least 80%, at least 85%, at least 90%, at least 95%, at least 95%, 96%, 97%, 98% or 99% sequence identity to one of a polynucleotide having a sequence as set forth in SEQ ID NO: 1, 3, 6, 7, 8, 9, 14, 19, 35, 36, 37, 38, 39, 40, 41, 42, 43, 44, 45, 46, 47, 48, or 49, or a variant thereof.

The polynucleotides of the disclosure include sequences that are degenerate as a result of the genetic code, e.g., optimized codon usage for a specific host. As used herein, "optimized" refers to a polynucleotide that is genetically engineered to increase its expression in a given species. To provide optimized polynucleotides coding for CDV HA polypeptides or GM-CSF polypeptides, the DNA sequence of the CDV HA gene or GM-CSF gene can be modified to 1) comprise codons preferred by highly expressed genes in a particular species; 2) comprise an A+T or G+C content in nucleotide base composition to that substantially found in said species; 3) form an initiation sequence of said species; or 4) eliminate sequences that cause destabilization, inappropriate polyadenylation, degradation and termination of RNA, or that form secondary structure hairpins or RNA splice sites. Increased expression of CDV HA protein or GM-CSF protein in said species can be achieved by utilizing the distribution frequency of codon usage in eukaryotes and prokaryotes, or in a particular species. The term "frequency of preferred codon usage" refers to the preference exhibited by a specific host cell in usage of nucleotide codons to specify a given amino acid. There are 20 natural amino acids, most of which are specified by more than one codon. Therefore, all degenerate nucleotide sequences are included in the disclosure as long as the amino acid sequence of the CDV HA polypeptide or the GM-CSF polypeptide encoded by the nucleotide sequence is functionally unchanged.

The sequence identity between two amino acid sequences may be established by the NCBI (National Center for Biotechnology Information) pairwise blast and the blosum62 matrix, using the standard parameters (see, e.g., the BLAST or BLASTX algorithm available on the "National Center for Biotechnology Information" (NCBI, Bethesda, Md., USA) server, as well as in Altschul et al.).

The "identity" with respect to sequences can refer to the number of positions with identical nucleotides or amino acids divided by the number of nucleotides or amino acids in the shorter of the two sequences wherein alignment of the two sequences can be determined in accordance with the Wilbur and Lipman algorithm (Wilbur and Lipman), for instance, using a window size of 20 nucleotides, a word length of 4 nucleotides, and a gap penalty of 4, and computer-assisted analysis and interpretation of the sequence data including alignment can be conveniently performed using commercially available programs (e.g., Intelligenetics™ Suite, Intelligenetics Inc. CA). When RNA sequences are said to be similar, or have a degree of sequence identity or homology with DNA sequences, thymidine (T) in the DNA sequence is considered equal to uracil (U) in the RNA sequence. Thus, RNA sequences are within the scope of the invention and can be derived from DNA sequences, by thymidine (T) in the DNA sequence being considered equal to uracil (U) in RNA sequences.

The sequence identity or sequence similarity of two amino acid sequences, or the sequence identity between two nucleotide sequences can be determined using Vector NTI software package (Invitrogen, 1600 Faraday Ave., Carlsbad, Calif.).

The following documents provide algorithms for comparing the relative identity or homology of sequences, and additionally or alternatively with respect to the foregoing, the teachings in these references can be used for determining percent homology or identity: Needleman S B and Wunsch C D; Smith T F and Waterman M S; Smith T F, Waterman M S and Sadler J R; Feng D F and Dolittle R F; Higgins D G and Sharp P M; Thompson J D, Higgins D G and Gibson T J; and, Devereux J, Haeberlie P and Smithies O. And, without undue experimentation, the skilled artisan can consult with many other programs or references for determining percent homology.

Hybridization reactions can be performed under conditions of different "stringency." Conditions that increase stringency of a hybridization reaction are well known. See for example, "Molecular Cloning: A Laboratory Manual", second edition (Sambrook et al., 1989).

The invention encompasses the CDV polynucleotide or GM-CSF polynucleotide or both contained in a vector molecule or an expression vector and operably linked to a promoter element and optionally to an enhancer.

The present invention further encompasses a canine vaccine or composition which may comprise an aforementioned recombinant vector comprising a polynucleotide encoding a CDV HA polypeptide or antigen and a polynucleotide encoding a GM-CSF polypeptide or antigen, a pharmaceutically or veterinarily acceptable carrier, excipient, adjuvant, or vehicle, and additionally one or more antigens from canine. The present invention further relates to a canine vaccine or composition which may comprise an aforementioned recombinant or expression vector comprising a polynucleotide encoding a GM-CSF polypeptide, a pharmaceutically or veterinarily acceptable carrier, excipient, adjuvant, or vehicle, and additionally one or more antigens from canine. The antigen may be canine antigen selected from the group consisting of rabies, canine parvovirus, canine coronavirus, canine influenza, canine distemper, infectious canine hepatitis, canine herpesvirus, pseudorabies, canine minute virus, *Leptospira*, *Neospora caninum*, *Borrelia burgdorferi*, *Ehrlichia canis*, *Rickettsia rickettsii*, *Bordetella bronchiseptica*, *Blastomyces dermatitidis*, *Histoplasma capsulatum*, *Coccidioides immitis*, *Cryptococcus neoformans*, *Microsporum canis*, *Sporothrix schenckii*, *Aspergillus fumigatus*, and *P. insidiosum*. The antigen may comprise a whole organism, killed, attenuated or live; a subunit or portion of an organism; a recombinant vector containing an insert with immunogenic properties; a piece or fragment of DNA capable of inducing an immune response upon presentation to a host animal; a polypeptide, an epitope, a hapten, or any combination thereof.

A "vector" refers to a recombinant DNA or RNA plasmid or virus that comprises a heterologous polynucleotide to be delivered to a target cell, either in vitro or in vivo. The heterologous polynucleotide may comprise a sequence of interest for purposes of prevention or therapy, and may optionally be in the form of an expression cassette. As used herein, a vector needs not be capable of replication in the ultimate target cell or subject. The term includes cloning vectors and viral vectors.

The term "recombinant" means a polynucleotide with semisynthetic or synthetic origin which either does not occur in nature or is linked to another polynucleotide in an arrangement not found in nature.

"Heterologous" means derived from a genetically distinct entity from the rest of the entity to which it is being compared. For example, a polynucleotide may be placed by genetic engineering techniques into a plasmid or vector derived from a different source, and is a heterologous polynucleotide. A promoter removed from its native coding sequence and operatively linked to a coding sequence other than the native sequence is a heterologous promoter.

The polynucleotides of the invention may comprise additional sequences, such as additional encoding sequences within the same transcription unit, controlling elements such as promoters, ribosome binding sites, 5'UTR, 3'UTR, transcription terminators, polyadenylation sites, additional transcription units under control of the same or a different promoter, sequences that permit cloning, expression, homologous recombination, and transformation of a host cell, and any such construct as may be desirable to provide embodiments of this invention.

Elements for the expression of a CDV HA polypeptide, antigen, epitope or immunogen or a GM-CSF polypeptide are present in an inventive vector. In minimum manner, this comprises an initiation codon (ATG), a stop codon and a promoter, and optionally also a polyadenylation sequence for certain vectors such as plasmid and certain viral vectors, e.g., viral vectors other than poxviruses. When the polynucleotide encodes a polypeptide fragment, e.g. a CDV HA polypeptide, in the vector, an ATG is placed at 5' of the reading frame and a stop codon is placed at 3'. Other elements for controlling expression may be present, such as enhancer sequences, stabilizing sequences, such as intron and signal sequences permitting the secretion of the protein.

The present invention also relates to compositions or vaccines comprising vectors. The composition or vaccine can comprise one or more vectors, e.g., expression vectors, such as in vivo expression vectors, comprising and expressing one or more CDV HA or GM-CSF polypeptides, antigens, epitopes or immunogens. In one embodiment, the vector contains and expresses a polynucleotide that comprises a polynucleotide coding for and/or expressing a CDV HA antigen, epitope or immunogen, in a pharmaceutically or veterinarily acceptable carrier, excipient, adjuvant, or vehicle. Thus, according to an embodiment of the invention, the other vector or vectors in the preparation comprises, consists essentially of or consists of a polynucleotide that encodes, and under appropriate circumstances the vector expresses one or more other proteins of a CDV HA polypeptide, antigen, epitope or immunogen (e.g., hemagglutinin, neuraminidase, nucleoprotein) or a fragment thereof.

According to another embodiment, the vector or vectors in the composition or vaccine comprise, or consist essentially of, or consist of polynucleotide(s) encoding one or more proteins or fragment(s) of a CDV HA polypeptide, antigen, epitope or immunogen, or a GM-CSF polypeptide, antigen, epitope or immunogen, or a combination thereof. In another embodiment, the composition or vaccine comprises one, two, or more vectors comprising polynucleotides encoding and expressing, advantageously in vivo, a CDV HA polypeptide, antigen, fusion protein or an epitope thereof. The invention is also directed at mixtures of vectors that comprise polynucleotides encoding and expressing different CDV HA polypeptides, antigens, epitopes, fusion protein, or immunogens, e.g., a CDV HA polypeptide, antigen, epitope or immunogen from different species such as, but not limited to, humans, pigs, cows or cattle, dogs, cats, and avian.

In the present invention a recombinant viral vector is used to express a CDV coding sequence or fragments thereof encoding a CDV polypeptide or fragment or variant thereof. Specifically, the viral vector can express a CDV sequence, more specifically a CDV HA gene or fragment thereof that encodes an antigenic polypeptide. Viral vector contemplated herein includes, but not limited to, poxvirus [e.g., vaccinia virus or attenuated vaccinia virus, avipox virus or attenuated avipox virus (e.g., canarypox, fowlpox, dovepox, pigeonpox, quailpox, ALVAC, TROVAC; see e.g., U.S. Pat. No. 5,505,941, U.S. Pat. No. 5,494,8070), raccoonpox virus, swinepox virus, etc.], adenovirus (e.g., human adenovirus, canine adenovirus), herpesvirus (e.g. canine herpesvirus, feline herpesvirus, bovine herpesvirus, swine herpesvirus), baculovirus, retrovirus, etc. In another embodiment, the avipox expression vector may be a canarypox vector, such as, ALVAC. In yet another embodiment, the avipox expression vector may be a fowlpox vector, such as, TROVAC. The CDV polypeptide, antigen, epitope or immunogen may be a CDV HA. For example, the poxvirus vectors comprising the CDV HA may be vectors as described in U.S. Pat. No. 5,756,102. The CDV HA polypeptide or antigen of the invention to be expressed is inserted under the control of a specific poxvirus promoter, e.g., the vaccinia promoter 7.5 kDa (Cochran et al., 1985), the vaccinia promoter I3L (Riviere et al., 1992), the vaccinia promoter HA (Shida, 1986), the cowpox promoter ATI (Funahashi et al., 1988), the vaccinia promoter H6 (Taylor et al., 1988b; Guo et al., 1989; Perkus et al., 1989), inter alia.

According to a yet further embodiment of the invention, the expression vector is a plasmid vector, in particular an in vivo expression vector. In a specific, non-limiting example, the pVR1020 or 1012 plasmid (VICAL Inc.; Luke et al., 1997; Hartikka et al., 1996, see, e.g., U.S. Pat. Nos. 5,846,946 and 6,451,769) can be utilized as a vector for the insertion of a polynucleotide sequence. The pVR1020 plasmid is derived from pVR1012 and contains the human tPA signal sequence. In one embodiment the human tPA signal comprises from amino acid M(1) to amino acid S(23) of GenBank accession number HUMTPA14. In another specific, non-limiting example, the plasmid utilized as a vector for the insertion of a polynucleotide sequence can contain the signal peptide sequence of equine IGF1 from amino acid M(24) to amino acid A(48) of GenBank accession number U28070. Additional information on DNA plasmids which may be consulted or employed in the practice are found, for example, in U.S. Pat. Nos. 6,852,705; 6,818,628; 6,586,412; 6,576,243; 6,558,674; 6,464,984; 6,451,770; 6,376,473 and 6,221,362. The DNA plasmid based vaccines expressing CDV antigens may be found in U.S. patent application Ser. No. 09/587,964.

The term plasmid covers any DNA transcription unit comprising a polynucleotide according to the invention and the elements necessary for its in vivo expression in a cell or cells of the desired host or target; and, in this regard, it is noted that a supercoiled or non-supercoiled, circular plasmid, as well as a linear form, are intended to be within the scope of the invention.

Each plasmid comprises or contains or consists essentially of, in addition to the polynucleotide encoding a CDV HA polypeptide, antigen, epitope or immunogen, optionally fused with a heterologous peptide sequence, variant, analog or fragment, operably linked to a promoter or under the control of a promoter or dependent upon a promoter. In general, it is advantageous to employ a strong promoter functional in eukaryotic cells. The strong promoter may be, but not limited to, the immediate early cytomegalovirus promoter (CMV-IE) of human or murine origin, or optionally having another origin such as the rat or guinea pig.

In more general terms, the promoter has either a viral, or a cellular origin. A strong viral promoter other than CMV-IE that may be usefully employed in the practice of the invention is the early/late promoter of the SV40 virus or the LTR promoter of the Rous sarcoma virus. A strong cellular promoter that may be usefully employed in the practice of the invention is the promoter of a gene of the cytoskeleton, such as e.g. the desmin promoter (Kwissa et al., 2000), or the actin promoter (Miyazaki et al., 1989).

As to the polyadenylation signal (polyA) for the plasmids and viral vectors other than poxviruses, use can be made of the poly(A) signal of the bovine growth hormone (bGH) gene (see U.S. Pat. No. 5,122,458), or the poly(A) signal of the rabbit (3-globin gene or the poly(A) signal of the SV40 virus.

A "host cell" denotes a prokaryotic or eukaryotic cell that has been genetically altered, or is capable of being genetically altered by administration of an exogenous polynucleotide, such as a recombinant plasmid or vector. When referring to genetically altered cells, the term refers both to the originally altered cell and to the progeny thereof.

Methods of Use and Article of Manufacture

The present invention includes the following method embodiments. In an embodiment, a method of vaccinating an animal comprising administering composition comprising a vector comprising a polynucleotide encoding a CDV HA polypeptide or fragment or variant thereof and a pharmaceutical or veterinarily acceptable carrier, excipient, vehicle, or adjuvant to an animal is disclosed. In one aspect of this embodiment, the animal is an avian, an equine, a canine, a feline, a ferret, a seal, or a porcine.

In another embodiment, a method of vaccinating an animal comprising a composition comprising a vector comprising a polynucleotide encoding a CDV HA polypeptide and a polynucleotide encoding a GM-CSF polypeptide and a pharmaceutical or veterinarily acceptable carrier, excipient, vehicle, or adjuvant and one or more compositions comprising canine antigens is disclosed.

In yet another embodiment, a method of vaccinating an animal comprising a composition comprising a vector comprising a polynucleotide encoding a GM-CSF polypeptide and a pharmaceutical or veterinarily acceptable carrier, excipient, vehicle, or adjuvant and one or more compositions comprising canine antigens is disclosed.

In one embodiment of the invention, a prime-boost regime can be employed, which is comprised of at least one primary administration and at least one booster administration using at least one common polypeptide, antigen, epitope or immunogen. The administration may comprise one, two, or more vaccines or compositions comprising same or different antigens. Typically the immunological composition(s) or vaccine(s) used in primary administration is different in nature from those used as a booster. However, it is noted that the same composition(s) can be used as the primary administration and the booster administration. This administration protocol is called "prime-boost".

A prime-boost regimen comprises at least one prime-administration and at least one boost administration using at least one common polypeptide and/or variants or fragments thereof. The prime-administration may comprise one or more administrations. Similarly, the boost administration may comprise one or more administrations. The prime-administration may comprise one or more antigens and the boost administration may comprise one or more antigens.

In one aspect of the prime-boost protocol or regime of the invention, a prime-boost protocol may comprise the administration of a composition comprising a recombinant viral vector that contains and expresses a CDV HA polypeptide, antigen and/or variants or fragments thereof in vivo followed by the administration of a recombinant CDV HA polypeptide or antigen, or an inactivated viral composition or vaccine comprising the CDV HA polypeptide or antigen, or a DNA plasmid-based composition or vaccine expressing the CDV HA polypeptide or antigen. Likewise, a prime-boost protocol may comprise the administration of a composition comprising a recombinant CDV HA antigen, or an inactivated viral composition or vaccine comprising the CDV HA polypeptide or antigen, or a DNA plasmid-based composition or vaccine expressing the CDV HA polypeptide or antigen followed by the administration of a recombinant viral vector that contains and expresses a CDV HA polypeptide or antigen and/or variants or fragments thereof in vivo. It is further noted that both the primary and the secondary administrations may comprise the recombinant viral vector that contains and expresses a CDV HA polypeptide of the invention. Thus, the recombinant CDV viral vector of the invention may be administered in any order with a recombinant CDV antigen, an inactivated viral composition or vaccine comprising the CDV antigen, or a DNA plasmid-based composition or vaccine expressing the CDV antigen, or alternatively may be used alone as both the primary and secondary compositions.

The dose volume of compositions for target species that are mammals, e.g., the dose volume of dog compositions, based on viral vectors, e.g., non-poxvirus-viral-vector-based compositions, is generally between about 0.1 to about 2.0 ml, between about 0.1 to about 1.0 ml, and between about 0.5 ml to about 1.0 ml.

The efficacy of the vaccines may be tested about 2 to 4 weeks after the last immunization by challenging animals, such as dog, with a virulent strain of CDV. Both homologous and heterologous strains are used for challenge to test the efficacy of the vaccine. The animal may be challenged orally, by IV injection or by IC inoculation. For each different challenge strain and each route of administration used, the virus is at a sufficiently high titre to induce clinical symptoms in unvaccinated animals. The volume of challenge virus is about 0.5 to 2.0 ml. Animals may be observed for 21 to 42 days following challenge for clinical signs such as conjunctivitis, rhinitis, diarrhoea, vomiting, depression, dehydration, hyperthermia, pneumonia, ataxia, myoclonus, hyperesthesia, paralysis, paresis, seizures, eye symptoms (such as keratoconjunctivitis, chorioretinitis) and optic neuritis. During the challenge the animals may be blood sampled for complete blood counts and serology study (presence of CDV specific antibodies). In addition PCR may be carried out on samples of urine, tears, saliva, faeces and blood.

The compositions comprising the recombinant antigenic polypeptides of the invention used in the prime-boost protocols are contained in a pharmaceutically or veterinary acceptable vehicle, adjuvant, diluent or excipient. The protocols of the invention protect the animal from CDV and/or prevent disease progression in an infected animal.

The various administrations are preferably carried out 1 to 6 weeks apart. Preferred time interval is 3 to 5 weeks, and optimally 4 weeks According to one embodiment, an annual booster is also envisioned. The animals, for examples dogs, may be at least 8 weeks of age at the time of the first administration.

It should be understood by one of skill in the art that the disclosure herein is provided by way of example and the present invention is not limited thereto. From the disclosure herein and the knowledge in the art, the skilled artisan can determine the number of administrations, the administration route, and the doses to be used for each injection protocol, without any undue experimentation.

The present invention contemplates at least one administration to an animal of an efficient amount of the therapeutic composition made according to the invention. The animal may be male, female, pregnant female and newborn. This administration may be via various routes including, but not limited to, intramuscular (IM), intradermal (ID) or subcutaneous (SC) injection or via intranasal or oral administration. The therapeutic composition according to the invention can also be administered by a needleless apparatus (as, for example with a Pigjet, Dermojet, Biojector, Avijet (Merial, Ga., USA), Vetjet or Vitajet apparatus (Bioject, Oregon, USA)). Another approach to administering plasmid compositions is to use electroporation (see, e.g. Tollefsen et al., 2002; Tollefsen et al., 2003; Babiuk et al., 2002; PCT Application No. WO99/01158). In another embodiment, the therapeutic composition is delivered to the animal by gene gun or gold particle bombardment. In an advantageous embodiment, the animal is a dog, ferret or seal.

In one embodiment, the invention provides for the administration of a therapeutically effective amount of a formulation for the delivery and expression of a CDV antigen or epitope in a target cell. Determination of the therapeutically effective amount is routine experimentation for one of ordinary skill in the art. In one embodiment, the formulation comprises an expression vector comprising a polynucleotide that expresses a CDV antigen or epitope and a pharmaceutically or veterinarily acceptable carrier, vehicle, adjuvant, or excipient. In another embodiment, the pharmaceutically or veterinarily acceptable carrier, vehicle, adjuvant, or excipient facilitates transfection or infection and/or improves preservation of the vector or protein in a host.

In one embodiment, the invention provides for the administration of a therapeutically effective amount of a composition for the delivery and expression of a CDV HA polypeptide or antigen or epitope in a target cell. Determination of the therapeutically effective amount is routine experimentation for one of ordinary skill in the art. In one embodiment, the composition comprises an expression vector comprising a polynucleotide that expresses a CDV HA polypeptide or antigen or epitope and a pharmaceutically or veterinarily acceptable carrier, adjuvant, vehicle or excipient. In another embodiment, the pharmaceutically or veterinarily acceptable carrier, vehicle, adjuvant, or excipient facilitates transfection or infection and/or improves preservation of the vector or protein.

The pharmaceutically or veterinarily acceptable carriers or vehicles or excipients or adjuvants are well known to the one skilled in the art. For example, a pharmaceutically or veterinarily acceptable carrier or vehicle or excipient or adjuvant can be a 0.9% NaCl (e.g., saline) solution or a phosphate buffer. Other pharmaceutically or veterinarily acceptable carrier or vehicle or excipient or adjuvant that can be used for methods of this invention include, but are not limited to, poly-(L-glutamate) or polyvinylpyrrolidone. The pharmaceutically or veterinarily acceptable carrier or vehicle or excipient or adjuvant may be any compound or combination of compounds facilitating the administration of the vector (or protein expressed from an inventive vector in vitro); advantageously, the carrier, vehicle or excipient or adjuvant may facilitate transfection and/or improve preservation of the vector (or protein). Doses and dose volumes are herein discussed in the general description and can also be determined by the skilled artisan from this disclosure read in conjunction with the knowledge in the art, without any undue experimentation.

The cationic lipids containing a quaternary ammonium salt which are advantageously but not exclusively suitable for plasmids, are those having the following formula:

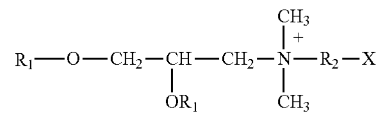

in which R1 is a saturated or unsaturated straight-chain aliphatic radical having 12 to 18 carbon atoms, R2 is another aliphatic radical containing 2 or 3 carbon atoms and X is an amine or hydroxyl group, e.g. the DMRIE. In another embodiment the cationic lipid can be associated with a neutral lipid, e.g. the DOPE.

Among these cationic lipids, preference is given to DMRIE (N-(2-hydroxyethyl)-N,N-dimethyl-2,3-bis(tetradecyloxy)-1-propane ammonium; WO96/34109), advantageously associated with a neutral lipid, advantageously DOPE (dioleoyl-phosphatidyl-ethanol amine; Behr, 1994), to form DMRIE-DOPE.

When DOPE is present, the DMRIE:DOPE molar ratio is advantageously about 95:about 5 to about 5:about 95, more advantageously about 1: about 1, e.g., 1:1.

In another embodiment, pharmaceutically or veterinarily acceptable carrier, excipient, vehicle or adjuvant may be a water-in-oil emulsion. Examples of suitable water-in-oil emulsions include oil-based water-in-oil vaccinal emulsions which are stable and fluid at 4° C. containing: from 6 to 50 v/v % of an antigen-containing aqueous phase, preferably from 12 to 25 v/v %, from 50 to 94 v/v % of an oil phase containing in total or in part a non-metabolizable oil (e.g., mineral oil such as paraffin oil) and/or metabolizable oil (e.g., vegetable oil, or fatty acid, polyol or alcohol esters), from 0.2 to 20 p/v % of surfactants, preferably from 3 to 8 p/v %, the latter being in total or in part, or in a mixture either polyglycerol esters, said polyglycerol esters being preferably polyglycerol (poly)ricinoleates, or polyoxyethylene ricin oils or else hydrogenated polyoxyethylene ricin oils. Examples of surfactants that may be used in a water-in-oil emulsion include ethoxylated sorbitan esters (e.g., polyoxyethylene (20) sorbitan monooleate (TWEEN 80®), available from AppliChem, Inc., Cheshire, Conn.) and sorbitan esters (e.g., sorbitan monooleate (SPAN 80®), available from Sigma Aldrich, St. Louis, Mo.). In addition, with respect to a water-in-oil emulsion, see also U.S. Pat. No. 6,919,084. In some embodiments, the antigen-containing aqueous phase comprises a saline solution comprising one or more buffering agents. An example of a suitable buffering solution is phosphate buffered saline. In one embodiment, the water-in-oil emulsion may be a water/oil/water (W/O/W) triple emulsion (U.S. Pat. No. 6,358,500). Examples of other suitable emulsions are described in U.S. Pat. No. 7,371,395.

The immunological compositions and vaccines according to the invention may comprise or consist essentially of one or more pharmaceutically or veterinarily acceptable carriers, excipients, vehicles or adjuvants. Suitable adjuvants for use in the practice of the present invention are (1) polymers of acrylic or methacrylic acid, maleic anhydride and alkenyl derivative polymers, (2) immunostimulating sequences (ISS), such as oligodeoxyribonucleotide sequences having one or more non-methylated CpG units (Klinman et al., 1996; WO98/16247), (3) an oil in water emulsion, such as the SPT emulsion described on page 147 of "Vaccine Design, The Subunit and Adjuvant Approach" published by M. Powell, M. Newman, Plenum Press 1995, and the emulsion MF59 described on page 183 of the same work, (4) cation lipids containing a quaternary ammonium salt, e.g., DDA (5) cytokines, (6) aluminum hydroxide or aluminum phosphate, (7) saponin or (8) other adjuvants discussed in any document cited and incorporated by reference into the instant application, or (9) any combinations or mixtures thereof.

The oil in water emulsion (3), which is especially appropriate for viral vectors, can be based on: light liquid paraffin oil (European pharmacopoeia type), isoprenoid oil such as squalane, squalene, oil resulting from the oligomerization of alkenes, e.g. isobutene or decene, esters of acids or alcohols having a straight-chain alkyl group, such as vegetable oils, ethyl oleate, propylene glycol, di(caprylate/caprate), glycerol tri(caprylate/caprate) and propylene glycol dioleate, or esters of branched, fatty alcohols or acids, especially isostearic acid esters.

The oil is used in combination with emulsifiers to form an emulsion. The emulsifiers may be nonionic surfactants, such as: esters of on the one hand sorbitan, mannide (e.g. anhydromannitol oleate), glycerol, polyglycerol or propylene glycol and on the other hand oleic, isostearic, ricinoleic or hydroxystearic acids, said esters being optionally ethoxylated, or polyoxypropylene-polyoxyethylene copolymer blocks, such as Pluronic, e.g., L121.

Among the type (1) adjuvant polymers, preference is given to polymers of crosslinked acrylic or methacrylic acid, especially crosslinked by polyalkenyl ethers of sugars or polyalcohols. These compounds are known under the name carbomer (Pharmeuropa, vol. 8, no. 2, June 1996). One skilled in the art can also refer to U.S. Pat. No. 2,909,462, which provides such acrylic polymers crosslinked by a polyhydroxyl compound having at least three hydroxyl groups, preferably no more than eight such groups, the hydrogen atoms of at least three hydroxyl groups being replaced by unsaturated, aliphatic radicals having at least two carbon atoms. The preferred radicals are those containing 2 to 4 carbon atoms, e.g. vinyls, allyls and other ethylenically unsaturated groups. The unsaturated radicals can also contain other substituents, such as methyl. Products sold under the name Carbopol (BF Goodrich, Ohio, USA) are especially suitable. They are crosslinked by allyl saccharose or by allyl pentaerythritol. Among them, reference is made to Carbopol 974P, 934P and 971P.

As to the maleic anhydride-alkenyl derivative copolymers, preference is given to EMA (Monsanto), which are straight-chain or crosslinked ethylene-maleic anhydride copolymers and they are, for example, crosslinked by divinyl ether.

With regard to structure, the acrylic or methacrylic acid polymers and EMA are preferably formed by basic units having the following formula:

$$----\overset{R_1}{\underset{COOH}{C}}-(CH_2)_x-\overset{R_2}{\underset{COOH}{C}}-(CH_2)_y----$$

in which:
R1 and R2, which can be the same or different, represent H or CH3
x=0 or 1, preferably x=1
y=1 or 2, with x+y=2.

For EMA, x=0 and y=2 and for carbomers x=y=1.

These polymers are soluble in water or physiological salt solution (20 g/l NaCl) and the pH can be adjusted to 7.3 to 7.4, e.g., by soda (NaOH), to provide the adjuvant solution in which the expression vector(s) can be incorporated. The polymer concentration in the final immunological or vaccine composition can range between about 0.01 to about 1.5% w/v, about 0.05 to about 1% w/v, and about 0.1 to about 0.4% w/v.

The cytokine or cytokines (5) can be in protein form in the immunological or vaccine composition, or can be co-expressed in the host with the immunogen or immunogens or epitope(s) thereof. Preference is given to the co-expression of the cytokine or cytokines, either by the same vector as that expressing the immunogen or immunogens or epitope(s) thereof, or by a separate vector thereof.

The invention comprehends preparing such combination compositions; for instance by admixing the active components, advantageously together and with an adjuvant, carrier, cytokine, and/or diluent.

Cytokines that may be used in the present invention include, but are not limited to, granulocyte colony stimulating factor (G-CSF), granulocyte/macrophage colony stimulating factor (GM-CSF), interferon α (IFNα), interferon β (IFNβ), interferon γ, (IFNγ), interleukin-1α(IL-1α), interleukin-1β (IL-1β), interleukin-2 (IL-2), interleukin-3 (IL-3), interleukin-4 (IL-4), interleukin-5 (IL-5), interleukin-6 (IL-6), interleukin-7 (IL-7), interleukin-8 (IL-8), interleukin-9 (IL-9), interleukin-10 (IL-10), interleukin-11 (IL-11), interleukin-12 (IL-12), tumor necrosis factor α (TNFα), tumor necrosis factor β (TNFβ), and transforming growth factor β (TGFβ). It is understood that cytokines can be co-administered and/or sequentially administered with the immunological or vaccine composition of the present invention. Thus, for instance, the vaccine of the instant invention can also contain an exogenous nucleic acid molecule that expresses in vivo a suitable cytokine, e.g., a cytokine matched to this host to be vaccinated or in which an immunological response is to be elicited (for instance, a canine cytokine for preparations to be administered to canine).

The invention will now be further described by way of the following non-limiting examples.

EXAMPLES

Without further elaboration, it is believed that one skilled in the art can, using the preceding descriptions, practice the present invention to its fullest extent. The following detailed examples are to be construed as merely illustrative, and not limitations of the preceding disclosure in any way whatsoever. Those skilled in the art will promptly recognize appropriate variations from the procedures both as to reactants and as to reaction conditions and techniques.

Construction of DNA inserts, plasmids and recombinant viral or plant vectors was carried out using the standard molecular biology techniques described by J. Sambrook et al. (Molecular Cloning: A Laboratory Manual, 2nd Edition, Cold Spring Harbor Laboratory, Cold Spring Harbor, N.Y., 1989).

Example 1

Construction of Plasmid Containing CDV HA—pC5 H6 CDV HA, pCXL1557.1

The plasmid containing codon-optimized CDV HA gene (SEQ ID NO:1) (from Danish CDV strain) was digested with EcoRV and XhoI. The 1849 bP fragment containing 3' sequence of vaccinia H6 promoter and full-length codon-optimized CDV HA gene was gel purified. Plasmid pCXL148.2 (pC5 donor plasmid, Merial proprietary material) was digested with EcoRV and Xho I to generate a 49851 by vector containing 5' sequence of H6 promoter. The 1849 by insert was ligated to the 49851 by vector to generate the pC5 H6 CDV HA (pCXL1557.1). The construct was sequenced to confirm the correct sequence. FIG. 3 displays plasmid pCXL1557.1 map.

Example 2

Construction of Plasmid Containing Canine GM-CSF—pC3 H6p Canine GM-CSF, pJSY2218.1

The plasmid containing the codon-optimized canine GM-CSF gene was digested with NruI/XhoI. The resulting canine GM-CSF DNA fragment was isolated and ligated to NruI/XhoI digested pJY19131.1 (Merial proprietary material) to create a C3 donor plasmid pJSY2218.1, which contains the expression cassette H6p (vaccinia H6 promoter)-canine GM-CSF in an opposite orientation against C3 arms. Plasmid pJSY2218.1 was sequenced and confirmed to have the correct sequence. FIG. 3 displays plasmid pJSY2218.1 map.

Example 3

Generation and Characterization of ALVAC Recombinant Containing CDV Synthetic HA Gene in C5 Loci of ALVAC (vCP2263)

A. Generation of vCP2263

The donor plasmid pCXL1557.1 contains codon-optimized canine CDV HA gene (SEQ ID NO:1). Primary chicken embryo fibroblast (1° CEF) cells were used for in vitro recombination. 1° CEF cells were grown in 10% FBS (JRH: γ-irradiated #12107-500M), DMEM (BRL/Gibco #11960-051 or 11960-044) supplemented with 4 mM Glutamine (BRL/Gibco #25030-081) and 1 mM Sodium Pyruvate (BRL/Gibco #11360-070) in the presence of 1× antibiotics/antimycotics (P/S/A/A, BRL/Gibco #15240-062). Plaque hybridization with horseradish peroxidase (HRP)-labeled CDV synthetic HA specific probe was used for recombinant selection.

The IVR (in vitro recombinant) was performed by transfection of 1° CEF cells with 12 μg of Not I-linearized donor plasmid pCXL1557.1 using FuGENE-6® reagent (Roche). The transfected cells were subsequently infected with ALVAC as rescue virus at MOI (multiplicity of infection) of 10 (ALVAC Stock, $6.3 \times 10^9$ pfu/ml). After 24 hours, the transfected-infected cells were harvested, sonicated and used for recombinant virus screening. Recombinant plaques were screened based on the plaque lift hybridization method using a 1232 by synthetic HA specific probe labeled with horse radish peroxidase (HRP) according to the manufacturer's protocol (Amersham Cat #RPN3001,). After four sequential rounds of plaque purification, the recombinants designated as vCP2263.1.2.1.1 and vCP2263.6.1.1.1 were generated and confirmed by hybridization as 100% positive for the HA insert and 100% negative for the empty C5 site. Single plaques were selected from the $4^{th}$ round of plaque purification, and expanded to obtain P1 (1×T25 flask per sister), P2 (1×T75 flask per sister) and P3 (4× roller bottles for vCP2263.1.2.1.1.) stocks to amplify vCP2263. The infected cell culture fluid from the roller bottles was harvested and concentrated to produce the virus stock.

B. Genomic Analysis

Genomic DNA from vCP2263.1.2.1.1 and vCP2263.6.1.1.1 was extracted, digested with BamHI, HindIII or Pst I and run on 0.8% agarose gel. The results revealed the correct insertion of CDV synthetic HA sequence.

Southern blot: The gel with BamHI, HindIII or PstI digested genomic DNA was transferred to nylon membrane and Southern blot analysis was performed by probing with a synthetic CDV HA specific probe. Single or double bands from all three digests were observed at the expected sizes: 1984 by BamHI, 12294 by HindIII and 6465 and 12119 bp PstI (see FIG. 4), indicating the correct insertion of CDV synthetic HA into the C5 loci.

Primers for Amplifying the Synthetic CDV HA Probe:

```
13220CXL:
5' AGGTGTCCACCTCCAACATGGAGT 3'    (SEQ ID NO: 10)

13225CXL:
5' GAACTGGTCGCCCCTGGAGGCCTT 3'    (SEQ ID NO: 11)
```

C. Expression Analysis

Figure 5:
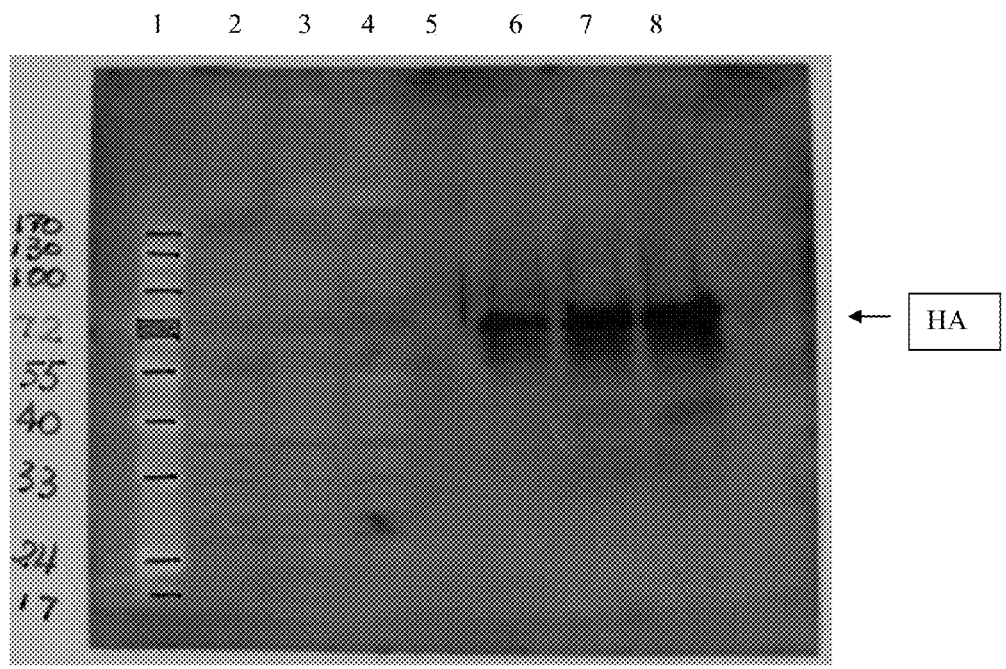
FIG. 5 shows the Western blot of vCP2263.

Western blot: 1° CEF cells were infected with the P2 stock at a MOI of 10 and incubated at 37° C. for 25 hrs. The cells and culture supernatant were then harvested. Sample proteins were separated on a 10% SDS-PAGE gel, transferred to Immobilon nylon membrane, and probed with rabbit anti-CDV polyclonal antibody (pool sera from rabbit A151, and 152 at 1 in 100 dilution). Peroxidase-conjugated Donkey anti-rabbit antiserum was used as a secondary antibody and the bands were visualized using luminol reagents. vCP2263.1211 showed a very weak single band at 73 kDa in the cell supernatant fraction, but no CDV specific band was detected in the cell pellet fraction (see FIG. 5).

Immunoplaque: The homogeneity of the population was 100% for vCP2263.1.2.1.1, as evidenced by an immunoplaque assay, using the Rabbit anti-CDV antibody (see FIG. 6).

D. Sequence Analysis

A more detailed analysis of the P3 stock genomic DNA was performed by PCR amplification and sequence analysis of the flanking arms of the C5 locus and the CDV synthetic HA insert. Primers 7931DC and 7932DC, located beyond the arms of the C5 locus in the ALVAC genome, were used to amplify the entire C5L-CDV synthetic HA-05R fragment. The results showed that the sequences of the CDV synthetic HA and C5L and C5R of ALVAC are correct.

Primers for PCR Amplification:

```
7931DC:
5' GAATCTGTTAGTTAGTTACTTGGAT 3'    (SEQ ID NO: 12)

7932DC:
5' TGATTATAGCTATTATCACAGACTC 3'    (SEQ ID NO: 13)
```

The DNA sequence flanked by primers 7931DC and 7932DC containing C5 arms, H6 promoter, and CDV synthetic HA is designated SEQ ID NO:14.

Example 4

Generation and Characterization of ALVAC Recombinant Containing H6p Synthetic Codon Optimized Canine GM-CSF Gene Inserted at C3 Locus of ALVAC—vCP2391

A. Generation of vCP2391

The donor plasmid pJSY2218.1 contains codon-optimized canine GM-CSF gene (SEQ ID NO:3). Primary chicken embryo fibroblast cells (1° CEF) were used for in vitro recombination. Plaque hybridization with horseradish peroxidase (HRP)-labeled Canine GM-CSF specific probe was used for recombinant selection.

The IVR was performed by transfection of 1° CEF cells with 10 μng of Not I-linearized donor plasmid pJSY2218.1 using FuGENE-6® reagent (Roche). The transfected cells were subsequently infected with ALVAC as rescue virus at MOI of 10. After 24 hours, the transfected-infected cells were harvested, sonicated and used for recombinant virus screening. Recombinant plaques were screened based on the plaque lift hybridization method using a 382 base canine GM-CSF specific probe labeled with horse radish peroxidase (HRP) according to the manufacturer's protocol (Amersham Cat #RPN3001). After two sequential rounds of plaque purification, the recombinant designated as vCP2391.4.4 was generated and confirmed by hybridization as 100% positive for the canine GM-CSF insert and 100% negative for the C3 ORF. Single plaque was selected from the 2nd round of plaque purification, and expanded to obtain P1 (1×T25 flask), P2 (1×T75 flask) and P3 (6× roller bottles).

B. Genomic Analysis—Southern Blot

Genomic DNA from vCP2391 was extracted, digested with BamHI, HindIII or Pst I and run on 0.8% agarose gel. The gel with BamHI, HindIII or PstI digested genomic DNA was transferred to a nylon membrane and Southern blot analysis was performed by probing with the 382 base caGM-CSF probe. Multiple bands were observed at the expected sizes, indicating the correct insertion of the caGM-CSF gene into the C3 locus.

| Restriction enzyme | Fragment (bp) |
| --- | --- |
| Bam HI | 7598 16674 |
| Hind III | 16344 |
| Pst I | 219 1696 11293 |

Primers for Amplifying the Canine GM-CSF Probe

```
18071BK:
5' GATGTTGAACAGGAAGTCCTTCAGGT 3'    (SEQ ID NO: 15)

18073BK:
5' GTTCCTGGGCACCGTGGTGTGCAGCA 3'    (SEQ ID NO: 16)
```

C. Expression Analysis

Figure 7:
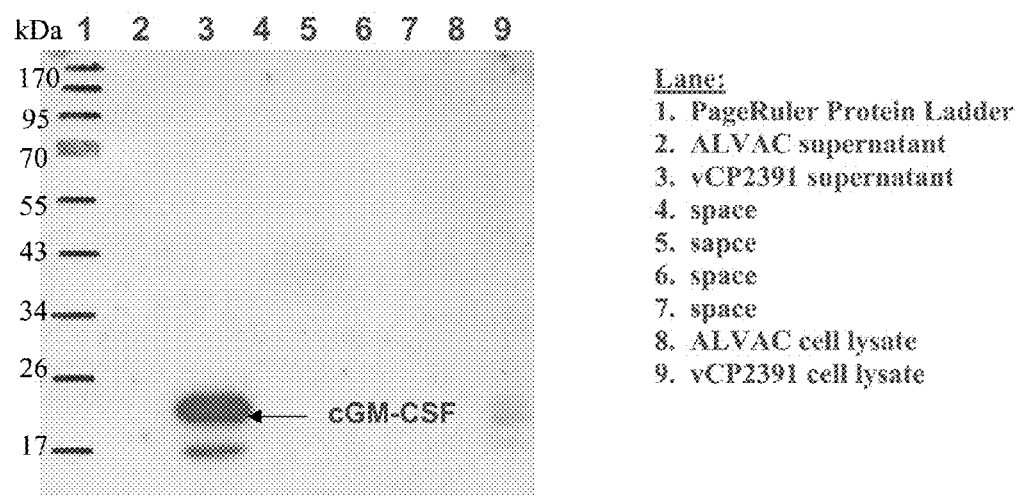
FIG. 7 shows the western blot of vCP2391.
Figure 9:
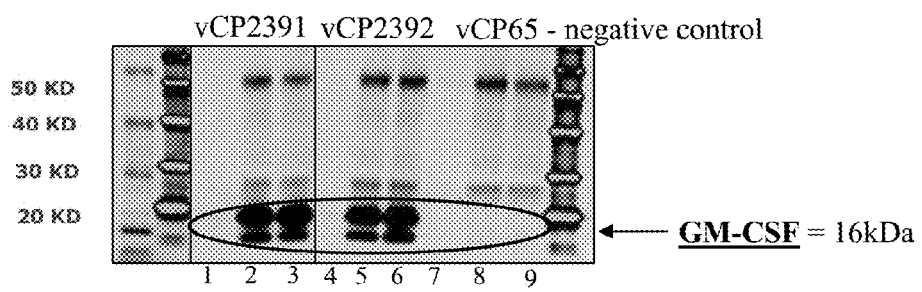
FIG. 9 shows the western blot of vCP2391 and vCP2392 for GM-CSF.

Western blot: Primary CEF cells were infected with the P3 stock of vCP2391.4.4 at MOI of 10 and incubated at 37° C. for 24 hrs. All the culture supernatant and cells were then harvested. Cell pellet was lysed with Reporter Gene Assay Lysis Buffer manufactured by Roche (Cat. 1 897 675). Both supernatant and cell lysate were prepared with the NuPage® System with addition of antioxidant. Proteins were separated on a NuPage® 10% Bis-Tris Pre-cast gel, and then transferred to a PVDF membrane. Purified goat anti-canine GM-CSF IgG (R&D Systems, Cat AF1546) was used as primary antibody. Western blot detected a major protein of ~20 kDa and a minor protein of ~17 kDa secreted from the supernatant of vCP2391.4.4 (see FIGS. 7 and 9). FIG. 9 showed good expression of GM-CSF in crude and supernatant.

D. Sequence Analysis

A more detailed analysis of the P3 stock genomic DNA of vCP2391.4.4 was performed by PCR amplification and sequence analysis of the flanking arms of the C3 locus and the canine GM-CSF insert. Primers 8103JY and 8104JY, located beyond the arms of the C3 locus in the ALVAC genome were used to amplify the entire C3L-caGM-CSF-C3R fragment. The results showed that the sequences of the canine GM-CSF insert and C3L and C3R of ALVAC are correct (SEQ ID NO: 19).

Primers for PCR amplification of C3L-Canine GM-CSF-C3R cassette:

```
                                            (SEQ ID NO: 17)
8103JY: 5' GAGGCATCCAACATATAAAGAAGACTAAAG 3'
```

```
                                            (SEQ ID NO: 18)
8104JY: 5' TAGTTAAATACTCATAACTCATATCTG 3'
```

Example 5

Generation and Characterization of ALVAC Recombinant Containing H6p Synthetic Codon Optimized Canine GM-CSF Gene Inserted at C3 Locus of vCP2263—vCP2392

ALVAC C5 H6p CDV (vCP2263.1.2.1.1) was used as a parental virus. pJSY2218.1 containing the codon-optimized canine GM-CSF gene was used as a donor plasmid. Primary chicken embryo fibroblast cells (1° CEF) were used for in vitro recombination. Plaque hybridization with horseradish peroxidase (HRP)-labeled Canine GM-CSF specific probe was used for recombinant selection.

The IVR was performed by transfection of 1° CEF cells with 10 µg of Not I-linearized donor plasmid pJSY2218.1 using FuGENE-6® reagent (Roche). The transfected cells were subsequently infected with vCP2263.1.2.1.1 as rescue virus at MOI of 10. After 24 hours, the transfected-infected cells were harvested, sonicated and used for recombinant virus screening. Recombinant plaques were screened based on the plaque lift hybridization method using a 382 base canine GM-CSF specific probe (example 4) labeled with horse radish peroxidase (HRP) according to the manufacturer's protocol (Amersham Cat #RPN3001). After four sequential rounds of plaque purification, the recombinant designated as vCP2392.5.3.1.1 was generated and confirmed by hybridization as 100% positive for the canine GM-CSF insert and 100% negative for the C3 ORF. Single plaque was selected from the 4th round of plaque purification, and expanded to obtain P1 (1×T25 flask), P2 (1×T75 flask) and P3 (6× roller bottles).

A. Genomic Analysis—Southern Blot

Genomic DNA from vCP2392 was extracted, digested with BamHI, HindIII or Pst I and run on 0.8% agarose gel. The gel with BamHI, HindIII or PstI digested genomic DNA was transferred to a nylon membrane and Southern blot analysis was performed by probing with the 382 base canine GM-CSF probe (example 4). Multiple bands were observed at the expected sizes, indicating the correct insertion of the canine GM-CSF gene into the C3 locus.

| Restriction enzyme | Fragment (bp) |
| --- | --- |
| Bam HI | 7598 16674 |
| Hind III | 16344 |
| Pst I | 219 1696 11293 |

B. Expression Analysis

Figure 8:
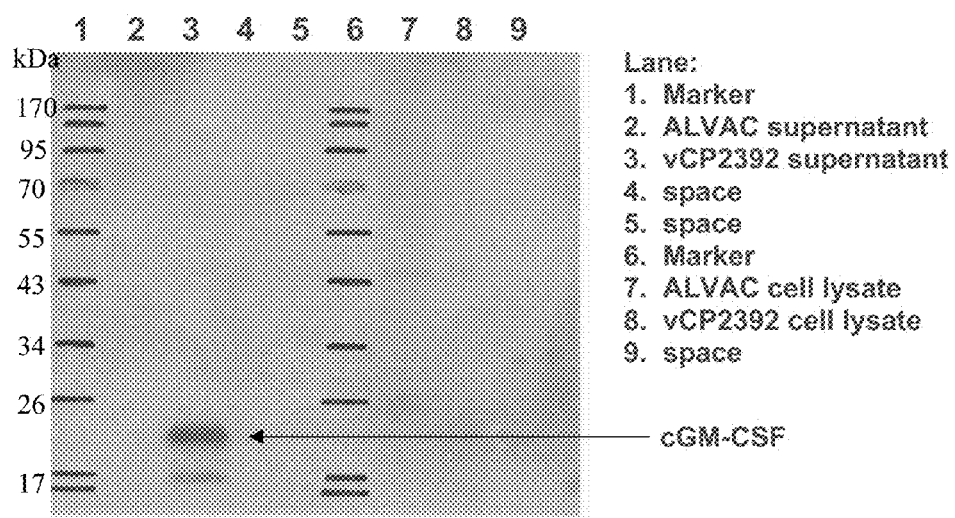
FIG. 8 shows the western blot of vCP2392.

Western blot: Primary CEF cells were infected with the P3 stock of vCP2392.5.3.1.1 at MOI of 10 and incubated at 37° C. for 24 hrs. All the culture supernatant and cells were then harvested. Cell pellet was lysed with Reporter Gene Assay Lysis Buffer manufactured by Roche (Cat. 1 897 675). Both supernatant and cell lysate were prepared with the NuPage® System with addition of antioxidant. Proteins were separated on a NuPage® 10% Bis-Tris Pre-cast gel, and then transferred to a PVDF membrane. Purified goat anti-canine GM-CSF IgG (R&D Systems, Cat AF1546) was used as primary antibody. Western blot detected a major protein of ~20 kDa and a minor protein of ~17 kDa secreted from the supernatant of vCP2392.5.3.1.1. (see FIGS. 8 and 9). The result of CDV HA expression is shown in FIG. 10. The result showed good expression of CDV HA protein with vCP2392.

C. Sequence Analysis

A more detailed analysis of the P3 stock genomic DNA of vCP2392.5.3.1.1 was performed by PCR amplification and sequence analysis of the flanking arms of the C3 locus and the canine GM-CSF insert. Primers 8103JY and 8104JY (see example 4), located beyond the arms of the C3 locus in the ALVAC genome, were used to amplify the entire C3L-caGM-CSF-C3R fragment. The results showed that the sequences of the canine GM-CSF insert and C3L and C3R of ALVAC are correct.

Example 6

Comparison of the Efficacy of the Recombinant Canarypox-Canine CDV HA and Canine GM-CSF (vCP2392) and the Recombinant Canarypox-Canine CDV HA (vCP2263) by Challenge in Dogs Eighteen CDV specific pathogen free dogs were used. The 4 month old male and female dogs were grouped into three groups, and were vaccinated and sampled as shown in Table 1 below.

TABLE 1

| Group (n = 6) | Antigen (titer in $\log_{10}$ $TCID_{50}/ml$) | Vaccination | Post vaccination clinical examinations | Monitoring of Serological and CMI responses |
|---|---|---|---|---|
| A | vCP2392 CDV + GM-CSF (6.21) | D0 & D28, 1 ml by the SQ route | General and local clinical signs | Serology: CDV SN CDV SN on Vero SLAM cells GM-CSF ELISA CMI: T-cell responses |
| B | vCP2263 CDV (6.38) | | | |
| C | Not Vaccinated | — | | |

SN: seroneutralization test
SLAM: signaling lymphocyte-activation molecule
CMI: cell mediated immunity Clinical examinations were performed on days: (V1) 0, 0+4/5 h, 1, 2, (V2) 28, 28+4/5 h, 29, 30, or until all symptoms had disappeared. Clinical monitoring included monitoring general condition of the dogs, such as rectal temperature, pain on palpation of injection site, local swelling, local heat, pruritus and local hair loss.

Figure 11:
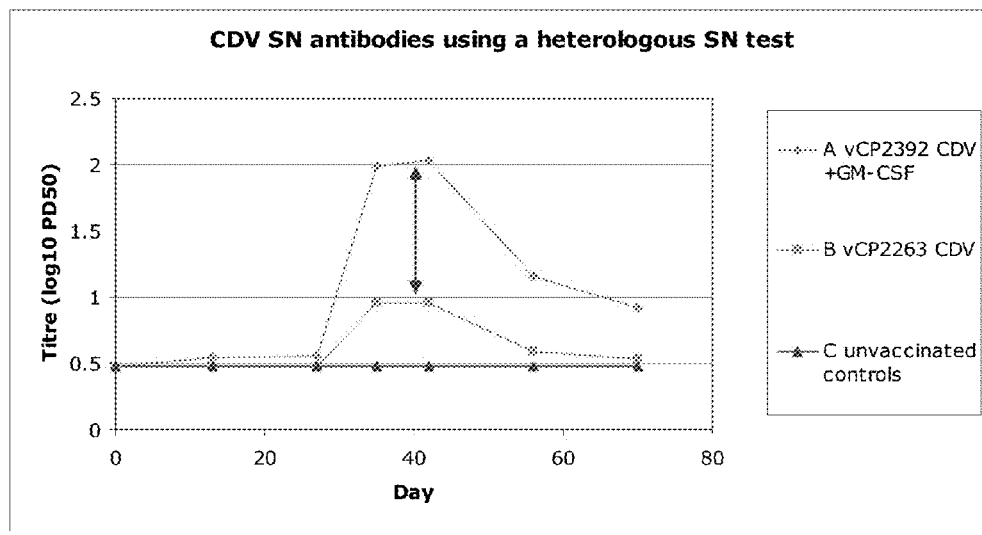
FIG. 11 provides the serology results of vCP2392 and vCP2263 using a heterologous SN test.
Figure 12:
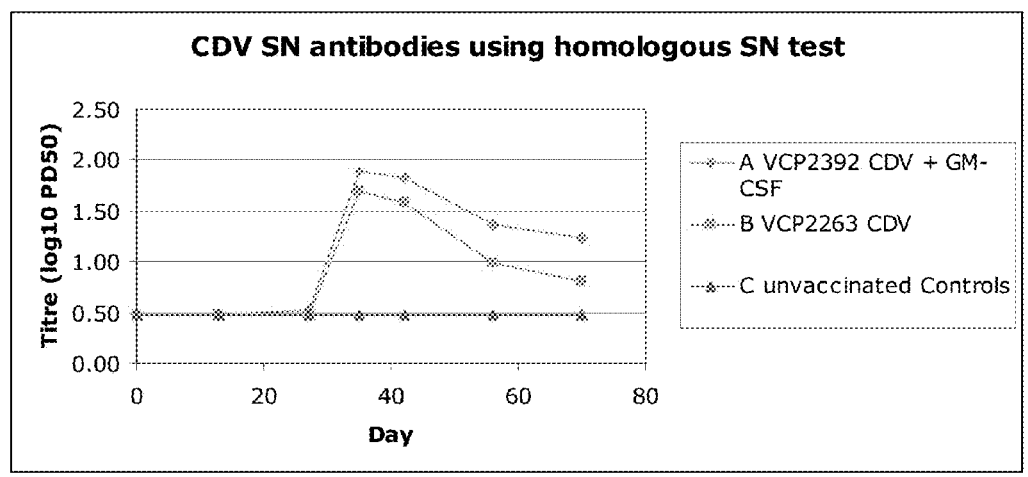
FIG. 12 provides the serology results of vCP2392 and vCP2263 using a homologous SN test.

Sampling in plain tubes for serology was performed on days: 0, 13, 27, 35, 42, 56, and 70. Two types of SN were performed. CDV strain (BA5) which is heterologous to the CDV HA insert in vCP2392 and vCP2263 was used. The result is shown in FIG. 11. The result showed that the titre in group A is higher than the titre in group B (1 log 10), p=0.009, p=0.019 and p=0.03 at D35, D42 and D70 respectively. In group B on D42, there were 3 dogs with titre <0.8 log 10PD50. The second type of SN using vero SLAM cells and CDV strain 5804-GFP which is homologous to the CDV HA insert in vCP2392 and vCP2263 was performed. The result is shown in FIG. 12. The result showed that group A titres are higher than group B titres. The result also showed that there were two dogs in group B that have attire of 0.48 on D70 while in group A all dogs had serological titres of 0.72 or more.

Sampling in heparinated tubes for monitoring of CMI was performed on days: 13, 42, and 70. The production of IFNγ was monitored using ELIspot assay upon PBMCs (peripheral blood mononuclear cells) re-stimulation with PBMCs nucleofected. The frequency of antigen specific IFNγ producing cells was calculated. The data is shown in FIG. 16.

In summary: vCP2392 (CDV HA+canine GM-CSF) induces significantly higher serology responses compared to vCP2263 (CDV HA).

Example 7

Effect of vCP2392 on the Immunogenicity of Other Vaccine Antigens

This study was designed to investigate whether vCP2392 (co-expressing CDV HA and canine GM-CSF) has a positive impact on the immunogenicity of other vaccine antigens.

A modified live canine parvovirus vaccine was used at a dose (2.6 $\log_{10}$ TCID50) which is well below the normal commercial dose. Twelve SPF (specific pathogen free) male and female beagle puppies (2-3 month old) were randomly assigned into two groups and vaccinated as shown in Table 2 below.

TABLE 2

| | *Vaccination D0 & D28 | | | | | |
|---|---|---|---|---|---|---|
| | CDV antigen | | CPV2 antigen | | CDV & | |
| Group N = 6 | vCP | Dose ($\log_{10}$ $TCID_{50}/ml$) | MLV** | Dose ($\log_{10}$ $TCID_{50}/ml$) | CPV2 Serology | Clinical monitoring |
| A | 2392 (CDV HA + GM-CSF) | 6.75 | CPV2 | 2.6 | D0, D7, D14, D28, D35, D42, D56 | D0, D0 + 4-5 h, D1 & D2 |
| B | 2263 (CDV HA) | 6.91 | CPV2 | 2.6 | | D28 D28 + 4-5 h, D29 & D30 |

*2 ml (vCP + MLV-CPV2 in PBS) by the SC route on the right shoulder (D0) then on the left shoulder (D28)
**modified live virus - canine parvovirus type 2 (MLV-CPV2)

Clinical monitoring included general condition, rectal temperature, pain on palpation of injection site, local swelling, local heat and pruritus. The vaccines received were well tolerated by dogs in both groups A and B. vCP2392 (CDV HA+GM-CSF) and vCP2263 (CDV HA) in combination with MLV-CPV2 was considered safe based on the clinical study result.

Sera were titrated for antibodies against CPV2 and CDV (using homologous and heterologous CDV in seroneutralization test).

FIG. 17 shows the CVP2 ELISA result. None of the animals in groups A and B had antibodies against CPV2 at the start of the study. In group B, only one dog mounted an antibody response following vaccination. This response was detected from D28 onwards. In group A, 4 out of 6 dogs showed high antibody responses and responses were detected as early as D7 in some of the dogs. None of the dogs showed a booster response after the second injection on D28. Statistical analyses on the incidence of responders showed that the groups were significantly different (p=0.046). The result indicated that the GM-CSF insert included in vCP2392 had a positive effect on CPV2 serology.

FIG. 18 shows the result of CDV homologous SN (seroneutralization) test. Before vaccination, none of the animals had antibodies against CDV. Group A and B titres were similar on D35 and D56. However 5/6 dogs from group A had antibodies on D28 while none of the dogs in group B had antibodies on D28. On D42 serological titres were significantly higher in group A (Student t-test, p=0.01).

Figure 19:
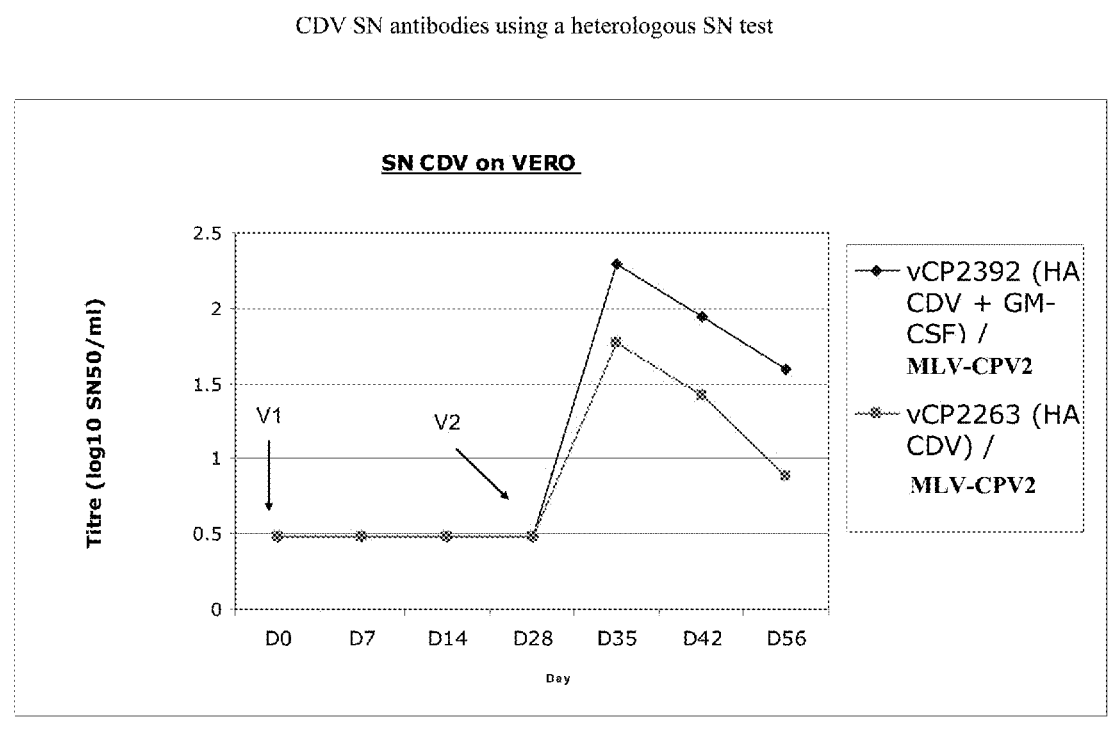

FIG. 19 shows the result of CDV heterologous SN test. Before vaccination, none of the animals had antibodies against CDV. Antibody titres in group A tended to be higher than group B titres on days 35, 42 and 56. On D56, antibody titres in group A were significantly higher than in group B (Wilcoxon, p=0.016).

The study results showed that a dose of 2.6 $\log_{10}$ TCID50 of MLV-CPV2 per dog was under the minimum dose that can confer seroconversion, as shown in group B's result. Interestingly and surprisingly, the inclusion of GM-CSF in canarypox vector (vCP2392) induced different antibody response, as shown in group A's result. The results demonstrated that the presence of caGM-CSF in canarypox vector can have an effect on the immunogenicity of another vaccine component injected into the same site.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

All documents cited or referenced in the application cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

What is claimed is:

1. A composition comprising a canarypox vector ALVAC, wherein the ALVAC vector is vCP2392 comprising the polynucleotide of SEQ ID NO: 14.

2. The composition of claim 1, wherein the ALVAC vector comprises a second polynucleotide encoding the canine GM-CSF polypeptide of SEQ ID NO: 4.

3. The composition of claim 1, further comprising one or more additional antigens.

4. The composition of claim 3, wherein the additional antigen is associated with canine parvovirus.

5. The composition of claim 2, wherein the second polynucleotide comprises SEQ ID NO: 3.

6. The composition of claim 5, wherein the composition further comprises one or more antigens.

7. The composition of claim 6, wherein the antigen is associated with canine parvovirus.

8. The composition of claim 3 or 1, wherein the composition further comprises a pharmaceutically or veterinary acceptable vehicle, adjuvant, diluent or excipient.

9. The composition of claim 2, wherein the polynucleotide encoding the canine GM-CSF polypeptide is inserted at C3 locus of the ALVAC.

10. A canarypox vector ALVAC, wherein the ALVAC vector is vCP2392 comprising the polynucleotide of SEQ ID NO: 14.

11. The vector of claim 10, wherein the ALVAC vector comprises a second polynucleotide encoding the canine GM-CSF polypeptide of SEQ ID NO: 4.

12. The composition of claim 11, wherein the second polynucleotide comprises SEQ ID NO: 3.

13. The vector of claim 11, wherein the polynucleotide encoding the canine GM-CSF polypeptide is inserted at C3 locus of the ALVAC.

14. A method of inducing an immune response in an animal comprising at least one administration of an effective amount of the composition of claim 1 or the vector of claim 10.

15. The method of claim 14, wherein the method comprises a prime-boost administration regime.

* * * * *

SEQUENCE LISTING

<160> NUMBER OF SEQ ID NOS: 51

<210> SEQ ID NO 1
<211> LENGTH: 1821
<212> TYPE: DNA
<213> ORGANISM: artificial sequence
<220> FEATURE:
<223> OTHER INFORMATION: codon-optimized CDV HA gene

<400> SEQUENCE: 1

```
atgctgagct accaggacaa agtgggcgcc ttctacaagg acaacgccag ggccaatagc      60
agcaagctga gcctggtgac cgaggagcag ggcggcagga gaccccccta cctgctgttc     120
gtgctgctga tccttcttgt gggcatcatg accctgctgg ccatcaccgg agtgagattc     180
caccaggtgt ccacctccaa catggagttc agccggctgc tgaaagagga catggagaag     240
agcgaggccg tgcaccacca ggtgatcgat gtgctgaccc ccctgttcaa gatcatcggc     300
gacgaagtgg gcctgagact gccccagaag ctgaacgaga tcaagcagtt catcctgcag     360
aaaaccaact tcttcaaccc caaccgggag ttcgacttca gagacctgca ctggtgcatc     420
aaccccccca gcaagatcaa agtgaacttc accaactact gcgacaccat cggcatcagg     480
aagagcatcg ccagcgccgt gaatcccatc ctgctgagcg ccctgagcgg cggcagaggc     540
gacatcttcc cccctacag atgcagcggc gccaccacct ctgtgggcag agtgttccct     600
ctgagcgtgt ccctgagcat gagcctgatc agcaagacca gcgagatcac caacatgctg     660
accgccatca gcgacggcgt gtacggcaag acctatctgc tggtgcccga ctacatcgag     720
ggcgagttcg acacccagaa gatccgcgtg ttcgagatcg gcttcatcaa gcggtggctg     780
aacaacatgc ccctgctgca gaccaccaac tacatggtgc tgcccgagaa cagcaaggcc     840
aaagtgtgca ccatcgctgt gggcgagctg accctggcca gcctgtgcgt ggacgagagc     900
accgtgctgc tgtaccacga cagcaacggc agccaggacg gcatcctggt ggtgaccctg     960
ggcatcttcg gcgccacccc tatggaccag gtggaggaag tgatccccgt ggcccacccc    1020
agcgtggaga agatccacat caccaaccac cggggcttta tcaaggacag catcgccacc    1080
tggatggtgc ccgcctggt gtctgagaag caggaggagc agaagaactg cctggagagc    1140
```

```
gcctgccaga gaaagaccta ccccatgtgc aaccagacca gctgggagcc ctttggcggc    1200
ggacagctgc ccagctacgg cagactgacc ctgagcctgg accctagcat cgacctgcag    1260
ctgaacatca gcttcaccta cggccccgtg atcctgaacg gcgacggcat ggattactac    1320
ggcagcagcc tgagcgacag cggctggctg accatccctc ccaagaacgg cacagtgctg    1380
ggcctgatca acaaggcctc cagggggcgac cagttcaccg tgatccctca cgtgctgacc    1440
```

```
ttcgccccca gagagagcag cggcaactgc tacctgccta ccagaccctc ccagatcatg    1500
gacaaggacg tgctgacaga gagcaacctg gtggtgctgc ctacccagaa cttccggtac    1560
gtgatcgcca cctacgacat cagcagaggc gatcacgcca tcgtgtacta cgtgtacgac    1620
cccatccgga ccatcagcta cacatacccc ttccggctga ccaccaaggg cagacccgac    1680
ttcctgcgga tcgagtgctt tgtgtgggac gacgacctgt ggtgccacca gttctacaga    1740
ttcgaggccg acatcaccaa tagcaccacc tccgtggaga accttgtgag gatccggttc    1800
agctgcgaca gaagcaagcc c                                              1821
```

<210> SEQ ID NO 2
<211> LENGTH: 607
<212> TYPE: PRT
<213> ORGANISM: artificial sequence
<220> FEATURE:
<223> OTHER INFORMATION: CDV HA protein encoded by codon-optimized gene
      (SEQ ID NO:1)

<400> SEQUENCE: 2

Met Leu Ser Tyr Gln Asp Lys Val Gly Ala Phe Tyr Lys Asp Asn Ala
1               5                   10                  15

Arg Ala Asn Ser Ser Lys Leu Ser Leu Val Thr Glu Glu Gln Gly Gly
                20                  25                  30

Arg Arg Pro Pro Tyr Leu Leu Phe Val Leu Leu Ile Leu Leu Val Gly
            35                  40                  45

Ile Met Thr Leu Leu Ala Ile Thr Gly Val Arg Phe His Gln Val Ser
        50                  55                  60

Thr Ser Asn Met Glu Phe Ser Arg Leu Leu Lys Glu Asp Met Glu Lys
65                  70                  75                  80

Ser Glu Ala Val His His Gln Val Ile Asp Val Leu Thr Pro Leu Phe
                85                  90                  95

Lys Ile Ile Gly Asp Glu Val Gly Leu Arg Leu Pro Gln Lys Leu Asn
            100                 105                 110

Glu Ile Lys Gln Phe Ile Leu Gln Lys Thr Asn Phe Phe Asn Pro Asn
        115                 120                 125

Arg Glu Phe Asp Phe Arg Asp Leu His Trp Cys Ile Asn Pro Pro Ser
    130                 135                 140

Lys Ile Lys Val Asn Phe Thr Asn Tyr Cys Asp Thr Ile Gly Ile Arg
145                 150                 155                 160

Lys Ser Ile Ala Ser Ala Val Asn Pro Ile Leu Leu Ser Ala Leu Ser
                165                 170                 175

Gly Gly Arg Gly Asp Ile Phe Pro Pro Tyr Arg Cys Ser Gly Ala Thr
            180                 185                 190

Thr Ser Val Gly Arg Val Phe Pro Leu Ser Val Ser Leu Ser Met Ser
        195                 200                 205

Leu Ile Ser Lys Thr Ser Glu Ile Thr Asn Met Leu Thr Ala Ile Ser
    210                 215                 220

Asp Gly Val Tyr Gly Lys Thr Tyr Leu Leu Val Pro Asp Tyr Ile Glu
225                 230                 235                 240

Gly Glu Phe Asp Thr Gln Lys Ile Arg Val Phe Ile Gly Phe Ile
            245                 250                 255

Lys Arg Trp Leu Asn Asn Met Pro Leu Leu Gln Thr Thr Asn Tyr Met
        260                 265                 270

Val Leu Pro Glu Asn Ser Lys Ala Lys Val Cys Thr Ile Ala Val Gly
            275                 280                 285

Glu Leu Thr Leu Ala Ser Leu Cys Val Asp Glu Ser Thr Val Leu Leu
        290                 295                 300

Tyr His Asp Ser Asn Gly Ser Gln Asp Gly Ile Leu Val Val Thr Leu
305                 310                 315                 320

Gly Ile Phe Gly Ala Thr Pro Met Asp Gln Val Glu Glu Val Ile Pro
                325                 330                 335

Val Ala His Pro Ser Val Glu Lys Ile His Ile Thr Asn His Arg Gly
            340                 345                 350

Phe Ile Lys Asp Ser Ile Ala Thr Trp Met Val Pro Ala Leu Val Ser
        355                 360                 365

Glu Lys Gln Glu Glu Gln Lys Asn Cys Leu Glu Ser Ala Cys Gln Arg
    370                 375                 380

Lys Thr Tyr Pro Met Cys Asn Gln Thr Ser Trp Glu Pro Phe Gly Gly
385                 390                 395                 400

Gly Gln Leu Pro Ser Tyr Gly Arg Leu Thr Leu Ser Leu Asp Pro Ser
                405                 410                 415

Ile Asp Leu Gln Leu Asn Ile Ser Phe Thr Tyr Gly Pro Val Ile Leu
            420                 425                 430

Asn Gly Asp Gly Met Asp Tyr Tyr Gly Ser Ser Leu Ser Asp Ser Gly
        435                 440                 445

Trp Leu Thr Ile Pro Pro Lys Asn Gly Thr Val Leu Gly Leu Ile Asn
    450                 455                 460

Lys Ala Ser Arg Gly Asp Gln Phe Thr Val Ile Pro His Val Leu Thr
465                 470                 475                 480

Phe Ala Pro Arg Glu Ser Ser Gly Asn Cys Tyr Leu Pro Ile Gln Thr
                485                 490                 495

Ser Gln Ile Met Asp Lys Asp Val Leu Thr Glu Ser Asn Leu Val Val
            500                 505                 510

Leu Pro Thr Gln Asn Phe Arg Tyr Val Ile Ala Thr Tyr Asp Ile Ser
        515                 520                 525

Arg Gly Asp His Ala Ile Val Tyr Val Tyr Asp Pro Ile Arg Thr
    530                 535                 540

Ile Ser Tyr Thr Tyr Pro Phe Arg Leu Thr Thr Lys Gly Arg Pro Asp
545                 550                 555                 560

Phe Leu Arg Ile Glu Cys Phe Val Trp Asp Asp Leu Trp Cys His
                565                 570                 575

Gln Phe Tyr Arg Phe Glu Ala Asp Ile Thr Asn Ser Thr Thr Ser Val
            580                 585                 590

Glu Asn Leu Val Arg Ile Arg Phe Ser Cys Asp Arg Ser Lys Pro
        595                 600                 605

<210> SEQ ID NO 3
<211> LENGTH: 435
<212> TYPE: DNA
<213> ORGANISM: artificial sequence
<220> FEATURE:
<223> OTHER INFORMATION: codon-optimized canine GM-CSF gene

<400> SEQUENCE: 3

```
atgtggctgc agaacctgct gttcctgggc accgtggtgt gcagcatcag cgcccccacc      60
agatccccca ccctggtgac ccggcccagc cagcacgtgg acgccatcca ggaagccctg     120
agcctgctga acaacagcaa cgacgtgacc gccgtgatga acaaggccgt gaaggtggtg     180
tccgaggtgt tcgaccccga gggccccacc tgcctggaaa cccggctgca gctgtacaaa     240
gagggcctgc agggcagcct gaccagcctg aagaaccccc tgaccatgat ggccaaccac     300
tacaagcagc actgcccccc cacccccgag agcccttgcg ccacccagaa catcaacttc     360
aagagcttca agagaaacct gaaggacttc ctgttcaaca tccccttcga ctgctggaag     420
cccgtgaaga agtga                                                      435
```

```
<210> SEQ ID NO 4
<211> LENGTH: 144
<212> TYPE: PRT
<213> ORGANISM: artificial sequence
<220> FEATURE:
<223> OTHER INFORMATION: canine GM-CSF protein encoded by
      codon-optimized gene (SEQ ID NO:3)

<400> SEQUENCE: 4
```

```
Met Trp Leu Gln Asn Leu Leu Phe Leu Gly Thr Val Val Cys Ser Ile
1               5                   10                  15

Ser Ala Pro Thr Arg Ser Pro Thr Leu Val Thr Arg Pro Ser Gln His
            20                  25                  30

Val Asp Ala Ile Gln Glu Ala Leu Ser Leu Leu Asn Asn Ser Asn Asp
        35                  40                  45

Val Thr Ala Val Met Asn Lys Ala Val Lys Val Ser Glu Val Phe
    50                  55                  60

Asp Pro Glu Gly Pro Thr Cys Leu Glu Thr Arg Leu Gln Leu Tyr Lys
65                  70                  75                  80

Glu Gly Leu Gln Gly Ser Leu Thr Ser Leu Lys Asn Pro Leu Thr Met
                85                  90                  95

Met Ala Asn His Tyr Lys Gln His Cys Pro Pro Thr Pro Glu Ser Pro
            100                 105                 110

Cys Ala Thr Gln Asn Ile Asn Phe Lys Ser Phe Lys Glu Asn Leu Lys
        115                 120                 125

Asp Phe Leu Phe Asn Ile Pro Phe Asp Cys Trp Lys Pro Val Lys Lys
    130                 135                 140
```

```
<210> SEQ ID NO 5
<211> LENGTH: 604
<212> TYPE: PRT
<213> ORGANISM: artificial sequence
<220> FEATURE:
<223> OTHER INFORMATION: CDV HA protein from vCP258

<400> SEQUENCE: 5
```

```
Ser Glu Ala Val His His Gln Val Ile Asp Val Leu Thr Pro Leu Phe
                85                  90                  95

Lys Ile Ile Gly Asp Glu Ile Gly Leu Arg Leu Pro Gln Lys Leu Asn
            100                 105                 110

Glu Ile Lys Gln Phe Ile Leu Gln Lys Thr Asn Phe Phe Asn Pro Asn
        115                 120                 125

Arg Glu Phe Asp Phe Arg Asp Leu His Trp Cys Ile Asn Pro Pro Ser
130                 135                 140

Thr Val Lys Val Asn Phe Thr Asn Tyr Cys Glu Ser Ile Gly Ile Arg
145                 150                 155                 160

Lys Ala Ile Ala Ser Ala Ala Asn Pro Ile Leu Leu Ser Ala Leu Ser
                165                 170                 175

Gly Gly Arg Gly Asp Ile Phe Pro Pro His Arg Cys Ser Gly Ala Thr
            180                 185                 190

Thr Ser Val Gly Lys Val Phe Pro Leu Ser Val Ser Leu Ser Met Ser
        195                 200                 205

Leu Ile Ser Arg Thr Ser Glu Val Ile Asn Met Leu Thr Ala Ile Ser
    210                 215                 220

Asp Gly Val Tyr Gly Lys Thr Tyr Leu Leu Val Pro Asp Asp Ile Glu
225                 230                 235                 240

Arg Glu Phe Asp Thr Arg Glu Ile Arg Val Phe Glu Ile Gly Phe Ile
                245                 250                 255

Lys Arg Trp Leu Asn Asp Met Pro Leu Leu Gln Thr Thr Asn Tyr Met
            260                 265                 270

Val Leu Pro Lys Asn Ser Lys Ala Lys Val Cys Thr Ile Ala Val Gly
        275                 280                 285

Glu Leu Thr Leu Ala Ser Leu Cys Val Glu Glu Ser Thr Val Leu Leu
    290                 295                 300

Tyr His Asp Ser Ser Gly Ser Gln Asp Gly Ile Leu Val Val Thr Leu
305                 310                 315                 320

Gly Ile Phe Trp Ala Thr Pro Met Asp His Ile Glu Glu Val Ile Pro
                325                 330                 335

Val Ala His Pro Ser Met Lys Lys Ile His Ile Thr Asn His Arg Gly
            340                 345                 350

Phe Ile Lys Asp Ser Ile Ala Thr Trp Met Val Pro Ala Leu Ala Ser
        355                 360                 365

Glu Lys Gln Glu Glu Gln Lys Gly Cys Leu Glu Ser Ala Cys Gln Arg
    370                 375                 380

Lys Thr Tyr Pro Met Cys Asn Gln Ala Ser Trp Glu Pro Phe Gly Gly
385                 390                 395                 400

Arg Gln Leu Pro Ser Tyr Gly Arg Leu Thr Leu Pro Leu Asp Ala Ser
                405                 410                 415

Val Asp Leu Gln Leu Asn Ile Ser Phe Thr Tyr Gly Pro Val Ile Leu
            420                 425                 430

Asn Gly Asp Gly Met Asp Tyr Tyr Glu Ser Pro Leu Leu Asn Ser Gly
        435                 440                 445

Trp Leu Thr Ile Pro Pro Lys Asp Gly Thr Ile Ser Gly Leu Ile Asn
    450                 455                 460

Lys Ala Gly Arg Gly Asp Gln Phe Thr Val Leu Pro His Val Leu Thr
465                 470                 475                 480

Phe Ala Pro Arg Glu Ser Ser Gly Asn Cys Tyr Leu Pro Ile Gln Thr
                485                 490                 495
```

-continued

```
Ser Gln Ile Arg Asp Arg Asp Val Leu Ile Glu Ser Asn Ile Val Val
            500                 505                 510

Leu Pro Thr Gln Ser Ile Arg Tyr Val Ile Ala Thr Tyr Asp Ile Ser
        515                 520                 525

Arg Ser Asp His Ala Ile Val Tyr Tyr Val Tyr Asp Pro Ile Arg Thr
    530                 535                 540

Ile Ser Tyr Thr His Pro Phe Arg Leu Thr Thr Lys Gly Arg Pro Asp
545                 550                 555                 560

Phe Leu Arg Ile Glu Cys Phe Val Trp Asp Asp Asn Leu Trp Cys His
                565                 570                 575

Gln Phe Tyr Arg Phe Glu Ala Asp Ile Ala Asn Ser Thr Thr Ser Val
            580                 585                 590

Glu Asn Leu Val Arg Ile Arg Phe Ser Cys Asn Arg
        595                 600
```

```
<210> SEQ ID NO 6
<211> LENGTH: 4140
<212> TYPE: DNA
<213> ORGANISM: artificial sequence
<220> FEATURE:
<223> OTHER INFORMATION: part of pCXL1557.1 containing arms and insert
<220> FEATURE:
<221> NAME/KEY: misc_feature
<222> LOCATION: (43)..(1578)
<223> OTHER INFORMATION: this is the C5L region
<220> FEATURE:
<221> NAME/KEY: promoter
<222> LOCATION: (1676)..(1799)
<223> OTHER INFORMATION: this is the H6 promoter region
<220> FEATURE:
<221> NAME/KEY: CDS
<222> LOCATION: (1800)..(3620)
<223> OTHER INFORMATION: this is the CDV-HA coding region
<220> FEATURE:
<221> NAME/KEY: misc_feature
<222> LOCATION: (3677)..(4081)
<223> OTHER INFORMATION: this is the C5R region

<400> SEQUENCE: 6
ggaaacagct atgaccatga ttacgaattg cggccgcaat tctgaatgtt aaatgttata     60
ctttggatga agctataaat atgcattgga aaaataatcc atttaaagaa aggattcaaa    120
tactacaaaa cctaagcgat aatatgttaa ctaagcttat tcttaacgac gctttaaata    180
tacacaaata aacataattt ttgtataacc taacaaataa ctaaaacata aaaataataa    240
aaggaaatgt aatatcgtaa ttattttact caggaatggg gttaaatatt tatatcacgt    300
gtatatctat actgttatcg tatactcttt acaattacta ttacgaatat gcaagagata    360
ataagattac gtatttaaga gaatcttgtc atgataattg ggtacgacat agtgataaat    420
gctatttcgc atcgttacat aaagtcagtt ggaaagatgg atttgacaga tgtaacttaa    480
taggtgcaaa aatgttaaat aacagcattc tatcggaaga taggatacca gttatattat    540
acaaaaatca ctggttggat aaaacagatt ctgcaatatt cgtaaaagat gaagattact    600
gcgaatttgt aaactatgac aataaaaagc catttatctc aacgacatcg tgtaattctt    660
ccatgtttta tgtatgtgtt tcagatatta tgagattact ataaactttt tgtatactta    720
tattccgtaa actatattaa tcatgaagaa aatgaaaaag tatagaagct gttcacgagc    780
ggttgttgaa aacaacaaaa ttatacattc aagatggctt acatatacgt ctgtgaggct    840
atcatggata atgacaatgc atctctaaat aggtttttgg acaatggatt cgaccctaac    900
acggaatatg gtactctaca atctcctctt gaaatggctg taatgttcaa gaataccgag    960
```

```
gctataaaaa tcttgatgag gtatggagct aaacctgtag ttactgaatg cacaacttct    1020
tgtctgcatg atgcggtgtt gagagacgac tacaaaatag tgaaagatct gttgaagaat    1080
aactatgtaa acaatgttct ttacagcgga ggctttactc ctttgtgttt ggcagcttac    1140
cttaacaaag ttaatttggt taaacttcta ttggctcatt cggcggatgt agatatttca    1200
aacacggatc ggttaactcc tctacatata gccgtatcaa ataaaaattt aacaatggtt    1260
aaacttctat tgaacaaagg tgctgatact gacttgctgg ataacatggg acgtactcct    1320
ttaatgatcg ctgtacaatc tggaaatatt gaaatatgta gcacactact taaaaaaaat    1380
aaaatgtcca gaactgggaa aaattgatct tgccagctgt aattcatggt agaaaagaag    1440
tgctcaggct acttttcaac aaaggagcag atgtaaacta catctttgaa agaaatggaa    1500
aatcatatac tgttttggaa ttgattaaag aaagttactc tgagacacaa aagaggtagc    1560
tgaagtggta ctctcaaagg tacgtgacta attagctata aaaaggatcc gggttaatta    1620
attagtcatc aggcagggcg agaacgagac tatctgctcg ttaattaatt agagcttctt    1680
tattctatac ttaaaaagtg aaaataaata caaaggttct tgagggttgt gttaaattga    1740
aagcgagaaa taatcataaa ttatttcatt atcgcgatat ccgttaagtt tgtatcgtaa    1800
tgctgagcta ccaggacaaa gtgggcgcct tctacaagga caacgccagg ccaatagca    1860 gcaagctgag cctggtgacc gaggagcagg gcggcaggag accccctac ctgctgttcg    1920 tgctgctgat ccttccttgtg gcatcatga ccctgctggc catcaccgga gtgagattcc    1980
accaggtgtc cacctccaac atggagttca gccggctgct gaaagaggac atggagaaga    2040
gcgaggccgt gcaccaccag gtgatcgatg tgctgacccc cctgttcaag atcatcggcg    2100
acgaagtggg cctgagactg ccccagaagc tgaacgagat caagcagttc atcctgcaga    2160
aaaccaactt cttcaacccc aaccgggagt tcgacttcag agacctgcac tggtgcatca    2220 accccccccag caagatcaaa gtgaacttca ccaactactg cgacaccatc ggcatcagga    2280
agagcatcgc cagcgccgtg aatcccatcc tgctgagcgc cctgagcggc ggcagaggcg    2340
acatcttccc ccctacaga tgcagcggcg ccaccacctc tgtgggcaga gtgttccctc    2400
tgagcgtgtc cctgagcatg agcctgatca gcaagaccag cgagatcacc aacatgctga    2460
ccgccatcag cgacggcgtg tacggcaaga cctatctgct ggtgcccgac tacatcgagg    2520
gcgagttcga cacccagaag atccgcgtgt cgagatcgg cttcatcaag cggtggctga    2580
acaacatgcc cctgctgcag accaccaact acatggtgct gcccgagaac agcaaggcca    2640
aagtgtgcac catcgctgtg ggcgagctga ccctggccag cctgtgcgtg gacgagagca    2700
ccgtgctgct gtaccacgac agcaacggca gccaggacgg catcctggtg gtgacccggg    2760
gcatcttcgg cgcccacccct atggaccagg tggaggaagt gatccccgtg gcccaccca    2820 gcgtggagaa gatccacatc accaaccacc ggggctttat caaggacagc atcgccacct    2880
ggatggtgcc cgccctggtg tctgagaagc aggaggagca aagaactgc ctggagagcg    2940 cctgccagag aaagacctac cccatgtgca accagaccag ctgggagccc tttgcggcg    3000 gacagctgcc cagctacggc agactgaccc tgagcctgga ccctagcatc gacctgcagc    3060
tgaacatcag cttcacctac ggccccgtga tcctgaacgg cgacggcatg gattactacg    3120
gcagcagcct gagcgacagc ggctggctga ccatccctcc caagaacggc acagtgctgg    3180
gcctgatcaa caaggcctcc aggggcgacc agttcaccgt gatccctcac gtgctgacct    3240
tcgcccccag agagagcagc ggcaactgct acctgcctat ccagacctcc cagatcatgg    3300
acaaggacgt gctgacagag agcaacctgg tggtgctgcc tacccagaac ttccggtacg    3360
```

```
tgatcgccac ctacgacatc agcagaggcg atcacgccat cgtgtactac gtgtacgacc    3420
ccatccggac catcagctac acataccct tccggctgac caccagggc agacccgact      3480 tcctgcggat cgagtgcttt gtgtgggacg acgacctgtg gtgccaccag ttctacagat    3540
tcgaggccga catcaccaat agcaccacct ccgtggagaa ccttgtgagg atccggttca    3600
gctgcgacag aagcaagccc tgatagctcg agtctagaat cgatcccggg ttttttatgac  3660 tagttaatca cggccgctta taaagatcta aaatgcataa tttctaaata atgaaaaaaa   3720
gtacatcatg agcaacgcgt tagtatattt tacaatggag attaacgctc tataccgttc   3780
tatgtttatt gattcagatg atgttttaga aagaaagtt attgaatatg aaaactttaa    3840
tgaagatgaa gatgacgacg atgattattg ttgtaaatct gttttagatg aagaagatga   3900
cgcgctaaag tatactatgg ttacaaagta taagtctata ctactaatgg cgacttgtgc   3960
aagaaggtat agtatagtga aaatgttgtt agattatgat tatgaaaaac caaataaatc   4020
agatccatat ctaaaggtat ctcctttgca cataatttca tctattccta gtttagaata   4080
cctgcagcca agcttggcac tggccgtcgt tttacaacgt cgtgactggg aaaaccctgg   4140
```

<210> SEQ ID NO 7
<211> LENGTH: 6700
<212> TYPE: DNA
<213> ORGANISM: artificial sequence
<220> FEATURE:
<223> OTHER INFORMATION: pCXL1557.1 plasmid entire sequence

<400> SEQUENCE: 7

```
acatatagcc gtatcaaata aaaatttaac aatggttaaa cttctattga acaaaggtgc      60
tgatactgac ttgctggata acatgggacg tactcctta atgatcgctg tacaatctgg     120
aaatattgaa atatgtagca cactacttaa aaaaaataaa atgtccagaa ctgggaaaaa     180
ttgatcttgc cagctgtaat tcatggtaga aaagaagtgc tcaggctact tttcaacaaa     240
ggagcagatg taaactacat cttttgaaaga aatggaaaat catatactgt tttggaattg    300
attaaagaaa gttactctga gacacaaaag aggtagctga agtggtactc tcaaaggtac    360
gtgactaatt agctataaaa aggatccggg ttaattaatt agtcatcagg cagggcgaga    420
acgagactat ctgctcgtta attaattaga gcttctttat tctatactta aaaagtgaaa    480
ataaatacaa aggttcttga gggttgtgtt aaattgaaag cgagaaataa tcataaatta    540
tttcattatc gcgatatccg ttaagtttgt atcgtaatgc tgagctacca ggacaaagtg    600
ggcgccttct acaaggacaa cgccaggggc aatagcagca agctgagcct ggtgaccgag    660
gagcagggcg gcaggagacc ccctacctg ctgttcgtgc tgctgatcct tcttgtgggc    720
atcatgaccc tgctggccat caccggagtg agattccacc aggtgtccac ctccaacatg    780
gagttcagcc ggctgctgaa agaggacatg gagaagagcg aggccgtgca ccaccaggtg    840
atcgatgtgc tgaccccct gttcaagatc atcggcgacg aagtgggcct gagactgccc    900
cagaagctga acgagatcaa gcagttcatc ctgcagaaaa ccaacttctt caaccccaac    960
cgggagttcg acttcagaga cctgcactgg tgcatcaacc ccccagcaa gatcaaagtg   1020 aacttcacca actactgcga caccatcggc atcaggaaga catcgccag cgccgtgaat   1080 cccatcctgc tgagcgccct gagcggcggc agaggcgaca tcttccccc ctacagatgc   1140 agcggcgcca ccacctctgt gggcagagtg ttccctctga gcgtgccct gagcatgagc   1200 ctgatcagca agaccagcga gatcaccaac atgctgaccg ccatcagcga cggcgtgtac   1260
```

-continued

```
ggcaagacct atctgctggt gcccgactac atcgagggcg agttcgacac ccagaagatc    1320
cgcgtgttcg agatcggctt catcaagcgg tggctgaaca acatgcccct gctgcagacc    1380
accaactaca tggtgctgcc cgagaacagc aaggccaaag tgtgcaccat cgctgtgggc    1440
gagctgaccc tggccagcct gtgcgtggac gagagcaccg tgctgctgta ccacgacagc    1500
aacggcagcc aggacggcat cctggtggtg accctgggca tcttcggcgc caccctatg    1560
gaccaggtgg aggaagtgat ccccgtggcc caccccagcg tggagaagat ccacatcacc    1620
aaccaccggg gctttatcaa ggacagcatc gccacctgga tggtgcccgc cctggtgtct    1680
gagaagcagg aggagcagaa gaactgcctg gagagcgcct gccagagaaa gacctacccc    1740
atgtgcaacc agaccagctg ggagcccttt ggcggcggac agctgcccag ctacggcaga    1800
ctgaccctga gcctggaccc tagcatcgac ctgcagctga acatcagctt cacctacggc    1860
cccgtgatcc tgaacggcga cggcatggat tactacggca gcagcctgag cgacagcggc    1920
tggctgacca tccctcccaa gaacggcaca gtgctgggcc tgatcaacaa ggcctccagg    1980
ggcgaccagt tcaccgtgat ccctcacgtg ctgaccttcg cccccagaga gagcagcggc    2040
aactgctacc tgcctatcca gacctcccag atcatggaca aggacgtgct gacagagagc    2100
aacctggtgg tgctgcctac ccagaacttc cggtacgtga tcgccaccta cgacatcagc    2160
agaggcgatc acgccatcgt gtactacgtg tacgacccca tccggaccat cagctacaca    2220
tacccctcc ggctgaccac caagggcaga cccgacttcc tgcggatcga gtgctttgtg    2280
tgggacgacg acctgtggtg ccaccagttc tacagattcg aggccgacat caccaatagc    2340
accacctccg tggagaacct tgtgaggatc cggttcagct gcgacagaag caagccctga    2400
tagctcgagt ctagaatcga tcccgggttt ttatgactag ttaatcacgg ccgcttataa    2460
agatctaaaa tgcataattt ctaaataatg aaaaaaagta catcatgagc aacgcgttag    2520
tatattttac aatggagatt aacgctctat accgttctat gtttattgat tcagatgatg    2580
ttttagaaaa gaaagttatt gaatatgaaa actttaatga agatgaagat gacgacgatg    2640
attattgttg taaatctgtt ttagatgaag aagatgacgc gctaaagtat actatggtta    2700
caaagtataa gtctatacta ctaatggcga cttgtgcaag aaggtatagt atagtgaaaa    2760
tgttgttaga ttatgattat gaaaaaccaa ataaatcaga tccatatcta aaggtatctc    2820
ctttgcacat aatttcatct attcctagtt tagaatacct gcagccaagc ttggcactgg    2880
ccgtcgtttt acaacgtcgt gactgggaaa accctggcgt tacccaactt aatcgccttg    2940
cagcacatcc cccttcgcc agctggcgta atagcgaaga ggcccgcacc gatcgccctt    3000
cccaacagtt gcgcagcctg aatggcgaat ggcgcctgat gcggtatttt ctccttacgc    3060
atctgtgcgg tatttcacac cgcatatggt gcactctcag tacaatctgc tctgatgccg    3120
catagttaag ccagccccga cacccgccaa cacccgctga cgcgccctga cgggcttgtc    3180
tgctcccggc atccgcttac agacaagctg tgaccgtctc cgggagctgc atgtgtcaga    3240
ggttttcacc gtcatcaccg aaacgcgcga acgaaaggg cctcgtgata cgcctatttt    3300
tataggttaa tgtcatgata taatggttt cttagacgtc aggtggcact tttcggggaa    3360
atgtgcgcg aaccctatt tgtttatttt tctaaataca ttcaaatatg tatccgctca    3420
tgagacaata accctgataa atgcttcaat aatattgaaa aaggaagagt atgagtattc    3480
aacatttccg tgtcgccctt attcctttt ttgcggcatt ttgccttcct gttttttgctc    3540
acccagaaac gctggtgaaa gtaaaagatg ctgaagatca gttgggtgca cgagtgggtt    3600
acatcgaact ggatctcaac agcggtaaga tccttgagag ttttcgcccc gaagaacgtt    3660
```

```
ttccaatgat gagcactttt aaagttctgc tatgtggcgc ggtattatcc cgtattgacg    3720
ccgggcaaga gcaactcggt cgccgcatac actattctca gaatgacttg gttgagtact    3780
caccagtcac agaaaagcat cttacggatg gcatgacagt aagagaatta tgcagtgctg    3840
ccataaccat gagtgataac actgcggcca acttacttct gacaacgatc ggaggaccga    3900
aggagctaac cgcttttttg cacaacatgg gggatcatgt aactcgcctt gatcgttggg    3960
aaccggagct gaatgaagcc ataccaaacg acgagcgtga caccacgatg cctgtagcaa    4020
tggcaacaac gttgcgcaaa ctattaactg gcgaactact tactctagct tcccggcaac    4080
aattaataga ctggatggag gcggataaag ttgcaggacc acttctgcgc tcggcccttc    4140
cggctggctg gtttattgct gataaatctg gagccggtga gcgtgggtct cgcggtatca    4200
ttgcagcact ggggccagat ggtaagccct cccgtatcgt agttatctac acgacgggga    4260
gtcaggcaac tatggatgaa cgaaatagac agatcgctga taggtgcc tcactgatta    4320 agcattggta actgtcagac caagtttact catatatact ttagattgat ttaaaacttc    4380 attttaatt taaaaggatc taggtgaaga tccttttga taatctcatg accaaaatcc    4440
cttaacgtga gttttcgttc cactgagcgt cagaccccgt agaaaagatc aaaggatctt    4500
cttgagatcc ttttttctg cgcgtaatct gctgcttgca acaaaaaaa ccaccgctac    4560 cagcggtggt ttgtttgccg gatcaagagc taccaactct ttttccgaag gtaactggct    4620
tcagcagagc gcagatacca atactgtcc ttctagtgta gccgtagtta ggccaccact    4680
tcaagaactc tgtagcaccg cctacatacc tcgctctgct aatcctgtta ccagtggctg    4740
ctgccagtgg cgataagtcg tgtcttaccg ggttggactc aagacgatag ttaccggata    4800
aggcgcagcg gtcgggctga acggggggtt cgtgcacaca gcccagcttg gagcgaacga    4860
cctacaccga actgagatac ctacagcgtg agctatgaga aagcgccacg cttcccgaag    4920
ggagaaaggc ggacaggtat ccggtaagcg cagggtcgg aacaggagag cgcacgaggg    4980
agcttccagg gggaaacgcc tggtatcttt atagtcctgt cgggtttcgc cacctctgac    5040
ttgagcgtcg attttgtga tgctcgtcag ggggcggag cctatggaaa acgccagca    5100 acgcggcctt tttacggttc ctggcctttt gctggccttt tgctcacatg ttctttcctg    5160
cgttatcccc tgattctgtg gataaccgta ttaccgcctt tgagtgagct gataccgctc    5220
gccgcagccg aacgaccgag cgcagcgagt cagtgagcga ggaagcggaa gagcgcccaa    5280
tacgcaaacc gcctctcccc gcgcgttggc cgattcatta atgcagctgg cacgacaggt    5340
ttcccgactg gaaagcgggc agtgagcgca acgcaattaa tgtgagttag ctcactcatt    5400
aggcacccca ggctttacac tttatgcttc cggctcgtat gttgtgtgga attgtgagcg    5460
gataacaatt tcacacagga aacagctatg accatgatta cgaattgcgg ccgcaattct    5520
gaatgttaaa tgttatactt tggatgaagc tataaatatg cattggaaaa ataatccatt    5580
taaagaaagg attcaaatac tacaaaacct aagcgataat atgttaacta agcttattct    5640
taacgacgct ttaaatatac acaaataaac ataattttg tataacctaa caaataacta    5700
aaacataaaa ataataaaag gaatgtaat atcgtaatta ttttactcag gaatggggtt    5760
aaatatttat atcacgtgta tatctatact gttatcgtat actctttaca attactatta    5820
cgaatatgca agagataata agattacgta tttaagagaa tcttgtcatg ataattgggt    5880
acgacatagt gataaatgct atttcgcatc gttacataaa gtcagttgga aagatggatt    5940
tgacagatgt aacttaatag gtgcaaaaat gttaaataac agcattctat cggaagatag    6000
```

| | |
|---|---|
| gataccagtt atattataca aaaatcactg gttggataaa acagattctg caatattcgt | 6060 |
| aaaagatgaa gattactgcg aatttgtaaa ctatgacaat aaaaagccat ttatctcaac | 6120 |
| gacatcgtgt aattcttcca tgttttatgt atgtgtttca gatattatga gattactata | 6180 |
| aacttttgt atacttatat tccgtaaact atattaatca tgaagaaaat gaaaagtat | 6240 |
| agaagctgtt cacgagcggt tgttgaaaac aacaaaatta tacattcaag atggcttaca | 6300 |
| tatacgtctg tgaggctatc atggataatg acaatgcatc tctaaatagg ttttttggaca | 6360 |
| atggattcga ccctaacacg gaatatggta ctctacaatc tcctcttgaa atggctgtaa | 6420 |
| tgttcaagaa taccgaggct ataaaaatct tgatgaggta tggagctaaa cctgtagtta | 6480 |
| ctgaatgcac aacttcttgt ctgcatgatg cggtgttgag agacgactac aaaatagtga | 6540 |
| aagatctgtt gaagaataac tatgtaaaca atgttcttta cagcggaggc tttactcctt | 6600 |
| tgtgtttggc agcttacctt aacaaagtta atttggttaa acttctattg gctcattcgg | 6660 |
| cggatgtaga tatttcaaac acggatcggt taactcctct | 6700 |

<210> SEQ ID NO 8
<211> LENGTH: 4193
<212> TYPE: DNA
<213> ORGANISM: artificial sequence
<220> FEATURE:
<223> OTHER INFORMATION: pJSY2218.1 seq containing arms and insert

<400> SEQUENCE: 8

| | |
|---|---|
| ctttatacta ctgggttaca acagctggtg ataacagaat gtaaatcatt attacttaat | 60 |
| agttccatta ttatatgttt gatatctata ggtaacctac ctattattcc tagattctta | 120 |
| ctctctttta cagctttaac tattagctga tgtctatgaa agctaatga tttattttc | 180 |
| cgtattaatt ccctatatat acgtatacat gcaggtatct tattaactct aggattagtt | 240 |
| acgaactta ccataagatc tatgttattg tcaagaaaga tattaaaaga atatatagaa | 300 |
| tttaacttta tatgtgttat aacatctagt tcttttttcgc atgattcttt tatagatagt | 360 |
| agtcttttat tactgtttat atgttccatg tttactataa aaccttctga attagctatt | 420 |
| tcaggatttt tagatatttc taacatcatt ttagatatta tcataatagc tatcttgtca | 480 |
| tctaaaaagc taacacaagt tagaggcgta ttaccgtgat tatttagaga attatagtcg | 540 |
| gcgttataag ataaaagtaa ttttatatta ttaaaactat tagataacat agctttatgt | 600 |
| aaggagtat ttccagataa cttagcttta gcatttacgt aagcaccgtg gtcaagtaag | 660 |
| agtttaacaa attctgtttt catagaacta actgccatgt atagaggagt gaaaccttta | 720 |
| tgattataga cgtttacata gcaaccatat aataagatcg cattcagtat attaatatct | 780 |
| ttcatttcta tagctatgtg aataacatgt ttatctaatc ctaccaactt tgtatcagta | 840 |
| ccgtacttca gtaataagtt tactatagtt ttgtttttag atgcaacagc tatatttaga | 900 |
| acggtatcta tatgattatt aaccacatta acattagatc ctctttctaa aagtgtcttt | 960 |
| gttgtttcga tatcgttacg tgaaacagcg taatgtaagg gactgcccat acagtcatct | 1020 |
| attacgttta tcagctccc tagatttaac agaagtgctg ttacatcttt tcttctatta | 1080 |
| attaccgaat gatgtaatgg ggttttacct aaatcatctt gttcgtttat aggcactccg | 1140 |
| tgatttataa gtaacgctat tatatcgtaa ctacaattat ttttaagtgc ctttatgaga | 1200 |
| tactgtttat gcaaaaataa acttttatct attttaatac tattatctaa caatatccta | 1260 |
| attaaatcta tattcttata ctttatagcg taatgtaacg gagttcaaaa atttctagtt | 1320 |
| tgtatattaa gatcaatatt aaaatctata aatattttat acatatcatc agatatctta | 1380 |

```
tcatacagta catcgtaata atttagaaag aatctattac aattaacacc ttttttaat      1440 aaatatctag ttaatgactt attgtttcta tatacagaaa tatataacgg actatttcca     1500
gaatgtatct gttctatgtc agcgccagaa tctattagta gtttagcaat ttctgtatta    1560
tctaaactag cagctttatg aagaggagga ttttacatt ttaaaatatc ggcaccgtgt     1620
tctagtaata atttaccat ttctatatca gaaatactta cggctaaata caaagacgtt     1680
gatagtatat ttacgttatt gtatttgcat tttttaagta tataccttac taaatttata   1740
tctctatacc ttatagcttt atgcagttca tttataagtc ttccattact catttctggt    1800
aatgaagtat tatatatcat tatgatatta tctctatttt attctaataa aaaccgttat    1860
catgttattt attatttgtt ataattatac tatttaataa attataccaa atacttagat    1920
acttattaat accatcctag aacttgtatt tcttgccccc taaacttgga catgcactcc    1980
attaggcgtt tcttgttttc gacatcgtcc tccttaacat atcctactgt tatgtgagga   2040
ttccacggat tatctactgt gatatcacca aacacgtcct tcgaacaggg taccgcattc    2100
agcagaacat ttcttagggc tctaagttca tcagatacct ccagtttcat aactacagcg    2160
catcctttcg ctcccaactg tttagaggcg ttactctgag gaaaacacat ctcttcttta   2220
cagactatag aaatagtctg taaatcttga tcagttattt gctttttgaa attttcaaat    2280
ctatcacatt gatccatatt tgctattcca agagttatat gaggaaaaat atcacatcct    2340
gtcatgtatt ttattgtaac attattataa tctgtaacat cagtatctaa cctaacgtcg    2400
taaaagttaa cagatgccca gttactataa tcccaaggaa ccttaacatc taatcccatt    2460
aaaatagtat cctttctact attttttca ttggcaagta tgtggcttag tttacacaaa     2520
attcctgcca ttttgtaacg atagcgaagc aatagcttgt atgcttttta tttgattaac    2580
taggggttaa ttaattagtc atcaggcagg gcgagaacga gactatctgc tcgttaatta    2640
attagagctt cttattcta tacttaaaaa gtgaaaataa atacaaaggt tcttgagggt    2700
tgtgttaaat tgaaagcgag aaataatcat aaattatttc attatcgcga tatccgttaa   2760
gtttgtatcg taatgtggct gcagaacctg ctgttcctgg gcaccgtggt gtgcagcatc    2820
agcgccccca ccagatcccc caccctggtg acccggccca gccagcacgt ggacgccatc    2880
caggaagccc tgagcctgct gaacaacagc aacgacgtga ccgccgtgat gaacaaggcc   2940
gtgaaggtgg tgtccgaggt gttcgacccc gagggcccca cctgcctgga aacccggctg   3000
cagctgtaca agagggcct gcagggcagc ctgaccagcc tgaagaaccc cctgaccatg    3060
atggccaacc actacaagca gcactgcccc cccaccccg agagcccttg cgccacccag    3120
aacatcaact tcaagagctt caaagagaac ctgaaggact tcctgttcaa catcccttc     3180 gactgctgga agcccgtgaa gaagtgatga ctcgagttt tattgactag ggttttttat    3240
agctaattag tcaaatgtga gttaatatta gtatactaca ttactaattt attacatatt    3300
catttatatc aatctagtag catttagctt ttataaaaca atataactga atagtacata   3360
ctttactaat aagttataaa taagagatac atatttatag tattttactt tctacactga    3420
atataataat ataattatac aaatataatt tttaatacta tatagtatat aactgaaata    3480
aaataccagt gtaatatagt tattatacat ttataccaca tcaaagatga gttataacat   3540
cagtgtcact gttagcaaca gtagttatac gatgagtagt tactctcgta tggcgttagt    3600
atgtatgtat cttctagttt tcttagtagg cattatagga aacgtcaagc ttataaggtt    3660
attaatggta tctagaaata tatctattat accgtttctc aacttgggaa tagccgattt    3720
```

```
gctgtttgtg atattcatac ctttatacat tatatacata ctaagtaatt tccattggca    3780
ttttggtaaa gcactttgta aaattagttc tttctttttt acttctaaca tgtttgcaag    3840
tatattttta ataactgtaa taagcgtata tagatatgta aaaattaccc ttcctggatt    3900
tacctataaa tatgttaaca ttagaaatat gtacattact atattttca tatggattat     3960 ttctattata ctagggattc ctgctcttta ctttagaaat actatcgtaa caaaaataa     4020 cgacacgctg tgtattaatc attatcatga taatagagaa attgctgaat tgatttacaa    4080
agttattatc tgtatcagat ttattttagg atacctacta cctacgataa ttatactcgt    4140
atgctatacg ttactgatct acagaactaa caatgcatgt cgacgcggcc gca           4193

<210> SEQ ID NO 9
<211> LENGTH: 6842
<212> TYPE: DNA
<213> ORGANISM: artificial sequence
<220> FEATURE:
<223> OTHER INFORMATION: pJSY2218.1 entire plasmid sequence

<400> SEQUENCE: 9
tgcggccgcg tcgacatgca ttgttagttc tgtagatcag taacgtatag catacgagta      60
taattatcgt aggtagtagg tatcctaaaa taaatctgat acagataata actttgtaaa     120
tcaattcagc aatttctcta ttatcatgat aatgattaat acacagcgtg tcgttatttt     180
ttgttacgat agtatttcta aagtaaagag caggaatccc tagtataata gaataatcc      240 atatgaaaaa tatagtaatg tacatatttc taatgttaac atatttatag gtaaatccag     300
gaagggtaat ttttacatat ctatatacgc ttattacagt tattaaaaat atacttgcaa     360
acatgttaga agtaaaaaag aaagaactaa ttttacaaag tgctttacca aaatgccaat     420
ggaaattact tagtatgtat ataatgtata aaggtatgaa atcacaaaac agcaaatcgg     480
ctattcccaa gttgagaaac ggtataatag atatatttct agataccatt aataacctta     540
taagcttgac gttcctata atgcctacta agaaaactag aagatacata catactaacg     600
ccatacgaga gtaactactc atcgtataac tactgttgct aacagtgaca ctgatgttat     660
aactcatctt tgatgtggta taatgtata ataactatat tacactggta tttttatttca    720 gttatatact atatagtatt aaaaattata tttgtataat tatattatta tattcagtgt     780
agaaagtaaa atactataaa tatgtatctc ttatttataa cttattagta aagtatgtac     840
tattcagtta tattgtttta taaagctaa atgctactag attgatataa atgaatatgt      900
aataaattag taatgtagta tactaatatt aactcacatt tgactaatta gctataaaaa     960
cccctagtca ataaaaactc gagtcatcac ttcttcacgg gcttccagca gtcgaagggg    1020
atgttgaaca ggaagtcctt caggttctct ttgaagctct tgaagttgat gttctgggtg    1080
gcgcaagggc tctcggggt gggggggcag tgctgcttgt agtggttggc catcatggtc     1140
agggggttct tcaggctggt caggctgccc tgcaggccct ctttgtacag ctgcagccgg    1200
gtttccaggc aggtggggcc ctcggggtcg aacacctcgg acaccacctt cacggccttg    1260
ttcatcacgg cggtcacgtc gttgctgttg ttcagcaggc tcagggcttc ctggatggcg    1320
tccacgtgct ggctgggccg ggtcaccagg gtggggatc tggtggggc gctgatgctg      1380 cacaccacgg tgcccaggaa cagcaggttc tgcagccaca ttacgataca aacttaacgg    1440
atatcgcgat aatgaaataa tttatgatta tttctcgctt tcaatttaac acaaccctca    1500
agaacctttg tatttatttt cacttttaa gtatagaata aagaagctct aattaattaa     1560
cgagcagata gtctcgttct cgccctgcct gatgactaat taattaaccc ctagttaatc    1620
```

```
aaataaaaag catacaagct attgcttcgc tatcgttaca aaatggcagg aattttgtgt    1680
aaactaagcc acatacttgc caatgaaaaa aatagtagaa aggatactat tttaatggga    1740
ttagatgtta aggttccttg ggattatagt aactgggcat ctgttaactt ttacgacgtt    1800
aggttagata ctgatgttac agattataat aatgttacaa taaaatacat gacaggatgt    1860 gatattttc ctcatataac tcttggaata gcaaatatgg atcaatgtga tagatttgaa     1920
aatttcaaaa agcaaataac tgatcaagat ttacagacta tttctatagt ctgtaaagaa    1980
gagatgtgtt ttcctcagag taacgcctct aaacagttgg gagcgaaagg atgcgctgta    2040
gttatgaaac tggaggtatc tgatgaactt agagccctaa gaaatgttct gctgaatgcg    2100
gtaccctgtt cgaaggacgt gtttggtgat atcacagtag ataatccgtg gaatcctcac    2160
ataacagtag gatatgttaa ggaggacgat gtcgaaaaca agaaacgcct aatggagtgc    2220
atgtccaagt ttaggggggca agaaatacaa gttctaggat ggtattaata agtatctaag    2280
tatttggtat aatttattaa atagtataat tataacaaat aataaataac atgataacgg    2340 ttttttattag aataaaatag agataatatc ataatgatat ataatacttc attaccagaa    2400
atgagtaatg gaagacttat aaatgaactg cataaagcta taaggtatag agatataaat    2460
ttagtaaggt atatacttaa aaaatgcaaa tacaataacg taaatatact atcaacgtct    2520
ttgtatttag ccgtaagtat ttctgatata gaaatggtaa aattattact agaacacggt    2580
gccgatattt taaaatgtaa aaatcctcct cttcataaag ctgctagttt agataataca    2640
gaaattgcta aactactaat agattctggc gctgacatag aacagataca ttctggaaat    2700
agtccgttat atatttctgt atatagaaac aataagtcat taactagata tttattaaaa    2760
aaaggtgtta attgtaatag attctttcta aattattacg atgtactgta tgataagata    2820
tctgatgata tgtataaaat atttatagat tttaatattg atcttaatat acaaactaga    2880
aattttgaaa ctccgttaca ttacgctata aagtataaga atagatttt aattaggata     2940 ttgttagata atagtattaa aatagataaa agtttatttt tgcataaaca gtatctcata    3000
aaggcactta aaaataattg tagttacgat ataatagcgt tacttataaa tcacggagtg    3060
cctataaacg aacaagatga tttaggtaaa acccccattac atcattcggt aattaataga    3120
agaaaagatg taacagcact tctgttaaat ctaggagctg atataaacgt aatagatgac    3180
tgtatgggca gtcccttaca ttacgctgtt tcacgtaacg atatcgaaac aacaaagaca    3240
cttttagaaa gaggatctaa tgttaatgtg gttaataatc atatagatac cgttctaaat    3300
atagctgttg catctaaaaa caaaactata gtaaacttat tactgaagta cggtactgat    3360
acaaagttgg taggattaga taaacatgtt attcacatag ctatagaaat gaaagatatt    3420
aatatactga atgcgatctt attatatggt tgctatgtaa acgtctataa tcataaaggt    3480
ttcactcctc tatacatggc agttagttct atgaaaacag aatttgttaa actcttactt    3540
gaccacggtg cttacgtaaa tgctaaagct aagttatctg gaaatactcc tttacataaa    3600
gctatgttat ctaatagttt taataatata aaattacttt tatcttataa cgccgactat    3660
aattctctaa ataatcacgg taatacgcct ctaacttgtg ttagcttttt agatgacaag    3720
atagctatta tgataatatc taaaatgatg ttagaaatat ctaaaatcc tgaaatagct     3780 aattcagaag gttttatagt aaacatggaa catataaaca gtaataaaag actactatct    3840 ataaagaat catgcgaaaa agaactagat gttataacac atataaagtt aaattctata    3900
tattctttta atatctttct tgacaataac atagatctta tggtaaagtt cgtaactaat    3960
```

```
cctagagtta ataagatacc tgcatgtata cgtatatata gggaattaat acggaaaaat    4020
aaatcattag cttttcatag acatcagcta atagttaaag ctgtaaaaga gagtaagaat    4080
ctaggaataa taggtaggtt acctatagat atcaaacata taataatgga actattaagt    4140
aataatgatt tacattctgt tatcaccagc tgttgtaacc cagtagtata aagagctcga    4200
attaattcac tggccgtcgt tttacaacgt cgtgactggg aaaaccctgg cgttacccaa    4260
cttaatcgcc ttgcagcaca tccccctttc gccagctggc gtaatagcga agaggcccgc    4320
accgatcgcc cttcccaaca gttgcgcagc ctgaatggcg aatggcgcct gatgcggtat    4380
tttctcctta cgcatctgtg cggtatttca caccgcatat ggtgcactct cagtacaatc    4440
tgctctgatg ccgcatagtt aagccagccc cgacacccgc caacacccgc tgacgcgccc    4500
tgacgggctt gtctgctccc ggcatccgct tacagacaag ctgtgaccgt ctccgggagc    4560
tgcatgtgtc agaggttttc accgtcatca ccgaaacgcg cgagacgaaa gggcctcgtg    4620
atacgcctat ttttataggt taatgtcatg ataataatgg tttcttagac gtcaggtggc    4680
acttttcggg gaaatgtgcg cggaacccct atttgtttat ttttctaaat acattcaaat    4740
atgtatccgc tcatgagaca ataaccctga taaatgcttc aataatattg aaaaaggaag    4800
agtatgagta ttcaacattt ccgtgtcgcc cttattccct tttttgcggc attttgcctt    4860 cctgttttg ctcacccaga aacgctggtg aaagtaaaag atgctgaaga tcagttgggt    4920
gcacgagtgg gttacatcga actggatctc aacagcggta agatccttga gttttcgc     4980 cccgaagaac gttttccaat gatgagcact tttaaagttc tgctatgtgg cgcggtatta    5040
tcccgtattg acgccgggca agagcaactc ggtcgccgca tacactattc tcagaatgac    5100
ttggttgagt actcaccagt cacagaaaag catcttacgg atggcatgac agtaagagaa    5160
ttatgcagtg ctgccataac catgagtgat aacactgcgg ccaacttact tctgacaacg    5220
atcggaggac cgaaggagct aaccgctttt ttgcacaaca tgggggatca tgtaactcgc    5280
cttgatcgtt gggaaccgga gctgaatgaa gccataccaa acgacgagcg tgacaccacg    5340
atgcctgtag caatggcaac aacgttgcgc aaactattaa ctggcgaact acttactcta    5400
gcttcccggc aacaattaat agactggatg gaggcggata agttgcagg accacttctg     5460 cgctcggccc ttccggctgg ctggtttatt gctgataaat ctggagccgg tgagcgtggg    5520
tctcgcggta tcattgcagc actggggcca gatggtaagc cctcccgtat cgtagttatc    5580
tacacgacgg ggagtcaggc aactatggat gaacgaaata gacagatcgc tgagataggt    5640
gcctcactga ttaagcattg gtaactgtca gaccaagttt actcatatat actttagatt    5700
gatttaaaac ttcattttta atttaaaagg atctaggtga agatcctttt tgataatctc    5760
atgaccaaaa tcccttaacg tgagttttcg ttccactgag cgtcagaccc cgtagaaaag    5820
atcaaaggat cttcttgaga tcctttttt ctgcgcgtaa tctgctgctt gcaaacaaaa    5880
aaaccaccgc taccagcggt ggtttgtttg ccggatcaag agctaccaac tcttttccg    5940 aaggtaactg gcttcagcag agcgcagata ccaaatactg tccttctagt gtagccgtag    6000
ttaggccacc acttcaagaa ctctgtagca ccgcctacat acctcgctct gctaatcctg    6060
ttaccagtgg ctgctgccag tggcgataag tcgtgtctta ccgggttgga ctcaagacga    6120
tagttaccgg ataaggcgca gcggtcgggc tgaacggggg gttcgtgcac acagcccagc    6180
ttggagcgaa cgacctacac cgaactgaga tacctacagc gtgagctatg agaaagcgcc    6240
acgcttcccg aagggagaaa ggcggacagg tatccggtaa gcggcagggt cggaacagga    6300
gagcgcacga gggagcttcc agggggaaac gcctggtatc tttatagtcc tgtcgggttt    6360
```

-continued

```
cgccacctct gacttgagcg tcgattttg tgatgctcgt caggggggcg gagcctatgg    6420
aaaaacgcca gcaacgcggc cttttttacgg ttcctggcct tttgctggcc ttttgctcac   6480
atgttctttc ctgcgttatc ccctgattct gtggataacc gtattaccgc ctttgagtga    6540
gctgataccg ctcgccgcag ccgaacgacc gagcgcagcg agtcagtgag cgaggaagcg   6600
gaagagcgcc caatacgcaa accgcctctc cccgcgcgtt ggccgattca ttaatgcagc   6660
tggcacgaca ggtttcccga ctggaaagcg ggcagtgagc gcaacgcaat taatgtgagt    6720
tagctcactc attaggcacc ccaggcttta cactttatgc ttccggctcg tatgttgtgt    6780
ggaattgtga gcggataaca atttcacaca ggaaacagct atgaccatga ttacgccaag   6840
ct                                                                    6842
```

<210> SEQ ID NO 10
<211> LENGTH: 24
<212> TYPE: DNA
<213> ORGANISM: artificial sequence
<220> FEATURE:
<223> OTHER INFORMATION: 13220CXL primer

<400> SEQUENCE: 10
aggtgtccac ctccaacatg gagt                                            24

<210> SEQ ID NO 11
<211> LENGTH: 24
<212> TYPE: DNA
<213> ORGANISM: artificial sequence
<220> FEATURE:
<223> OTHER INFORMATION: 13225CXL primer

<400> SEQUENCE: 11
gaactggtcg cccctggagg cctt                                            24

<210> SEQ ID NO 12
<211> LENGTH: 25
<212> TYPE: DNA
<213> ORGANISM: artificial sequence
<220> FEATURE:
<223> OTHER INFORMATION: 7931DC primer

<400> SEQUENCE: 12
gaatctgtta gttagttact tggat                                           25

<210> SEQ ID NO 13
<211> LENGTH: 25
<212> TYPE: DNA
<213> ORGANISM: artificial sequence
<220> FEATURE:
<223> OTHER INFORMATION: 7932DC primer

<400> SEQUENCE: 13
tgattatagc tattatcaca gactc                                           25

<210> SEQ ID NO 14
<211> LENGTH: 4279
<212> TYPE: DNA
<213> ORGANISM: artificial sequence
<220> FEATURE:
<223> OTHER INFORMATION: vCP2263 containing arms and insert
<220> FEATURE:
<221> NAME/KEY: misc_feature
<222> LOCATION: (126)..(1661)
<223> OTHER INFORMATION: this is the C5 arm region
<220> FEATURE:

```
<221> NAME/KEY: promoter
<222> LOCATION: (1759)..(1882)
<220> FEATURE:
<221> NAME/KEY: CDS
<222> LOCATION: (1883)..(3703)
<223> OTHER INFORMATION: this is the HA protein encoding region
<220> FEATURE:
<221> NAME/KEY: misc_feature
<222> LOCATION: (3760)..(4164)
<223> OTHER INFORMATION: this is the C5 arm region

<400> SEQUENCE: 14
```

| | | |
|---|---|---|
| gaatctgtta gttagttact tggataaatt aatcgagacg cgtgataaaa tgactatgta | 60 |
| ccgttattgc atgaacgata tttataaatat aggttctcgt aggagagaac tattgactat | 120 |
| ggcaatgaat gttaaatgtt atactttgga tgaagctata aatatgcatt ggaaaaataa | 180 |
| tccatttaaa gaaaggattc aaatactaca aaacctaagc gataatatgt taactaagct | 240 |
| tattcttaac gacgctttaa atatacacaa ataaacataa ttttgtata acctaacaaa | 300 |
| taactaaaac ataaaaataa taaaggaaa tgtaatatcg taattatttt actcaggaat | 360 |
| ggggttaaat atttatatca cgtgtatatc tatactgtta tcgtatactc tttacaatta | 420 |
| ctattacgaa tatgcaagag ataataagat tacgtattta agagaatctt gtcatgataa | 480 |
| ttgggtacga catagtgata aatgctattt cgcatcgtta cataaagtca gttggaaaga | 540 |
| tggatttgac agatgtaact taataggtgc aaaaatgtta ataacagca ttctatcgga | 600 |
| agataggata ccagttatat tatacaaaaa tcactggttg gataaaacag attctgcaat | 660 |
| attcgtaaaa gatgaagatt actgcgaatt tgtaaactat gacaataaaa agccatttat | 720 |
| ctcaacgaca tcgtgtaatt cttccatgtt ttatgtatgt gtttcagata ttatgagatt | 780 |
| actataaact ttttgtatac ttatattccg taaactatat taatcatgaa gaaaatgaaa | 840 |
| aagtatagaa gctgttcacg agcggttgtt gaaaacaaca aaattataca ttcaagatgg | 900 |
| cttacatata cgtctgtgag gctatcatgg ataatgacaa tgcatctcta aataggtttt | 960 |
| tggacaatgg attcgaccct aacacggaat atggtactct acaatctcct cttgaaatgg | 1020 |
| ctgtaatgtt caagaatacc gaggctataa aaatcttgat gaggtatgga gctaaacctg | 1080 |
| tagttactga atgcacaact tcttgtctgc atgatgcggt gttgagagac gactacaaaa | 1140 |
| tagtgaaaga tctgttgaag aataactatg taaacaatgt tctttacagc ggaggcttta | 1200 |
| ctcctttgtg tttggcagct taccttaaca agttaatttt ggttaaactt ctattggctc | 1260 |
| attcggcgga tgtagatatt tcaaacacgg atcggttaac tcctctacat atagccgtat | 1320 |
| caaataaaaa tttaacaatg gttaaacttc tattgaacaa aggtgctgat actgacttgc | 1380 |
| tggataacat gggacgtact cctttaatga tcgctgtaca atctggaaat attgaaatat | 1440 |
| gtagcacact acttaaaaaa aataaaatgt ccagaactgg gaaaaattga tcttgccagc | 1500 |
| tgtaattcat ggtagaaaag aagtgctcag gctactttc aacaaggag cagatgtaaa | 1560 |
| ctacatcttt gaaagaaatg gaaaatcata tactgttttg gaattgatta agaaagtta | 1620 |
| ctctgagaca caaaagaggt agctgaagtg gtactctcaa aggtacgtga ctaattagct | 1680 |
| ataaaaagga tccgggttaa ttaattagtc atcaggcagg gcgagaacga gactatctgc | 1740 |
| tcgttaatta attagagctt ctttattcta tacttaaaaa gtgaaaataa atacaaaggt | 1800 |
| tcttgagggt tgtgttaaat tgaaagcgag aaataatcat aaattatttc attatcgcga | 1860 |
| tatccgttaa gtttgtatcg taatgctgag ctaccaggaa aaagtgggcg ccttctacaa | 1920 |
| ggacaacgcc agggccaata gcagcaagct gagcctggtg accgaggagc agggcggcag | 1980 |

```
gagacccccc tacctgctgt tcgtgctgct gatccttctt gtgggcatca tgaccctgct   2040
ggccatcacc ggagtgagat tccaccaggt gtccacctcc aacatggagt tcagccggct   2100
gctgaaagag gacatggaga agagcgaggc cgtgcaccac caggtgatcg atgtgctgac   2160 cccctgttc aagatcatcg cgacgaagt gggcctgaga ctgccccaga agctgaacga    2220
gatcaagcag ttcatcctgc agaaaaccaa cttcttcaac cccaaccggg agttcgactt   2280
cagagacctg cactggtgca tcaacccccc cagcaagatc aaagtgaact tcaccaacta   2340
ctgcgacacc atcggcatca ggaagagcat cgccagcgcc gtgaatccca tcctgctgag   2400
cgccctgagc ggcggcagag cgacatcttc cccccctac agatgcagcg cgccaccac    2460 ctctgtgggc agagtgttcc ctctgagcgt gtccctgagc atgagcctga tcagcaagac   2520
cagcgagatc accaacatgc tgaccgccat cagcgacggc gtgtacggca agacctatct   2580
gctggtgccc gactacatcg agggcgagtt cgacacccag aagatccgcg tgttcgagat   2640
cggcttcatc aagcggtggc tgaacaacat gcccctgctg cagaccacca actacatggt   2700
gctgcccgag aacagcaagg ccaaagtgtg caccatcgct gtgggcgagc tgaccctggc   2760
cagcctgtgc gtggacgaga gcaccgtgct gctgtaccac gacagcaacg gcagccagga   2820
cggcatcctg gtggtgaccc tgggcatctt cggcgccacc cctatggacc aggtggagga   2880
agtgatcccc gtggcccacc ccagcgtgga agatccac atcaccaacc accggggctt    2940
tatcaaggac agcatcgcca cctggatggt gcccgccctg gtgtctgaga agcaggagga   3000
gcagaagaac tgcctggaga gcgcctgcca gagaaagacc tacccccatgt gcaaccagac   3060 cagctgggag ccctttggcg gcggacagct gcccagctac ggcagactga ccctgagcct   3120
ggaccctagc atcgacctgc agctgaacat cagcttcacc tacggccccg tgatcctgaa   3180
cggcgacggc atggattact acggcagcag cctgagcgac agcggctggc tgaccatccc   3240
tcccaagaac ggcacagtgc tgggcctgat caacaaggcc tccaggggcg accagttcac   3300
cgtgatccct cacgtgctga ccttcgcccc cagagagagc agcggcaact gctacctgcc   3360
tatccagacc tcccagatca tggacaagga cgtgctgaca gagagcaacc tggtggtgct   3420
gcctacccag aacttccggt acgtgatcgc cacctcgac atcagcagag gcgatcacgc    3480
catcgtgtac tacgtgtacg acccatccg gaccatcagc tacacatacc ccttccggct   3540
gaccaccaag ggcagacccg acttcctgcg gatcgagtgc tttgtgtggg acgacgacct   3600
gtggtgccac cagttctaca gattcgaggc cgacatcacc aatagcacca cctccgtgga   3660
gaaccttgtg aggatccggt tcagctgcga cagaagcaag ccctgatagc tcgagtctag   3720
aatcgatccc gggttttat gactagttaa tcacggccgc ttataaagat ctaaaatgca    3780
taatttctaa ataatgaaaa aaagtacatc atgagcaacg cgttagtata ttttacaatg   3840
gagattaacg ctctataccg ttctatgttt attgattcag atgatgtttt agaaaagaaa   3900
gttattgaat atgaaaactt taatgaagat gaagatgacg acgatgatta ttgttgtaaa   3960 tctgtttttag atgaagaaga tgacgcgcta aagtatacta tggttacaaa gtataagtct   4020
atactactaa tggcgacttg tgcaagaagg tatagtatag tgaaaatgtt gttagattat   4080
gattatgaaa aaccaaataa atcagatcca tatctaaagg tatctccttt gcacataatt   4140
tcatctattc ctagtttaga atactttca ttatatttgt ttacagctga agacgaaaaa    4200
aatatatcga taatagaaga ttatgttaac tctgctaata agatgaaatt gaatgagtct   4260 gtgataaatag ctataatca                                             4279
```

```
<210> SEQ ID NO 15
<211> LENGTH: 26
<212> TYPE: DNA
<213> ORGANISM: artificial sequence
<220> FEATURE:
<223> OTHER INFORMATION: 18071BK primer

<400> SEQUENCE: 15
gatgttgaac aggaagtcct tcaggt                                            26

<210> SEQ ID NO 16
<211> LENGTH: 26
<212> TYPE: DNA
<213> ORGANISM: artificial sequence
<220> FEATURE:
<223> OTHER INFORMATION: 18073BK primer

<400> SEQUENCE: 16
gttcctgggc accgtggtgt gcagca                                            26

<210> SEQ ID NO 17
<211> LENGTH: 30
<212> TYPE: DNA
<213> ORGANISM: artificial sequence
<220> FEATURE:
<223> OTHER INFORMATION: 8103JY primer

<400> SEQUENCE: 17
gaggcatcca acatataaag aagactaaag                                        30

<210> SEQ ID NO 18
<211> LENGTH: 27
<212> TYPE: DNA
<213> ORGANISM: artificial sequence
<220> FEATURE:
<223> OTHER INFORMATION: 8104JY primer

<400> SEQUENCE: 18
tagttaaata ctcataactc atatctg                                           27

<210> SEQ ID NO 19
<211> LENGTH: 4350
<212> TYPE: DNA
<213> ORGANISM: artificial sequence
<220> FEATURE:
<223> OTHER INFORMATION: part of vCP2391 containing C3L-canine
      GM-CSF-C3R
<220> FEATURE:
<221> NAME/KEY: misc_feature
<222> LOCATION: (72)..(2643)
<223> OTHER INFORMATION: this is the C3 arm region
<220> FEATURE:
<221> NAME/KEY: promoter
<222> LOCATION: (2658)..(2843)
<220> FEATURE:
<221> NAME/KEY: CDS
<222> LOCATION: (2844)..(3281)
<223> OTHER INFORMATION: this is the GM_CSF coding region
<220> FEATURE:
<221> NAME/KEY: misc_feature
<222> LOCATION: (3323)..(4249)
<223> OTHER INFORMATION: this is the C3 arm region

<400> SEQUENCE: 19
ctttagttaa atactcataa ctcatatctg ttaacaaatt taatgtttat cttcgtaatt       60
gaataaaatc actttatact actgggttac aacagctggt gataacagaa tgtaaatcat      120
tattacttaa tagttccatt attatatgtt tgatatctat aggtaaccta cctattattc      180
```

```
ctagattctt actctctttt acagctttaa ctattagctg atgtctatga aaagctaatg      240 atttatttt ccgtattaat tccctatata tacgtataca tgcaggtatc ttattaactc       300
taggattagt tacgaacttt accataagat ctatgttatt gtcaagaaag atattaaaag      360
aatatataga atttaacttt atatgtgtta taacatctag ttcttttcg catgattctt       420 ttatagatag tagtcttta ttactgttta tatgttccat gtttactata aaaccttctg       480
aattagctat ttcaggattt ttagatattt ctaacatcat tttagatatt atcataatag      540
ctatcttgtc atctaaaaag ctaacacaag ttagaggcgt attaccgtga ttatttagag      600
aattatagtc ggcgttataa gataaaagta attttatatt attaaaacta ttagataaca      660
tagctttatg taaaggagta tttccagata acttagcttt agcatttacg taagcaccgt      720
ggtcaagtaa gagtttaaca aattctgttt tcatagaact aactgccatg tatagaggag      780
tgaaaccttt atgattatag acgtttacat agcaaccata taataagatc gcattcagta      840
tattaatatc tttcatttct atagctatgt gaataacatg tttatctaat cctaccaact      900
ttgtatcagt accgtacttc agtaataagt ttactatagt tttgttttta gatgcaacag      960
ctatatttag aacggtatct atatgattat taaccacatt aacattagat cctctttcta     1020
aaagtgtctt tgttgtttcg atatcgttac gtgaaacagc gtaatgtaag ggactgccca     1080
tacagtcatc tattacgttt atatcagctc ctagatttaa cagaagtgct gttacatctt     1140
ttcttctatt aattaccgaa tgatgtaatg gggtttacc taaatcatct tgttcgttta      1200
taggcactcc gtgatttata agtaacgcta ttatatcgta actacaatta ttttaagtg      1260 cctttatgag atactgttta tgcaaaaata aacttttatc tattttaata ctattatcta     1320
acaatatcct aattaaatct atattcttat actttatagc gtaatgtaac ggagtttcaa     1380
aatttctagt ttgtatatta agatcaatat taaaatctat aaatatttta tacatatcat     1440
cagatatctt atcatacagt acatcgtaat aatttagaaa gaatctatta caattaacac     1500 cttttttaa taaatatcta gttaatgact tattgtttct atatacagaa atatataacg     1560
gactatttcc agaatgtatc tgttctatgt cagcgccaga atctattagt agtttagcaa     1620
tttctgtatt atctaaacta gcagcttat gaagaggagg attttacat tttaaaatat      1680 cggcaccgtg ttctagtaat aatttttacca tttctatatc agaaatactt acggctaaat     1740
acaaagacgt tgatagtata tttacgttat tgtatttgca ttttttaagt atataccta     1800 ctaaatttat atctctatac cttatagctt tatgcagttc atttataagt cttccattac     1860
tcatttctgg taatgaagta ttatatatca ttatgatatt atctctatt tattctaata    1920 aaaaccgtta tcatgttatt tattatttgt tataattata ctatttaata aattataccca    1980 aatacttaga tacttattaa taccatccta gaacttgtat ttcttgcccc ctaaacttgg     2040
acatgcactc cattaggcgt ttcttgtttt cgacatcgtc ctccttaaca tatcctactg     2100
ttatgtgagg attccacgga ttatctactg tgatatcacc aaacacgtcc ttcgaacagg     2160
gtaccgcatt cagcagaaca tttcttaggg ctctaagttc atcagatacc tccagtttca     2220
taactacagc gcatcctttc gctcccaact gtttagaggc gttactctga ggaaaacaca     2280
tctcttcttt acagactata gaaatagtct gtaaatcttg atcagttatt tgcttttga    2340 aattttcaaa tctatcacat tgatccatat ttgctattcc aagagttata tgaggaaaaa    2400
tatcacatcc tgtcatgtat tttattgtaa cattattata atctgtaaca tcagtatcta    2460
acctaacgtc gtaaaagtta acagatgccc agttactata atcccaagga accttaacat    2520
ctaatcccat taaaatagta tcctttctac tattttttc attggcaagt atgtggctta     2580
```

-continued

```
gtttacacaa aattcctgcc attttgtaac gatagcgaag caatagcttg tatgctttt      2640 atttgattaa ctaggggtta attaattagt catcaggcag ggcgagaacg agactatctg      2700
ctcgttaatt aattagagct tctttattct atacttaaaa agtgaaaata aatacaaagg      2760
ttcttgaggg ttgtgttaaa ttgaaagcga gaaataatca taaattattt cattatcgcg      2820
atatccgtta agtttgtatc gtaatgtggc tgcagaacct gctgttcctg ggcaccgtgg      2880
tgtgcagcat cagcgccccc accagatccc cacccctggt gacccggccc agccagcacg      2940
tggacgccat ccaggaagcc ctgagcctgc tgaacaacag caacgacgtg accgccgtga      3000
tgaacaaggc cgtgaaggtg gtgtccgagg tgttcgaccc cgagggcccc acctgcctgg      3060
aaacccggct gcagctgtac aaagagggcc tgcagggcag cctgaccagc ctgaagaacc      3120
ccctgaccat gatggccaac cactacaagc agcactgccc ccccaccccc gagagccctt      3180
gcgccaccca gaacatcaac ttcaagagct tcaaagagaa cctgaaggac ttcctgttca      3240 acatccccctt cgactgctgg aagcccgtga agaagtgatg actcgagttt ttattgacta      3300 ggggtttta tagctaatta gtcaaatgtg agttaatatt agtatactac attactaatt      3360
tattacatat tcatttatat caatctagta gcatttagct tttataaaac aatataactg      3420
aatagtacat actttactaa taagttataa ataagagata catatttata gtattttact      3480
ttctacactg aatataataa tataattata caaatataat ttttaatact atatagtata      3540
taactgaaat aaaataccag tgtaatatag ttattataca tttataccac atcaaagatg      3600
agttataaca tcagtgtcac tgttagcaac agtagttata cgatgagtag ttactctcgt      3660
atggcgttag tatgtatgta tcttctagtt ttcttagtag gcattatagg aaacgtcaag      3720
cttataaggt tattaatggt atctagaaat atatctatta taccgtttct caacttggga      3780
atagccgatt tgctgtttgt gatattcata cctttataca ttatatacat actaagtaat      3840
ttccattggc attttggtaa agcactttgt aaaattagtt ctttcttttt tacttctaac      3900
atgtttgcaa gtatatttt aataactgta ataagcgtat atagatatgt aaaaattacc      3960
cttcctggat ttacctataa atatgttaac attagaaata tgtacattac tatattttc      4020 atatggatta tttctattat actagggatt cctgctcttt actttagaaa tactatcgta      4080
acaaaaaata cgacacgct gtgtattaat cattatcatg ataatagaga aattgctgaa      4140
ttgatttaca aagttattat ctgtatcaga tttattttag gataccctact acctacgata      4200 attatactcg tatgctatac gttactgatc tacagaacta acaatgcatc taatatatct      4260
gataagatat tcttcataac agcttctaca gctttagtct tctttatatg ttggatgcct      4320
catcacataa ttaatgtaat atctcttttg                                       4350
```

<210> SEQ ID NO 20
<211> LENGTH: 607
<212> TYPE: PRT
<213> ORGANISM: artificial sequence
<220> FEATURE:
<223> OTHER INFORMATION: AAQ05828

<400> SEQUENCE: 20

```
Met Leu Ser Tyr Gln Asp Lys Val Gly Ala Phe Tyr Lys Asp Asn Ala
1               5                   10                  15

Arg Ala Asn Ser Ser Lys Leu Ser Leu Val Thr Glu Glu Gln Gly Gly
            20                  25                  30

Arg Arg Pro Pro Tyr Leu Leu Phe Val Leu Leu Ile Leu Leu Val Gly
        35                  40                  45
```

```
Ile Met Thr Leu Leu Ala Ile Thr Gly Val Arg Phe His Gln Val Ser
     50                  55                  60
Thr Ser Asn Met Glu Phe Ser Arg Leu Leu Lys Glu Asp Met Glu Lys
 65                  70                  75                  80
Ser Glu Ala Val His His Gln Val Ile Asp Val Leu Thr Pro Leu Phe
                     85                  90                  95
Lys Ile Ile Gly Asp Glu Val Gly Leu Arg Leu Pro Gln Lys Leu Asn
                100                 105                 110
Glu Ile Lys Gln Phe Ile Leu Gln Lys Thr Asn Phe Phe Asn Pro Asn
            115                 120                 125
Arg Glu Phe Asp Phe Arg Asp Leu His Trp Cys Ile Asn Pro Pro Ser
130                 135                 140
Lys Ile Lys Val Asn Phe Thr Asn Tyr Cys Asp Thr Ile Gly Ile Arg
145                 150                 155                 160
Lys Ser Ile Ala Ser Ala Val Asn Pro Ile Leu Leu Ser Ala Leu Ser
                165                 170                 175
Gly Gly Arg Gly Asp Ile Phe Pro Pro Tyr Arg Cys Ser Gly Ala Thr
                180                 185                 190
Thr Ser Val Gly Arg Val Phe Pro Leu Ser Val Ser Leu Ser Met Ser
                195                 200                 205
Leu Ile Ser Lys Thr Ser Glu Ile Thr Asn Met Leu Thr Ala Ile Ser
210                 215                 220
Asp Gly Val Tyr Gly Lys Thr Tyr Leu Leu Val Pro Asp Tyr Ile Glu
225                 230                 235                 240
Gly Glu Phe Asp Thr Gln Lys Ile Arg Val Phe Glu Ile Gly Phe Ile
                245                 250                 255
Lys Arg Trp Leu Asn Asn Met Pro Leu Leu Gln Thr Thr Asn Tyr Met
                260                 265                 270
Val Leu Pro Glu Asn Ser Lys Ala Lys Val Cys Thr Ile Ala Val Gly
                275                 280                 285
Glu Leu Thr Leu Ala Ser Leu Cys Val Asp Glu Ser Thr Val Leu Leu
290                 295                 300
Tyr His Asp Ser Asn Gly Ser Gln Asp Gly Ile Leu Val Val Thr Leu
305                 310                 315                 320
Gly Ile Phe Gly Ala Thr Pro Met Asp Gln Val Glu Glu Val Ile Pro
                325                 330                 335
Val Ala His Pro Ser Val Glu Lys Ile His Ile Thr Asn His Arg Gly
                340                 345                 350
Phe Ile Lys Asp Ser Ile Ala Thr Trp Met Val Pro Ala Leu Val Ser
                355                 360                 365
Glu Lys Gln Glu Glu Gln Lys Asn Cys Leu Glu Ser Ala Cys Gln Arg
370                 375                 380
Lys Thr Tyr Pro Met Cys Asn Gln Thr Ser Trp Glu Pro Phe Gly Gly
385                 390                 395                 400
Gly Gln Leu Pro Ser Tyr Gly Arg Leu Thr Leu Ser Leu Asp Pro Ser
                405                 410                 415
Ile Asp Leu Gln Leu Asn Ile Ser Phe Thr Tyr Gly Pro Val Ile Leu
                420                 425                 430
Asn Gly Asp Gly Met Asp Tyr Tyr Gly Ser Ser Leu Ser Asp Ser Gly
                435                 440                 445
Trp Leu Thr Ile Pro Pro Lys Asn Gly Thr Val Leu Gly Leu Ile Asn
450                 455                 460
```

```
Lys Ala Ser Arg Gly Asp Gln Phe Thr Val Ile Pro His Val Leu Thr
465                 470                 475                 480

Phe Ala Pro Arg Glu Ser Ser Gly Asn Cys Tyr Leu Pro Ile Gln Thr
                485                 490                 495

Ser Gln Ile Met Asp Lys Asp Val Leu Thr Glu Ser Asn Leu Val Val
            500                 505                 510

Leu Pro Thr Gln Asn Phe Arg Tyr Val Ile Ala Thr Tyr Asp Ile Ser
        515                 520                 525

Arg Gly Asp His Ala Ile Val Tyr Asp Val Tyr Asp Pro Ile Arg Thr
    530                 535                 540

Ile Ser Tyr Thr His Pro Phe Arg Leu Thr Thr Lys Gly Arg Pro Asp
545                 550                 555                 560

Phe Leu Arg Ile Glu Cys Phe Val Trp Asp Asp Asp Leu Trp Cys His
                565                 570                 575

Gln Phe Tyr Arg Phe Glu Ala Asp Ile Thr Asn Ser Thr Thr Ser Val
            580                 585                 590

Glu Asn Leu Val Arg Ile Arg Phe Ser Cys Asp Arg Ser Lys Pro
        595                 600                 605

<210> SEQ ID NO 21
<211> LENGTH: 607
<212> TYPE: PRT
<213> ORGANISM: artificial sequence
<220> FEATURE:
<223> OTHER INFORMATION: ABF55673

<400> SEQUENCE: 21

Met Leu Ser Tyr Gln Asp Lys Val Gly Ala Phe Tyr Lys Asp Asn Ala
1               5                   10                  15

Arg Ala Asn Ser Ser Lys Leu Ser Leu Val Thr Glu Glu Gln Gly Gly
                20                  25                  30

Arg Arg Pro Pro Tyr Leu Leu Phe Val Leu Leu Ile Leu Leu Val Gly
            35                  40                  45

Ile Met Thr Leu Leu Ala Ile Thr Gly Val Arg Phe His Gln Val Ser
50                  55                  60

Thr Ser Asn Met Glu Phe Ser Arg Leu Leu Lys Glu Asp Met Glu Lys
65                  70                  75                  80

Ser Glu Ala Val His His Gln Val Ile Asp Val Leu Thr Pro Leu Phe
                85                  90                  95

Lys Ile Ile Gly Asp Glu Val Gly Leu Arg Leu Pro Gln Lys Leu Asn
            100                 105                 110

Glu Ile Lys Gln Phe Ile Leu Gln Lys Thr Asn Phe Phe Asn Pro Asn
        115                 120                 125

Arg Glu Phe Asp Phe Arg Asp Leu His Trp Cys Ile Asn Pro Pro Ser
130                 135                 140

Lys Ile Lys Val Asn Phe Thr Asn Tyr Cys Asp Thr Ile Gly Ile Arg
145                 150                 155                 160

Lys Ser Ile Ala Ser Ala Ala Asn Pro Ile Leu Leu Ser Ala Leu Ser
                165                 170                 175

Gly Gly Arg Gly Asp Ile Phe Pro Pro Tyr Arg Cys Ser Gly Ala Thr
            180                 185                 190

Thr Ser Val Gly Arg Val Phe Pro Leu Ser Val Ser Leu Ser Met Ser
        195                 200                 205

Leu Ile Ser Lys Thr Ser Glu Ile Thr Asn Met Leu Thr Ala Ile Ser
210                 215                 220
```

Asp Gly Val Tyr Gly Lys Thr Tyr Leu Leu Val Pro Asp Tyr Ile Glu
225                 230                 235                 240

Gly Glu Phe Asp Thr Gln Lys Ile Arg Val Phe Glu Ile Gly Phe Ile
            245                 250                 255

Lys Arg Trp Leu Asn Asn Met Pro Leu Leu Gln Thr Thr Asn Tyr Met
            260                 265                 270

Val Leu Pro Glu Asn Ser Lys Ala Lys Val Cys Thr Ile Ala Val Gly
        275                 280                 285

Glu Leu Thr Leu Ala Ser Leu Cys Val Asp Glu Ser Thr Val Leu Leu
        290                 295                 300

Tyr His Asp Ser Asn Gly Ser Gln Asp Gly Ile Leu Val Val Thr Leu
305                 310                 315                 320

Gly Ile Phe Gly Ala Thr Pro Met Asp Gln Val Gly Glu Val Ile Pro
                325                 330                 335

Val Ala His Pro Ser Val Glu Lys Ile His Ile Thr Asn His Arg Gly
                340                 345                 350

Phe Ile Lys Asp Ser Ile Ala Thr Trp Met Val Pro Ala Leu Val Ser
                355                 360                 365

Glu Lys Gln Glu Glu Gln Lys Asn Cys Leu Glu Ser Ala Cys Gln Arg
370                 375                 380

Lys Thr Tyr Pro Met Cys Asn Gln Thr Ser Trp Glu Pro Phe Gly Gly
385                 390                 395                 400

Gly Gln Leu Pro Ser Tyr Gly Arg Leu Thr Leu Pro Leu Asp Pro Ser
                405                 410                 415

Ile Asp Pro Gln Leu Asn Ile Ser Phe Thr Tyr Gly Pro Val Ile Leu
                420                 425                 430

Asn Gly Asp Gly Met Asp Tyr Tyr Glu Ser Ser Leu Ser Asp Ser Gly
                435                 440                 445

Trp Leu Thr Ile Pro Pro Lys Asn Gly Thr Val Leu Gly Leu Ile Asn
450                 455                 460

Lys Ala Ser Arg Gly Asp Gln Phe Thr Val Ile Pro His Val Leu Thr
465                 470                 475                 480

Phe Ala Pro Arg Glu Ser Ser Gly Asn Cys Tyr Leu Pro Ile Gln Thr
                485                 490                 495

Ser Gln Ile Met Asp Lys Asp Val Leu Thr Glu Ser Asn Leu Val Val
                500                 505                 510

Leu Pro Thr Gln Asn Phe Arg Tyr Val Ile Ala Thr Tyr Asp Ile Ser
        515                 520                 525

Arg Gly Asp His Ala Ile Val Tyr Tyr Val Tyr Asp Pro Ile Arg Thr
530                 535                 540

Ile Ser Tyr Thr Tyr Pro Phe Arg Leu Thr Thr Lys Gly Arg Pro Asp
545                 550                 555                 560

Phe Leu Arg Ile Glu Cys Phe Val Trp Asp Asp Leu Trp Cys His
                565                 570                 575

Gln Phe Tyr Arg Phe Glu Ala Asp Ile Thr Asn Ser Thr Ser Val
        580                 585                 590

Glu Asn Leu Val Arg Ile Arg Phe Ser Cys Asn Arg Ser Lys Pro
        595                 600                 605

<210> SEQ ID NO 22
<211> LENGTH: 607
<212> TYPE: PRT
<213> ORGANISM: artificial sequence
<220> FEATURE:
<223> OTHER INFORMATION: CAA55672

<400> SEQUENCE: 22

```
Met Leu Ser Tyr Gln Asp Lys Val Gly Ala Phe Tyr Lys Asp Asn Ala
 1               5                  10                  15

Arg Ala Asn Ser Ser Lys Leu Ser Leu Val Thr Glu Glu Gln Gly Gly
             20                  25                  30

Arg Arg Pro Pro Tyr Leu Leu Phe Val Leu Leu Ile Leu Leu Val Gly
         35                  40                  45

Ile Met Thr Leu Leu Ala Ile Thr Gly Val Arg Phe His Gln Val Ser
     50                  55                  60

Thr Ser Asn Met Glu Phe Ser Arg Leu Leu Lys Glu Asp Met Glu Lys
 65                  70                  75                  80

Ser Glu Ala Val His His Gln Val Ile Asp Val Leu Thr Pro Leu Phe
                 85                  90                  95

Lys Ile Ile Gly Asp Glu Val Gly Leu Arg Leu Pro Gln Lys Leu Asn
            100                 105                 110

Glu Ile Lys Gln Phe Ile Leu Gln Lys Thr Asn Phe Phe Asn Pro Asn
        115                 120                 125

Arg Glu Phe Asp Phe Arg Asp Leu His Trp Cys Ile Asn Pro Pro Ser
    130                 135                 140

Lys Ile Lys Val Asn Phe Thr Asn Tyr Cys Asp Thr Ile Gly Ile Arg
145                 150                 155                 160

Lys Ser Ile Ala Ser Ala Ala Asn Pro Ile Leu Leu Ser Ala Leu Ser
                165                 170                 175

Gly Gly Arg Gly Asp Ile Phe Pro Pro Tyr Arg Cys Ser Gly Ala Thr
            180                 185                 190

Thr Ser Val Gly Arg Val Phe Pro Leu Ser Val Ser Leu Ser Met Ser
        195                 200                 205

Leu Ile Ser Lys Thr Ser Glu Ile Thr Asn Met Leu Thr Ala Ile Ser
    210                 215                 220

Asp Gly Val Tyr Gly Lys Thr Tyr Leu Leu Val Pro Asp Tyr Ile Glu
225                 230                 235                 240

Gly Glu Phe Asp Thr Gln Met Ile Arg Val Phe Glu Ile Gly Phe Ile
                245                 250                 255

Lys Arg Trp Leu Asn Asn Met Pro Leu Leu Gln Thr Thr Asn Tyr Met
            260                 265                 270

Val Leu Pro Glu Asn Ser Lys Ala Lys Val Cys Thr Ile Ala Val Gly
        275                 280                 285

Glu Leu Thr Leu Ala Ser Leu Cys Val Asp Glu Ser Thr Val Leu Leu
    290                 295                 300

Tyr His Asp Ser Asn Gly Ser Gln Asp Gly Ile Leu Val Val Thr Leu
305                 310                 315                 320

Gly Ile Phe Gly Ala Thr Pro Met Asp Gln Val Gly Glu Val Ile Pro
                325                 330                 335

Val Ala His Pro Ser Val Glu Lys Ile His Ile Thr Asn His Arg Gly
            340                 345                 350

Phe Ile Lys Asp Ser Ile Ala Thr Trp Met Val Pro Ala Leu Val Ser
        355                 360                 365

Glu Lys Gln Glu Glu Lys Asn Cys Leu Glu Ser Ala Cys Gln Arg
    370                 375                 380

Lys Thr Tyr Pro Met Cys Asn Gln Thr Ser Trp Glu Pro Phe Gly Gly
385                 390                 395                 400

Gly Gln Leu Pro Ser Tyr Gly Arg Leu Thr Leu Pro Leu Asp Pro Ser
```

```
                405              410              415
Ile Asp Pro Gln Leu Asn Ile Ser Phe Thr Tyr Gly Pro Val Ile Leu
            420              425              430

Asn Gly Asp Gly Met Asp Tyr Tyr Glu Ser Ser Leu Ser Asp Ser Gly
            435              440              445

Trp Leu Thr Ile Pro Pro Lys Asn Gly Thr Val Leu Gly Leu Ile Asn
        450              455              460

Lys Ala Ser Arg Gly Asp Gln Phe Thr Val Ile Pro His Val Leu Thr
465              470              475              480

Phe Ala Pro Arg Glu Ser Ser Gly Asn Cys Tyr Leu Pro Ile Gln Thr
                485              490              495

Ser Gln Ile Met Asp Lys Asp Val Leu Thr Glu Ser Asn Leu Val Val
            500              505              510

Leu Pro Thr Gln Asn Phe Arg Tyr Val Ile Ala Thr Tyr Asp Ile Ser
        515              520              525

Arg Gly Asp His Ala Ile Val Tyr Tyr Val Tyr Asp Pro Ile Arg Thr
530              535              540

Ile Ser Tyr Thr Tyr Pro Phe Arg Leu Thr Thr Lys Gly Arg Pro Asp
545              550              555              560

Phe Leu Arg Ile Glu Cys Phe Val Trp Asp Asp Leu Trp Cys His
                565              570              575

Gln Phe Tyr Arg Phe Glu Ala Asp Ile Thr Asn Ser Thr Ser Val
            580              585              590

Glu Asn Leu Val Arg Ile Arg Phe Ser Cys Asn Arg Ser Lys Pro
            595              600              605

<210> SEQ ID NO 23
<211> LENGTH: 607
<212> TYPE: PRT
<213> ORGANISM: artificial sequence
<220> FEATURE:
<223> OTHER INFORMATION: AAQ96308

<400> SEQUENCE: 23

Met Leu Ser Tyr Gln Asp Lys Val Gly Ala Phe Tyr Lys Asp Asn Ala
1               5                   10                  15

Arg Ala Asn Ser Ser Lys Leu Ser Leu Val Thr Glu Glu Gln Gly Gly
            20                  25                  30

Arg Arg Pro Pro Tyr Leu Leu Phe Val Leu Ile Leu Leu Val Gly
            35                  40                  45

Ile Met Thr Leu Leu Ala Ile Thr Gly Val Arg Phe His Gln Val Ser
    50                  55                  60

Thr Ser Asn Met Glu Phe Ser Arg Leu Leu Lys Glu Asp Met Glu Lys
65                  70                  75                  80

Ser Glu Ala Val His His Gln Val Ile Asp Val Leu Thr Pro Leu Phe
                85                  90                  95

Lys Ile Ile Gly Asp Glu Val Gly Leu Gln Leu Pro Gln Lys Leu Asn
            100                 105                 110

Glu Ile Lys Gln Phe Ile Leu Gln Lys Thr Asn Phe Phe Asn Pro Asn
        115                 120                 125

Arg Glu Phe Asp Phe Arg Asp Leu His Trp Cys Ile Asn Pro Pro Ser
    130                 135                 140

Lys Ile Lys Val Asn Phe Thr Asn Tyr Cys Asp Thr Ile Gly Ile Lys
145                 150                 155                 160

Lys Ser Ile Ala Ser Ala Ala Asn Pro Ile Leu Leu Ser Ala Leu Ser
```

-continued

```
                165                 170                 175
Gly Gly Arg Gly Asp Ile Phe Pro Pro Tyr Arg Cys Ser Gly Ala Thr
            180                 185                 190

Thr Ser Val Gly Arg Val Phe Pro Leu Ser Val Ser Leu Ser Met Ser
        195                 200                 205

Leu Ile Ser Lys Thr Ser Glu Ile Thr Ser Met Leu Thr Ala Ile Ser
    210                 215                 220

Asp Gly Val Tyr Gly Lys Thr Tyr Leu Val Pro Asp Tyr Ile Glu
225                 230                 235                 240

Gly Glu Phe Asp Thr Gln Lys Ile Arg Val Phe Glu Ile Gly Phe Ile
            245                 250                 255

Lys Arg Trp Leu Asn Asn Met Pro Leu Leu Gln Thr Thr Asn Tyr Met
        260                 265                 270

Val Leu Pro Glu Asn Ser Lys Ala Lys Val Cys Thr Ile Ala Val Gly
    275                 280                 285

Glu Leu Thr Leu Ala Ser Leu Cys Val Asp Glu Ser Thr Val Leu Leu
    290                 295                 300

Tyr His Asp Ser Asn Gly Ser Gln Asp Gly Ile Leu Val Val Thr Leu
305                 310                 315                 320

Gly Ile Phe Gly Ala Thr Pro Met Asp Gln Val Glu Glu Val Ile Pro
            325                 330                 335

Val Ala His Pro Ser Val Glu Lys Ile His Ile Thr Asn His Arg Gly
        340                 345                 350

Phe Ile Lys Asp Ser Ile Ala Thr Trp Met Val Pro Ala Leu Val Ser
    355                 360                 365

Glu Lys Gln Glu Glu Gln Lys Asn Cys Leu Glu Ser Ala Cys Gln Arg
    370                 375                 380

Lys Thr Tyr Pro Met Cys Asn Gln Thr Ser Trp Glu Pro Phe Gly Gly
385                 390                 395                 400

Gly Gln Leu Pro Ser Tyr Gly Arg Leu Thr Leu Pro Leu Asp Pro Ser
            405                 410                 415

Ile Asp Leu Gln Leu Asn Ile Ser Phe Thr Tyr Gly Pro Val Ile Leu
        420                 425                 430

Asn Gly Asp Gly Met Asp Tyr Tyr Glu Ser Pro Leu Ser Asp Ser Gly
    435                 440                 445

Trp Leu Thr Ile Pro Pro Arg Asn Gly Thr Val Leu Gly Leu Ile Asn
    450                 455                 460

Lys Ala Ser Arg Gly Asp Gln Phe Thr Val Ile Pro His Val Leu Thr
465                 470                 475                 480

Phe Ala Pro Arg Glu Ser Ser Gly Asn Cys Tyr Leu Pro Ile Gln Thr
            485                 490                 495

Ser Gln Ile Met Asp Lys Asp Val Leu Thr Glu Ser Asn Leu Val Val
        500                 505                 510

Leu Pro Thr Gln Asn Phe Arg Tyr Val Ile Ala Thr Tyr Asp Ile Ser
    515                 520                 525

Arg Gly Asp His Ala Ile Val Tyr Tyr Val Tyr Asp Pro Ile Arg Thr
530                 535                 540

Ile Ser Tyr Thr His Pro Phe Arg Leu Thr Thr Lys Gly Arg Pro Asp
545                 550                 555                 560

Phe Leu Arg Ile Glu Cys Phe Val Trp Asp Asp Leu Trp Cys His
            565                 570                 575

Gln Phe Tyr Arg Phe Glu Ala Asp Ile Thr Asn Ser Thr Thr Ser Val
        580                 585                 590
```

Glu Asn Leu Val Arg Ile Arg Phe Ser Cys Asn Arg Ser Lys Pro
        595                 600                 605

<210> SEQ ID NO 24
<211> LENGTH: 607
<212> TYPE: PRT
<213> ORGANISM: artificial sequence
<220> FEATURE:
<223> OTHER INFORMATION: ABF55671
<220> FEATURE:
<221> NAME/KEY: misc_feature
<222> LOCATION: (53)..(53)
<223> OTHER INFORMATION: Xaa can be any naturally occurring amino acid

<400> SEQUENCE: 24

Met Leu Ser Tyr Gln Asp Lys Val Gly Ala Phe Tyr Lys Asp Asn Ala
1               5                   10                  15

Arg Ala Asn Ser Ser Lys Leu Ser Leu Val Thr Glu Glu Gln Gly Gly
            20                  25                  30

Arg Arg Pro Pro Tyr Leu Leu Phe Val Leu Leu Ile Leu Leu Val Gly
        35                  40                  45

Val Met Thr Leu Xaa Ala Ile Thr Gly Val Arg Ile His Gln Val Ser
50                  55                  60

Thr Ser Asn Met Glu Phe Ser Arg Leu Leu Lys Glu Asp Met Glu Lys
65                  70                  75                  80

Ser Glu Ala Val His His Gln Val Ile Asp Val Leu Thr Pro Leu Phe
                85                  90                  95

Lys Ile Ile Gly Asp Glu Val Gly Leu Arg Leu Pro Gln Lys Leu Asn
            100                 105                 110

Glu Ile Lys Gln Phe Ile Leu Gln Lys Thr Asn Phe Phe Asn Pro Asn
        115                 120                 125

Arg Glu Phe Asp Phe Arg Asp Leu His Trp Cys Ile Asn Pro Pro Ser
130                 135                 140

Lys Ile Lys Val Asn Phe Thr Asn Tyr Cys Asp Thr Val Gly Ile Arg
145                 150                 155                 160

Lys Ser Ile Ala Ser Ala Ala Asn Pro Ile Leu Leu Ser Ala Leu Ser
                165                 170                 175

Gly Gly Arg Gly Asp Ile Phe Pro Pro Tyr Arg Cys Ser Gly Ala Thr
            180                 185                 190

Thr Ser Val Gly Arg Val Phe Pro Leu Ser Val Ser Leu Ser Met Ser
        195                 200                 205

Leu Ile Ser Lys Thr Ser Glu Ile Thr Asn Met Leu Thr Ala Ile Ser
    210                 215                 220

Asp Gly Val Tyr Gly Lys Thr Tyr Leu Leu Val Pro Asp Tyr Ile Glu
225                 230                 235                 240

Gly Glu Phe Asp Thr Gln Lys Ile Arg Val Phe Glu Ile Gly Phe Ile
                245                 250                 255

Arg Arg Trp Leu Asn Asn Met Pro Leu Leu Gln Thr Thr Asn Tyr Met
            260                 265                 270

Val Leu Pro Glu Asn Ser Lys Ala Lys Val Cys Thr Ile Ala Val Gly
        275                 280                 285

Glu Leu Thr Leu Ala Ser Leu Cys Val Asp Glu Ser Thr Val Leu Leu
    290                 295                 300

Tyr His Asp Ser Asn Gly Ser Gln Asp Gly Ile Leu Val Val Thr Leu
305                 310                 315                 320

Gly Ile Phe Gly Ala Thr Pro Met Asp Gln Val Glu Glu Val Ile Pro

```
                325                 330                 335
Val Ala His Pro Ser Val Glu Lys Ile His Ile Thr Asn His Arg Gly
            340                 345                 350

Phe Ile Lys Asp Ala Ile Ala Thr Trp Met Val Pro Ala Leu Val Ser
        355                 360                 365

Glu Lys Gln Glu Gln Lys Asn Cys Leu Glu Ser Ala Cys Gln Arg
    370                 375                 380

Lys Thr Tyr Pro Met Cys Asn Gln Thr Ser Trp Glu Pro Phe Gly Gly
385                 390                 395                 400

Gly Gln Leu Pro Ser Tyr Gly Arg Leu Thr Leu Pro Leu Asp Pro Ser
                405                 410                 415

Ile Asp Leu Gln Leu Asn Ile Ser Phe Thr Tyr Gly Pro Val Ile Leu
            420                 425                 430

Asn Gly Asp Gly Met Asp Tyr Tyr Glu Ser Ser Leu Ser Asp Ser Gly
        435                 440                 445

Trp Leu Thr Ile Pro Pro Lys Asn Gly Thr Val Leu Gly Leu Ile Asn
    450                 455                 460

Lys Ala Ser Arg Gly Asp Gln Phe Thr Val Thr Pro His Val Leu Thr
465                 470                 475                 480

Ser Ala Pro Arg Glu Ser Ser Gly Asn Cys Tyr Leu Pro Ile Gln Thr
                485                 490                 495

Ser Gln Ile Met Asp Lys Asp Val Leu Thr Glu Ser Asn Leu Val Val
            500                 505                 510

Leu Pro Thr Gln Asn Phe Arg Tyr Val Ile Ala Thr Tyr Asp Ile Ser
        515                 520                 525

Arg Gly Asp His Ala Ile Val Tyr Val Tyr Asp Pro Ile Arg Thr
    530                 535                 540

Ile Ser Tyr Thr Tyr Pro Phe Arg Leu Thr Thr Lys Gly Arg Pro Asp
545                 550                 555                 560

Phe Leu Arg Ile Glu Cys Phe Val Trp Asp Asp Asp Met Trp Cys His
                565                 570                 575

Gln Phe Tyr Arg Phe Glu Ala Asp Ile Thr Asn Ser Thr Thr Ser Val
            580                 585                 590

Glu Asn Leu Val Arg Ile Arg Phe Ser Cys Asn Arg Ser Lys Pro
        595                 600                 605

<210> SEQ ID NO 25
<211> LENGTH: 607
<212> TYPE: PRT
<213> ORGANISM: artificial sequence
<220> FEATURE:
<223> OTHER INFORMATION: ACS88240

<400> SEQUENCE: 25

Met Leu Ser Tyr Gln Asp Lys Val Gly Ala Phe Tyr Lys Asp Asn Ala
1               5                   10                  15

Arg Ala Asn Ser Ser Lys Leu Ser Leu Val Thr Glu Glu Gln Gly Gly
            20                  25                  30

Arg Arg Pro Pro Tyr Leu Leu Phe Val Leu Leu Ile Leu Leu Val Gly
        35                  40                  45

Ile Met Thr Leu Leu Ala Ile Thr Gly Val Arg Phe His Gln Val Ser
    50                  55                  60

Thr Ser Asn Met Glu Phe Ser Arg Leu Leu Lys Glu Asp Met Glu Lys
65                  70                  75                  80

Ser Glu Ala Val His His Gln Val Ile Asp Val Leu Thr Pro Leu Phe
```

```
                85                  90                  95
Lys Ile Ile Gly Asp Glu Val Gly Leu Arg Leu Pro Gln Lys Leu Asn
            100                 105                 110

Glu Ile Lys Gln Phe Ile Leu Gln Lys Thr Asn Phe Asn Pro Asn
            115                 120                 125

Arg Glu Phe Asp Phe Arg Asp Leu His Trp Cys Ile Asn Pro Pro Ser
    130                 135                 140

Lys Ile Lys Val Asn Phe Thr Asn Tyr Cys Asp Thr Ile Gly Ile Arg
145                 150                 155                 160

Gln Ser Ile Ala Ser Ala Ala Asn Pro Ile Leu Leu Ser Ala Leu Ser
                165                 170                 175

Gly Gly Arg Gly Asp Ile Phe Pro Pro Tyr Arg Cys Ser Gly Ala Thr
            180                 185                 190

Thr Ser Val Gly Arg Val Phe Pro Leu Ser Val Ser Leu Ser Met Ser
            195                 200                 205

Val Ile Ser Lys Thr Ser Glu Ile Thr Asn Met Leu Thr Ala Ile Ser
    210                 215                 220

Asp Gly Val Tyr Gly Lys Thr Tyr Leu Leu Val Pro Asp Tyr Ile Glu
225                 230                 235                 240

Gly Glu Phe Asp Thr Gln Lys Ile Arg Val Phe Glu Ile Gly Phe Ile
                245                 250                 255

Lys Arg Trp Leu Asn Asn Met Pro Leu Leu Gln Thr Thr Asn Tyr Met
            260                 265                 270

Val Leu Pro Glu Asn Ser Lys Ala Lys Val Cys Thr Ile Ala Val Gly
            275                 280                 285

Glu Leu Thr Leu Ala Ser Leu Cys Val Asp Glu Asn Thr Val Leu Leu
    290                 295                 300

Tyr His Asp Ser Asn Gly Ser Gln Asp Gly Ile Leu Val Val Thr Leu
305                 310                 315                 320

Gly Ile Phe Gly Ala Thr Pro Met Asp Gln Val Glu Glu Val Ile Pro
                325                 330                 335

Val Ala His Pro Ser Ile Glu Lys Ile His Ile Thr Asn His Arg Gly
            340                 345                 350

Phe Ile Lys Asp Ser Ile Ala Thr Trp Met Val Pro Ala Leu Val Ser
            355                 360                 365

Glu Lys Gln Glu Glu Gln Lys Asn Cys Leu Glu Ser Ala Cys Gln Arg
    370                 375                 380

Lys Thr Tyr Pro Met Cys Asn Gln Thr Ser Trp Glu Pro Phe Gly Gly
385                 390                 395                 400

Arg Gln Leu Pro Ser Tyr Gly Arg Leu Thr Leu Pro Leu Asp Pro Ser
                405                 410                 415

Met Asp Leu Gln Leu Asn Ile Ser Phe Thr Tyr Gly Pro Val Ile Leu
            420                 425                 430

Asn Gly Asp Gly Met Asp Tyr Tyr Glu Ser Pro Leu Pro Asp Ser Gly
            435                 440                 445

Trp Leu Thr Ile Pro Pro Lys Asn Gly Thr Val Leu Gly Leu Ile Asn
    450                 455                 460

Lys Ala Ser Arg Gly Asp Gln Phe Thr Val Ile Pro His Val Leu Thr
465                 470                 475                 480

Phe Ala Pro Arg Glu Ser Ser Gly Asn Cys Tyr Leu Pro Ile Gln Thr
                485                 490                 495

Ser Gln Ile Met Asp Lys Asp Val Leu Thr Glu Ser Asn Leu Val Val
            500                 505                 510
```

```
Leu Pro Thr Gln Asn Phe Arg Tyr Val Ile Ala Thr Tyr Asp Ile Ser
            515                 520                 525

Arg Gly Asp His Ala Ile Val Tyr Val Tyr Asp Pro Ile Arg Thr
530                 535                 540

Ile Ser Tyr Thr Tyr Pro Phe Arg Leu Thr Thr Lys Gly Arg Pro Asp
545                 550                 555                 560

Phe Leu Arg Ile Glu Cys Phe Val Trp Asp Asp Leu Trp Cys His
            565                 570                 575

Gln Phe Tyr Arg Phe Glu Ala Asp Ile Thr Asn Ser Thr Thr Ser Val
            580                 585                 590

Glu Asn Leu Val Cys Ile Arg Phe Ser Cys Asn Arg Ser Lys Pro
            595                 600                 605
```

<210> SEQ ID NO 26
<211> LENGTH: 607
<212> TYPE: PRT
<213> ORGANISM: artificial sequence
<220> FEATURE:
<223> OTHER INFORMATION: ABK35770

<400> SEQUENCE: 26

```
Met Leu Ser Tyr Gln Asp Lys Val Gly Ala Phe Tyr Lys Asp Asn Ala
1               5                   10                  15

Arg Ala Asn Ser Ser Lys Leu Ser Leu Val Thr Glu Glu Gln Gly Gly
            20                  25                  30

Arg Arg Pro Pro Tyr Leu Leu Phe Val Leu Leu Ile Leu Leu Val Gly
            35                  40                  45

Ile Met Thr Leu Leu Ala Ile Thr Gly Val Arg Phe His Gln Val Ser
50                  55                  60

Thr Ser Asn Met Glu Phe Ser Arg Leu Leu Lys Glu Asp Met Glu Lys
65                  70                  75                  80

Ser Glu Ala Val His His Gln Val Ile Asp Val Leu Thr Pro Leu Phe
            85                  90                  95

Lys Ile Ile Gly Asp Glu Val Gly Leu Arg Leu Pro Gln Lys Leu Asn
            100                 105                 110

Glu Ile Lys Gln Phe Ile Leu Gln Lys Thr Asn Phe Phe Asn Pro Asn
            115                 120                 125

Arg Glu Phe Asp Phe Arg Asp Leu His Trp Cys Ile Asn Pro Pro Ser
            130                 135                 140

Lys Ile Lys Val Asn Phe Thr Asn Tyr Cys Asp Thr Ile Gly Ile Arg
145                 150                 155                 160

Lys Ser Ile Ala Ser Ala Ala Asn Pro Ile Leu Leu Ser Ala Leu Ser
            165                 170                 175

Gly Gly Arg Gly Asp Ile Phe Pro Pro Tyr Arg Cys Ser Gly Ala Thr
            180                 185                 190

Thr Ser Val Gly Arg Val Phe Pro Leu Ser Val Ser Leu Ser Met Ser
            195                 200                 205

Leu Ile Ser Lys Thr Ser Gly Ile Thr Asn Met Leu Thr Ala Ile Ser
            210                 215                 220

Asp Gly Val Tyr Gly Lys Thr Tyr Leu Leu Val Pro Asp Tyr Ile Glu
225                 230                 235                 240

Gly Glu Phe Asp Thr Gln Lys Ile Arg Val Phe Glu Ile Gly Phe Ile
            245                 250                 255

Lys Arg Trp Leu Asn Asn Met Pro Leu Phe Gln Thr Thr Asn Tyr Met
            260                 265                 270
```

Val Leu Pro Glu Asn Ser Lys Ala Lys Val Cys Thr Ile Ala Val Gly
             275                 280                 285

Glu Leu Thr Leu Ala Ser Leu Cys Val Asp Glu Ser Thr Val Leu Leu
        290                 295                 300

Tyr His Asp Ser Asn Gly Ser Gln Gly Gly Val Leu Val Val Thr Leu
305                 310                 315                 320

Gly Ile Phe Gly Ala Thr Pro Met Asp Gln Val Glu Glu Met Ile Pro
                325                 330                 335

Val Ala His Pro Ser Val Glu Lys Ile His Ile Thr Asn His Arg Gly
                340                 345                 350

Phe Ile Lys Asp Ser Ile Ala Thr Trp Met Val Pro Val Leu Val Ser
             355                 360                 365

Glu Lys Gln Glu Glu Gln Lys Asn Cys Leu Glu Ser Ala Cys Gln Arg
        370                 375                 380

Lys Thr Tyr Pro Met Cys Asn Gln Thr Ser Trp Glu Pro Phe Gly Gly
385                 390                 395                 400

Gly Gln Leu Pro Ser Tyr Gly Arg Leu Thr Leu Pro Leu Asp Pro Ser
                405                 410                 415

Ile Asp Leu Gln Leu Asn Ile Ser Phe Thr Tyr Gly Pro Val Ile Leu
                420                 425                 430

Asn Gly Asp Gly Met Asp Tyr Tyr Glu Ser Pro Leu Leu Asp Ser Gly
             435                 440                 445

Trp Leu Thr Ile Pro Pro Lys Asn Gly Thr Val Leu Gly Leu Ile Asn
        450                 455                 460

Lys Ala Ser Arg Gly Asp Gln Phe Thr Val Ile Pro His Val Leu Thr
465                 470                 475                 480

Phe Ala Pro Arg Glu Ser Ser Gly Asn Cys Tyr Leu Pro Ile Gln Thr
                485                 490                 495

Ser Gln Ile Met Asp Lys Asp Val Leu Thr Glu Ser Asn Leu Val Val
                500                 505                 510

Leu Pro Thr Gln Asn Phe Arg Tyr Val Ile Ala Thr Tyr Asp Ile Ser
             515                 520                 525

Arg Gly Asp His Ala Ile Val Tyr Tyr Val Tyr Asp Pro Ile Arg Thr
        530                 535                 540

Ile Ser Tyr Thr Tyr Pro Phe Arg Leu Thr Thr Lys Gly Arg Pro Glu
545                 550                 555                 560

Phe Leu Arg Ile Glu Cys Phe Val Trp Asp Asp Leu Trp Cys His
                565                 570                 575

Gln Phe Tyr Arg Phe Glu Ala Asp Ile Thr Asn Ser Thr Ile Ser Val
                580                 585                 590

Glu Asn Leu Val His Ile Arg Phe Ser Cys Asn Arg Ser Lys Pro
             595                 600                 605

<210> SEQ ID NO 27
<211> LENGTH: 607
<212> TYPE: PRT
<213> ORGANISM: artificial sequence
<220> FEATURE:
<223> OTHER INFORMATION: ACD92997

<400> SEQUENCE: 27

Met Leu Ser Tyr Gln Asp Lys Val Gly Ala Phe Tyr Lys Asp Asn Ala
1               5                   10                  15

Arg Ala Asn Ser Ser Lys Leu Ser Ser Val Thr Glu Glu Gln Gly Gly
            20                  25                  30

```
Arg Arg Pro Pro Tyr Leu Leu Phe Val Leu Ile Leu Leu Val Gly
        35              40              45
Ile Met Ala Leu Leu Ala Ile Thr Gly Val Arg Phe His Gln Val Ser
 50              55              60
Thr Asn Asn Met Glu Phe Ser Arg Leu Leu Lys Glu Asp Met Glu Lys
 65              70              75              80
Ser Glu Ala Val His His Gln Val Ile Asp Val Leu Thr Pro Leu Phe
                85              90              95
Lys Ile Ile Gly Asp Glu Val Gly Leu Arg Leu Pro Gln Lys Leu Asn
                100             105             110
Glu Ile Lys Gln Phe Ile Leu Gln Lys Thr Asn Phe Asn Pro Asn
            115             120             125
Arg Glu Phe Asp Phe Arg Asp Leu His Trp Cys Ile Asn Pro Pro Ser
        130             135             140
Lys Ile Lys Val Asn Phe Thr Asn Tyr Cys Asp Thr Ile Glu Ile Arg
145             150             155             160
Lys Ser Ile Ala Leu Ala Ala Asn Pro Ile Leu Leu Ser Ala Leu Ser
                165             170             175
Gly Gly Arg Gly Asp Ile Phe Pro Pro Tyr Ser Cys Ser Gly Ala Thr
        180             185             190
Thr Ser Val Gly Arg Val Phe Pro Leu Ser Val Ser Leu Ser Met Ser
        195             200             205
Leu Ile Ser Lys Thr Ser Glu Ile Ile Asn Met Leu Thr Ala Ile Ser
    210             215             220
Asp Gly Val Tyr Gly Lys Thr Tyr Leu Leu Val Pro Asp Tyr Ile Glu
225             230             235             240
Gly Gly Phe Asp Thr Gln Lys Ile Arg Val Phe Glu Ile Gly Phe Ile
            245             250             255
Lys Arg Trp Leu Asn Asp Met Pro Leu Leu Gln Thr Thr Asn Tyr Met
        260             265             270
Val Leu Pro Glu Asn Ser Lys Ala Lys Val Cys Thr Ile Ala Val Gly
        275             280             285
Glu Leu Thr Leu Ala Ser Leu Cys Val Asp Ser Thr Val Leu Leu
    290             295             300
Tyr His Asp Ser Asp Gly Ser Gln Asp Gly Ile Leu Val Val Thr Leu
305             310             315             320
Gly Ile Phe Gly Ala Thr Pro Met Asp Gln Val Glu Glu Val Ile Pro
            325             330             335
Val Ala His Pro Ser Val Glu Lys Ile His Ile Thr Asn His Arg Gly
            340             345             350
Phe Ile Lys Asp Ser Ile Ala Thr Trp Met Val Pro Ala Leu Val Ser
        355             360             365
Glu Lys Gln Glu Glu Lys Asn Cys Leu Glu Ser Ala Cys Gln Arg
    370             375             380
Lys Ser Tyr Pro Met Cys Asn Gln Thr Ser Trp Glu Pro Phe Gly Gly
385             390             395             400
Gly Gln Leu Pro Ser Tyr Gly Arg Leu Thr Leu Pro Leu Asp Pro Ser
            405             410             415
Ile Asp Leu Gln Leu Asn Ile Ser Phe Thr Tyr Gly Pro Val Ile Leu
            420             425             430
Asn Gly Asp Gly Met Asp Tyr Tyr Glu Ser Pro Leu Leu Asp Ser Gly
        435             440             445
```

```
Trp Leu Thr Ile Pro Pro Lys Asn Gly Thr Val Leu Gly Leu Ile Asn
    450                 455                 460

Lys Ala Ser Arg Gly Asp Gln Phe Thr Val Ile Pro His Val Leu Thr
465                 470                 475                 480

Phe Ala Pro Arg Glu Ser Ser Gly Asn Cys Tyr Leu Pro Ile Gln Thr
                485                 490                 495

Ser Gln Ile Met Asp Lys Asp Val Leu Thr Glu Ser Asn Leu Val Val
                500                 505                 510

Leu Pro Thr Gln Asn Phe Arg Tyr Val Ile Ala Thr Tyr Asp Ile Ser
                515                 520                 525

Arg Gly Asp His Ala Ile Val Tyr Tyr Val Tyr Asp Pro Ile Arg Ala
530                 535                 540

Ile Ser Tyr Thr Tyr Pro Phe Arg Leu Thr Thr Lys Gly Arg Pro Asp
545                 550                 555                 560

Phe Leu Arg Ile Glu Cys Phe Val Trp Asp Asp Leu Trp Cys His
                565                 570                 575

Gln Phe Tyr Arg Phe Glu Ala Asp Ser Thr Asn Ser Thr Thr Ser Val
                580                 585                 590

Glu Asn Leu Val Arg Ile Arg Phe Ser Cys Asn Arg Ser Lys Pro
                595                 600                 605

<210> SEQ ID NO 28
<211> LENGTH: 607
<212> TYPE: PRT
<213> ORGANISM: artificial sequence
<220> FEATURE:
<223> OTHER INFORMATION: ACI28389

<400> SEQUENCE: 28

Met Leu Ser Tyr Gln Asp Lys Val Gly Ala Phe Tyr Lys Asp Asn Ala
1               5                   10                  15

Arg Ala Asn Ser Ser Lys Leu Ser Leu Val Thr Glu Glu Gln Gly Gly
                20                  25                  30

Arg Arg Pro Pro Tyr Leu Leu Phe Val Leu Leu Ile Leu Leu Val Gly
            35                  40                  45

Ile Met Thr Leu Leu Ala Ile Thr Gly Val Arg Phe His Gln Val Ser
    50                  55                  60

Thr Ser Asn Met Glu Phe Ser Arg Leu Leu Lys Glu Asp Met Glu Lys
65                  70                  75                  80

Ser Glu Ala Val His His Gln Val Ile Asp Val Leu Thr Pro Leu Phe
                85                  90                  95

Lys Ile Ile Gly Asp Glu Val Gly Leu Arg Leu Pro Gln Lys Leu Asn
                100                 105                 110

Glu Ile Lys Gln Phe Ile Leu Gln Lys Thr Asn Phe Phe Asn Pro Asn
            115                 120                 125

Arg Glu Phe Asp Phe Arg Asp Leu His Trp Cys Ile Asn Pro Pro Ser
130                 135                 140

Lys Ile Lys Val Asn Phe Thr Asn Tyr Cys Asp Thr Ile Glu Ile Arg
145                 150                 155                 160

Lys Ser Ile Ala Ser Ala Ala Asn Pro Ile Leu Leu Ser Ala Leu Ser
                165                 170                 175

Gly Gly Arg Gly Asp Ile Phe Pro Pro Tyr Arg Cys Ser Gly Ala Thr
                180                 185                 190

Thr Ser Val Gly Arg Val Phe Pro Leu Ser Val Ser Leu Ser Met Ser
            195                 200                 205
```

```
Leu Ile Ser Arg Thr Ser Glu Ile Thr Asn Met Leu Thr Ala Ile Ser
210                 215                 220

Asp Gly Val Tyr Gly Lys Thr Tyr Leu Leu Val Pro Asp Tyr Phe Glu
225                 230                 235                 240

Gly Glu Phe Asp Thr Gln Lys Ile Arg Val Phe Glu Ile Gly Phe Ile
                245                 250                 255

Lys Arg Trp Leu Asn Asp Met Pro Leu Leu Gln Thr Thr Asn Tyr Met
                260                 265                 270

Phe Leu Pro Glu Asn Ser Lys Ala Lys Val Cys Thr Ile Ala Val Gly
            275                 280                 285

Glu Leu Thr Leu Ala Ser Leu Cys Val Asp Glu Ser Thr Val Ser Leu
290                 295                 300

Tyr His Asp Gly Ser Gly Ser Gln Asp Gly Ile Leu Val Val Thr Leu
305                 310                 315                 320

Gly Ile Phe Gly Ala Thr Pro Met Asp Gln Val Glu Val Ile Pro
                325                 330                 335

Val Ala His Pro Ser Val Glu Lys Ile His Ile Thr Asn His Arg Gly
            340                 345                 350

Phe Ile Lys Asp Ser Ile Ala Thr Trp Met Val Pro Ala Leu Val Ser
            355                 360                 365

Glu Lys Gln Glu Glu Gln Lys Asn Cys Leu Glu Ser Ala Cys Gln Arg
370                 375                 380

Lys Thr Tyr Pro Met Cys Asn Gln Thr Ser Trp Glu Pro Phe Gly Gly
385                 390                 395                 400

Gly Gln Leu Pro Ser Tyr Gly Arg Trp Thr Leu Pro Leu Asp Pro Ser
                405                 410                 415

Ile Asp Leu Gln Leu Asn Ile Ser Val Thr Tyr Gly Pro Val Ile Leu
                420                 425                 430

Asn Gly Asp Gly Met Asp Tyr Tyr Glu Ser Pro Leu Ser Asp Ser Gly
            435                 440                 445

Trp Leu Thr Ile Pro Pro Lys Asn Gly Thr Ile Leu Gly Leu Ile Asn
450                 455                 460

Lys Ala Ser Arg Gly Asp Gln Phe Thr Val Ile Pro His Val Leu Thr
465                 470                 475                 480

Phe Ala Pro Arg Glu Ser Ser Gly Asn Cys Tyr Leu Pro Ile Gln Thr
                485                 490                 495

Ser Gln Ile Met Asp Lys Asp Val Leu Thr Glu Ser Asn Leu Val Val
            500                 505                 510

Leu Pro Thr Gln Asn Phe Arg Tyr Val Ile Ala Thr Tyr Asp Ile Ser
            515                 520                 525

Arg Gly Asp His Ala Ile Val Tyr Tyr Val Tyr Asp Pro Ile Arg Thr
530                 535                 540

Ile Ser Tyr Thr Tyr Pro Phe Arg Leu Thr Thr Lys Gly Arg Pro Val
545                 550                 555                 560

Ser Leu Arg Ile Glu Cys Phe Val Trp Asp Asp Leu Trp Cys His
                565                 570                 575

Gln Phe Tyr Gln Phe Glu Ala Asp Ile Thr Asn Ser Thr Thr Ser Val
            580                 585                 590

Glu Asn Leu Val Arg Ile Arg Phe Ser Cys Asn Arg Ser Lys Pro
595                 600                 605

<210> SEQ ID NO 29
<211> LENGTH: 607
<212> TYPE: PRT
```

<213> ORGANISM: artificial sequence
<220> FEATURE:
<223> OTHER INFORMATION: ACI28390

<400> SEQUENCE: 29

Met Leu Ser Tyr Gln Asp Lys Val Gly Ala Phe Tyr Lys Asp Asn Ala
1               5                   10                  15

Arg Ala Asn Ser Ser Lys Leu Ser Leu Val Thr Glu Glu Gln Gly Gly
            20                  25                  30

Arg Arg Pro Pro Tyr Leu Leu Phe Val Leu Leu Ile Leu Leu Val Gly
        35                  40                  45

Ile Met Thr Leu Leu Ala Ile Thr Gly Val Arg Phe His Gln Val Ser
50                  55                  60

Thr Ser Asn Met Glu Phe Ser Arg Leu Leu Lys Glu Asp Met Glu Lys
65                  70                  75                  80

Ser Glu Ala Val His His Gln Val Met Asp Val Leu Thr Pro Leu Phe
                85                  90                  95

Lys Ile Ile Gly Asp Glu Val Gly Leu Arg Leu Pro Gln Lys Leu Asn
            100                 105                 110

Glu Ile Lys Gln Phe Ile Leu Gln Lys Thr Asn Phe Phe Asn Pro Asn
        115                 120                 125

Arg Glu Phe Asp Phe Arg Asp Leu His Trp Cys Ile Asn Pro Pro Ser
130                 135                 140

Lys Ile Lys Val Asn Phe Ser Asn Tyr Cys Asp Thr Ile Gly Ile Arg
145                 150                 155                 160

Lys Ser Ile Ala Ser Ala Ala Asn Pro Ile Leu Leu Ser Ala Leu Ser
                165                 170                 175

Gly Gly Arg Gly Asp Ile Phe Pro Pro Tyr Arg Cys Asn Gly Ala Ala
            180                 185                 190

Thr Ser Ile Gly Arg Val Phe Pro Leu Ser Val Ser Leu Ser Met Ser
        195                 200                 205

Leu Ile Ser Arg Thr Ala Glu Ile Ile Asn Met Leu Thr Ala Ile Ser
210                 215                 220

Asp Gly Val Asp Gly Lys Thr Tyr Leu Leu Val Pro Asp Tyr Ile Glu
225                 230                 235                 240

Gly Glu Phe Glu Thr Gln Lys Ile Arg Val Phe Glu Ile Gly Phe Ile
                245                 250                 255

Lys Arg Trp Leu Asn Asp Met Ser Leu Leu Gln Thr Thr Asn Tyr Met
            260                 265                 270

Val Leu Pro Glu Asn Ser Lys Ala Lys Val Cys Thr Ile Ala Val Gly
        275                 280                 285

Glu Leu Thr Leu Ala Ser Leu Cys Val Asp Glu Ser Thr Val Leu Leu
290                 295                 300

Tyr His Asp Ser Asn Gly Ser Gln Asp Gly Ile Leu Val Val Thr Leu
305                 310                 315                 320

Gly Ile Phe Trp Gly Thr Pro Met Asp Gln Val Glu Glu Val Ile Pro
                325                 330                 335

Val Ala His Pro Ser Val Glu Lys Ile His Ile Thr Asn His Arg Gly
            340                 345                 350

Phe Ile Lys Asp Ser Lys Ala Ile Trp Met Val Pro Ala Leu Val Ser
        355                 360                 365

Glu Lys Gln Glu Glu Gln Lys Asn Cys Leu Glu Ser Ala Cys Gln Arg
370                 375                 380

Lys Thr Tyr Pro Met Cys Asn Gln Thr Ser Trp Glu Pro Phe Gly Gly

```
            385                 390                 395                 400
        Gly Gln Leu Pro Ser Tyr Gly Arg Leu Thr Leu Pro Leu Asp Pro Ser
                        405                 410                 415

Ile Asp Leu Gln Leu Asn Ile Ser Phe Thr Tyr Gly Pro Val Ile Leu
                        420                 425                 430

Asn Gly Asp Gly Met Asp Tyr Tyr Glu Ser Pro Leu Leu Asp Ser Gly
                        435                 440                 445

Trp Leu Thr Ile Pro Pro Lys Asn Gly Thr Val Leu Gly Leu Met Asn
                450                 455                 460

Lys Ala Ser Arg Gly Asp Gln Phe Thr Val Ile Pro His Val Leu Thr
        465                 470                 475                 480

Phe Ala Pro Arg Glu Ser Gly Gly Asn Cys Tyr Leu Pro Ile Gln Thr
                        485                 490                 495

Ser Gln Ile Met Asp Lys Asp Val Leu Ala Glu Ser Asn Leu Val Val
                        500                 505                 510

Leu Pro Thr Gln Asn Phe Arg Tyr Val Ile Ala Thr Tyr Asp Ile Ser
                        515                 520                 525

Arg Asp Asp His Ala Ile Val Tyr Val Tyr Asp Pro Ile Arg Thr
                530                 535                 540

Ile Ser Tyr Thr Tyr Pro Phe Arg Leu Thr Thr Lys Gly Arg Pro Asp
        545                 550                 555                 560

Phe Leu Arg Ile Glu Cys Phe Val Trp Asp Asp Leu Trp Cys His
                        565                 570                 575

Gln Phe Tyr Arg Phe Glu Ala Asp Ile Thr Asn Ser Thr Thr Ser Val
                        580                 585                 590

Glu Asn Leu Val Arg Ile Arg Phe Ser Cys Asn Arg Ser Lys Pro
                        595                 600                 605

<210> SEQ ID NO 30
<211> LENGTH: 607
<212> TYPE: PRT
<213> ORGANISM: artificial sequence
<220> FEATURE:
<223> OTHER INFORMATION: ACN58242

<400> SEQUENCE: 30

Met Leu Ser Tyr Gln Asp Lys Val Gly Ala Phe Tyr Lys Asp Asn Ala
1               5                   10                  15

Arg Ala Asn Ser Ser Lys Leu Ser Leu Val Thr Glu Glu Gln Gly Gly
                20                  25                  30

Arg Arg Pro Pro Tyr Leu Leu Phe Val Leu Leu Ile Leu Leu Thr Gly
            35                  40                  45

Ile Leu Ala Leu Leu Ala Ile Thr Arg Val Arg Phe His Gln Val Ser
        50                  55                  60

Thr Ser Asn Met Glu Phe Ser Arg Leu Leu Lys Glu Asp Met Glu Lys
65                  70                  75                  80

Ser Glu Ala Val His His Gln Val Ile Asp Val Leu Thr Pro Leu Phe
                85                  90                  95

Lys Ile Ile Gly Asp Glu Ile Gly Leu Arg Leu Pro Gln Lys Leu Asn
            100                 105                 110

Glu Ile Lys Gln Phe Ile Leu Gln Lys Thr Asn Phe Asn Pro Asn
        115                 120                 125

Arg Glu Phe Asp Phe Arg Asp Leu His Trp Cys Ile Asn Pro Pro Ser
130                 135                 140

Lys Ile Lys Val Asn Phe Thr Asn Tyr Cys Asp Thr Val Gly Val Lys
```

```
            145                 150                 155                 160
        Lys Ser Ile Ala Ser Ala Ala Asn Pro Ile Ile Leu Ser Ala Leu Ser
                        165                 170                 175
        Gly Ala Arg Gly Asp Ile Phe Pro Pro Cys Arg Cys Ser Gly Ala Thr
                        180                 185                 190
        Thr Ser Val Gly Arg Val Phe Pro Leu Ser Val Ser Leu Ser Met Ser
                        195                 200                 205
        Leu Ile Ser Arg Thr Ser Glu Ile Ile Asn Met Leu Thr Ala Ile Ser
        210                 215                 220
        Asp Gly Met Tyr Gly Lys Thr Tyr Leu Leu Val Pro Asp Tyr Ile Glu
        225                 230                 235                 240
        Gly Glu Phe Asp Ser Gln Lys Ile Arg Val Phe Glu Ile Gly Phe Ile
                        245                 250                 255
        Arg Arg Trp Leu Asn Asp Met Pro Leu Leu Gln Thr Thr Asn Tyr Met
                        260                 265                 270
        Val Leu Pro Glu Thr Ser Lys Ala Lys Val Cys Thr Ile Ala Val Gly
                        275                 280                 285
        Glu Leu Thr Leu Ala Ser Leu Cys Val Asp Glu Ser Thr Val Leu Leu
                        290                 295                 300
        Tyr His Asp Ser Asn Gly Ser Gln Asn Gly Ile Leu Val Val Thr Leu
        305                 310                 315                 320
        Gly Ile Phe Gly Ala Thr Pro Met Asp Gln Val Glu Glu Val Ile Pro
                        325                 330                 335
        Ile Ala His Pro Ser Val Glu Arg Ile His Ile Thr Asn His Arg Gly
                        340                 345                 350
        Phe Ile Lys Asp Ser Ile Val Thr Trp Met Val Pro Val Leu Val Ser
                        355                 360                 365
        Glu Lys Gln Glu Glu Gln Lys Asn Cys Leu Glu Ser Ala Cys Gln Arg
                        370                 375                 380
        Lys Thr Tyr Pro Met Cys Asn Gln Thr Ser Trp Glu Pro Phe Gly Gly
        385                 390                 395                 400
        Gly Gln Leu Pro Ser Tyr Gly Arg Leu Thr Leu Pro Leu Asp Pro Ser
                        405                 410                 415
        Ile Asp Leu Gln Leu Asn Ile Ser Phe Thr Tyr Gly Pro Val Ile Leu
                        420                 425                 430
        Asn Gly Asp Gly Met Asp Tyr Tyr Glu Ser Pro Leu Leu Asp Ser Gly
                        435                 440                 445
        Trp Leu Thr Ile Pro Pro Lys Asn Gly Thr Val Leu Gly Leu Ile Asn
        450                 455                 460
        Lys Ala Ser Arg Gly Asp Gln Phe Thr Val Thr Pro His Val Leu Thr
        465                 470                 475                 480
        Phe Ala Pro Arg Glu Ser Ser Gly Asn Cys Tyr Leu Pro Ile Gln Thr
                        485                 490                 495
        Ser Gln Ile Met Asp Lys Asp Val Leu Thr Glu Ser Asn Leu Val Val
                        500                 505                 510
        Leu Pro Thr Gln Asn Phe Arg Tyr Val Ile Ala Thr Tyr Asp Ile Ser
                        515                 520                 525
        Arg Gly Asp His Ala Ile Val Tyr Tyr Val Tyr Asp Pro Ile Arg Thr
                        530                 535                 540
        Ile Ser Tyr Thr Tyr Pro Phe Arg Leu Thr Thr Lys Gly Arg Pro Asp
        545                 550                 555                 560
        Phe Leu Arg Ile Glu Cys Phe Val Trp Asp Asp Leu Trp Cys His
                        565                 570                 575
```

```
Gln Phe Tyr Arg Phe Glu Ala Asn Ile Thr Asn Ser Thr Thr Ser Val
                580                 585                 590

Glu Asn Leu Val Arg Ile Arg Phe Ser Cys Asn Arg Ser Lys Pro
            595                 600                 605

<210> SEQ ID NO 31
<211> LENGTH: 607
<212> TYPE: PRT
<213> ORGANISM: artificial sequence
<220> FEATURE:
<223> OTHER INFORMATION: ABB51156
<220> FEATURE:
<221> NAME/KEY: misc_feature
<222> LOCATION: (343)..(343)
<223> OTHER INFORMATION: Xaa can be any naturally occurring amino acid

<400> SEQUENCE: 31

Met Leu Ser Tyr Gln Asp Lys Val Gly Ala Phe Tyr Lys Asp Asn Ala
1               5                   10                  15

Arg Ala Asn Ser Ser Lys Leu Ser Leu Val Thr Glu Glu Gln Gly Gly
            20                  25                  30

Arg Arg Pro Pro Phe Leu Leu Phe Val Leu Leu Val Leu Leu Val Gly
        35                  40                  45

Ile Met Ala Leu Leu Ala Ile Thr Gly Val Arg Phe His Gln Val Ser
    50                  55                  60

Thr Ser Asn Met Glu Phe Ser Arg Leu Leu Lys Glu Asp Met Glu Lys
65                  70                  75                  80

Ser Glu Ala Val His His Gln Val Ile Asp Val Leu Thr Pro Leu Phe
                85                  90                  95

Lys Ile Ile Gly Asp Glu Ile Gly Leu Arg Leu Pro Gln Lys Leu Asn
            100                 105                 110

Glu Ile Lys Gln Phe Ile Leu Gln Lys Thr Asn Phe Phe Asn Pro Asn
        115                 120                 125

Arg Glu Phe Asp Phe Arg Asp Leu His Trp Cys Ile Asn Pro Pro Ser
    130                 135                 140

Lys Ile Lys Val Asn Phe Thr Asn Tyr Cys Asp Thr Ile Gly Ile Arg
145                 150                 155                 160

Lys Ser Ile Ala Ser Ala Ala Asn Pro Ile Leu Leu Ser Ala Leu Ser
                165                 170                 175

Gly Gly Arg Gly Asp Ile Phe Pro Pro Tyr Lys Cys Asn Gly Ala Ala
            180                 185                 190

Thr Ser Val Gly Arg Val Phe Pro Leu Ser Val Ser Leu Ser Met Ser
        195                 200                 205

Leu Ile Ser Lys Thr Ser Gly Ile Ile Asn Met Leu Thr Ala Ile Ser
    210                 215                 220

Asp Gly Val Tyr Gly Lys Thr Tyr Leu Leu Met Pro Asp Tyr Ile Glu
225                 230                 235                 240

Gly Glu Phe Asp Thr Gln Lys Ile Arg Val Phe Glu Ile Gly Phe Ile
                245                 250                 255

Lys Arg Trp Leu Asn Asp Met Pro Leu Leu Gln Thr Thr Asn Tyr Ile
            260                 265                 270

Val Leu Pro Glu Asn Ser Lys Ala Lys Val Cys Thr Ile Ala Val Gly
        275                 280                 285

Glu Leu Thr Leu Ala Ser Leu Cys Val Asp Glu Ser Thr Val Leu Leu
    290                 295                 300

Tyr His Asp Ser Asn Gly Ser Gln Asp Gly Ile Leu Val Val Thr Leu
```

```
                305                 310                 315                 320
        Gly Ile Phe Gly Ala Thr Pro Met Asp Gln Val Glu Val Ile Pro
                        325                 330                 335

Val Ala His Pro Ser Val Xaa Lys Ile His Ile Thr Asn His Arg Gly
                        340                 345                 350

Phe Ile Lys Asp Ser Ile Ala Thr Trp Met Val Pro Ala Leu Ile Ser
                        355                 360                 365

Gly Glu Gln Glu Glu Lys Asn Cys Leu Glu Ser Ala Cys Gln Arg
                370                 375                 380

Lys Ser Tyr Pro Met Cys Asn Gln Thr Ser Trp Lys Pro Phe Gly Gly
        385                 390                 395                 400

Gly Gln Leu Pro Ser Tyr Gly Arg Leu Thr Leu Pro Leu Asp Pro Gly
                        405                 410                 415

Ile Asp Leu Gln Leu Asn Ile Ser Phe Thr Tyr Gly Pro Val Ile Leu
                        420                 425                 430

Asn Gly Asp Gly Met Asp Tyr Tyr Glu Ser Pro Leu Leu Asp Ser Gly
                        435                 440                 445

Trp Leu Thr Ile Pro Pro Lys Asn Gly Thr Ile Leu Gly Leu Ile Asn
                450                 455                 460

Lys Ala Ser Arg Gly Asp Gln Phe Thr Val Ile Pro His Val Leu Thr
        465                 470                 475                 480

Phe Ala Pro Arg Glu Ser Ser Gly Asn Cys Tyr Leu Pro Ile Gln Thr
                        485                 490                 495

Ser Gln Ile Met Asp Lys Asp Val Leu Thr Glu Ser Asn Leu Val Val
                        500                 505                 510

Leu Pro Thr Gln Asn Phe Arg Tyr Val Ile Ala Thr Tyr Asp Ile Ser
                        515                 520                 525

Arg Asn Asp His Ala Ile Val Tyr Tyr Val Tyr Asp Pro Ile Arg Thr
                530                 535                 540

Ile Ser Tyr Thr His Pro Phe Arg Leu Thr Thr Lys Gly Arg Pro Asp
        545                 550                 555                 560

Phe Leu Arg Ile Glu Cys Phe Val Trp Asp Asp Leu Trp Cys His
                        565                 570                 575

Gln Phe Tyr Arg Phe Glu Ala Asp Ile Thr Asn Ser Ala Thr Ser Val
                        580                 585                 590

Glu Asn Leu Val Arg Ile Arg Phe Ser Cys Asn Arg Ser Lys Pro
                        595                 600                 605

<210> SEQ ID NO 32
<211> LENGTH: 607
<212> TYPE: PRT
<213> ORGANISM: artificial sequence
<220> FEATURE:
<223> OTHER INFORMATION: ABK35780

<400> SEQUENCE: 32

Met Leu Ser Tyr Gln Asp Lys Val Ser Ala Phe Tyr Lys Asp Asn Ala
1               5                   10                  15

Arg Ala Asn Ser Ser Lys Leu Ser Leu Val Thr Glu Glu His Gly Ser
                20                  25                  30

Arg Arg Pro Pro Tyr Leu Leu Phe Ile Leu Leu Ile Leu Leu Val Gly
                35                  40                  45

Ile Met Ala Leu Leu Ala Ile Thr Gly Ala Arg Phe His Gln Val Ser
                50                  55                  60

Thr Ser Asn Met Glu Phe Ser Arg Leu Leu Lys Glu Asp Met Glu Lys
```

```
            65                  70                  75                  80
Ser Glu Ala Val His His Gln Val Ile Asp Val Leu Thr Pro Leu Phe
                    85                  90                  95

Lys Ile Ile Gly Asp Glu Ile Gly Leu Arg Leu Pro Gln Lys Leu Asn
                    100                 105                 110

Glu Ile Lys Gln Phe Ile Leu Gln Lys Thr Asn Phe Phe Asn Pro Lys
                    115                 120                 125

Arg Glu Phe Asp Phe Arg Asp Leu His Trp Cys Ile Asn Pro Pro Ser
                    130                 135                 140

Lys Ile Lys Val Asn Phe Thr Asn Tyr Cys Asp Thr Ile Gly Ile Arg
145                 150                 155                 160

Lys Ser Ile Ala Leu Ala Ala Asn Pro Ile Leu Leu Ser Ala Leu Ser
                    165                 170                 175

Arg Gly Arg Gly Asp Ile Phe Pro Pro Tyr Arg Cys Ser Gly Ala Ala
                    180                 185                 190

Thr Ser Val Gly Arg Val Phe Pro Leu Ser Val Ser Leu Ser Met Ser
                    195                 200                 205

Leu Ile Ser Arg Thr Ser Glu Ile Ile Asn Met Leu Thr Ala Ile Ser
    210                 215                 220

Asp Gly Val Tyr Gly Lys Thr Tyr Leu Leu Val Pro Asp Tyr Ile Glu
225                 230                 235                 240

Gly Glu Phe Asp Thr Gln Lys Ile Arg Val Phe Glu Ile Gly Phe Ile
                    245                 250                 255

Lys Arg Trp Leu Asn Asp Met Pro Leu Leu Gln Thr Thr Asn Tyr Met
                    260                 265                 270

Val Leu Pro Glu Asn Ser Lys Ala Lys Val Cys Thr Ile Ala Val Gly
                    275                 280                 285

Glu Leu Thr Leu Ala Ser Leu Cys Val Asp Glu Ser Thr Val Leu Leu
            290                 295                 300

Tyr His Asp Ser Asn Gly Ser Gln Asp Gly Ile Leu Val Val Thr Leu
305                 310                 315                 320

Gly Ile Phe Gly Ala Thr Pro Met Asp Gln Val Glu Glu Val Ile Pro
                    325                 330                 335

Val Ala His Pro Ser Val Glu Lys Ile His Ile Thr Asn His Arg Gly
                    340                 345                 350

Phe Ile Lys Asp Ser Ile Ala Thr Trp Met Val Pro Val Leu Val Ser
                    355                 360                 365

Glu Asn Gln Glu Glu Gln Lys Asn Cys Leu Glu Ser Ala Cys Gln Arg
            370                 375                 380

Lys Ser Tyr Pro Met Cys Asn Gln Thr Ser Trp Glu Pro Phe Gly Gly
385                 390                 395                 400

Gly Gln Leu Pro Ser Tyr Gly Arg Leu Thr Leu Pro Leu Asp Pro Gly
                    405                 410                 415

Ile Asp Leu Gln Leu Asn Leu Ser Phe Thr Tyr Gly Pro Ile Ile Leu
                    420                 425                 430

Asn Gly Asp Gly Met Asp Tyr Tyr Glu Ser Pro Leu Leu Asn Ser Gly
            435                 440                 445

Trp Leu Thr Ile Pro Pro Lys Asn Gly Thr Ile Leu Gly Leu Ile Asn
                    450                 455                 460

Lys Ala Ser Arg Gly Asp Gln Phe Thr Val Thr Pro His Val Leu Thr
465                 470                 475                 480

Phe Ala Pro Arg Glu Ser Ser Gly Asn Cys Tyr Leu Pro Ile Gln Thr
                    485                 490                 495
```

```
Ser Gln Ile Met Asp Lys Asp Val Leu Thr Glu Ser Asn Leu Val Val
            500                 505                 510

Leu Pro Thr Gln Asn Phe Arg Tyr Val Ile Ala Thr Tyr Asp Ile Ser
        515                 520                 525

Arg Asp Asp His Ala Ile Val Tyr Val Tyr Asp Pro Ile Arg Thr
    530                 535                 540

Ile Ser Tyr Thr Tyr Pro Phe Arg Leu Thr Thr Lys Gly Arg Pro Asp
545                 550                 555                 560

Phe Leu Arg Ile Glu Cys Phe Val Trp Asp Tyr Asp Leu Trp Cys His
            565                 570                 575

Gln Phe Tyr Arg Phe Glu Ala Asp Ile Thr Asn Ser Thr Thr Ser Val
            580                 585                 590

Glu Asn Leu Val Arg Ile Arg Phe Ser Cys Asn Arg Ser Lys Pro
            595                 600                 605
```

<210> SEQ ID NO 33
<211> LENGTH: 607
<212> TYPE: PRT
<213> ORGANISM: artificial sequence
<220> FEATURE:
<223> OTHER INFORMATION: ACJ46470

<400> SEQUENCE: 33

```
Met Leu Ser Tyr Gln Asp Lys Val Gly Ala Phe Tyr Lys Asp Asn Ala
1               5                   10                  15

Arg Ala Asn Ser Ser Lys Leu Ser Leu Val Thr Glu Glu Gln Gly Gly
            20                  25                  30

Arg Arg Pro Pro Tyr Leu Phe Phe Val Leu Leu Thr Leu Leu Ile Gly
        35                  40                  45

Ile Leu Ala Leu Leu Ala Ile Thr Gly Val Arg Phe His Gln Val Ser
    50                  55                  60

Thr Ser Asn Met Glu Phe Ser Arg Leu Leu Lys Glu Asp Met Glu Lys
65              70                  75                  80

Ser Glu Ala Val His His Gln Val Ile Asp Val Leu Thr Pro Leu Phe
            85                  90                  95

Lys Ile Ile Gly Asp Glu Ile Gly Leu Arg Leu Pro Gln Lys Leu Asn
            100                 105                 110

Glu Ile Lys Gln Phe Ile Leu Gln Lys Thr Asn Phe Asn Pro Asn
            115                 120                 125

Arg Glu Phe Asp Phe Arg Asp Leu His Trp Cys Ile Asn Pro Pro Ser
        130                 135                 140

Lys Ile Lys Val Asn Phe Thr Asn Tyr Cys Asp Thr Val Gly Val Lys
145                 150                 155                 160

Lys Ser Ile Thr Ser Ala Ala Asn Pro Ile Ile Leu Ser Ala Leu Ser
            165                 170                 175

Gly Ala Arg Gly Asp Ile Phe Pro Pro Tyr Arg Cys Ser Gly Ala Thr
        180                 185                 190

Thr Ser Val Gly Arg Val Phe Pro Leu Ser Val Ser Leu Ser Met Ser
    195                 200                 205

Leu Ile Ser Arg Thr Ser Glu Ile Ile Asn Met Leu Thr Ala Ile Ser
    210                 215                 220

Asp Gly Val Tyr Gly Lys Thr Tyr Leu Leu Val Pro Asp Tyr Ile Glu
225                 230                 235                 240

Gly Glu Phe Asp Ser Gln Lys Ile Arg Val Phe Glu Ile Gly Phe Ile
            245                 250                 255
```

Lys Arg Trp Leu Asn Asp Met Pro Leu Leu Gln Thr Thr Asn Tyr Met
            260                 265                 270

Val Leu Pro Glu Thr Ser Lys Ala Lys Val Cys Thr Ile Ala Val Gly
        275                 280                 285

Glu Leu Thr Leu Ala Ser Leu Cys Val Asp Ser Thr Val Leu Leu
    290                 295                 300

Tyr His Asp Ser Asn Gly Ser Gln Asn Gly Ile Leu Val Val Thr Leu
305                 310                 315                 320

Gly Ile Phe Gly Ala Thr Ser Met Asp Gln Val Glu Val Ile Pro
                325                 330                 335

Ile Ala His Pro Ser Val Glu Arg Ile His Ile Thr Asn His Arg Gly
            340                 345                 350

Phe Ile Lys Asp Ser Ile Val Thr Trp Met Val Pro Val Leu Val Ser
        355                 360                 365

Glu Lys Gln Glu Glu Gln Lys Asn Cys Leu Glu Ser Ala Cys Gln Arg
    370                 375                 380

Lys Ser Tyr Pro Met Cys Asn Gln Thr Ser Trp Glu Pro Phe Gly Gly
385                 390                 395                 400

Gly Gln Leu Pro Ser Tyr Gly Arg Leu Thr Leu Pro Leu Asp Pro Ser
                405                 410                 415

Ile Asp Leu Gln Leu Asn Ile Ser Phe Thr Tyr Gly Pro Val Ile Leu
            420                 425                 430

Asn Gly Asp Gly Met Asp Tyr Tyr Glu Ser Pro Leu Leu Glu Ser Gly
        435                 440                 445

Trp Leu Thr Ile Pro Pro Lys Asn Gly Thr Val Leu Gly Leu Ile Asn
    450                 455                 460

Lys Ala Ser Arg Gly Asp Gln Phe Thr Ala Thr Pro His Val Leu Thr
465                 470                 475                 480

Phe Ala Pro Arg Glu Ser Ser Gly Asn Cys Tyr Leu Pro Ile Gln Thr
                485                 490                 495

Ser Gln Ile Met Asp Lys Asp Val Leu Thr Glu Ser Asn Leu Val Val
            500                 505                 510

Leu Pro Thr Gln Asn Phe Arg Tyr Val Ile Ala Thr Tyr Asp Ile Ser
        515                 520                 525

Arg Gly Asp His Ala Ile Val Tyr Tyr Val Tyr Asp Pro Ile Arg Thr
530                 535                 540

Ile Ser Tyr Thr Tyr Pro Phe Arg Leu Thr Thr Lys Gly Arg Pro Asp
545                 550                 555                 560

Phe Leu Arg Ile Glu Cys Phe Val Trp Asp Asp Leu Trp Cys His
                565                 570                 575

Gln Phe Tyr Arg Phe Glu Ala Asn Ile Thr Asn Ser Thr Thr Ser Val
            580                 585                 590

Glu Asn Leu Val Arg Ile Arg Phe Ser Cys Asn Arg Ser Lys Pro
        595                 600                 605

<210> SEQ ID NO 34
<211> LENGTH: 607
<212> TYPE: PRT
<213> ORGANISM: artificial sequence
<220> FEATURE:
<223> OTHER INFORMATION: ABX84040

<400> SEQUENCE: 34

Met Leu Ser Tyr Gln Asp Lys Val Gly Ala Phe Tyr Lys Asp Asn Ala
1               5                   10                  15

```
Arg Ala Asn Ser Ser Lys Leu Ser Leu Val Thr Glu Glu Gln Gly Gly
            20                  25                  30

Arg Arg Pro Pro Tyr Leu Leu Phe Val Leu Leu Ile Leu Leu Ile Gly
        35                  40                  45

Ile Leu Ala Leu Leu Ala Ile Thr Gly Val Arg Phe His Gln Val Ser
 50                  55                  60

Thr Ser Asn Met Glu Phe Ser Arg Leu Leu Lys Glu Asp Met Glu Lys
 65                  70                  75                  80

Ser Glu Ala Val His His Gln Val Ile Asp Val Leu Thr Pro Leu Phe
                85                  90                  95

Lys Ile Ile Gly Asp Glu Ile Gly Leu Arg Leu Pro Gln Lys Leu Asn
            100                 105                 110

Glu Ile Lys Gln Phe Ile Leu Gln Lys Thr Asn Phe Phe Asn Pro Asn
        115                 120                 125

Arg Glu Phe Asp Phe Arg Asp Leu His Trp Cys Ile Asn Pro Pro Ser
130                 135                 140

Lys Ile Lys Val Asn Phe Thr Asn Tyr Cys Asp Thr Val Gly Val Lys
145                 150                 155                 160

Lys Ser Ile Ala Ser Ala Ala Asn Pro Ile Ile Leu Ser Ala Leu Ser
                165                 170                 175

Gly Ala Arg Gly Asp Ile Phe Pro Pro Tyr Arg Cys Ser Gly Ala Thr
            180                 185                 190

Thr Ser Val Gly Arg Val Phe Pro Leu Ser Val Ser Leu Ser Met Ser
        195                 200                 205

Leu Ile Ser Arg Thr Ser Glu Ile Ile Asn Met Leu Thr Ala Ile Ser
210                 215                 220

Asp Gly Val Tyr Gly Lys Thr Tyr Met Leu Val Pro Asp Tyr Ile Glu
225                 230                 235                 240

Gly Glu Phe Asp Ser Gln Lys Ile Arg Val Phe Glu Ile Gly Phe Ile
                245                 250                 255

Lys Arg Trp Leu Asn Asn Met Pro Leu Leu Gln Thr Thr Asn Tyr Met
            260                 265                 270

Val Leu Pro Glu Thr Ser Lys Ala Lys Val Cys Thr Ile Ala Val Gly
        275                 280                 285

Glu Leu Thr Leu Ala Ser Leu Cys Val Asp Glu Ser Thr Val Leu Leu
290                 295                 300

Tyr His Asp Ser Asn Gly Ser Gln Asn Gly Ile Leu Val Val Thr Leu
305                 310                 315                 320

Gly Ile Phe Gly Ala Thr Pro Met Asp Gln Val Glu Glu Val Ile Pro
                325                 330                 335

Ile Ala His Pro Ser Val Glu Arg Ile His Ile Thr Asn His Arg Gly
            340                 345                 350

Phe Ile Lys Asp Ser Val Val Thr Trp Met Val Pro Val Leu Val Ser
        355                 360                 365

Glu Lys Gln Glu Glu Gln Lys Asn Cys Leu Glu Ser Ala Cys Gln Arg
370                 375                 380

Lys Ser Tyr Pro Met Cys Asn Gln Thr Ser Trp Glu Pro Phe Gly Gly
385                 390                 395                 400

Gly Gln Leu Pro Ser Tyr Gly Arg Leu Thr Leu Pro Leu Asp Pro Ser
                405                 410                 415

Val Asp Leu Gln Leu Asn Ile Ser Phe Thr Tyr Gly Pro Val Ile Leu
            420                 425                 430
```

-continued

Asn Gly Asp Gly Met Asp Tyr Tyr Glu Ser Pro Leu Leu Glu Ser Gly
                435                 440                 445

Trp Leu Ala Ile Pro Pro Lys Asn Gly Thr Val Leu Gly Leu Ile Asn
    450                 455                 460

Lys Ala Ser Arg Gly Asp Gln Phe Thr Val Thr Pro His Val Leu Thr
465                 470                 475                 480

Phe Ala Pro Arg Glu Ser Ser Gly Asn Cys Tyr Leu Pro Ile Gln Thr
                485                 490                 495

Ser Gln Ile Met Asp Lys Asp Val Leu Thr Glu Ser Asn Leu Val Val
            500                 505                 510

Leu Pro Thr Gln Asn Phe Arg Tyr Val Ile Ala Thr Tyr Asp Ile Ser
        515                 520                 525

Arg Gly Asp His Ala Ile Val Tyr Tyr Val Tyr Asp Pro Ile Arg Thr
    530                 535                 540

Ile Ser Tyr Thr Tyr Pro Phe Arg Leu Thr Thr Lys Gly Arg Pro Asp
545                 550                 555                 560

Phe Leu Arg Ile Glu Cys Phe Val Trp Asp Asp Leu Trp Cys His
                565                 570                 575

Gln Phe Tyr Arg Phe Glu Ala Asn Ile Thr Asn Ser Thr Thr Ser Val
            580                 585                 590

Glu Asn Leu Val Arg Ile Arg Phe Ser Cys Asn Arg Ser Lys Pro
        595                 600                 605

<210> SEQ ID NO 35
<211> LENGTH: 1824
<212> TYPE: DNA
<213> ORGANISM: artificial sequence
<220> FEATURE:
<223> OTHER INFORMATION: wildtype DNA encoding CDV HA (AAQ05830)

<400> SEQUENCE: 35

| | |
|---|---|
| atgctctcct accaagacaa ggtgggtgcc ttctataagg ataatgcaag agctaattca | 60 |
| tccaagctgt ccttagtgac agaagagcaa ggggcagga gaccacccta tttgctgttt | 120 |
| gtccttctca tccttctggt tggaatcatg accttgcttg ctatcactgg agttcgattt | 180 |
| caccaagtat caactagcaa tatggaattt agcagattgc tgaaagagga tatgagaaa | 240 |
| tcagaggccg tacatcacca agtcatagat gtcttgacac cgctcttcaa aattattgga | 300 |
| gatgaggttg ggttacggtt gccacaaaaa ctaaacgaga tcaaacaatt tatccttcaa | 360 |
| aagacaaact tcttcaatcc gaacagggaa ttcgacttcc gcgatctcca ctggtgcatt | 420 |
| aatccaccta gtaagatcaa ggtgaatttt actaattact gcgatacaat gggatcaga | 480 |
| aaatctattg catcggcagt aaatcccatc cttttatcag cactctccgg aggcagaggt | 540 |
| gacatattcc caccatacag atgcagtgga gctactactt cagtgggcag agttttcccc | 600 |
| ctatcagtat cattgtccat gtctttgatc tcaaaaacat cagagataac caatatgcta | 660 |
| actgctatct cagacggagt gtatggtaaa acctatttgc tagtgcctga ttacattgaa | 720 |
| ggggagttcg acacgcaaaa gattcgagtc tttgagatag ggttcatcaa acggtggctg | 780 |
| aataacatgc cattactcca gacaaccaac tacatggtcc tcccggagaa ttccaaagcc | 840 |
| aaggtatgta ctatagcagt gggcgagttg acactggctt ccttgtgtgt agatgagagc | 900 |
| accgtattgt tatatcatga cagcaatggt tcacaagatg gtattctagt agtgacgctg | 960 |
| gggatatttg ggcaacacc tatggatcaa gttgaagaag tgatacctgt cgctcaccca | 1020 |
| tcagtagaaa aatacatat aacaaatcac cgtgggttca aaagattc aatagcaacc | 1080 |

| | |
|---|---|
| tggatggtgc ctgcattggt ctctgagaaa caagaggaac aaaaaaattg tctggagtcg | 1140 |
| gcttgtcaaa gaaaaaccta ccctatgtgc aaccaaacgt catgggaacc ctttggaggg | 1200 |
| ggacagttgc catcttatgg gcggttgaca ttatctctag atccaagcat tgaccttcaa | 1260 |
| cttaacatat catttacata cggtccagtt atactgaatg gagacggtat ggattattat | 1320 |
| ggaagctcac tttcggactc cggatggctt accattcctc ccaagaatgg aacagtcctt | 1380 |
| ggattgataa acaaagcaag tagaggagac cagttcactg taatccccca tgtgttgaca | 1440 |
| tttgcgccca gggaatcaag tggaaattgt tatttaccta ttcaaacatc ccagattatg | 1500 |
| gataaagatg tcctgactga gtccaattta gtggtgttgc ctacacagaa tttttagatat | 1560 |
| gtcatagcaa catatgatat atctcggggc gatcatgcaa ttgtttatta tgtttatgac | 1620 |
| ccaatccgga cgatttctta tacgtaccca tttagactaa ctaccaaggg tagacctgat | 1680 |
| ttcctaagaa ttgaatgttt tgtgtgggat gacgatttgt ggtgtcacca atttaccga | 1740 |
| tttgaggctg acatcaccaa ctctacaacc agtgttgaga atttagtccg tataagattc | 1800 |
| tcatgtgacc gttcaaaacc ttga | 1824 |

<210> SEQ ID NO 36
<211> LENGTH: 1824
<212> TYPE: DNA
<213> ORGANISM: artificial sequence
<220> FEATURE:
<223> OTHER INFORMATION: AF478543 encoding CDV HA AAQ05828

<400> SEQUENCE: 36

| | |
|---|---|
| atgctctcct accaagacaa ggtgggtgcc ttctataagg ataatgcaag agctaattca | 60 |
| tccaagctgt ccttagtgac agaagagcaa gggggcagga gaccacccta tttgctgttt | 120 |
| gtccttctca tccttctggt tggaatcatg accttgcttg ctatcactgg agttcgattt | 180 |
| caccaagtat caactagcaa tatggaattt agcagattgc tgaaagagga tatggagaaa | 240 |
| tcagaggccg tacatcacca agtcatagat gtcttgacac cgctcttcaa aattattgga | 300 |
| gatgaggttg ggttacggtt gccacaaaaa ctaaacgaga tcaaacaatt tatccttcaa | 360 |
| aagacaaact tcttcaatcc gaacagggaa ttcgacttcc gcgatctcca ctggtgcatt | 420 |
| aatccaccta gtaagatcaa ggtgaatttt actaattact gcgatacaat gggatcaga | 480 |
| aaatctattg catcggcagt aaatcccatc cttttatcag cactctccgg aggcagaggt | 540 |
| gacatattcc caccatacag atgcagtgga gctactactt cagtgggcag agttttcccc | 600 |
| ctatcagtat cattgtccat gtcttttgatc tcaaaaacat cagagataac caatatgcta | 660 |
| actgctatct cagacggagt gtatggtaaa acctatttgc tagtgcctga ttacattgaa | 720 |
| ggggagttcg acacgcaaaa gattcgagtc tttgagatag ggttcatcaa acggtggctg | 780 |
| aataacatgc cattactcca gacaaccaac tacatggtcc tcccggagaa ttccaaagcc | 840 |
| aaggtatgta ctatagcagt gggcgagttg acactggctt ccttgtgtgt agatgagagc | 900 |
| accgtattgt tatatcatga cagcaatggt tcacaagatg gtattctagt agtgacgctg | 960 |
| gggatatttg gggcaacacc tatggatcaa gttgaagaag tgatacctgt cgctcaccca | 1020 |
| tcagtagaaa aaatacatat aacaaatcac cgtgggttca taaagattc aatagcaacc | 1080 |
| tggatggtgc ctgcattggt ctctgagaaa caagaggaac aaaaaaattg tctggagtcg | 1140 |
| gcttgtcaaa gaaaaaccta ccctatgtgc aaccaaacgt catgggaacc ctttggaggg | 1200 |
| ggacagttgc catcttatgg gcggttgaca ttatctctag atccaagcat tgaccttcaa | 1260 |
| cttaacatat catttacata cggtccagtt atactgaatg gagacggtat ggattattat | 1320 |

```
ggaagctcac tttcggactc cggatggctt accattcctc ccaagaatgg aacagtcctt    1380
ggattgataa acaaagcaag tagaggagac cagttcactg taatccccca tgtgttgaca    1440
tttgcgccca gggaatcaag tggaaattgt tatttaccta ttcaaacatc ccagattatg    1500
gataaagatg tcctgactga gtccaattta gtggtgttgc ctacacagaa ttttagatat    1560
gtcatagcaa catatgatat atctcggggc gatcatgcaa ttgtttatga tgtttatgac    1620
ccaatccgga cgatttctta tacgcaccca tttagactaa ctaccaaggg tagacctgat    1680
ttcctaagaa ttgaatgttt tgtgtgggat gacgatttgt ggtgtcacca attttaccga    1740
tttgaggctg acatcaccaa ctctacaacc agtgttgaga atttagtccg tataagattc    1800
tcatgtgacc gttcaaaacc ttga                                           1824
```

<210> SEQ ID NO 37
<211> LENGTH: 1824
<212> TYPE: DNA
<213> ORGANISM: artificial sequence
<220> FEATURE:
<223> OTHER INFORMATION: DQ494318 encoding CDV HA ABF55672

<400> SEQUENCE: 37

```
atgctctcct accaagacaa ggtgggtgcc ttctataagg ataatgcaag agctaattca      60
tccaagctgt ccttagtgac agaagagcaa ggggcagga gaccacccta tttgctgttt      120
gtccttctca tccttctggt cggaatcatg accttgcttg ctatcactgg agttcgattt      180
caccaagtat caactagcaa tatggaattt agcagattgt tgaaagagga tatggagaaa     240
tcagaggccg tacatcacca agtcatagat gtcttgacac cgctcttcaa aattattgga     300
gatgaggttg ggttacggtt gccacaaaaa ctaaacgaga tcaaacaatt tatccttcaa     360
aagacaaact tcttcaatcc gaacagggaa ttcgacttcc gcgatctcca ctggtgcatt     420
aatccaccta gtaagatcaa ggtgaatttt actaattact gcgatacaat gggatcaga     480 aaatctattg catcggcagc aaatcccatc cttttatcag cactctccgg aggcagaggt     540
gacatattcc caccatacag atgcagtgga gctactactt cagtgggcag agttttcccc     600
ctatcagtat cattgtccat gtctttgatc tcaaaaacat cagagataac caatatgcta     660
actgctatct cagacggagt gtatggtaaa acctatttgc tagtgcctga ttacattgaa     720
ggggagttcg acacgcaaat gattcgagtc tttgagtagg ggttcatcaa acggtggctg     780
aataacatgc cattactcca gacaaccaac tacatggtcc tcccggagaa ttccaaagcc     840
aaggtatgta ctatagcagt gggcgagttg acactagctt cttgtgtgt agatgagagc      900 accgtattgt tatatcatga cagcaatggt tcacaagatg gtattctagt agtgacgctg     960
gggatatttg ggcaacacc tatggatcaa gttggagaag tgatacctgt cgctcacccc    1020
tcagtagaaa aaatacatat aacaaatcac cgtgggttca taaaagattc aatagcaacc    1080
tggatggtgc ctgcattggt ctctgagaaa caagaggaac aaaaaaattg tctgagtcg    1140 gcttgtcaaa gaaaaaccta cccaatgtgc aaccaaacgt catgggaacc ctttggaggg    1200
ggacagttac catcttatgg gcggttgaca ttacctctag atccaagcat tgaccctcaa    1260
cttaacatat catttacata cggtccagtt atactgaatg agacggtat ggattattat    1320 gaaagctcac tttcggactc tggatggctt accattcctc ccaagaacgg aacagtcctt    1380
ggattgataa acaaagcaag tagaggagac cagttcactg taatccccca tgtgttgaca    1440
tttgcgccca gggaatcaag tggaaattgt tatttaccta ttcaaacatc ccagattatg    1500
```

| | |
|---|---|
| gataaagatg tcctgactga gtccaattta gtggtgttgc ctacacagaa tttttagatat | 1560 |
| gtcatagcaa catatgatat atctcggggc gatcatgcca ttgttttatta tgtttatgac | 1620 |
| ccaatccgga cgatttctta tacgtaccca tttagactga ctaccaaggg tagacctgat | 1680 |
| ttcctaagaa ttgaatgttt tgtgtgggat gacgatttgt ggtgtcacca attttaccga | 1740 |
| tttgaggctg acatcaccaa ctctacaacc agtgttgaga atttagtccg tataagattc | 1800 |
| tcatgtaatc gttcaaaacc ttga | 1824 |

```
<210> SEQ ID NO 38
<211> LENGTH: 1824
<212> TYPE: DNA
<213> ORGANISM: artificial sequence
<220> FEATURE:
<223> OTHER INFORMATION: AY386316

<400> SEQUENCE: 38
```

| | |
|---|---|
| atgctctcct accaagacaa ggtgggtgcc ttctataagg ataatgcaag agctaattca | 60 |
| tccaagctgt ccttagtgac agaagagcaa ggggcagga gaccaccta tttgctgttt | 120 |
| gtccttctca tccttctggt tggaatcatg accttgcttg ctatcactgg agttcgattt | 180 |
| caccaagtat caactagcaa tatggaattt agcagattgc tgaaagagga tatggagaaa | 240 |
| tcagaggccg tacatcacca agtcatagat gtcttgacac cgctcttcaa aattattgga | 300 |
| gatgaggttg ggttacagtt gccacaaaaa ctaaacgaga tcaaacaatt tatccttcaa | 360 |
| aagacaaact tcttcaatcc gaacagggaa ttcgacttcc gcgatctcca ctggtgcatt | 420 |
| aatccaccta gtaagatcaa ggtgaatttt actaattact gcgatacaat tgggatcaaa | 480 |
| aagtctattg catcggcagc aaatcccatc cttttatcag cactctccgg aggcagaggt | 540 |
| gacatattcc caccatacag atgcagtgga gctactactt cagtgggcag agttttcccc | 600 |
| ctatcagtat cattgtccat gtctttgatc tcaaaaacat cagagataac cagtatgcta | 660 |
| actgctatct cagacggagt gtatggtaaa acctattgc tagtgcctga ttacattgaa | 720 |
| ggggagttcg acacgcaaaa gattcgagtc tttgagatag ggttcatcaa acggtggctg | 780 |
| aataacatgc cattactcca gacaaccaac tacatggtcc tcccggagaa ttccaaagcc | 840 |
| aaggtatgta ctatagcagt gggcgagttg acactggctt ccttgtgtgt agatgagagc | 900 |
| accgtattgt tatatcatga cagcaatggt tcacaagatg gtattctagt agtgacgctg | 960 |
| gggatatttg gagcaacacc tatggatcaa gttgaagaag tgatacctgt cgctcaccca | 1020 |
| tcagtagaaa aaatacatat aacaaatcac cgtgggttca taaagattc aatagcaacc | 1080 |
| tggatggtgc ctgcattggt ctctgagaaa caagaggaac aaaaaaattg tctggagtcg | 1140 |
| gcttgtcaaa gaaaaactta ccctatgtgc aaccaaacgt catgggaacc ctttggaggg | 1200 |
| ggacagttgc catcttatgg gcggttgaca ttacctctag atccaagcat tgaccttcaa | 1260 |
| cttaacatat catttacata cggtccggtt atactgaatg agacggtat ggattattat | 1320 |
| gaaagcccac tttcggactc cggatggctt accattcctc ccaggaacgg aacagtcctt | 1380 |
| ggattgataa acaaagcaag tagaggagac cagttcactg taatcccccca tgtgttgaca | 1440 |
| tttgcgccca gggaatcaag tggaaattgt tatttaccta ttcaaacatc ccagattatg | 1500 |
| gataaagatg tccttactga gtccaattta gtggtgttgc ctacacagaa tttttagatat | 1560 |
| gtcatagcaa catatgatat atcccggggc gatcatgcaa ttgttttatta tgtttatgac | 1620 |
| ccaatccgga cgatttctta tacgcaccca tttagactaa ccaccaaggg tagacctgat | 1680 |
| ttcctaagga ttgaatgttt tgtgtgggat gacgatttgt ggtgtcacca attttaccga | 1740 |

```
tttgaggctg acatcaccaa ctctacaacc agtgttgaga atttagtccg tataagattc   1800
tcatgtaacc gttcaaaacc ttga                                          1824

<210> SEQ ID NO 39
<211> LENGTH: 1824
<212> TYPE: DNA
<213> ORGANISM: artificial sequence
<220> FEATURE:
<223> OTHER INFORMATION: DQ494317 encoding CDV HA ABF55671
<220> FEATURE:
<221> NAME/KEY: misc_feature
<222> LOCATION: (158)..(158)
<223> OTHER INFORMATION: n is a, c, g, or t

<400> SEQUENCE: 39
atgctctcct accaagacaa ggtgggtgcc ttctataagg ataatgcaag agctaattca     60
tccaagctgt ccttagtgac agaagagcaa gggggcagga gaccacccta tttgctgttt    120
gtccttctca tccttctggt tggagtcatg accttgcntg ctatcactgg agttcgaatt    180
caccaagtat caactagcaa tatggaattt agcagattgc tgaaagagga tatggagaaa    240
tcagaggccg tacatcacca agtcatagat gtcttgacac cgctcttcaa aattattgga    300
gatgaggttg ggttacggtt gccacaaaaa ctaaacgaga tcaaacaatt tatccttcaa    360
aagacaaact tcttcaatcc gaacagggaa ttcgacttcc gcgatctcca ctggtgcatt    420
aatccaccta gtaagatcaa ggtgaatttt actaattact gcgatacagt tgggatcaga    480
aaatctattg catcggcagc aaatcccatc cttttatcag cactctccgg aggcagaggt    540
gacatattcc caccatacag atgcagtgga gctactactt cagtgggcag agttttcccc    600
ctatcagtat cattgtccat gtctttgatc tcaaaaacat cagagataac caatatgcta    660
actgctatct cagacggagt gtatggtaaa acctatttgc tagtgcctga ttacattgaa    720
ggggagttcg acacgcaaaa gattcgagtc tttgagattg ggttcatcag acggtggctg    780
aataacatgc cattactcca gacaaccaac tacatggtcc tcccggagaa ttccaaagcc    840
aaggtatgta ctatagcagt gggcgagttg acactggctt ccttgtgtgt agatgagagc    900
accgtattgt tatatcatga cagcaatggt tcacaagatg gtattctagt agtgacgctg    960
gggatatttg ggcaacacc tatggatcaa gttgaagaag tgatacctgt cgctcaccca   1020
tcagtagaaa aaatacatat aacaaatcac cgtgggttca taaaagatgc aatagcaacc   1080
tggatggtgc ctgcattggt ctctgagaaa caagaggaac aaaaaaattg tctggagtcg   1140
gcttgtcaaa gaaaaaccta tcctatgtgc aaccaaacgt catgggaacc ctttggagga   1200
ggacagttgc catcttatgg gcggttgaca ttacctctag atccaagcat tgaccttcaa   1260
cttaacatat catttacata cggtccagtt atactgaatg gagacggtat ggattattat   1320
gaaagctcac tttcggactc cggatggctt accattcctc ccaagaacgg aacagtcctt   1380
ggattgataa acaaagcaag tagaggagac cagttcactg taacccccca tgtgttgaca   1440
tctgcgccca gggaatcaag tggaaattgt tatttaccta ttcaaacatc ccagattatg   1500
gataaagatg tcctgactga gtccaattta gtggtgttgc ctacacagaa ttttagatat   1560
gtcatagcaa catatgatat atctcggggc gatcatgcaa ttgtttatta tgtttatgac   1620
ccaatccgga cgatttctta tacgtaccca tttagactaa ctaccaaggg tagacctgat   1680
ttcctaagaa ttgaatgttt tgtgtgggat gacgatatgt ggtgtcacca attttaccga   1740
tttgaggctg acatcaccaa ctctacaacc agtgttgaga atttagtccg tataagattc   1800
```
tcatgtaacc gttcaaaacc ttga                                          1824

<210> SEQ ID NO 40
<211> LENGTH: 1824
<212> TYPE: DNA
<213> ORGANISM: artificial sequence
<220> FEATURE:
<223> OTHER INFORMATION: GQ214376 encoding CDV HA ACS88240

<400> SEQUENCE: 40
atgctctcct accaagacaa ggtgggtgcc ttctataagg ataatgcaag agctaattca     60
tccaagctgt ccttagtgac agaagagcaa gggggcagga gaccaccta tttgctgttt    120
gtccttctca tccttctggt tggaatcatg accttgcttg ctatcactgg agttcgattt    180
caccaagtat caactagcaa tatggaattt agcagattgc tgaaagagga tatggagaaa    240
tcagaggccg tacatcacca agtcatagat gtcttgacac cgctcttcaa aattattgga    300
gatgaggttg ggttacggtt gccacaaaaa ctaaacgaga tcaaacaatt tatccttcaa    360
aagacaaact tcttcaatcc gaacagggaa ttcgacttcc gcgatctcca ctggtgcatt    420
aatccaccta gtaagatcaa ggtgaatttt actaattact gcgatacaat gggatcaga    480
caatctattg catcggcagc aaatcccatc cttttatcag cactctccgg aggcagaggt    540
gacatattcc caccatacag atgcagtgga gctactactt cagtgggcag agttttcccc    600
ctgtcagtat cattgtccat gtctgtgatc tcaaaaacat cagagataac caatatgcta    660
actgctatct cagacggagt gtatggtaaa acctatttgc tagtgcctga ttacattgaa    720
ggggagttcg acacgcaaaa gattcgagtc tttgagatag ggttcatcaa acggtggctg    780
aataacatgc cattactcca gacaaccaac tatatggtcc tcccggagaa ttccaaagcc    840
aagtatgta ctatagcagt gggcgagttg acactggctt ccttgtgtgt agatgagaac    900
accgtattgt tatatcatga cagcaatggt tcacaagatg gtattctagt agtgacgctg    960
gggatatttg gggcaacacc tatggatcaa gttgaagaag tgatacctgt cgcccaccca   1020
tcaatagaaa aaatacatat aacaaatcac cgtgggttca taaagattc aatagcaacc   1080
tggatggtgc ctgcattggt ctctgagaaa caagaggaac aaaaaaattg tctggagtcg   1140
gcttgtcaaa gaaaaaccta ccctatgtgc aaccaaacgt catgggaacc ctttggaggg   1200
agacagttgc catcttatgg gcggttgaca ttacctctag atccaagtat ggaccttcaa   1260
cttaacatat catttacata cggtccagtt atactgaatg gagacggtat ggattattat   1320
gaaagcccac ttccggactc cggatggctt accattccac ccaagaacgg aacagtcctt   1380
ggactgataa acaaagcaag tagaggagac cagttcactg taatccccca tgtgttgaca   1440
tttgcgccca gggaatcaag tggaaattgt tatttaccta ttcaaacatc ccagattatg   1500
gataaagatg tccttactga gtccaattta gtggtgttgc ctacacagaa ttttagatat   1560
gtcatagcaa catatgatat atcccggggt gatcatgcaa ttgttttatta tgtttatgac    1620
ccaatccgga cgatttctta tacgtaccca tttagactaa ctaccaaggg tagacctgat   1680
ttcctaagga ttgaatgttt tgtgtgggat gacgatttgt ggtgtcacca attttatcga   1740
tttgaggctg acatcaccaa ctctacaacc agtgttgaga atttagtctg tataagattc   1800
tcatgtaacc gttcaaaacc ttga                                          1824

<210> SEQ ID NO 41
<211> LENGTH: 1824
<212> TYPE: DNA
<213> ORGANISM: artificial sequence
<220> FEATURE:
<223> OTHER INFORMATION: DQ889177 encoding CDV HA ABK35770

<400> SEQUENCE: 41

```
atgctctcct accaagacaa ggtgggtgcc ttctataagg ataatgcaag agctaattca      60
tccaagctgt ccttagtgac agaagagcaa ggggcagga gaccaccta tttgctgttt      120
gtccttctca tccttctggt tggaatcatg accttgcttg ctatcactgg agttcgattt     180
caccaagtat caactagcaa tatggaattt agcagattac tgaaagagga tatggagaaa     240
tcagaggccg tacatcacca agtcatagat gtcttgacac cgctcttcaa aattattgga     300
gatgaggttg ggttacggtt gccacaaaaa ctaaacgaga tcaaacaatt tatccttcaa     360
aagacaaact tcttcaatcc gaacagggaa ttcgacttcc gcgatctcca ctggtgcatt     420
aatccaccta gtaagatcaa ggtgaatttt actaattact gcgatacaat gggatcaga     480
aaatctattg catcggcagc aaatcccatc cttttatcag cactctcggg aggcagaggt     540
gacatattcc caccatacag atgcagtgga gctactactt cagtgggcag agttttcccc     600
ctatcagtat cattgtccat gtcttttgatt tcaaaaacat cagggataac caatatgcta     660
actgccatct cagacggagt gtatggtaaa acctatttgc tagtgcctga ttacattgaa     720
ggggagttcg acacgcaaaa gattcgagtc tttgagatag ggttcattaa acggtggctg     780
aataacatgc cattattcca gacaaccaac tacatggtcc tcccggagaa ttccaaagcc     840
aaggtatgta ctatagcagt gggcgaattg acactagctt ccttgtgtgt agatgagagc     900
accgtattgt tatatcatga tagcaatggt tcacaaggtg tgttctagt agtgacgctg     960
gggatatttg ggcaacacc tatggatcaa gttgaagaaa tgatacctgt cgctcaccca    1020
tcagtagaaa aaatacatat aacaaatcac cgtgggttca taaaagattc aatagcaacc    1080
tggatggtgc ctgtattggt ctctgagaaa caagaggaac aaaaaaattg tctggagtcg    1140
gcttgtcaaa gaaaaaccta ccctatgtgc aaccaaacgt catgggaacc ctttggaggg    1200
ggacagttgc catcttatgg gcggttgaca ttacctctag atccgagcat tgaccttcaa    1260
cttaacatat catttacata cggtccagtt atactgaatg gagacggtat ggattactat    1320
gaaagcccac ttttggactc tgggtggctt accattcctc caagaacgg aacagtcctt    1380
ggattgataa acaaagcaag tagaggagac cagttcactg taatccccca tgtgttaaca    1440
tttgcgccca gggaatcaag tggaaattgt tatttaccta ttcaaacatc ccagattatg    1500
gataaagatg tccttactga gtccaattta gtggtgttgc ctacacagaa ttttagatat    1560
gtcatagcaa catatgatat atcccggggc gatcatgcaa ttgtttatta tgtttatgac    1620
ccaatccgga cgatatccta tacgtaccca tttagactaa ctaccaaggg tagacctgaa    1680
ttcctaagga ttgaatgttt tgtgtgggat gacgatttgt ggtgtcacca atttaccga    1740
tttgaggctg acatcaccaa ctctacaatc agtgttgaga atttagtcca tataagattc    1800
tcatgtaacc gttcaaaacc ttga                                         1824
```

<210> SEQ ID NO 42
<211> LENGTH: 1824
<212> TYPE: DNA
<213> ORGANISM: artificial sequence
<220> FEATURE:
<223> OTHER INFORMATION: EU716337 encoding CDV HA ACD92997

<400> SEQUENCE: 42

```
atgctctcct accaagacaa ggtgggtgcc ttctataagg ataatgcaag agctaattca      60
```

```
tccaagctgt cctcagtgac agaagagcaa gggggcagga gaccacccta tttgctgttt    120
gtccttctca tcctactggt tggaatcatg gccttgcttg ctatcactgg agttcgattt    180
caccaagtat caactaacaa tatggaattt agcagattgc tgaaagagga tatggagaag    240
tcagaggccg tacatcacca agtcatagat gtcttgacac cgctcttcaa gattattgga    300
gatgaggttg ggttacggtt gccacaaaaa ctaaacgaga tcaaacaatt tatccttcaa    360
aagacaaact tcttcaatcc gaacagggag ttcgatttcc gcgatctcca ctggtgcatt    420
aacccaccta gtaagatcaa agtgaatttt actaattact gcgatacaat tgagatcaga    480
aaatctattg cattggcagc aaatcccatc cttttatcag cactctccgg tggcagaggt    540
gacatattcc caccatacag ttgcagtgga gctactactt cagtaggcag agttttccct    600
ctatcagtat cattgtccat gtctttgatc tcaaaaacat cagagataat caatatgcta    660
accgctatct cagacggggt gtatggtaaa acttatttgc tagttcctga ttatattgaa    720 gggggggttcg acacgcaaaa gattcgagtc tttgagatag ggttcatcaa acggtggctg    780
aatgacatgc cattactcca gacaaccaac tatatggtcc tcccggagaa ttccaaagcc    840
aaggtatgta ctatagcggt gggcgagttg acactggctt ccttgtgtgt agatgagagc    900
accgtattgt tatatcatga cagcgatggt tcacaagatg gtattctagt ggtgacgctg    960
ggaatatttg ggcaacacc tatggatcaa gttgaagagg tgatacctgt tgctcaccca    1020
tcagtagaaa aaatacatat aacaaatcac cgtgggttca taaagattc aatagcaacc    1080 tggatggtgc ctgcattggt atctgagaaa caagaggaac aaaaaaattg tctggagtcg    1140
gcttgtcaaa gaaaatccta ccctatgtgc aaccaaacgt catgggaacc ctttggagga    1200
ggacagttgc catcttatgg gcggttgaca ttacctctag atccaagcat tgaccttcaa    1260
cttaacatct cgtttacata cggtccggtt atactgaatg gagacggtat ggattattat    1320
gaaagcccac ttttggactc cggatggctt accattcccc ccaagaacgg aacagtcctt    1380
ggattgataa acaaagcaag tagaggagac caattcactg taatccccca tgtgttgaca    1440
tttgcgccca gggaatcaag tggaaattgt tatttaccta ttcaaacatc ccagattatg    1500
gataaagatg tccttactga gtccaattta gtggtgttgc ctacacagaa ttttagatat    1560
gtcatagcaa catatgatat atcccggggc gatcatgcga ttgtttatta tgtttatgac    1620
ccaatccggg cgatttctta tacgtacccca tttagactaa ctaccaaggg tagacctgat    1680
ttcctaagga ttgaatgttt tgtgtgggat gacgatttgt ggtgtcacca attttaccga    1740
ttcgaggctg acagcaccaa ctctacaacc agtgttgaga atttagtccg tataagattc    1800
tcatgtaatc gttcaaaacc ttga                                          1824
```

<210> SEQ ID NO 43
<211> LENGTH: 1821
<212> TYPE: DNA
<213> ORGANISM: artificial sequence
<220> FEATURE:
<223> OTHER INFORMATION: FJ011004 encoding CDV HA ACI28389

<400> SEQUENCE: 43

```
atgctctcct accaagacaa ggtgggtgcc ttctataagg ataatgcaag agctaattca     60
tccaagctgt ccttagtgac agaagagcaa gggggccgga gaccacccta tttgctgttt    120
gtccttctca tccttctggt tggaatcatg accttgcttg ctatcactgg agttcgattt    180
caccaagtat caactagcaa tatggaattt agcagattgc tgaaagagga tatggagaaa    240
tcagaggccg tacatcacca agtcatagat gtcttgacac cgctcttcaa aattattgga    300
```

```
gatgaggttg ggttacggtt gccacagaaa ctaaacgaga tcaagcaatt tatccttcaa      360
aagacaaact tcttcaatcc gaacagggaa ttcgacttcc gcgatctcca ctggtgcatt      420
aatccaccta gtaagatcaa ggtgaatttt actaattact gtgatacaat tgagatcaga      480
aaatctattg catcggcagc aaatcccatc cttttatcag cactctccgg aggcagaggt      540
gacatattcc caccatacag atgcagtgga gctactactt cagtgggcag agttttcccc      600
ctatcagtat cattgtccat gtctttgatc tcaagaacat cagagataac caatatgcta      660
actgctatct cagacggagt gtatggtaaa acctatttgc tagtgcctga ttactttgaa      720
ggggagttcg acacgcaaaa gattcgggtc tttgagatag ggttcatcaa acggtggctg      780
aatgacatgc cattactcca gacaaccaac tacatgttcc tcccggagaa ttccaaagcc      840
aaggtatgta ctatagcagt gggcgagttg acactggctt ccttgtgtgt agatgagagc      900
accgtatcgt tatatcatga cggcagtggt tcacaagatg gtattctagt agtgacgctg      960
gggatatttg gggcaacacc tatggatcaa gttgaagagg tgatacctgt cgctcaccca     1020
tcagtagaga aaatacatat aaccaatcac cgtggattca taaaagattc aatcgcaacc     1080
tggatggtgc ctgcattggt ctctgagaaa caagaggaac aaaaaaattg tctggagtcg     1140
gcttgtcaaa gaaaaaccta ccctatgtgc aaccaaacgt catgggaacc ctttggagga     1200
ggacagttgc catcttatgg gcggtggaca ttacctctag atccaagcat tgaccttcaa     1260
cttaacatat cagttacata cggtccagtt atactgaatg gagacggtat ggattattat     1320
gaaagcccac tttcagactc cggatggctt accattcctc caagaacgg aacaatcctt     1380
ggattgataa acaaagcaag tagaggagac cagttcactg taatccccca tgtgttgaca     1440
tttgcgccca gggaatcaag tggaaattgt tatttaccta ttcaaacatc ccagattatg     1500
gataaagatg tccttactga gtccaattta gtggtgttgc ctacacagaa ttttagatat     1560
gtcatagcaa catatgatat atcccggggc gatcatgcaa ttgtttatta tgtttatgac     1620
ccaatccgga cgatttctta tacttaccca tttagactaa ctaccaaggg tagacctgtt     1680
tccctaagga ttgaatgttt tgtgtgggat gacgatttgt ggtgtcacca attttaccaa     1740
tttgaggcag acatcaccaa ctctaccacc agtgttgaga atttagtccg tataagattc     1800
tcatgtaacc gttcaaaacc t                                               1821
```

<210> SEQ ID NO 44
<211> LENGTH: 1821
<212> TYPE: DNA
<213> ORGANISM: artificial sequence
<220> FEATURE:
<223> OTHER INFORMATION: FJ011005 encoding CDV HA ACI28390

<400> SEQUENCE: 44

```
atgctctcct accaagacaa ggtgggtgcc ttttataagg ataatgcaag agccaattca       60
tccaagctgt ctctagtgac agaagagcaa ggggtagga gaccacccta tctgctgttt      120
gtccttctca tcctactggt tggaatcatg accttgcttg ctatcaccgg agttcgattt      180
caccaggtat caactagcaa tatggaattc agcagattgc tgaaagagga tatggagaaa      240
tcagaggccg tacaccacca gtcatggat gtcttgcaca cgctcttcaa aattattgga      300
gatgaggttg ggttacggtt gccacaaaaa ctgaacgaga tcaaacaatt tatccttcaa      360
aagacaaact tcttcaatcc gaacagggaa ttcgacttcc gcgatctcca ctggtgcatt      420
aacccaccta gtaagatcaa ggtgaatttt tctaattact gtgatacaat tgggatcaga      480
```

-continued

```
aaatctattg catcagcagc aaatcctatc cttttatcag cactctccgg aggcagaggt    540
gacatattcc ctccatacag atgcaatgga gctgctactt caataggcag agttttccct    600
ctatctgtgt cattgtccat gtccttgatc tccagaacag cagagataat caatatgcta    660
accgctatct cagacggagt tgatggtaaa acttacttgc tagtgcctga ttatattgaa    720
ggggagttcg aaacgcagaa gattcgagtc tttgagatcg ggttcatcaa acggtggctg    780
aatgacatgt cattactcca gacaaccaac tatatggtcc tcccggagaa ttccaaagcc    840
aaggtatgta ctatagcagt gggcgagttg acactggctt ccttgtgtgt agatgagagc    900
actgtattgt tatatcatga cagcaatggt tcacaagatg gtattctagt agtgacgctg    960
ggaatatttt ggggcacacc tatggatcaa gttgaagagg tgatacctgt cgctcaccca   1020
tcagtagaaa aaatacatat aacaaatcac cgtgggttca taaaagattc aaaagcaatc   1080
tggatggtgc ctgcattggt ctctgagaaa caagaggaac aaaaaaattg tctggagtcg   1140
gcttgtcaaa gaaaaaccta ccctatgtgc aaccaaacgt catgggaacc ctttggggga   1200
ggacaattgc catcctatgg gcggctgaca ttacctctag atccaagtat tgaccttcaa   1260
cttaacatat cgtttacata cggtccggtt atactgaatg agacggtat ggattattat   1320 gaaagcccac ttttggactc cggatggctt accattcctc ccaaaaacgg aacagttctt   1380
ggattgatga acaaagcaag tagaggagac cagttcactg taatccccca tgtgttgaca   1440
tttgcgccta gggaatcagg tggaaaattgt tatttaccta ttcaaacctc ccagattatg   1500
gataaagatg tccttgctga gtccaattta gtggtgttgc ctacacagaa ttttagatat   1560
gtcatagcaa catatgatat atcccgggac gatcatgcga ttgtttatta tgtttatgat   1620
ccaatccgga cgatttctta tacgtaccca tttagactaa ctaccaaggg tagacctgat   1680
ttcctaagaa ttgaatgttt tgtatgggat gacgatttgt ggtgtcatca attttaccga   1740
ttcgaggctg acatcactaa ctctacaacc agtgttgaga atttagtccg tataagattc   1800
tcatgtaacc gttcaaaacc t                                             1821
```

<210> SEQ ID NO 45
<211> LENGTH: 1824
<212> TYPE: DNA
<213> ORGANISM: artificial sequence
<220> FEATURE:
<223> OTHER INFORMATION: FJ705233 encoding CDV HA ACN58242

<400> SEQUENCE: 45

```
atgctctcct accaagacaa ggtgggtgcc ttctataagg ataatgcaag agctaattca    60
tccaagctgt ccttagtgac agaagagcaa gggggaagga gaccacccta tttgctgttt   120
gtccttctca tcctactgac tggaatcctg gccttgcttg ccatcactag agttcgattt   180
caccaagtat caactagcaa tatggaattt agcagattgc tgaaagagga tatggagaaa   240
tcagaggccg tacatcacca agtcatagat gtcttgacgc cgctcttcaa aattattgga   300
gatgagattg ggttacggtt gccacaaaaa ctaaacgaga tcaaacaatt tatccttcaa   360
aagacaaact tcttcaatcc gaacagggaa ttcgacttcc gcgatctcca ctggtgcatt   420
aacccaccta gcaagatcaa ggtgaatttt actaattact gtgatacagt tgggtcaaa    480 aaatctattg catcggcagc aaatcccatc attttatcag cactctccgg agccagaggt   540
gacatattcc cgccgtgcag atgcagtgga gctactactt cagtaggcag agtattcccc   600
ctatccgtat cattatccat gtctttgata tcaagaacat cagagataat caatatgcta   660
accgctatct cagacggaat gtatggtaaa acttatttgc tagtgcctga ttatattgaa   720
```

```
ggggagttcg actcgcaaaa gattcgagtc tttgagatag ggtttatcag acggtggctg    780
aatgacatgc ctttactcca gacaaccaac tatatggtcc ttccggaaac ttccaaagcc    840
aaggtatgta ctatagcagt gggcgagctg acactagctt ccttgtgtgt agatgagagc    900
accgtattgt tatatcatga cagcaatggt tcacaaaatg gtattctagt agtgacattg    960
ggaatatttg ggcaacacc tatggatcaa gttgaagagg tgatacctat cgctcaccca   1020
tcagtggaga gaatacatat aacaaatcac cgtgggttca taaagattc aatagtaacc   1080
tggatggtgc ctgtattggt ctcagagaaa caagaggagc aaaaaaactg tctggagtct   1140
gcttgtcaaa gaaaaaccta tcctatgtgc aaccaaacgt catgggaacc ctttggagga   1200
ggacagttgc cctcttatgg gcggttgaca ttacctctag atccaagcat tgaccttcag   1260
cttaacatat catttacata tggtccggtt atactgaacg agacggtat ggattattat   1320
gaaagcccgc ttttggactc cggatggctt accatacctc taagaacgg aacagtcctt   1380
ggattgataa acaaagcaag tagaggagac cagttcactg tgaccccca tgtgttgaca   1440
tttgcgccca gggaatcaag tggaaattgt tatttgccta ttcaaacatc ccagattatg   1500
gataaagatg tccttactga gtccaatta gtagtgttac ctacacagaa ttttaggtat   1560
gtcatagcaa catatgatat atcccggggc gatcatgcaa ttgtttatta tgtttatgac   1620
ccaatccgga cgatttctta tacatacca tttagactaa ctaccaaggg tagacctgat   1680
ttcctaagga ttgaatgttt tgtgtgggat gacgatttgt ggtgtcatca atttaccga   1740
ttcgaggcta acattactaa ctctacaacc agtgttgaga atttagtccg tataagattc   1800
tcatgtaacc gttcaaaacc ttga                                          1824

<210> SEQ ID NO 46
<211> LENGTH: 1824
<212> TYPE: DNA
<213> ORGANISM: artificial sequence
<220> FEATURE:
<223> OTHER INFORMATION: DQ228166 encoding CDV HA ABB51156
<220> FEATURE:
<221> NAME/KEY: misc_feature
<222> LOCATION: (1027)..(1027)
<223> OTHER INFORMATION: n is a, c, g, or t

<400> SEQUENCE: 46
atgctctcct accaagacaa ggtgggtgcc ttctataaag ataatgcaag agccaattca     60
tccaagctgt ccttagtgac agaagagcaa gggggtagaa gaccacccett tttgctgttt   120
gtccttctcg tcctactggt tggaatcatg gccttgcttg ctatcactgg agttcgattt    180
catcaagtat caaccagcaa tatggaattt agtagattgc tgaaagagga tatggagaaa    240
tctgaggccg tacatcatca agtcatagat gttttgacac cgctcttcaa aatcatcgga    300
gatgagattg ggttacggtt gccacaaaaa ctaaacgaga ttaaacaatt tatccttcaa    360
aagacaaact tcttcaatcc gaacagggaa ttcgacttcc gcgatctcca ctggtgcatt    420
aacccaccta gtaagatcaa ggtgaatttt actaattact gcgatacaat tgggatcaga    480
aaatctattg catcggcagc aaatcctatc cttttatcag cactttctgg aggcagaggt    540
gacatattcc caccatacaa gtgcaatgga gctgctactt cagtaggcag agttttcccc    600
ctttcagtat cattgtccat gtctttgatc tcaaaaacat cagggataat caatatgcta    660
accgctatct cagacggagt gtatggtaaa acttacttgc taatgcctga ttatattgaa    720
ggggagttcg acacgcaaaa gattcgagtc tttgagatag ggttcatcaa acggtggctg    780
```

```
aatgacatgc cattactcca gacaaccaac tatattgtcc tcccggagaa ttccaaagcc      840
aaggtatgta ctatagcagt gggtgagttg acactggctt ccttgtgtgt agatgagagc      900
accgtattgt tatatcatga cagcaatggt tcacaagatg gtattctagt agtgacactg      960
ggaatattcg gggcaacacc tatggatcaa gttgaagagg tgatacctgt cgctcaccca     1020
tcagtanaaa aaatacatat aacaaatcac cgtgggttca taaaagattc aatagcaacc     1080
tggatggtgc ctgcattgat ctctggggaa caagaggaac aaaaaaattg tctggagtcg     1140
gcttgtcaaa gaaaatccta ccctatgtgc aaccaaacgt catggaaacc ctttggagga     1200
ggacagttgc catcttatgg gcggttgaca ttacctctag atccaggcat tgaccttcaa     1260
cttaacatat catttacata cggtccggtt atactgaatg gagacggtat ggattattat     1320
gaaagcccac ttttggactc cggatggctt accattcctc caagaacgg  aacaattctt     1380 ggattgataa acaaggcaag tagaggagac cagttcactg taatccccca tgtgttgaca     1440
tttgcgccca gggaatcaag tgggaattgt tatttaccta ttcaaacatc tcagattatg     1500
gataaagatg tccttactga gtccaattta gtggtattgc ctacacagaa ttttagatat     1560
gtcatagcaa catatgatat atcccggaac gatcatgcga ttgtttatta tgtttatgac     1620
ccaatccgga ctatttctta tacgcaccca tttagactaa ctactaaggg tagacctgat     1680
ttcctaagga ttgaatgttt tgtgtgggat gatgatttgt ggtgtcacca attttaccgg     1740
ttcgaggctc acatcaccaa ctctgcaacc agtgttgaga atttggtccg tataagattc     1800
tcatgtaacc gttcaaaacc ttga                                            1824

<210> SEQ ID NO 47
<211> LENGTH: 1824
<212> TYPE: DNA
<213> ORGANISM: artificial sequence
<220> FEATURE:
<223> OTHER INFORMATION: DQ889187 encoding CDV HA ABK35780

<400> SEQUENCE: 47
atgctctcct accaagacaa ggtgagtgcc ttctataagg ataatgcaag agccaattca       60
tccaaactgt ccttagtgac agaagaacat gggagcagga gaccacccta tttgctgttt      120
atccttctca tcctactggt tggaatcatg gccttgcttg ctatcactgg agctcgattt      180
caccaagtat caactagcaa tatggaattt agcagattgc tgaaagagga tatggagaaa      240
tcagaggccg tacatcacca agtcatagat gtcttgacac cgctctttaa aattattggt      300
gatgagattg gttacggtt  gccacaaaaa ctaaacgaga tcaaacagtt tatccttcaa      360 aagacaaaact tcttcaatcc gaaaagggaa ttcgacttcc gcgacctcca ctggtgcatt      420
aacccaccta gtaagatcaa ggtgaatttt actaattact gcgatacaat gggatcaga       480 aaatctattg cattggcagc aaatcccatc ctttgtcgg  cactctccag aggcagggt       540 gacatattcc caccatacag atgtagtgga gctgctactt cagtaggcag agttttcccc      600
ctctcagtat cattgtccat gtctttgatc tcaagaacat cagagataat caatatgcta      660
accgctatct cagatggagt gtatggtaaa acttacttgc tagtgcctga ttatattgaa      720
ggggaattcg acacacaaaa gattcgagtc tttgagatag ggttcatcaa acggtggctg      780
aatgacatgc cattactcca gacaaccaac tatatggtcc tcccggagaa ttccaaagcc      840
aaggtatgta ctatagcagt gggcgagttg acactggctt ccttgtgtgt agatgagagc      900
actgtattac tatatcatga cagcaatggt tcacaagatg gtattctagt agtgacgctg      960
ggaatatttg gggcaacacc tatggatcaa gttgaagagg tgatacctgt cgctcatcca     1020
```

```
tcagtagaaa aaatacatat aacaaatcac cgtgggttca taaaagattc aatagcaacc    1080
tggatggtgc ctgtattggt ctctgagaac caagaggaac aaaaaaattg tctggagtcg    1140
gcttgtcaaa gaaatccta ccctatgtgc aaccaaacgt catgggaacc ctttggagga    1200
ggacagctgc catcttatgg gcggttgaca ttacctctag atccaggcat tgaccttcaa    1260
cttaatctat cgtttacata cggtccgatt atactgaatg gagacggtat ggattattat    1320
gaaagcccac ttttgaactc cggatggctt accattcctc ccaagaacgg gacaattctt    1380
ggattgataa acaaagcaag tagaggagac cagttcactg taaccccca tgtgttgaca    1440 tttgcgccta gggaatcaag tgggaattgt tatttaccta ttcaaacatc tcagattatg    1500
gataaagatg tccttactga gtccaatttg gtggtgttgc ctacacagaa ttttagatat    1560
gtcatagcaa catatgatat atcccgggat gatcatgcga ttgtttatta tgtttatgac    1620
ccaatccgga cgatttctta tacgtaccca tttagactaa ctaccaaggg tagacctgat    1680
ttcctaagga ttgaatgttt tgtgtgggat tacgatttgt ggtgtcacca attttaccga    1740
ttcgaggctg acatcaccaa ctctacaacc agtgttgaga atttagtccg tataagattc    1800
tcatgtaacc gttcaaaacc ttga                                           1824

<210> SEQ ID NO 48
<211> LENGTH: 1824
<212> TYPE: DNA
<213> ORGANISM: artificial sequence
<220> FEATURE:
<223> OTHER INFORMATION: FJ423608 encoding CDV HA ACJ46470

<400> SEQUENCE: 48
atgctctctt accaagacaa ggtgggtgcc ttctataagg ataatgcaag agctaattca      60
tccaagctgt ccttagtgac agaagagcaa gggggaagga gaccacccta cttgttttt     120 gtccttctca ccctactgat tggaatcctg gccttgcttg ccatcactgg agttcgattt     180
caccaagtat caactagcaa tatggaattt agcagattgc tgaaagagga tatggagaaa    240
tcagaggccg tacatcacca agtcatagat gtcttgacac cgctcttcaa aattattgga    300
gatgagattg ggtacggtt gccacaaaaa ctaaacgaga tcaaacaatt tatccttcaa    360
aagacaaact tcttcaatcc gaacagggaa ttcgacttcc gcgatctcca ctggtgcatt    420
aacccaccta gcaagatcaa ggtgaatttt actaattact gtgatacagt tgggggtcaaa   480 aaatctatta catcggcagc aaatcccatc attttatcag cactctccgg agccagaggt    540
gacatattcc cgccgtacag atgcagtgga gctactactt cagtaggcag agtattcccc    600
ctatctgtat cattatccat gtctttgata tcaagaacat cagagataat caatatgcta    660
accgctatct cagacggagt gtatggtaaa acttatttgc tagtgcctga ttatattgaa    720
ggggagttcg actcgcaaaa gattcgagtc tttgagatag ggtttatcaa acggtggctg    780
aatgacatgc cttactccca gacaaccaac tatatggttc tcccggaaac ttccaaagcc    840
aaggtatgta ctatagcagt gggcgagctg acactagctt ccttgtgtgt agatgagagc    900
actgtattat tatatcatga cagcaatggt tcacaaaatg gtattctagt agtgacattg    960
ggaatatttg gggcaacatc tatggatcaa gttgaagagg tgatacctat cgctcaccca    1020
tcagtggaga gaatacatat aacaaatcac cgtgggttca taaaagattc aatagtaacc   1080
tggatggtgc ctgtattggt ctctgagaaa caagaggagc aaaaaaactg tctggagtct   1140
gcttgtcaaa gaaatccta ccctatgtgc aaccaaacgt catgggaacc ctttggagga    1200
```

```
ggacagttgc cttcttatgg gcggttgaca ttacctctag atccaagcat tgaccttcaa   1260
cttaacatat catttacata tggtccggtt atactgaacg gggacggtat ggattattat   1320
gaaagcccac ttttggaatc cggatggctt accataccc ctaagaacgg aacagtcctt   1380
ggattgataa acaaagcaag tagaggagac cagttcactg cgaccccca tgtgttgaca   1440 tttgcgccca gggaatcaag tggaaattgt tatttgccta ttcaaacatc ccagattatg   1500
gataaagatg tccttactga gtccaattta gtggtgttac ctacacagaa ttttagatat   1560
gtcatagcaa catatgatat atcccggggc gatcatgcaa ttgtttatta tgtttatgac   1620
cctatccgga cgatttctta tacataccca tttagactaa ctaccaaagg tagacctgat   1680
ttcctaagga ttgaatgttt tgtgtgggat gacgatttgt ggtgtcatca attttaccga   1740
ttcgaggcta acatcactaa ctctacaacc agtgttgaga atttagtccg tataagattc   1800
tcatgtaacc gttcaaaacc ttga                                          1824

<210> SEQ ID NO 49
<211> LENGTH: 1824
<212> TYPE: DNA
<213> ORGANISM: artificial sequence
<220> FEATURE:
<223> OTHER INFORMATION: EU325730 encoding CDV HA ABX84040

<400> SEQUENCE: 49
atgctctctt accaagacaa ggtgggtgcc ttctataagg acaatgcaag agctaattca     60
tccaagctgt ccttagtgac agaagagcaa gggggaagga gaccacccta tttgctgttt    120
gtccttctca tcctactgat tggaatcctg gccttgcttg ccatcactgg agttcgattt    180
caccaagtat caactagcaa tatggaattt agcagattgc tgaaagagga tatggagaaa    240
tcagaggccg tacatcacca agtcatagat gtcttgacac cgctcttcaa aattattgga    300
gatgagattg ggttgcggtt gccacaaaaa ctaaacgaga tcaaacaatt tatccttcaa    360
aagacaaact tcttcaatcc gaacagggaa ttcgacttcc gcgatctcca ctggtgcatt    420
aacccaccta gcaagatcaa ggtgaatttt actaattact gtgatacagt tggggtcaaa    480
aaatctattg catcggcagc aaatcccatc attttatcag cactctccgg agccagaggc    540
gacatattcc cgccgtacag atgcagtgga gctactactt cagtaggcag agtattcccc    600
ctatccgtat cattatccat gtctttgata tcaagaacat cagagataat caatatgcta    660
accgctatct cagacggagt gtatggtaaa acttatatgc tagtgcctga ttatattgaa    720
ggggagttcg actcgcaaaa gattcgagtc tttgagatag ggtttatcaa cggtggctg    780 aataacatgc ctttactcca gacaaccaac tatatggtcc tcccggaaac ttccaaagcc    840
aaggtatgta ctatagcagt gggcgagctg acactagctt ccttgtgtgt agatgagagc    900
accgtattgt tatatcatga cagcaatggt tcacaaaatg gtattctagt agtgacattg    960
ggaatatttg ggcaacacc tatggatcaa gttgaagagg tgatacctat cgctcaccca   1020
tcagtggaga gaatacatat aacaaatcac cgtgggttca taaaagattc agtagtaacc   1080
tggatggtgc ctgtattggt ctctgagaaa caagaggagc aaaaaaactg tctggagtct   1140
gcttgtcaaa gaaatcctaa cccgatgtgc aaccaaacgt catgggaacc ctttggagga   1200
ggacagttgc cttcttatgg gcggttgaca ttacctctag atccaagcgt tgaccttcaa   1260
cttaacatat catttacata tggtccggtt atactgaacg agacggtat ggattattat    1320 gaaagcccac ttttggaatc cggatggctt gccataccc ctaagaacgg aacagtcctt   1380
ggattgataa acaaagcaag tagaggagac cagttcactg tgaccccca tgtgttgaca   1440
```

```
tttgcgccca gggaatcaag tgggaattgt tatttgccta ttcaaacatc ccagattatg    1500
gataaagatg tccttactga gtccaattta gtggtgttac ctacacagaa ttttagatat    1560
gtcatagcaa catatgatat atcccggggc gatcatgcaa ttgtttatta tgtttatgac    1620
cctatccgga cgatttctta tacatacccca tttagactaa ctaccaaggg tagacctgat    1680
```

```
ttcctaagga ttgaatgttt tgtgtgggat gacgatttgt ggtgtcatca attttaccga    1740
ttcgaggcta acatcactaa ctctacaacc agtgttgaga atttagtccg tataagattc    1800
tcatgtaacc gttcaaaacc ttga                                            1824
```

<210> SEQ ID NO 50
<211> LENGTH: 4178
<212> TYPE: DNA
<213> ORGANISM: artificial sequence
<220> FEATURE:
<223> OTHER INFORMATION: vCP2392 part containing C3 arms, H6 promoter
      and GM-CSF
<220> FEATURE:
<221> NAME/KEY: misc_feature
<222> LOCATION: (1)..(2586)
<223> OTHER INFORMATION: this is the C3 arm region
<220> FEATURE:
<221> NAME/KEY: promoter
<222> LOCATION: (2587)..(2772)
<223> OTHER INFORMATION: this is the H6 promoter region
<220> FEATURE:
<221> NAME/KEY: CDS
<222> LOCATION: (2773)..(3207)
<223> OTHER INFORMATION: this is the caGM-CSF coding region
<220> FEATURE:
<221> NAME/KEY: misc_feature
<222> LOCATION: (3208)..(4178)
<223> OTHER INFORMATION: this is the C3 arm region

<400> SEQUENCE: 50

```
ctttatacta ctgggttaca acagctggtg ataacagaat gtaaatcatt attacttaat      60
agttccatta ttatatgttt gatatctata ggtaacctac ctattattcc tagattctta    120
ctctctttta cagctttaac tattagctga tgtctatgaa aagctaatga tttatttttc    180
cgtattaatt ccctatatat acgtatacat gcaggtatct tattaactct aggattagtt    240
acgaacttta ccataagatc tatgttattg tcaagaaaga tattaaaaga atatatagaa    300
tttaacttta tatgtgttat aacatctagt tcttttttcgc atgattcttt tatagatagt    360
agtcttttat tactgtttat atgttccatg tttactataa aaccttctga attagctatt    420
tcaggatttt tagatatttc taacatcatt ttagatatta tcataatagc tatcttgtca    480
tctaaaaagc taacacaagt tagaggcgta ttaccgtgat tatttagaga attatagtcg    540
gcgttataag ataaaagtaa ttttatatta ttaaaactat tagataacat agctttatgt    600
aaaggagtat ttccagataa cttagcttta gcatttacgt aagcaccgtg gtcaagtaag    660 agttaacaa attctgtttt catagaacta actgccatgt atagaggagt gaaaccttta    720
tgattataga cgtttacata gcaaccatat aataagatcg cattcagtat attaatatct    780
ttcatttcta tagctatgtg aataacatgt ttatctaatc ctaccaactt tgtatcagta    840
ccgtacttca gtaataagtt tactatagtt ttgttttttag atgcaacagc tatatttaga    900
acggtatcta tatgattatt aaccacatta acattagatc ctcttttctaa aagtgtcttt    960 gttgtttcga tatcgttacg tgaaacagcg taatgtaagg gactgcccat acagtcatct   1020
attacgttta tatcagctcc tagatttaac agaagtgctg ttacatcttt tcttctatta   1080
attaccgaat gatgtaatgg ggttttacct aaatcatctt gttcgtttat aggcactccg   1140
```

```
tgatttataa gtaacgctat tatatcgtaa ctacaattat ttttaagtgc ctttatgaga    1200
tactgtttat gcaaaaataa acttttatct attttaatac tattatctaa caatatccta    1260
attaaatcta tattcttata ctttatagcg taatgtaacg gagtttcaaa atttctagtt    1320
tgtatattaa gatcaatatt aaaatctata aatattttat acatatcatc agatatctta    1380
tcatacagta catcgtaata atttagaaag aatctattac aattaacacc ttttttaat     1440 aaatatctag ttaatgactt attgtttcta tatacagaaa tatataacgg actatttcca    1500
gaatgtatct gttctatgtc agcgccagaa tctattagta gtttagcaat ttctgtatta    1560
tctaaactag cagctttatg aagaggagga ttttacatt ttaaaatatc ggcaccgtgt     1620
tctagtaata attttaccat ttctatatca gaaatactta cggctaaata caaagacgtt    1680
gatagtatat ttacgttatt gtatttgcat ttttaagta tataccttac taaatttata    1740
tctctatacc ttatagcttt atgcagttca tttataagtc ttccattact catttctggt    1800
aatgaagtat tatatatcat tatgatatta tctctatttt attctaataa aaaccgttat    1860
catgttattt attatttgtt ataattatac tatttaataa attataccaa atacttagat    1920
acttattaat accatcctag aacttgtatt tcttgccccc taaacttgga catgcactcc    1980
attaggcgtt tcttgttttc gacatcgtcc tccttaacat atcctactgt tatgtgagga    2040
ttccacggat tatctactgt gatatcacca aacacgtcct tcgaacaggg taccgcattc    2100
agcagaacat ttcttagggc tctaagttca tcagatacct ccagtttcat aactacagcg    2160
catcctttcg ctcccaactg tttagaggcg ttactctgag gaaaacacat ctcttcttta    2220
cagactatag aaatagtctg taaatcttga tcagttattt gcttttgaa attttcaaat     2280 ctatcacatt gatccatatt tgctattcca agagttatat gaggaaaaat atcacatcct    2340
gtcatgtatt ttattgtaac attattataa tctgtaacat cagtatctaa cctaacgtcg    2400
taaaagttaa cagatgccca gttactataa tcccaaggaa ccttaacatc taatcccatt    2460
aaaatagtat cctttctact attttttca ttggcaagta tgtggcttag tttacacaaa     2520
attcctgcca ttttgtaacg atagcgaagc aatagcttgt atgcttttta tttgattaac    2580 tagggggttaa ttaattagtc atcaggcagg gcgagaacga gactatctgc tcgttaatta    2640
attagagctt ctttattcta tacttaaaaa gtgaaaataa atacaaaggt tcttgagggt    2700
tgtgttaaat tgaaagcgag aaataatcat aaattatttc attatcgcga tatccgttaa    2760
gtttgtatcg taatgtggct gcagaacctg ctgttcctgg gcaccgtggt gtgcagcatc    2820
agcgccccca ccagatcccc caccctggtg acccggccca gccagcacgt ggacgccatc    2880
caggaagccc tgagcctgct gaacaacagc aacgacgtga ccgccgtgat gaacaaggcc    2940
gtgaaggtgg tgtccgaggt gttcgacccc gagggcccca cctgcctgga acccggctg     3000 cagctgtaca agagggcct gcagggcagc ctgaccagcc tgaagaaccc cctgaccatg    3060
atggccaacc actacaagca gcactgcccc cccaccccg agagcccttg cgccacccag     3120
aacatcaact tcaagagctt caaagagaac ctgaaggact tcctgttcaa catcccttc     3180 gactgctgga gcccgtgaa gaagtgatga ctcgagtttt tattgactag gggttttat     3240 agctaattag tcaatgtga gttaatatta gtatactaca ttactaattt attacatatt    3300
catttatatc aatctagtag catttagctt ttataaaaca atataactga atagtacata    3360
ctttactaat aagttataaa taagagatac atatttatag tatttactt tctcactga     3420 atataataat ataattatac aaatataatt tttaatacta tatagtatat aactgaaata    3480
```

```
aaataccagt gtaatatagt tattatacat ttataccaca tcaaagatga gttataacat    3540
cagtgtcact gttagcaaca gtagttatac gatgagtagt tactctcgta tggcgttagt    3600
atgtatgtat cttctagttt tcttagtagg cattatagga aacgtcaagc ttataaggtt    3660
attaatggta tctagaaata tatctattat accgtttctc aacttgggaa tagccgattt    3720
gctgtttgtg atattcatac ctttatacat tatatacata ctaagtaatt tccattggca    3780
ttttggtaaa gcactttgta aaattagttc tttcttttt  acttctaaca tgtttgcaag    3840
tatattttta ataactgtaa taagcgtata tagatatgta aaaattaccc ttcctggatt    3900
tacctataaa tatgttaaca ttagaaatat gtacattact atatttttca tatggattat    3960
ttctattata ctagggattc ctgctcttta ctttagaaat actatcgtaa caaaaaataa    4020
cgacacgctg tgtattaatc attatcatga taatagagaa attgctgaat tgatttacaa    4080
agttattatc tgtatcagat ttattttagg atacctacta cctacgataa ttatactcgt    4140
atgctatacg ttactgatct acagaactaa caatgcat                           4178

<210> SEQ ID NO 51
<211> LENGTH: 621
<212> TYPE: DNA
<213> ORGANISM: artificial sequence
<220> FEATURE:
<223> OTHER INFORMATION: vCP2392 part seq containing H6 promoter +
      caGM-CSF
<220> FEATURE:
<221> NAME/KEY: promoter
<222> LOCATION: (1)..(186)
<223> OTHER INFORMATION: this is the H6 promoter region
<220> FEATURE:
<221> NAME/KEY: CDS
<222> LOCATION: (187)..(621)
<223> OTHER INFORMATION: this is the caGM-CSF coding region

<400> SEQUENCE: 51
ttaattaatt agtcatcagg cagggcgaga acgagactat ctgctcgtta attaattaga     60
gcttctttat tctatactta aaaagtgaaa ataaatacaa aggttcttga gggttgtgtt    120
aaattgaaag cgagaaataa tcataaatta tttcattatc gcgatatccg ttaagtttgt    180
atcgtaatgt ggctgcagaa cctgctgttc ctgggcaccg tggtgtgcag catcagcgcc    240
cccaccagat ccccccaccct ggtgacccgg cccagccagc acgtggacgc catccaggaa   300
gccctgagcc tgctgaacaa cagcaacgac gtgaccgccg tgatgaacaa ggccgtgaag    360
gtggtgtccg aggtgttcga ccccgagggc cccacctgcc tggaaacccg gctgcagctg    420
tacaaagagg gcctgcaggg cagcctgacc agcctgaaga ccccctgac  catgatggcc    480 aaccactaca gcagcactg cccccccacc cccgagagcc cttgcgccac ccagaacatc    540
aacttcaaga gcttcaaaga gaacctgaag gacttcctgt tcaacatccc cttcgactgc    600
tggaagcccg tgaagaagtg a                                              621
```